US010550413B2

(12) United States Patent
David et al.

(10) Patent No.: US 10,550,413 B2
(45) Date of Patent: Feb. 4, 2020

(54) FUNGAL CELLS AND METHODS FOR PRODUCTION OF VERY LONG CHAIN FATTY ACID DERIVED PRODUCTS

(71) Applicant: BIOPETROLIA AB, Gothenburg (SE)

(72) Inventors: Florian David, Gothenburg (SE); Verena Siewers, Gothenburg (SE); Anastasia Krivoruchko, Gothenburg (SE); Leonie Wenning, Hisingsbacka (SE); Tao Yu, Gothenburg (SE); Yong-Jin Zhou, Gothenburg (SE); Jens Nielsen, Gothenburg (SE)

(73) Assignee: BIOPETROLIA AB, Gothenburg (SE)

( * ) Notice: Subject to any disclaimer, the term of this patent is extended or adjusted under 35 U.S.C. 154(b) by 109 days.

(21) Appl. No.: 15/562,951

(22) PCT Filed: Apr. 1, 2016

(86) PCT No.: PCT/SE2016/050274
§ 371 (c)(1),
(2) Date: Sep. 29, 2017

(87) PCT Pub. No.: WO2016/159869
PCT Pub. Date: Oct. 6, 2016

(65) Prior Publication Data

US 2018/0112240 A1 Apr. 26, 2018

Related U.S. Application Data

(60) Provisional application No. 62/142,236, filed on Apr. 2, 2015.

(51) Int. Cl.

| | |
|---|---|
| ***C12P 7/64*** | (2006.01) |
| ***C12N 9/00*** | (2006.01) |
| ***C12N 9/10*** | (2006.01) |
| ***C12P 7/04*** | (2006.01) |
| ***C12N 9/02*** | (2006.01) |

(52) U.S. Cl.
CPC .......... *C12P 7/6409* (2013.01); *C12N 9/0008* (2013.01); *C12N 9/1029* (2013.01); *C12P 7/04* (2013.01); *C12P 7/6463* (2013.01); *C12Y 102/0105* (2013.01); *C12Y 203/01075* (2013.01)

(58) Field of Classification Search
None
See application file for complete search history.

(56) References Cited

FOREIGN PATENT DOCUMENTS

| | | |
|---|---|---|
| WO | WO 01/94565 | 12/2001 |
| WO | WO 2008/119082 | 10/2008 |
| WO | WO 2012/087964 | 6/2012 |
| WO | WO 2015/042306 | 3/2015 |

OTHER PUBLICATIONS

Runguphan, Weerawat et al., "Metabolic engineering of *Saccharomyces cerevisiae* for production of fatty acid-derived biofuels and chemicals", *Metabolic Engineering*, vol. 21, pp. 103-113, (2014).

Shi, Shuobo et al, "Functional expression and characterization of five wax ester synthases in *Saccharomyces cerevisiae* and their utility for biodiesel production", Biotechnology for Biofuels, Biomed Central LTD, GB, (Feb. 24, 2012), vol. 5, No. 1, doi:10.1186/1754-6834-5-7, ISSN 1754-6834, p. 7.

Valle-Rodriguez, Juan Octabio et al., "Metabolic Metabolic engineering of *Saccharomyces cerevisiae* for production of fatty acid-derived biofuels and chemicals", Metabolic Engineering, US, (Jan. 1, 2014), vol. 21, doi:10.1016/j.ymben.2013.07.003, ISSN 1096-7176, pp. 103-113.

*Primary Examiner* — Suzanne M Noakes
(74) *Attorney, Agent, or Firm* — Myers Bigel, P.A.

(57) ABSTRACT

The present invention generally relates to a genetically modified fungal cell capable of producing a very long, chain fatty acid (VLCFA) and/or a VLCFA derivative. The genetically modified fungal cell comprises at least one exogenous gene encoding a fatty acyl-CoA reductase, and at least one gene encoding an elongase, and/or at least one gene encoding a fatty acid synthase.

21 Claims, 25 Drawing Sheets

Specification includes a Sequence Listing.

FUNGAL CELLS AND METHODS FOR PRODUCTION OF VERY LONG CHAIN FATTY ACID DERIVED PRODUCTS

STATEMENT OF PRIORITY

This application is a 35 U.S.C. § 371 national phase application of International Application Serial No. PCT/SE2016/050274, filed Apr. 1, 2016, which claims benefit, under 35 U.S.C. § 119 (a) of U.S. Patent Application No. 62/142,236, filed Apr. 2, 2015, the entire contents of each of which are incorporated by reference herein.

FIELD OF THE INVENTION

The present invention relates to the development of genetically engineered fungal cells, preferably yeasts, that can produce specific chain length fatty acid derived products in a controllable and economic fashion. More specifically the invention relates to the production of very long chain fatty acid (VLCFA) products and derivatives, such as very long chain fatty alcohols, e.g., docosanol, very long chain fatty acids, e.g., erucic acid, nervonic acid, and wax esters of such very long chain fatty alcohols and fatty acids, e.g., jojoba oil esters, that can be used in the production of a range of industrial chemicals and oils, as well as pharmaceutical and cosmetic products.

BACKGROUND OF THE INVENTION

Primary alcohols are a product class of compounds having a variety of industrial applications, this include a variety of biofuels and specialty chemicals. Primary alcohols also can be used to make a large number of additional industrial products including polymers and surfactants. Higher primary alcohols, also known as fatty alcohols, and their derivatives have numerous commercial applications, including use as surfactants, lubricants, plasticizers, solvents, emulsifiers, emollients, thickeners, flavors, fragrances, and fuels. Fatty alcohols can further be dehydrated to alpha-olefins, which have utility in the manufacture of polymers, lubricants, surfactants, plasticizers, and can also be used in fuel formulations.

Current technologies for producing fatty alcohols involve inorganic catalyst-mediated reduction of fatty acids to the corresponding primary alcohols. The fatty acids used in this process are derived from natural sources, e.g., plant and animal oils and fats, primarily coconut, palm, palm kernel, tallow and lard. These various sources have different fatty acid compositions; of particular importance are the varying acyl chain lengths that are present. As a consequence, the fatty alcohols derived from these fatty acids also have varying chain lengths. The chain length of fatty alcohols greatly impacts the chemical and physical properties of the molecules, and thus different chain lengths are used for different applications. Fatty alcohols are currently produced from, for example, hydrogenation of fatty acids, hydroformylation of terminal olefins, partial oxidation of n-paraffins and the Al-catalyzed polymerization of ethylene. Fatty alcohols can also be made by chemical hydration of alpha-olefins produced from petrochemical feedstocks. Unfortunately, it is not commercially viable to produce fatty alcohols directly from the oxidation of petroleum-based linear hydrocarbons (n-paraffins). This impracticality is because the oxidation of n-paraffins produces primarily secondary alcohols, tertiary alcohols or ketones, or a mixture of these compounds, but does not produce high yields of fatty alcohols. Additionally, currently known methods for producing fatty alcohols suffer from the disadvantage that they are restricted to feedstock which is relatively expensive, notably ethylene, which is produced via the thermal cracking of petroleum. In addition, current methods require several steps, and several catalyst types.

Plant primary fatty alcohols occur either in free form or are linked by an ester-bond with a fatty acid, e.g. palmitic acid, to give a wax ester or an aromatic compound, e.g. ferulic acid, to give an alkyl hydroxycinnamate. These various compounds are often components of plant extracellular lipid barriers: cuticle coating the aerial surfaces, suberin found in the cell walls of various internal and external tissue layers, and sporopollenin found in the outer walls of pollen grains. These waxes are usually complex mixtures of very-long-chain ($C_{20}$-$C_{34}$) fatty acids and derivatives including primary fatty alcohols and wax esters. Wax esters can also serve as energy storage, such as in the case of jojoba (*Simmondsia chinensis*) seed oil.

Unlike most other plants, the oil of jojoba seeds, which constitutes between 45-55%, by weight, of the seeds, is mainly composed of very long chain monoesters of fatty acids and alcohols (97-98%, by weight) rather than triglycerides. These esters, which are commonly referred to as wax esters, are straight chain esters predominantly 36-46 carbons in length, with an ester bond approximately in the center of the chain. The oil, which exists as a liquid at room temperature, is used extensively as a raw material in the cosmetic and pharmaceutical industries for its dermatological properties. Jojoba oil is also used as an alternative to sperm oil as a lubricant and as a plasticizer. Because it is not subject to lipase hydrolysis and is thus poorly digested, jojoba oil has also been investigated as a non-caloric fat replacement in foods.

However, the relatively short supply of jojoba oil and its extremely desirable properties have resulted in a rather high price, preventing its use for commercial preparation of a large number of useful derivatives and products.

Thus, there exists a need for alternative means for cost effectively producing commercial and scalable quantities of very long chain length fatty acid derived products, including jojoba oil.

Previously, synthesis of long chain fatty alcohols and very long chain wax ester have only been demonstrated in yeast and *Escherichia coli* when heterologous expression of particular enzymes, including fatty acid reductase (FAR) and wax ester synthases, is combined with feeding of fatty acid substrates or relevant precursors (Kalscheuer et al., 2006; Li et al., 2008; Teerawanichpan and Qiu, 2010). However, these solutions are not suitable for producing scalable quantities of very long chain fatty acid derived products in a cost-effective manner.

SUMMARY OF THE INVENTION

The present invention provides genetically engineered fungal cells, preferably yeasts, that include genes for the biosynthesis of very long chain fatty acid (VLCFA) products or derivatives, such as very long chain fatty acids, e.g., erucic acid, nervonic acid, very long chain fatty alcohols, e.g., docosanol, and/or wax esters, e.g. jojoba oil esters, and methods of producing such very long chain fatty acid products that can be used to produce a range of industrial chemicals and oils, e.g. lubricants, as well as pharmaceutical and cosmetic products, e.g. emulsifiers, emollients, in a controllable and economic fashion.

An aspect of the embodiments relates to genetically modified fungal cell capable of producing a VLCFA and/or a VLCFA derivative. The genetically modified fungal cell comprises at least one exogenous gene encoding a fatty acyl-CoA reductase and at least one gene encoding an elongase, and/or at least one gene encoding a fatty acid synthase. The at least one gene encoding the elongase is an overexpressed endogenous gene encoding the elongase and/or an exogenous gene encoding the elongase. Correspondingly, the at least one gene encoding the fatty acid synthase is an overexpressed endogenous gene encoding the fatty acid synthase and/or an exogenous gene encoding the fatty acid synthase.

Another aspect of the embodiments relates to a genetically modified fungal cell capable of producing a VLCFA or VLCFA derivative. The genetically fungal cell comprises at least one gene encoding a *Mycobacterium* fatty acid synthase.

A further aspect of the embodiments relates to a method for the production of a VLCFA and/or a VLCFA derivative. The method comprises culturing a genetically modified fungal cell according to the embodiments in a culture medium. The method also comprises isolating the VLCFA and/or said VLCFA derivative from the genetically modified fungal cell and/or from the culture medium.

The yeast *Saccharomyces cerevisiae* (*S. cerevisiae*) is a very important cell factory as it is already widely used for production of biofuels, chemicals and pharmaceuticals, and there is therefore much interest in developing platform strains of this yeast that can be used for production of a whole range of different products. It is however a problem that such a platform cell factory for efficient production of fatty acid derived products is not as efficient as needed for good industrial application. This invention is, in an embodiment, a multiple gene modification approach of the yeast generating a stable and scalable platform for production of very long chain fatty acid derived products by combining pathways for direct conversion from fatty acyl-CoA to long or very long chain fatty alcohols and/or wax esters.

In one embodiment, the VLCFA derivative, e.g., fatty alcohols, fatty acid, wax esters etc., produced by the recombinant fungal cell, such as yeast is a very long chain fatty alcohol, preferably docosanol which can be used for production of industrial chemicals or pharmaceutical and cosmetic products. In another embodiment, the VLCFA derivative is a very long chain fatty acid, preferably erucic acid ((Z)-docos-13-enoic acid) which is used as a component in industrial chemicals or pharmaceutical and cosmetic products. In yet another embodiment, the VLCFA derivative of this invention is nervonic acid ((Z)-Tetracos-15-enoic acid) which could be used in pharmaceutical and food products. For instance, nervonic acid can be used for the treatment of demyelinating diseases, including Multiple Sclerosis. In addition, nervonic acid can also be used for its nutritional value as a dietary supplement, for instance, in baby foods and/or infant formulas. In another embodiment, the VLCFA derivatives of this invention are wax esters, preferably jojoba oils/esters which can be used for production of industrial chemicals or pharmaceutical and cosmetic products. These and other aspects of the invention are set forth in more detail in the description of the invention below.

DETAILED DESCRIPTION OF THE INVENTION

Figure 1:
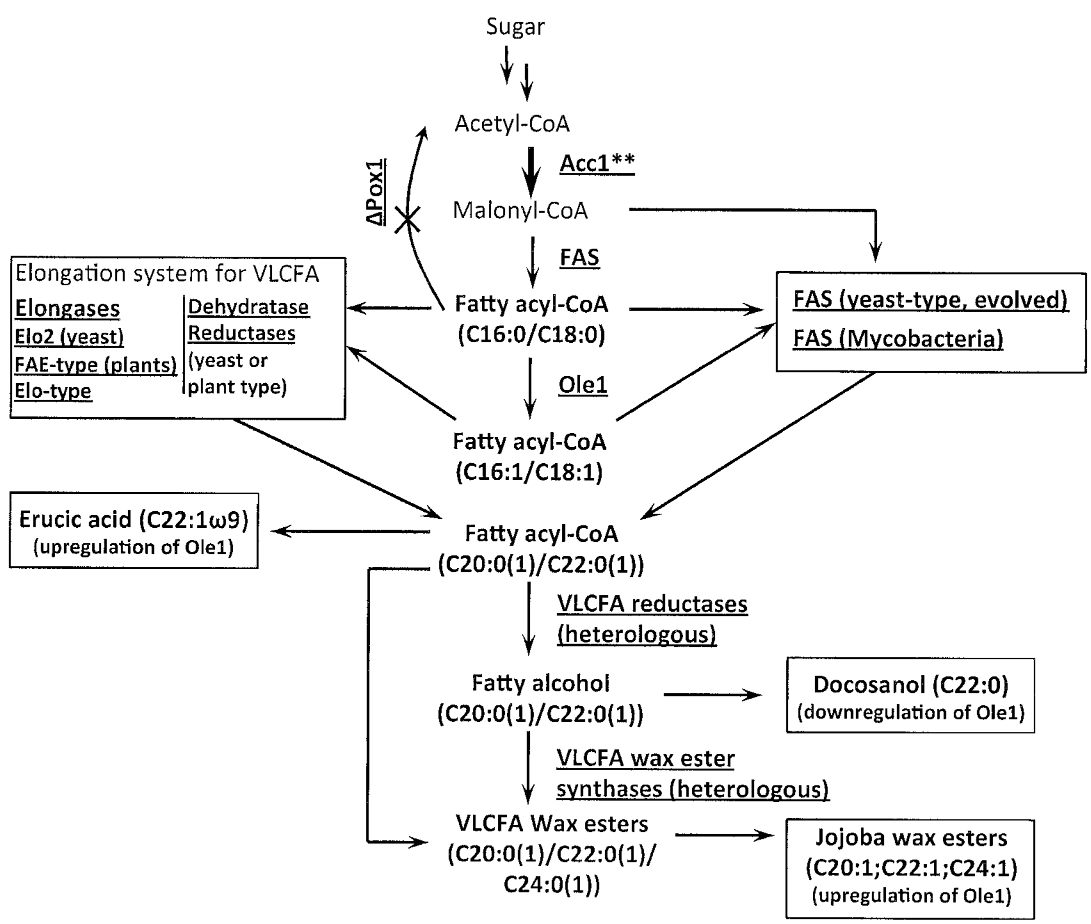
FIG. 1. Shows synthesis of VLCFA, VLC-fatty alcohols and the corresponding wax esters. The background yeast strain (Δpox1, ACC1**) provides enhanced precursor supply of malonyl-CoA for fatty acid elongation. The elongation towards very long chains was done via elongase or via fatty acid synthase (FAS) (Mycobacteria derived; evolved yeast FAS) systems. Heterologous very long chain specific reductases catalyze the reaction towards fatty alcohols. VLCFA wax ester synthases combine very long chain fatty acids with very long chain fatty alcohols producing very long chain wax esters. Depending on the product of interest the desaturase gene OLE1 is upregulated (mono-unsaturated FAs) or downregulated (saturated FAs).

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Definitions

Unless otherwise defined, all technical and scientific terms used herein have the same meaning as commonly understood by one of ordinary skill in the art to which this invention belongs. As such, the elongases, reductases, desaturases, fatty acid synthases and wax ester synthases, polypetides and genes encoding them, that may be used in this invention are any of those known in the art or homologues or derivatives thereof.

The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

To facilitate understanding of the invention, a number of terms are defined below.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein the term "recombinant" when used means that a particular nucleic acid (DNA or RNA) is the product of various combinations of cloning, restriction, and/or ligation steps resulting in a construct having a structural coding or non-coding sequence distinguishable from endogenous nucleic acids found in natural systems.

As used herein, the terms "protein" and "polypeptide" refer to compounds comprising amino acids joined via peptide bonds and are used interchangeably.

As used herein, the terms "increase," "increases," "increased," "increasing," "enhance," "enhanced," "enhancing," and "enhancement" (and grammatical variations thereof) indicate an elevation of at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more, or any range therein, as compared to a control.

As used herein, the terms "reduce," "reduces," "reduced," "reduction," "diminish," "suppress," and "decrease" and similar terms mean a decrease of at least about 0%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more, or any range therein, as compared to a control.

A reduced expression of a gene as used herein involves a gentical modification that reduces the transcription of the gene, reduces the translation of the mRNA transcribed from the gene and/or reduces post-translational processing of the protein translated from the mRNA. Such genetical modification includes insertion(s), deletion(s), replacement(s) or mutation(s) applied to the control sequence, such as a promoter and enhancer, of the gene. For instance, the promoter of the gene could be replaced by a less active or inducible promoter to thereby result in a reduced transcription of the gene. Also a knock-out of the promoter would result in reduced, typically zero, expression of the gene.

As used herein the terms "knock-out" or "deletion" or "disruption" refers to a gene that is inoperative or knocked out and/or a nonfunctional gene product, e.g. a polypeptide having essentially no activity, e.g. less than about 10% or even 5% as compared to the activity of the wild type polypeptide.

As used herein, the term "portion" or "fragment" of a nucleotide sequence of the invention will be understood to mean a nucleotide sequence of reduced length relative to a reference nucleic acid or nucleotide sequence and comprising, consisting essentially of and/or consisting of a nucleotide sequence of contiguous nucleotides identical or almost identical, e.g. 80%, 81%, 82%, 83%, 84%, 85%, 86%, 87%, 88%, 89%, 90%, 91%, 92%, 93%, 94%, 95%, 96%, 98%, 99% identical, to the reference nucleic acid or nucleotide sequence. Such a nucleic acid fragment or portion according to the invention may be, where appropriate, included in a larger polynucleotide of which it is a constituent.

Different nucleic acids or proteins having homology are referred to herein as “homologues.” The term homologue includes homologous sequences from the same and other species and orthologous sequences from the same and other species. “Homology” refers to the level of similarity between two or more nucleic acid and/or amino acid sequences in terms of percent of positional identity, i.e. sequence similarity or identity. Homology also refers to the concept of similar functional properties among different nucleic acids or proteins. Thus, the compositions and methods of the invention further comprise homologues to the nucleotide sequences and polypeptide sequences of this invention. “Orthologous,” as used herein, refers to homologous nucleotide sequences and/or amino acid sequences in different species that arose from a common ancestral gene during speciation. A homologue of a nucleotide sequence of this invention has a substantial sequence identity, e.g. at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, and/or 100%, to said nucleotide sequence.

The term “overexpress,” “overexpresses” or “overexpression” as used herein refers to higher levels of activity of a gene, e.g. transcription of the gene; higher levels of translation of mRNA into protein; and/or higher levels of production of a gene product, e.g. polypeptide, than would be in the cell in its native or control, e.g. not transformed with the particular heterologous or recombinant polypeptides being overexpressed, state. A typical example of an overexpressed gene is a gene under transcription control of another promoter as compared to the native promoter of the gene. Also, or alternatively, other changes in the control elements of a gene, such as enhancers, could be used to overexpress the particular gene. Furthermore, modifications that affect, i.e. increase, the translation of the mRNA transcribed from the gene could, alternatively or in addition, be used to achieve an overexpressed gene as used herein. These terms can also refer to an increase in the number of copies of a gene and/or an increase in the amount of mRNA and/or gene product in the cell. Overexpression can result in levels that are 25%, 50%, 100%, 200%, 500%, 1000%, 2000% or higher in the cell, as compared to control levels.

An “exogenous”, “heterologous” or a “recombinant” nucleotide sequence is a nucleotide sequence not naturally associated with a host cell into which it is introduced, including non-naturally occurring multiple copies of a naturally occurring nucleotide sequence. Such an exogenous gene could be a gene from another species or strain, a modified, mutated or evolved version of a gene naturally occurring in the host cell or a chimeric version of a gene naturally occurring in the host cell or fusion genes. In these former cases, the modification, mutation or evolution causes a change in the nucleotide sequence of the gene to thereby obtain a modified, mutated or evolved gene with another nucleotide sequence as compared to the gene naturally occurring in the host cell. Evolved gene refers to genes encoding evolved genes and obtained by geneticial modification, such as mutation or exposure to an evolutionary pressure, to derive a new gene with a different nucleotide sequence as compared to the wild type or native gene. A chimeric gene is formed through the combination of portions of one or more coding sequences to produce a new gene. These modifications are distinct from a fusion gene, which merges whole gene sequences into a single reading frame and often retain their original functions.

An “endogenous”, “native” or “wild type” nucleic acid, nucleotide sequence, polypeptide or amino acid sequence refers to a naturally occurring or endogenous nucleic acid, nucleotide sequence, polypeptide or amino acid sequence. Thus, for example, a “wild type mRNA” is an mRNA that is naturally occurring in or endogenous to the organism. A “homologous” nucleic acid sequence is a nucleotide sequence naturally associated with a host cell into which it is introduced.

Also as used herein, the terms “nucleic acid,” “nucleic acid molecule,” “nucleotide sequence” and “polynucleotide” refer to RNA or DNA that is linear or branched, single or double stranded, or a hybrid thereof. The term also encompasses RNA/DNA hybrids.

As used herein, the term “nucleotide sequence” refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic, e.g. chemically synthesized, DNA, plasmid DNA, mRNA, and anti-sense RNA, any of which can be single stranded or double stranded. The terms “nucleotide sequence” “nucleic acid,” “nucleic acid molecule,” “oligonucleotide” and “polynucleotide” are also used interchangeably herein to refer to a heteropolymer of nucleotides. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

As used herein, the term “gene” refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and non-coding regions, e.g. introns, regulatory elements, promoters, enhancers, termination sequences and/or 5' and 3' untranslated regions. A gene may be “isolated” by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

A codon optimized version of a gene refers to an exogenous gene introduced into a fungal cell and where the codons of the gene have been optimized with regard to the particular fungal cell. Generally, not all tRNAs are expressed equally or at the same level across species. Codon optimization of a gene sequence thereby involves changing codons to match the most prevalent tRNAs, i.e. to change a codon recoqnized by a low prevalent tRNA with a synonymous codon recognized by a tRNA that is comparatively more prevalent in the given fungal cell. This way the mRNA from the codon optimized gene will be more efficiently translated. The codon and the synonymous codon preferably encode the same amino acid.

“Introducing” in the context of a yeast cell means contacting a nucleic acid molecule with the cell in such a manner that the nucleic acid molecule gains access to the interior of the cell. Accordingly, polynucleotides and/or nucleic acid molecules can be introduced yeast cells in a single transformation event, in separate transformation events. Thus, the term “transformation” as used herein refers to the introduction of a heterologous nucleic acid into a cell. Transformation of a yeast cell can be stable or transient.

"Transient transformation" in the context of a polynucleotide means that a polynucleotide is introduced into the cell and does not integrate into the genome of the cell.

By "stably introducing" or "stably introduced" in the context of a polynucleotide introduced into a cell, it is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein includes the nuclear genome. Stable transformation as used herein can also refer to a nucleic acid molecule that is maintained extrachromasomally, for example, as a plasmid.

Transient transformation may be detected by, for example, an enzyme-linked immunosorbent assay (ELISA) or Western blot, which can detect the presence of a peptide or polypeptide encoded by one or more nucleic acid molecules introduced into an organism. Stable transformation of a cell can be detected by, for example, a Southern blot hybridization assay of genomic DNA of the cell with nucleic acid sequences which specifically hybridize with a nucleotide sequence of a nucleic acid molecule introduced into an organism, e.g. a yeast. Stable transformation of a cell can be detected by, for example, a Northern blot hybridization assay of RNA of the cell with nucleic acid sequences which specifically hybridize with a nucleotide sequence of a nucleic acid molecule introduced into a yeast or other organism. Stable transformation of a cell can also be detected by, e.g. a polymerase chain reaction (PCR) or other amplification reaction as are well known in the art, employing specific primer sequences that hybridize with target sequence(s) of a nucleic acid molecule, resulting in amplification of the target sequence(s), which can be detected according to standard methods Transformation can also be detected by direct sequencing and/or hybridization protocols well known in the art.

"Gentical modification" or "genetically modified" as used herein involves such genetic modifications to the genome of the fungal cell, such as yeast, and/or introduction of exogenous nucleotide sequences, such as in the form of one or more plasmids, into the fungal cell, such as yeast.

The term "fatty alcohol" as used herein, is intended to mean an aliphatic compound that comprises one or more hydroxyl groups. The fatty alcohol possesses the group —$CH_2OH$ that can be oxidized so as to form a corresponding aldehyde or acid having the same number of carbon atoms. A fatty alcohol can be a saturated fatty alcohol or an unsaturated fatty alcohol.

The term "fatty aldehyde" as used herein, is intended to mean an aliphatic compound that comprises an aldehyde (CHO) group. The fatty aldehyde can be reduced to form the corresponding alcohol or oxidized to form the carboxylic acid having the same number of carbon atoms. A fatty aldehyde can be a saturated fatty aldehyde or an unsatured fatty aldehyde.

The term "fatty acid" as used herein, is intended to mean an aliphatic compound that comprises at least one carboxylic acid group (COOH). The fatty acid can be reduced to form the corresponding alcohol or aldehyde having the same number of carbon atoms. A fatty acid can be a saturated fatty acid or an unsaturated fatty acid.

The term "fatty acid products" or "fatty acid derivatives" as used interchangeably herein, include a fatty acid or a fatty acid derivative; such as a fatty aldehyde, a fatty alcohol, an omega hydroxy fatty acid, a fatty ester, including a wax ester, a triglyceride, fatty-acyl-CoA, fatty acyl-ACP, or any other fatty acid derivatives. In a particular embodiment, a fatty acid product or derivative is selected among a group consisting of a fatty acid, a fatty alcohol and a wax ester.

The term "long chain" fatty acid (LCFA) or long chain fatty acid derivative, as used herein is a fatty acid or fatty acid derivative having an acyl chain length of 16 to 18 carbons.

The term "very long chain" fatty acid (VLCFA) or very long chain fatty acid derivative, as used herein is a fatty acid or fatty acid derivative having an acyl chain length of greater than 18 carbons. In a particular embodiment, the VLCFA product or derivative is a $C_{19}$-$C_{28}$ product or derivative, i.e. preferably has an acyl or alkyl length of 19 to 26 carbons or 19 to 24 carbons.

A VLCFA product or derivative is preferably selected from a group consisting of a very long chain fatty acid, a very long chain fatty alcohol or a wax ester that is an ester of i) a very long chain fatty acid and a fatty alcohol, ii) a fatty acid and a very long chain fatty alcohol, iii) a very long chain fatty acid and a very long chain fatty alcohol or iv) a fatty acid (B-side) and a fatty alcohol (A-side) and where the total length of the carbon chain, i.e. A-side+B-side, is greater than 18 carbons. In a particular embodiment, the A-side of the wax ester has a carbon chain length of C16-C28 and the B-side of the wax ester has a carbon chain length of C16-C28. In such a particular embodiment, the wax ester is an ester of i) a long chain or a very long chain fatty acid and ii) a long chain or a very long chain fatty alcohol.

The term "elongase" and that can be referred to by the abbreviation (ELO) as used herein, are enzymes that utilize malonyl-CoA to add a C2 unit to a growing acyl-CoA chain. This process also involves decarboxylation and is thus largely irreversible. Elongases are found in several compartments including the mitochondria, endoplasmic reticulum, and peroxisomes.

The endoplasmic reticulum also has an elongase system for synthesizing very long chain fatty acids (C18+) from acyl-CoA substrates of varying lengths. Genes involved in the elongase system include YBR159W, PHS1, TSC13, CER10, KCR1, PAS2, ELO1, ELO2 and ELO3.

In an embodiment, the fungal cell is a *Saccharomyces cerevisiae* cell and the at least one gene encoding the elongase comprises an overexpressed endogenous gene encoding an enzyme from an elongase system selected from the group consisting of a β-ketoacyl-CoA synthase (KCS) (Elo1 and/or Elo2), a β-ketoacyl-CoA reductase (YBR159W), a β-hydroxy acyl-CoA dehydratase (Phs1) and an enoyl-CoA reductase (Tsc13). This embodiment can be combined with the above described embodiment involving an exogenous gene encoding an elongase. In such a case, the *S. cerevisiae* cell comprises at least one exogenous gene encoding an elongase and at least one endogenous gene encoding an enzyme from the elongase system.

In an embodiment, the fungal cell further comprises an exogenous gene encoding an enzyumme from an elongase system selected from the group consisting of *Arabidopsis thaliana* reductase (CER10, KCR1) and dehydratase, and codon optimized versions thereof.

The term "fatty acyl-CoA reductase", or "fatty acyl reductase", "very long chain fatty acid reductase" or "fatty alcohol forming acyl-CoA reductase" and that can be referred to by the abbreviation "FAR" as used herein, produces alcohols as a product of a reduction reaction. FAR catalyzes the reduction of a fatty acyl-CoA, a fatty acyl-ACP, or other fatty acyl thioester complex to a fatty alcohol, in a reaction linked to the oxidation of NAD(P)H to $NAD(P)^+$. FARs catalyze this reaction through two steps, first creating an aldehyde and secondly the corresponding alcohol. Therefore these enzymes also take the aldehydes as substrates. FARs have been cloned from several plants, including *Simmondsia chinensis* (jojoba), *Arabidopsis thaliana*, rice and wheat, as well as insects, mammals, birds, a phytoflagellate protist, a planktonic crustacean, and from prokaryotes like *Marinobactor aquaeolei.*

The term "desaturase" as used herein, means an enzyme that can desaturate fatty acids to produce a mono- or poly-unsaturated fatty acid or precursor thereof of interest. Fatty acid desaturases catalyze the introduction of a double bond into an acyl chain with strict regioselectivity and stereoselectivity. Membrane bound fatty acid desaturases are expressed in eukaryotes and bacteria. It is a diverse family constituting at least 10 different types of regioselectivities and chain length specificities, such as Δ4-Δ6, Δ8-Δ13 and Δ15, including Δ9. Desaturase genes include OLE1 derived from *S. cerevisiae*, ChDes9-1 and ChDes9-2 from *Calanus hyperboreus* and a desaturase derived from *Simmondsia chinensis*

The term "wax synthases" or "wax ester synthases" as used herein, are used interchangeably and means enzymes capable of catalyzing the combination of acyl-thioesters and fatty alcohols to fatty acid alkyl esters (FAAEs). Wild-type yeast does not have the metabolic machinery for producing very long chain fatty acid alkyl esters (FAAEs). Wax synthases catalyzing the former reactions, are characteristics of organisms such as *Acinetobacter baylyi, Arabidopsis* thaliana, *Euglena gracilis, Marinobacter hydrocarbonoclasticus, Simmondsia chinensis, Marinobacter aquaeolei.*

The term "FAS" or "fatty acid synthases" as used herein, is an enzymatic system that catalyzes the initiation and elongation of acyl chains and thus plays a key role in fatty acid synthesis from acetyl-CoA and malonyl-CoA. In the yeast *S. cerevisiae*, fatty acids are synthesized by a 2.4 Mba multifunctional enzyme complex with two subunits encoded by two unlinked genes FAS1 and FAS 2. Alternative FAS systems for producing very long chain (up to C26) fatty acids include for example FASs from Mycobacteria.

In a general aspect, the present invention is directed towards a genetically modified fungal cell that is capable of producing a VLCFA and/or a VLCFA. In a particular embodiment, the fungal cell is a yeast cell or mold cell.

In some embodiments, *S. cerevisiae* can be a host for carrying out the invention, as it is a popular host in basic and applied research apart from being a good ethanol producer, a precursor of esters and specifically of fatty acid ethyl esters. In addition, other yeast cells useful with the present invention include, but are not limited to, other *Saccharomyces* species, *Hansenula polymorpha, Kluyveromyces* species, *Pichia* species, *Candida* species, *Trichoderma* species, *Yarrowia lipolytica, Rhodotorula graminis, Trichosporon oleaginosus, Rhodosporidium toruloides, Lipomyces starkeyi*, etc.

In industry, there is much interest in applying a limited number of platform cell factories for production of a wide range of fuels and chemicals as this allows for flexible use of production facilities, which are very capital intensive. One of these platform cell factories is the yeast *Saccharomyces cerevisiae*, which is widely used for the production of beer, bread, wine, bioethanol, nutraceuticals, chemicals and pharmaceuticals. These platform cell factories can efficiently convert raw materials, today typically glucose/fructose derived from starch or sucrose, but in the future also pentoses derived from lignocellulose, into so-called precursor metabolites can then be further converted into products of interest.

In the invention herein we have generated a yeast platform cell factory that can convert fatty acyl-CoA to very long chain fatty acid derivatives. The yeast *S. cerevisiae* does not naturally accumulate very long chain fatty acids and while it is difficult to introduce efficient pathways from fatty acyl-CoA to very long chain fatty acid derivatives, the inventors of the present invention have identified a possible route for this introduction. Strategies for reconstructing such a synthetic pathway from fatty acyl-CoA to very long chain fatty acid derivatives, leading to a cell factory for producing very long chain fatty acid derivatives, such as fatty acids, e.g. erucic acid, nervonic acid, fatty alcohols, e.g. docosanol, and wax esters, e.g. jojoba oil, or more correctly jojoba esters or jojoba wax esters, are described below.

The genetically modified fungal cell, preferably yeast, of this invention comprises one or more genetic modifications to improve production of the desired very long chain fatty acid derivatives. Such modifications can include, but are not limited to the introduction of new enzymes, and/or biosynthetic and/or metabolic pathways and/or heterologous expression of one or more genes (see FIG. 1). In addition, such modifications to improve production of very long chain fatty acid derivatives also comprise elimination or reduction of non-essential pathways, or pathways that compete with the production of very long chain fatty acid derivatives.

Accordingly, an aspect of the embodiments relates to a genetically modified fungal cell capable of producing a very long chain fatty acid (VLCFA) and/or a VLCFA derivative. In this aspect, the genetically modified fungal cell comprises at least one exogenous gene encoding a fatty acyl-CoA reductase. The genetically modified fungal cell also comprises, in this aspect i) at least one gene encoding an elongase, and/or at least one gene encoding a fatty acid synthase.

The at least one gene encoding the elongase is an overexpressed endogenous gene encoding the elongase and/or an exogenous gene encoding the elongase. Correspondingly, the at least one gene encoding the fatty acid synthase is an overexpressed endogenous gene encoding the fatty acid synthase and/or an exogenous gene encoding the fatty acid synthase.

In an embodiment, the at least one exogenous gene encoding the fatty acyl-CoA reductase (FAR) is selected from a group consisting of a FAR from *Apis mellifera* (AmFAR), a FAR from *Marinobacter aquaeoliei* VT8 (MaFAldhR), a FAR from *Simmondsia chinensis* (SciFAR), a FAR from *Triticum aestivum* (TaFAR), a FAR from *Arabidopsis thaliana* (At5FAR), a FAR from *Marinobacter algicola* DG893, a FAR from *Marinobacter adhaerens* HP15, a FAR from *Taxus baccata*, a FAR from *Euglena gracilis*, a FAR from *Oryza sativa*, a FAR from *Gallus gallus*, a FAR from *Yponomeuta evonymellus*, a FAR from *Mus musculus*, and codon optimized versions thereof.

In an embodiment, the at least one gene encoding the elongase comprises an exogenous gene encoding the elongase selected from a group consisting of an elongase from *Arabidopsis thaliana* (Fae1), a β-ketoacyl-CoA synthase (KCS) from *Brassica napus* (BnKCS), a KCS from *Crambe abyssinica* (CaKCS), a KCS from *Cardamine graeca* (CgKCS), a KCS from *Lunaria annua* (LaKCS), a KCS from

*Simmondsia chinensis* (SciKCS), a KCS from *Tropaeolum majus* (TmKCS), and codon optimized versions thereof.

In an embodiment, the fungal cell is a *Saccharomyces cerevisiae* cell and the at least one gene encoding the elongase comprises an overexpressed endogenous gene encoding an enzyme from an elongase system selected from the group consisting of a β-ketoacyl-CoA synthase (KCS) (Elo1 and/or Elo2), a β-ketoacyl-CoA reductase (YBR159W), a β-hydroxy acyl-CoA dehydratase (Phs1) and an enoyl-CoA reductase (Tsc13). This embodiment can be combined with the above described embodiment involving an exogenous gene encoding an elongase. In such a case, the *S. cerevisiae* cell comprises at least one exogenous gene encoding an elongase and at least one endogenous gene encoding an enzyme from the elongase system.

In an embodiment, the fungal cell further comprises an exogenous gene encoding an enzyumme from an elongase system selected from the group consisting of *Arabidopsis thaliana* reductase (CER10, KCR1) and dehydratase, and codon optimized versions thereof.

In an embodiment, the fungal cell is a *Saccharomyces cerevisiae* cell genetically modified for reduced expression of and/or knock-out of the gene encoding Elo3.

In an embodiment, the at least one gene encoding the fatty acid synthase comprises an exogenous gene encoding the fatty acid synthase (FAS) selected from a group consisting of a FAS from *Mycobacterium vaccae*, a FAS from *Mycobacterium diernhoferi* 41002, a FAS from *Mycobacterium neoaurum*, a FAS from *Mycobacterium parafortuitum* PA-1, a FAS from *Mycobacterium intracellulare*, a FAS from *Rhodosporidium toruloides*, and codon optimized versions thereof. In an embodiment, the exogenous gene is an envolved version of the gene encoding fatty acid synthase 1 (Fas1) and/or an envolved version of the gene encoding fatty acid synthase 2 (Fas 2).

In an embodiment, the fungal cell is a *Saccharomyces cerevisiae* cell and the at least one gene encoding the fatty acid synthase comprises an overexpressed endogenous gene encoding fatty acid synthase 1 (Fas1) and/or fatty acid synthase 2 (Fas2) or evolved versions thereof. This embodiment can be combined with the above described embodiment involving an exogenous gene encoding a fatty acid synthase. In such a case, the *S. cerevisiae* cell comprises at least one exogenous gene encoding a fatty acid synthase and at least one endogenous gene encoding a fatty acid synthase.

In an embodiment, the fungal cell comprises the at least one gene encoding the fatty acid synthase and a gene encoding an acyl-carrier protein synthase, such as a *Mycobacterium vaccae* acyl-carrier protein synthase.

In a particular embodiment, the fungal cell comprises an exogenous gene encoding a fatty acyl-CoA reductase (FAR) from *Arabidopsis thaliana* (At5FAR) and an overexpressed Elo2 gene encoding a β-ketoacyl-CoA synthase (KCS). The fungal cell is furthermore preferably a *Saccharomyces cerevisiae* cell genetically modified for reduced expression of and/or knock-out of the gene encoding Elo3.

In another particular embodiment, the *S. cerevisiae* cell further comprises an exogenous gene or an overexpressed endogenous gene encoding an acetyl-CoA carboxylase (ACC) and an overexpressed Elo1 gene encoding a KCS. The *S. cerevisiae* cell is preferably genetically modified for knock-out of the gal1 gene encoding a galactokinase.

In an embodiment, the fungal cell further comprises at least one exogenous gene encoding a wax synthase.

In an embodiment, the at least one gene encoding said wax synthase (WS) is selected from a group consisting of a WS from *Acinetobacter baylyi* ADP1 (AbWS), a WS from *Arabidopsis thaliana* (AtWS), a WS from *Euglena gracilis* (EgWS), a WS from *Marinobacter hydrocarbonoclasticus* DSM 8798 (MhWS), a WS from *Simmondsia chinensis* (SciWS), a WS from *Marinobacter aquaeolei* VT8, and codon optimized versions thereof.

In a particular embodiment, the fungal cell comprises an exogenous gene encoding a fatty acyl-CoA reductase (FAR) from *Marinobacter* aquaeoliei VT8 (MaFAldhR), or a codon optimized version thereof, an exogenous gene encoding a wax synthase (WS) selected from the group consisting of a WS from *Arabidopsis thaliana* (AtWS), a WS from *Euglena gracilis* (EgWS), a WS from *Simmondsia chinensis* (SciWS), or a codon optimized version thereof; and an overexpressed Elo2 gene encoding a β-ketoacyl-CoA synthase (KCS).

The fungal cell is preferably a *Saccharomyces cerevisiae* cell. The *S. cerevisiae* cell preferably further comprises an exogenous gene or an overexpressed endogenous gene encoding an acetyl-CoA carboxylase (ACC), and is genetically modified for reduced expression of and/or knock-out of the gene encoding Elo3.

In an embodiment, the fungal cell further comprises at least one gene encoding a desaturase. The at least one gene encoding the desaturase is an endogenous gene overexpressing the desaturase and/or an exogenous gene encoding the desaturase.

In an embodiment, the at least one gene encoding the desaturase comprises an exogenous gene encoding the desaturase selected from a group consisting of a desaturase from *Simmondsia chinensis* (SciFAD), a desaturase from *Calanus hyperboreus* (ChDes9-1 and/or ChDes9-2), and codon optimized versions thereof.

In an embodiment, the fungal cell is a *Saccharomyces cerevisiae* cell and the at least one gene encoding the desaturase comprises an overexpressed endogenous gene encoding Δ9-desaturase (Ole1). This embodiment can be combined with the above described embodiment involving an exogenous gene encoding a desaturase. In such a case, the *S. cerevisiae* cell comprises at least one exogenous gene encoding a desaturase and at least one endogenous gene encoding a desaturase.

In an embodiment, the fungal cell further comprises an overexpressed endogenous gene encoding an acetyl-CoA carboxylase (ACC), preferably ACC1 or mutated forms or evolved versions thereof having acetyl-CoA carboxylase activity.

In an embodiment, the fungal cell further comprises at least one exogenous gene encoding a long-chain acyl CoA synthetase, preferably selected from a group consisting of *Arabidopsis thaliana* LACS1, LACS2, LACS3, and codon optimized versions thereof.

In an embodiment, the fungal cell further comprising at least one exogenous gene encoding a non-phosphorylating NADP+-dependent glyceraldehydes-3-phosphate dehydrogenase (GAPN), preferably a GAPN from *Streptococcus mutans*.

In an embodiment, the fungal cell further comprises at least one exogenous gene encoding a phosphoketolase, preferably a phosphoketolase from *Aspergillus nidulans* (xpkA and/or ack).

In an embodiment, the fungal cell is a *Saccharomyces cerevisiae* cell genetically modified for reduced expression of and/or knock-out of the gene GDH1 encoding a NADP-dependent glutamate dehydrogenase.

In an embodiment, the fungal cell is a *Saccharomyces cerevisiae* cell genetically modified for overexpression of an endogenous GDH2 gene encoding a NAD-dependent glutamate dehydrogenase.

In an embodiment, the fungal cell is genetically modified for reduced expression of and/or knock-out of non-essential pathway genes selected from a group consisting of acyl-CoA:sterol acyltransferase (ARE1, ARE2), diacylglycerol acyltransferase (DGA1), lecithin cholesterol acyl transferase (LRO1), fatty-acyl coenzyme A oxidase (POX1), Elo3, Fat1, Faa1 and Faa4.

In an embodiment, the fungal cell further comprises at least one exogenous gene encoding a transport protein selected from a group consisting of an ATP-binding cassette (ABC) protein, a lipid transfer protein (LTP), a fatty acid transporter protein (FATP) and a plant wax ester transporter, preferably selected from the group consisting of ABCG11, ABCG12, LTPG1 and/or LTPG2.

Another aspect of the embodiments relates to a genetically modified fungal cell capable of producing a VLCFA or VLCFA derivative. The genetically fungal cell comprises at least one gene encoding a *Mycobacterium* fatty acid synthase.

In an embodiment, the at least one gene encoding said *Mycobacterium* fatty acid synthase (FAS) is selected from a group consisting of a gene encoding a FAS from *Mycobacterium vaccae*, a gene encoding a FAS from *Mycobacterium diernhoferi* 41002, a gene encoding a FAS from *Mycobacterium neoaurum*, a gene encoding a FAS from *Mycobacterium parafortuitum* PA-1, a gene encoding a FAS from *Mycobacterium intracellulare*, and codon optimized versions thereof.

In a particular embodiment, the fungal cell is a *Saccharomyces cerevisiae* cell genetically modified for reduced expression of and/or knock-out of the genes encoding Elo2 and Elo3. The *S. cerevisiae* cell also comprises a gene encoding a *Mycobacterium vaccae* fatty acid synthase, and a gene encoding a *M. vaccae* acyl-carrier protein synthase.

In another or additional particular embodiment, the fungal cell or *S. cerevisiae* cell further comprises at least one gene encoding a desaturase. The at least one gene encoding the desaturase is an endogenous gene overexpressing the desaturase and/or an exogenous gene encoding the desaturase. The previously described preferred examples of exogenous genes (SciFAD, ChDes9-1, ChDes9-2) and endogenous gene (Ole1) encoding desatures can also be applied to the present particular embodiment.

In an embodiment, the fungal cell of the various embodiments is preferably a genetically modified yeast cell, and more preferably a genetically modified *Saccharomyces cerevisiae* cell or a genetically modified *Yarrowia lipolytica* cell.

Yet another aspect of the embodiments relates a genetically modified fungal cell capable of producing a very long chain fatty acid (VLCFA) and/or a VLCFA derivative. In this aspect, the genetically modified fungal cell comprises at least one gene encoding an elongase and at least one gene encoding a desaturase. The at least one gene encoding the elongase is an overexpressed endogenous gene encoding the elongase and/or an exogenous gene encoding the elongase. Correspondingly, the at least one gene encoding the desaturase is an endogenous gene overexpressing the desaturase and/or an exogenous gene encoding the desaturase.

Preferred examples of such elongases and desaturases can be selected among the embodiments described herein.

Still another aspect of the embodiments relates a genetically modified fungal cell capable of producing a very long chain fatty acid (VLCFA) and/or a VLCFA derivative. In this aspect, the genetically modified fungal cell comprises at least one gene encoding a fatty acid synthase and at least one gene encoding a desaturase. The at least one gene encoding the fatty acid synthase is an overexpressed endogenous gene encoding the fatty acid synthase and/or an exogenous gene encoding the fatty acid synthase. Correspondingly, the at least one gene encoding the desaturase is an endogenous gene overexpressing the desaturase and/or an exogenous gene encoding the desaturase.

Preferred examples of such fatty acid synthases and desaturases can be selected among the embodiments described herein.

A further aspect of the embodiments relates to a a method for the production of a VLCFA and/or a VLCFA derivative. The method comprises culturing a genetically modified fungal cell according to any of the embodiments in a culture medium. The method also comprises isolating the VLCFA and/or the VLCFA derivative from the genetically modified fungal cell and/or from the culture medium.

In an embodiment, culturing the genetically modified fungal cell comprises culturing a genetically modified fungal cell comprising the fatty acyl-CoA reductase, the elongase and/or fatty acid synthase as described herein in the culture medium. In this embodiment, isolating the VLCFA and/or the VLCFA derivative comprises isolating a very long chain fatty alcohol, preferably docosanol, and more preferably N-docosanol C22:0, from the genetically modified fungal cell and/or from the culture medium.

In an embodiment, culturing the genetically modified fungal cell comprises culturing a genetically modified fungal cell comprising the fatty acyl-CoA reductase, the wax synthase, the elongase and/or fatty acid synthase as described herein in the culture medium. In this embodiment, isolating the VLCFA and/or the VLCFA derivative comprises isolating a wax ester from the genetically modified fungal cell and/or from the culture medium. The wax ester is preferably a wax ester of a C16:0 or C16:1 up to C28:0 or C28:1 fatty alcohol and a C16:0 or C16:1 up to C28:0 or C28:1 fatty acid.

In an embodiment, culturing the genetically modified fungal cell comprises culturing a genetically modified fungal cell comprising the *Mycobacterium* fatty acid synthase as described herein in the culture medium. In this embodiment, isolating the VLCFA and/or the VLCFA derivative comprises isolating a very long chain fatty acid, preferably eruric acid and/or nervonic acid, from the genetically modified fungal cell and/or the said culture medium.

One objective of the invention is to produce very long chain fatty acid derivatives like very long chain fatty alcohols or wax esters. In a first step fatty-acyl-CoA (C16:0, C18:0) is elongated to very long chain fatty-acyl-CoA, e.g. C22:0, either via the intrinsic yeast or heterologous elongase system or a heterologous or evolved FAS system. In a second step these very long chain fatty-acyl-CoA are reduced to the corresponding very long chain fatty alcohol by heterologously expressed FAR enzymes. The very long chain fatty acids and generated very long chain fatty alcohols are combined to the corresponding very long chain wax esters via expressing heterologous wax ester synthases.

In one embodiment the invention provides a genetically modified yeast that includes one or more exogenous genes that encode; (a) an elongase, or different components of an elongase system, e.g. from *S. cerevisiae, Arabidopsis thaliana, Simmondsia chinensis, Brassica napus, Crambe abyssinica, Taxus baccata* etc., and/or a fatty acid synthase (FAS) system, e.g. from *Rhodosporidium toruloides, S. cerevisiae*

, *Mycobacteria* etc. and (b) a very long chain fatty acid reductase, such as fatty acyl-CoA reductase (FAR), e.g. from *Apis mellifera, Marinobacter aquaeolei* VT8, *Simmondsia chinensis, Triticum aestivum, Arabidopsis thaliana, Marinobacter algicola* DG893, *Marinobacter adhaerens* HP15, *Taxus baccata, Euglena gracilis, Oryza sativa, Gallus gallus, Yponomeuta evonymellus, Mus musculus* etc., wherein the yeast produces at least one fatty alcohol, such as docosanol, preferably N-docosanol C22:0.

In a particular embodiment the elongase, or different components of an elongase system, is a yeast, plant, insect, or prokaryotic elongase.

In a particular embodiment, the recombinant yeast includes at least one gene encoding yeast elongase Elo1 and/or Elo2, including but not limited to from *S. cerevisiae.*

In a particular embodiment, the recombinant yeast includes at least one gene encoding Fas1 or Fas2 and/or mutants thereof.

In a particular embodiment, the recombinant yeast includes at least one or more genes encoding different components of the *S. cerevisiae* elongase systems, including but not limited to elongases, e.g., KCS, 3-keto acyl-CoA reductase, enoyl-CoA reductase, 3-hydroxy acyl-CoA dehydratase.

In a particular embodiment, the recombinant yeast includes at least one or more, exogenous genes encoding part of, or the entire elongase systems from plants, including respective elongases, reductases and dehydratases.

In a particular embodiment, fatty reductases derived from *Apis mellifera, Arabidopsis thaliana, Marinobacter aquaeolei* are preferred.

In a particular embodiment, FAS derived from *Mycobacterium* and/or yeast evolved FAS are preferred.

In a particular embodiment, elongase from *S. cerevisiae, Arabidopsis thaliana, Brassica napus, Crambe abyssinica Lunaria annua* (LaKCS), *Simmondsia chinensis* are preferred.

In another embodiment, the invention provides a method of producing a recombinant microorganism that includes one or more exogenous genes that encode; (a) an elongase, or different components of an elongase system, e.g. from *Arabidopsis thaliana, Simmondsia chinensis, Brassica napus, Crambe abyssinica, Taxus baccata* etc., and/or a fatty acid synthase (FAS) system, e.g. from *Rhodosporidium toruloides, S. cerevisiae*, Mycobacteria etc., and (b) a very long chain fatty acid reductase, such as fatty acyl-CoA reductase (FAR), e.g. from *Apis mellifera, Marinobacter aquaeolei* VT8, *Simmondsia chinensis, Triticum aestivum, Arabidopsis thaliana, Marinobacter algicola* DG893, *Marinobacter adhaerens* HP15, *Taxus baccata, Euglena gracilis, Oryza sativa, Gallus gallus, Yponomeuta evonymellus, Mus musculus* etc., wherein the yeast produces at least one fatty alcohol, such as docosanol, preferably N-docosanol C22:0.

Another objective of the invention is to produce very long chain fatty acid derivatives like very long chain fatty acids. In a first step fatty-acyl-CoA (C16:0, C18:0) is desaturated towards preferably C18:1 and elongated to very long chain fatty-acyl-CoA, e.g. C22:1, either via the intrinsic yeast or heterologous elongase system or a heterologous or evolved FAS system. In a second step VLCF acyl-CoA is modified towards free VLCFA via intrinsic thioesterases or by overexpression of heterologous thioesterases such as mammalian ACOT genes, for instance, *Homo sapiens* ACOT2 (GenBank: NP_006812.3), *Homo sapiens* ACOT9 (Genbank: NP_001028755.2), *Rattus norvegicus* ACOT2 (GenBank: NP_620262.2) or *Rattus norvegicus* ACOT1 (Genbank: NP_112605.1)

In an embodiment, the invention provides a genetically modified yeast that includes one or more exogenous genes that encode; (a) an elongase, or different components of an elongase system, e.g. from *Arabidopsis thaliana*, or *Simmondsia chinensis, Taxus baccata, Brassica napus, Crambe abyssinica* etc., and/or a fatty acid synthase (FAS) system, e.g. from *Rhodosporidium toruloides, S. cerevisiae, Mycobacteria* etc., and; (b) a desaturase, e.g. from *S. cerevisiae, Simmondsia chinensis, Calanus hyperboreus*, etc., wherein the yeast produces at least one fatty acid derivative, such as erucic acid, preferably C22:1 or nervonic acid, C24:1.

In a particular embodiment the elongase, or different components of an elongase system, is a yeast, plant, insect, or prokaryotic elongase.

In a particular embodiment, the recombinant yeast includes at least one gene encoding yeast elongase Elo1 and/or Elo2, including but not limited to from *S. cerevisiae.*

In a particular embodiment, the recombinant yeast includes at least one gene encoding Fas1 or Fas2 and/or mutants thereof.

In a particular embodiment, the recombinant yeast includes at least one or more genes encoding different components of the *S. cerevisiae* elongase systems, including but not limited to elongases, e.g., KCS, 3-keto acyl-CoA reductase, enoyl-CoA reductase, 3-hydroxy acyl-CoA dehydratase.

In a particular embodiment, the recombinant yeast includes at least one or more, exogenous genes encoding part of, or the entire elongase systems from plants, including elongases, reductases and dehydratases.

In a particular embodiment, the recombinant yeast includes at least one desaturase gene encoding Ole1, ChDes9_2 or other desaturases.

In a particular embodiment, FAS derived from *Mycobacterium* and/or yeast evolved FAS are preferred.

In a particular embodiment elongase from *S. cerevisiae, Arabidopsis thaliana, Brassica napus, Crambe abyssinica Lunaria annua* (LaKCS), *Simmondsia chinensis* are preferred.

In a particular embodiment, desaturase from *S. cerevisiae* is preferred.

In another embodiment, the invention provides a method of producing a recombinant microorganism that includes one or more exogenous genes that encode; (a) an elongase, or different components of an elongase system, e.g. from *Arabidopsis thaliana*, or *Simmondsia chinensis, Taxus baccata, Brassica napus, Crambe abyssinica* etc. and/or a fatty acid synthase (FAS) system, e.g. from *Rhodosporidium toruloides, S. cerevisiae*, Mycobacteria etc. and; (b) a desaturase, e.g. from *S. cerevisiae, Simmondsia chinensis, Calanus hyperboreus* etc., wherein the yeast produces at least one fatty acid derivative, such as erucic acid, preferably C22:1 or nervonic acid, C24:1.

Yet another objective of the invention is to produce very long chain fatty acid derivatives like wax esters.

In an embodiment, the invention provides a genetically modified yeast that includes one or more exogenous genes that encode; (a) a very long chain fatty acid reductase, such as fatty acyl-CoA reductase (FAR), e.g. from *Apis mellifera, Marinobacter aquaeoli, Marinobacter algicola, Marinobacter adhaerens, Simmondsia chinensis Triticum aestivum, Arabidopsis thaliana, Taxus baccata, Euglena gracilis, Oryza sativa, Gallus gallus, Yponomeuta evonymellus, Mus musculus* etc., and; (b) a wax synthase, e.g. from *Acineto-*

*bacter baylyi, Arabidopsis thaliana, Euglena gracilis, Marinobacter hydrocarbonoclasticus* DSM 8798, *Simmondsia chinensis* and *Marinobacter aquaeolei* VT8, *Acinetobacter calcoaceticus*, Mycobacteria, *Streptomyces coelicolor* etc., wherein the yeast produces at least one fatty acid derivative, such as a wax ester, preferably with C16 (C16):1 up to C28(C28):1 as the fatty alcohol (A side) and C16 (C16):1 up to C28(C28):1 as the fatty acid (B side).

In a particular embodiment, fatty reductases derived from *Apis mellifera, Arabidopsis thaliana, Marinobacter aquaeolei* are preferred.

In a particular embodiment, wax ester synthates derived from *Arabidopsis thaliana, Simmondsia chinensis, Euglena gracilis* are preferred.

In another embodiment, the invention provides a method of producing a recombinant microorganism that includes one or more exogenous genes that encode; (a) a very long chain fatty acid reductase, such as fatty acyl-CoA reductase (FAR), e.g. from *Apis mellifera, Marinobacter aquaeoli, Marinobacter algicola, Marinobacter adhaerens, Simmondsia chinensis Triticum aestivum, Arabidopsis thaliana, Taxus baccata, Euglena gracilis, Oryza sativa, Gallus gallus, Yponomeuta evonymellus, Mus musculus* etc. and; (b) a wax synthase, e.g. from *Acinetobacter baylyi, Arabidopsis thaliana, Euglena gracilis, Marinobacter hydrocarbonoclasticus, Simmondsia chinensis, Marinobacter aquaeoli, Acinetobacter calcoaceticus*, Mycobacteria, *Streptomyces coelicolor* etc., wherein the yeast produces at least one fatty acid derivative, such as a wax ester, preferably with C16 (C16):1 up to C28(C28):1 as the fatty alcohol (A side) and C16(C16):1 up to C28(C28):1 as the fatty acid (B side).

In a further embodiment, the invention provides a genetically modified yeast that includes one or more exogenous genes that encode; (a) an elongase, or different components of an elongase system, e.g. from *Arabidopsis thaliana*, or *Simmondsia chinensis, Taxus baccata, Brassica napus*, or *Crambe abyssinica* etc.) and/or a fatty acid synthase (FAS) system, e.g. from *Rhodosporidium toruloides, Saccharomyces cerevisiae*, Mycobacteria etc., and; (b) a very long chain fatty acid reductase, such as fatty acyl-CoA reductase (FAR), e.g. from *Apis mellifera, Marinobacter aquaeolei* VT8, *Simmondsia chinensis, Triticum aestivum, Arabidopsis thaliana, Marinobacter algicola* DG893, *Marinobacter adhaerens* HP15, *Taxus baccata, Euglena gracilis, Oryza sativa, Gallus gallus, Yponomeuta evonymellus, Mus musculus* etc., and; (c) a wax synthase, e.g. from *Acinetobacter baylyi, Arabidopsis thaliana, Euglena gracilis, Marinobacter hydrocarbonoclasticus* DSM 8798, *Simmondsia chinensis* and *Marinobacter aquaeolei* VT8, *Acinetobacter calcoaceticus*, Mycobacteria, *Streptomyces coelicolor* etc., wherein the yeast produces at least one fatty acid derivative, preferably with C22 (C20):1 as the fatty alcohol (A side) and C20(C22):1 as the fatty acid (B side).

In a particular embodiment, fatty reductases derived from *Apis mellifera, Arabidopsis thaliana, Marinobacter aquaeolei* are preferred.

In a particular embodiment, wax ester synthates derived from *Arabidopsis thaliana, Simmondsia chinensis, Euglena gracilis* are preferred.

In a particular embodiment, FAS derived from *Mycobacterium* and/or yeast evolved FAS are preferred.

In a particular embodiment, elongase derived from *S. cerevisiae, Arabidopsis thaliana, Brassica napus, Crambe abyssinica Lunaria annua* (LaKCS), *Simmondsia chinensis* are preferred.

In another embodiment, the invention provides a method of producing a recombinant microorganism that includes one or more exogenous genes that encode; (a) an elongase, or different components of an elongase system, e.g. from *Arabidopsis thaliana*, or *Simmondsia chinensis, Taxus baccata, Brassica napus*, or *Crambe abyssinica* etc.) and/or a fatty acid synthase (FAS) system, e.g. from *Rhodosporidium toruloides, Saccharomyces cerevisiae*, Mycobacteria etc., and; (b) a very long chain fatty acid reductase, such as fatty acyl-CoA reductase (FAR), e.g. from *Apis mellifera, Marinobacter aquaeolei* VT8, *Simmondsia chinensis, Triticum aestivum, Arabidopsis thaliana, Marinobacter algicola* DG893, *Marinobacter adhaerens* HP15, *Taxus baccata, Euglena gracilis, Oryza sativa, Gallus gallus, Yponomeuta evonymellus, Mus musculus* etc., and; (c) a wax synthase, e.g. from *Acinetobacter baylyi, Arabidopsis thaliana, Euglena gracilis, Marinobacter hydrocarbonoclasticus* DSM 8798, *Simmondsia chinensis* and *Marinobacter aquaeolei* VT8, *Acinetobacter calcoaceticus*, Mycobacteria, *Streptomyces coelicolor* etc., wherein the yeast produces at least one fatty acid derivative, preferably with C22 (C20):1 as the fatty alcohol (A side) and C20(C22):1 as the fatty acid (B side).

In still another embodiment, the invention provides a genetically modified yeast that includes one or more exogenous genes that encode; (a) an elongase, or different components of an elongase system, e.g. from *Arabidopsis thaliana*, or *Simmondsia chinensis, Taxus baccata, Brassica napus*, or *Crambe abyssinica* etc., and/or a fatty acid synthase (FAS) system, e.g. from *Rhodosporidium toruloides, Saccharomyces cerevisiae*, Mycobacteria etc., and; (b) a very long chain fatty acid reductase, such as fatty acyl-CoA reductase (FAR), e.g. from *Apis mellifera, Marinobacter aquaeolei* VT8, *Simmondsia chinensis, Triticum aestivum, Arabidopsis thaliana, Marinobacter algicola* DG893, *Marinobacter adhaerens* HP15, *Taxus baccata, Euglena gracilis, Oryza sativa, Gallus gallus, Yponomeuta evonymellus, Mus musculus* etc., and; (c) a desaturase, e.g. from *S. cerevisiae, Simmondsia chinensis, Calanus hyperboreus*, etc., and; (d) a wax synthase, e.g. from *Acinetobacter baylyi, Arabidopsis thaliana, Euglena gracilis, Marinobacter hydrocarbonoclasticus* DSM 8798, *Simmondsia chinensis* and *Marinobacter aquaeolei* VT8, *Acinetobacter calcoaceticus*, Mycobacteria, *Streptomyces coelicolor* etc., wherein the yeast produces at least one fatty acid derivative, such as jojoba oil, preferably with C22 (C20):1 as the fatty alcohol (A side) and C20(C22):1 as the fatty acid (B side).

In a particular embodiment, the recombinant yeast includes at least one exogenous gene encoding plant desaturase from *Simmondsia chinensis.*

In a particular embodiment, the recombinant yeast includes at least one gene encoding desaturase from *S. cerevisiae.*

In a particular embodiment, the recombinant yeast includes at least one gene encoding ChDes9-1 desaturase from *Calanus hyperboreus.*

In particular embodiments, the recombinant yeast includes an elongase, FAS and/or FAR as previously exemplified in connection with production of very long chain fatty alcohols and very long chain fatty acids.

In a particular embodiment, fatty reductase derived from *Apis mellifera, Arabidopsis thaliana, Marinobacter aquaeolei* are preferred.

In a particular embodiment, wax ester synthates derived from *Arabidopsis thaliana, Simmondsia chinensis, Euglena gracilis* are preferred.

In a particular embodiment, FAS derived from *Mycobacterium* and/or yeast evolved FAS are preferred.

In a particular embodiment, elongase derived from *S. cerevisiae, Arabidopsis thaliana, Brassica napus, Crambe abyssinica Lunaria annua* (LaKCS), *Simmondsia chinensis* are preferred.

In a particular embodiment, desaturase derived from *S. cerevisiae* is preferred.

In another embodiment, the invention provides a method of producing a recombinant microorganism that includes one or more exogenous genes that encode; (a) an elongase, or different components of an elongase system, e.g. from *Arabidopsis thaliana*, or *Simmondsia chinensis, Taxus baccata, Brassica napus*, or *Crambe abyssinica* etc., and/or a fatty acid synthase (FAS) system, e.g. from *Rhodosporidium toruloides, Saccharomyces cerevisiae*, Mycobacteria etc., and; (b) a very long chain fatty acid reductase, such as fatty acyl-CoA reductase (FAR), e.g. from *Apis mellifera, Marinobacter aquaeolei* VT8, *Simmondsia chinensis, Triticum aestivum, Arabidopsis thaliana, Marinobacter algicola* DG893, *Marinobacter adhaerens* HP15, *Taxus baccata, Euglena gracilis, Oryza sativa, Gallus gallus, Yponomeuta evonymellus, Mus musculus* etc., and; (c) a desaturase, e.g. from *S. cerevisiae, Simmondsia chinensis, Calanus hyperboreus*, etc., and; (d) a wax synthase, e.g. from *Acinetobacter baylyi, Arabidopsis thaliana, Euglena gracilis, Marinobacter hydrocarbonoclasticus* DSM 8798, *Simmondsia chinensis* and *Marinobacter aquaeolei* VT8, *Acinetobacter calcoaceticus*, Mycobacteria, *Streptomyces coelicolor* etc., wherein the yeast produces at least one fatty acid derivative, such as jojoba oil, preferably with C22 (C20):1 as the fatty alcohol (A side) and C20(C22):1 as the fatty acid (B side).

In additional aspects of the invention, the genetically modified yeast of the invention can be further modified to express heterologous fatty acid biosynthetic polypeptides for increased production of fatty acid derivatives. Non-limiting examples of genes encoding such heterologous polypeptides include ACC1, gapN, e.g. derived from *Streptococcus mutans*, OLE1 and LACS1, LACS2, LACS3, derived from *Arabidopsis thaliana.*

NADPH is a cofactor in the synthesis of fatty acids. To increase the availability of NADPH for fatty acid biosynthesis, the genetically modified yeast of the invention can be further modified for heterologous expression of non-phosphorylating NADP+-dependent glyceraldehydes-3-phosphate dehydrogenase (GAPN), e.g. from *Streptococcus mutans*, or a phosphoketolase pathway. In other aspects, the yeast can be modified to disrupt GDH1 encoding NADP-dependent glutamate dehydrogenase. In still other embodiments, the yeast of the invention can be further modified to overexpress GDH2 encoding NAD-dependent glutamate dehydrogenase. Also combinations of these embodiments are possible, i.e. the yeast is modified for i) heterologous expression of non-phosphorylating NADP+-dependent GAPN, ii) disruption of GDH1 encoding NADP-dependent glutamate dehydrogenase and/or iii) overexpression of GDH2 encoding NAD-dependent glutamate dehydrogenase.

In a particular embodiment, the recombinant yeast includes the expression of at least one gene encoding an acetyl-CoA carboxylase (ACC), including but not limited to ACC1 and mutated forms thereof as previously described (Shi et al., 2014), to increase the precursor supply of malonyl-CoA for the production of very long chain fatty acids.

In a particular embodiment, the recombinant yeast includes heterologous expression of at least one gene encoding a system to increase NADPH supply for elongation and reduction reactions, including but not limited to expression of GAPN, or a phosphoketolase pathway e.g. from *Aspergillus nidulans* (heterologous expression of xpkA and ack).

In a particular embodiment, the recombinant yeast includes heterologous expression of at least one gene encoding a desaturase, to increase the production of Δ9 unsaturated very long chain fatty acids, including precursors for erucic acid, nervonic acid and jojoba oil.

In a particular embodiment, the recombinant yeast includes heterologous expression of one or more genes of LACS1, LACS2, LACS3 derived from *Arabidopsis thaliana* to facilitate an activation of long chain fatty acids with CoA. This is important for subsequent reactions catalyzed by reductases and wax ester synthases in creating very long chain fatty alcohols and wax esters.

Also combinations of these particular embodiments are possible and within the scope of the embodiments.

In further aspects of this invention, the yeast strains of the invention can additionally, or alternatively, comprise genetic modifications that eliminate or reduce non-essential pathways. Such modifications can eliminate or reduce the utilization or consumption of fatty acids by enzymes or pathways that compete with the production of fatty acid derivatives such as fatty alcohols, fatty acid alkyl esters etc in the recombinant yeast strains. Exemplary embodiments of such non-essential pathways can include but are not limited to storage lipid (triacylglycerols, TAGs; sterol esters, SEs) formation, β-oxidation. In particular embodiments, storage lipid formation can be eliminated or reduced by disrupting the genes encoding, for example, acyl-CoA:sterol acyltransferase (ARE1, ARE2), diacylglycerol acyltransferase (DGA1), and/or lecithin cholesterol acyl transferase (LRO1). In other embodiments, β-oxidation can be eliminated or reduced by disrupting the genes encoding, for example, fatty-acyl coenzyme A oxidase (POX1). In yet another embodiment, the recombinant yeast strains of this invention can have reduced expression or activity of one or more additional enzymes that reduce the biosynthesis of the desired fatty acid derived products, including but not limited to genes encoding Ole1, Elo3, Fat1, Faa1 and Faa4.

Therefore, in a particular embodiment, the recombinant yeast includes reduced expression of and/or knock-out of at least one gene from competing pathways, including but not limited to TAGs, SEs, β-oxidation.

In a particular embodiment, the recombinant yeast includes reduced expression and/or knock-out of at least one gene encoding Ole1, to increase the production of saturated fatty acids and very long chain fatty acids such as docosanol.

In a particular embodiment, the recombinant yeast includes reduced expression of and/or knock-out of at least one gene encoding Fas1, for example, by putting the yeast FAS1 gene under a promoter such as pHXT1.

In a particular embodiment, the recombinant yeast includes reduced expression of and/or knock-out of at least one gene encoding Elo3, in order to allow accumulation of C22.

In a particular embodiment, the recombinant yeast includes reduced expression of and/or knock-out of at least one gene encoding Fat1, in order to allow accumulation of very long chain fatty acids of C24.

In a particular embodiment, the recombinant yeast includes reduced expression of and/or knock-out of at least one gene encoding Faa1 and/or Faa4.

Combinations of the above exemplified gene knock-outs or expression reductions are possible and within the scope of the embodiments.

In a particular embodiment, the recombinant yeast is the JV03 strain (MATa MAL2-8$^c$ SUC2 ura3-52 are1Δ dga1Δ are2Δ Iro1Δ pox1Δ).

Combinations of the above exemplified heterologous gene expressions and gene knock-outs are also possible and within the scope of the embodiments.

In a particular embodiment, the recombinant yeast includes expression of a gene encoding acetyl-CoA carboxylase (ACC), including but not limited to ACC1 and mutated forms thereof as previously described by (Shi et al., 2014) in combination with knock-down of Elo3.

Transporter proteins, such as ATP-binding cassette (ABC) proteins can be introduced into a host that includes an exogenous fatty acyl-CoA reductase gene, fatty aldehyde reductase gene, or carboxylic acid reductase gene. For example, ABC transporters of *Arabidopsis* such as ABCG11 and/or ABCG12 as well as lipid transfer proteins (LTPs) such as LTPG1 and LTPG2 can be introduced into a host cell. In some embodiments, fatty acid transporter (FATP) genes from species including *Saccharomyces, Drosophila*, Mycobacteria, or mammalian species can be introduced into a host cell. In some embodiments, a transporter protein increases the amount of fatty alcohols or fatty alcohol derivatives released into the growth medium of a microorganism. Expression of a transporter protein can in some embodiments also increase production of fatty alcohols or fatty alcohol derivatives by a host strain. One embodiment the invention herein uses a plant wax ester transporter. For example, ABCG12/CER5 from *Arabidopsis* facilitates the export of very long chain aldehydes, ketones, alcohols, alkanes, esters and other possible fatty acids derivatives.

Therefore, in a particular embodiment, the recombinant yeast includes heterologous expression of at least one gene encoding ABCG11, ABCG12, LTPG1 and/or LTPG2.

At the same time genes encoding for intrinsic yeast transporters, including ABC transporters, such as ABCG11 and ABCG12, can be deleted to avoid secretion of particular products of interest and increase intracellular accumulation.

Other aspects of the invention provides methods for the production of VLCFA derivatives in genetically modified yeast, comprising culturing a genetically modified yeast of the invention and isolating at least one VLCFA derivative, such as very long chain fatty acid, very long chain fatty alcohol and/or wax ester, from the microorganism or the growth media.

Therefore, in one embodiment, the method includes culturing a microorganism that includes at least one exogenous gene encoding an elongase or a fatty acid synthase (FAS) system and a very long chain fatty acid reductase, such as fatty acyl-CoA reductase (FAR), that increases the amount of very long chain fatty alcohol products released into the media and isolating at least one very long chain fatty alcohol from the microorganism or the growth media.

In a particular embodiment, the fatty alcohol is docosanol, preferably N-docosanol C22:0.

In another embodiment, the method includes culturing a microorganism that includes at least one exogenous gene encoding an elongase or a fatty acid synthase (FAS) system and a desaturase, that increases the amount of very long chain fatty acids released into the media and isolating at least one very long chain fatty acid from the microorganism or the growth media.

In a particular embodiment, the fatty acid is erucic acid, preferably C22:1 or nervonic acid, C24:1.

In yet another embodiment, the method includes culturing a microorganism that includes at least one exogenous gene encoding a very long chain fatty acid reductase, such as fatty acyl-CoA reductase (FAR) and a wax synthase, that increases the amount of wax esters released into the media, and isolating at least one wax ester from the microorganism or the growth media.

In yet another embodiment, the method includes culturing a microorganism that includes at least one exogenous gene encoding an elongase or a fatty acid synthase (FAS) system, a very long chain fatty acid reductase, such as fatty acyl-CoA reductase (FAR), and a wax synthase, that increases the amount of wax esters released into the media, and isolating at least one wax ester from the microorganism or the growth media.

In yet another embodiment, the method includes culturing a microorganism that includes at least one exogenous gene encoding an elongase or a fatty acid synthase (FAS) system, a very long chain fatty acid reductase, such as fatty acyl-CoA reductase (FAR), a desaturase and a wax synthase, that increases the amount of wax esters released into the media, and isolating at least one wax ester from the microorganism or the growth media.

In a particular embodiment, the wax ester is jojoba oil, preferably comprising C22 (C20):1 as the fatty alcohol (A side) and C20(C22):1 as the fatty acid (B side).

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

In the examples below references are made to several primers, nucleotide and/or protein sequences, these primers, nucleotide and/or protein sequences are to be found in Table 4.

Example 1

Expression of a Wax Ester Biosynthetic Pathway Combining Heterologous Reductases (AmFAR, MaFAldhR, SciFAR or TaFAR) and Wax Ester Synthases (AbWS, AtWS, EgWS or SciWS) in *Saccharomyces cerevisiae*

Figure 2:
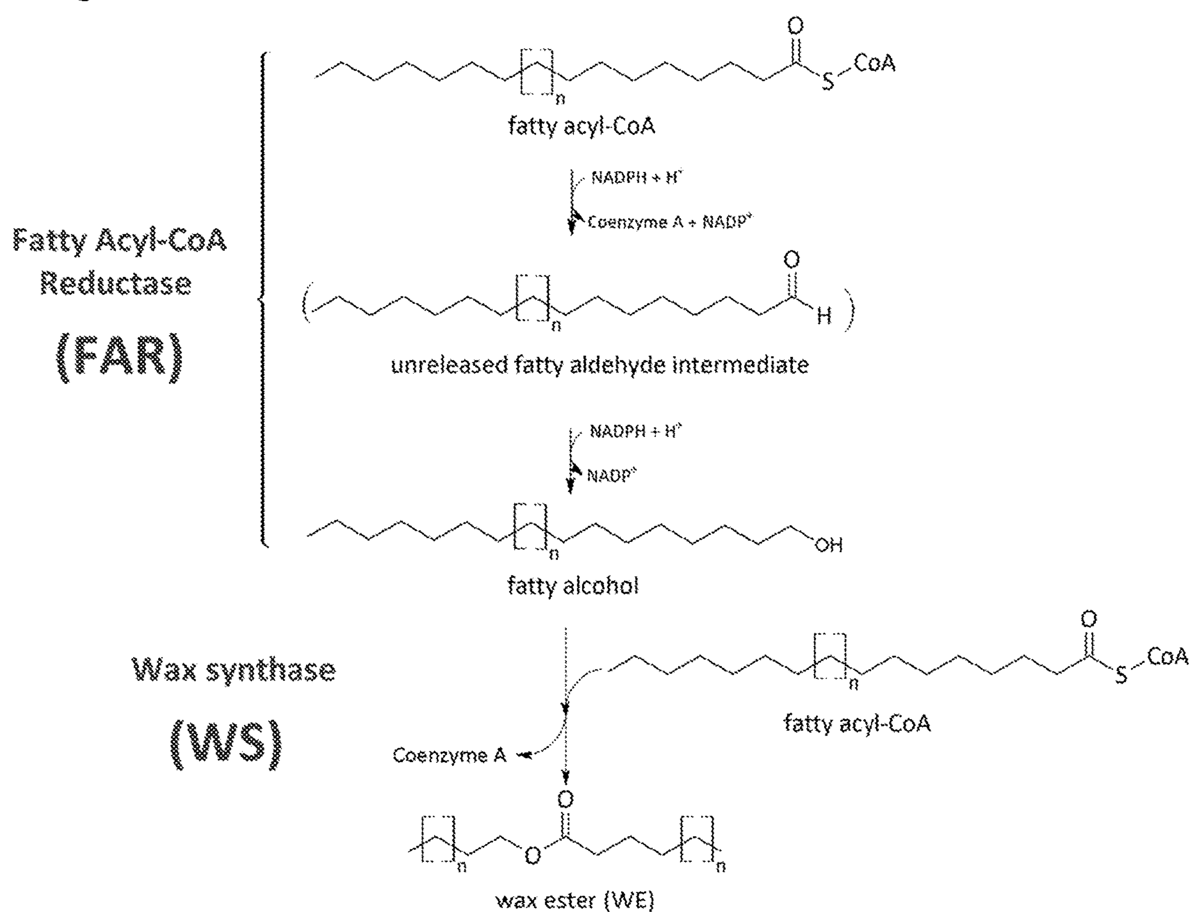
FIG. 2. Shows synthesis of wax esters, catalyzed by a fatty acyl-CoA reductase (FAR) and a wax synthase (WS).

This example includes the formation of wax esters in strains of *S. cerevisiae* by heterologous expression of different combinations of a fatty acyl-CoA reductase (FAR) and a wax ester synthase (WS). The FAR is responsible for formation of a fatty alcohol based on a fatty acyl-CoA and the WS catalyzes the esterification of the formed alcohol with a second fatty acyl-CoA molecule (see FIG. 2). The different combinations of the two enzymes were cloned into the expression vector pSP-GM2 (SEQ ID NO1, Plasmid ID 1) (Partow et al., 2010) and transformed into the yeast strains CEN.PK 113-5D (MATa MAL2-8$^c$ SUC2 ura3-52), CEN.PK113-11C (MATa MAL2-8c SUC2 his3Δ1 ura 3-52) pox1Δ and JV03 (MATa MAL2-8$^c$ SUC2 ura3-52 are1Δ dga1Δ are2Δ lro1Δ pox1Δ). Control strains harboring the empty plasmid pSP-GM2 were also constructed.

The FAR tested in this study include those from *Apis mellifera* (AmFAR) (codon optimized for *S. cerevisiae*: SEQ ID NO: 2; accession number ADJ56408), *Marinobacter aquaeolei* VT8 (MaFAldhR) (codon optimized for *S. cerevisiae*: SEQ ID NO: 3; accession number YP_959486), *Simmondsia chinensis* (SciFAR) (codon optimized for *S. cerevisiae*: SEQ ID NO: 4; accession number AAD38039), *Triticum aestivum* (TaFAR) (codon optimized for *S. cerevi-*

*siae*: SEQ ID NO: 5; accession number CAD30692), *Arabidopsis thaliana* (At5FAR) (codon optimized for yeast: SEQ ID NO: 42)

In addition, FAR1 and FAR4 from *Arabidopsis thaliana* (At) (SEQ ID NO: 6; accession number NP_197642.1 and SEQ ID NO: 7; accession number NP_190040.3, respectively) are tested. Moreover, the putative reductases from *Marinobacter algicola* DG893 (SEQ ID NO: 8, accession number ZP_01892457.1) and *Marinobacter adhaerens* HP15 (SEQ ID NO: 9; accession number ADP96574) which both have 78% identity to the *Marinobacter aquaeolei* VT8 protein (accession number YP_959486) are included in the study.

The WS in this study include those from *Acinetobacter baylyi* ADP1 (AbWS) (codon optimized for *S. cerevisiae*: SEQ ID NO: 10; accession number ENV55676), *Arabidopsis thaliana* (AtWS) (codon optimized for *S. cerevisiae*: SEQ ID NO: 11; accession number NP_568547), *Euglena gracilis* (EgWS) (codon optimized for *S. cerevisiae*: SEQ ID NO: 12; accession number ADI60058), *Marinobacter hydrocarbonoclasticus* DSM 8798 (MhWS) (codon optimized for *S. cerevisiae*: SEQ ID NO: 13; accession number ABO21021), *Simmondsia chinensis* (SciWS) (codon optimized for *S. cerevisiae*: SEQ ID NO: 14; accession number AF149919) and *Marinobacter aquaeolei* VT8 (SEQ ID NO: 15; accession number YP_957462).

The codon-optimized sequences for the genes AmFAR, MaFAldhR, SciFAR, TaFAR, AtWS, EgWS and SciWS were obtained from GenScript (860 Centennial Ave., Piscataway, N.J. 08854, U.S.), containing the Kozak sequence AAAAAA directly in front of the start codon ATG and restriction sites on both ends of the gene (NotI & SpeI in case of the FAR and BamHI & SalI in case of the WS) and cloned into the pUC57 vector (Plasmid ID 2).

In a first approach, the genes coding for the AmFAR, MaFAldhR, SciFAR and TaFAR were cloned into pSP-GM2 via the restriction enzymes NotI & SpeI, leading to the plasmids pSP-GM2::AmFAR, pSP-GM2::MaFAldhR, pSP-GM2::SciFAR and pSP-GM2::TaFAR (Plasmid ID 3-6).

The genes coding for the WS AtWS, EgWS and SciWS were cut out of the pUC57 vector using the restriction enzymes BamHI & SalI and were ligated into the plasmids pSPGM2::SciFAR and pSPGM2::TaFAR which have been cut with the respective restriction enzymes before. This led to the plasmids pSPGM2::SciFAR::AtWS, pSPGM2::SciFAR::EgWS, pSPGM2::SciFAR::SciWS, pSPGM2::TaFAR::AtWS, pSPGM2::TaFAR::EgWS and pSPGM2::TaFAR::SciWS (Plasmid ID 7-12). The genes AbWS and MhWS were amplified with specific primers (SEQ ID NO: 43-SEQ ID NO: 46) based on the plasmids pSPB1 (codon optimized AbWS gene cloned into the HindIII & BamHI restriction sites of pSP-GM2) (Plasmid ID 13) and pSPB2N (codon optimized MhWS gene cloned into the NotI & SacI restriction sites of pSP-GM2) (Plasmid ID 14).

The Gibson assembly method (Gibson et al., 2009) (SEQ ID NO: 47-SEQ ID NO: 56) was used to construct the plasmids pSPGM2::AmFAR::AbWS, pSPGM2::AmFAR::AtWS, pSPGM2::AmFAR::EgWS, pSPGM2::AmFAR::MhWS, pSPGM2::AmFAR::SciWS, pSPGM2::MaFAldhR::AbWS, pSPGM2::MaFAldhR::AtWS, pSPGM2::MaFAldhR::EgWS, pSPGM2::MaFAldhR::MhWS and pSPGM2::MaFAldhR::SciWS (Plasmid ID 15-24).

All plasmids were transformed into *Escherichia coli* DH5α by chemical transformation. The colonies carrying the desired plasmids were verified by colony PCR (SEQ ID NO: 57-SEQ ID NO: 60).

After isolation of the plasmids and verification of each gene by sequencing (SEQ ID NO: 61-SEQ ID NO: 76) (Eurofins Genomics, Ebersberg, Germany), they were transferred to the yeast strains CEN.PK 113-5D (MATa MAL2-$8^c$ SUC2 ura3-52), CEN.PK113-11C (MATa MAL2-8c SUC2 his3Δ1 ura 3-52) pox1Δ and JV03 (MATa MAL2-$8^c$ SUC2 ura3-52 are1Δ dga1Δ are2Δ lro1Δ pox1Δ) by chemical transformation (Gietz and Woods, 2002).

Three independent clones were isolated for each of the producer and control strains by streak purification onto fresh SD-Ura 2% glucose plates. Successful transformation of the producer was verified by colony PCR (SEQ ID NO: 51-SEQ ID NO: 66). Each clone was grown in precultures of 5 mL in SD-URA+2% glucose medium for 2 days, inoculated to fresh SD-URA+2% glucose medium at an $OD_{600}$ of 0.05-0.1 in 25 ml in 250 ml shake flasks. The cultures were incubated at 30° C. and 200 rpm. After 48 h, cell pellets were collected by centrifugation for 5 minutes at 1000 rcf and washed twice with 5 ml phosphate buffer (10 mM $KH_2PO_4$, pH 7.5). Extraction of lipids was carried out as described before with the exception that the final sample was dissolved in hexane (instead of chloroform/methanol) (Khoomrung et al., 2013). Subsequently, 2 μl injections were analyzed using a gas chromatograph (Focus GC, ThermoScientific) mass spectrometer (DSQII ThermoScientific) equipped with a ZB-5MS Guardian (L=30 m, ID 0.25 mm, df=0.25 μm, Phenomenex) column. The inlet temperature was set to 280° C., the helium (carrier) gas flow to 1 ml/min splitless. The initial oven temperature was set to 50° C. and held for 1 minute. Then the temperature was ramped to 280° C. by 25° C./min. In a second step the temperature was ramped to 350° C. by 10° C./min and hold for 5 min. The mass transfer line temperature was set to 250° C., the ion source temperature was set to 250° C. and a full scan for m/z of 50 to 650 was performed.

Figure 3:
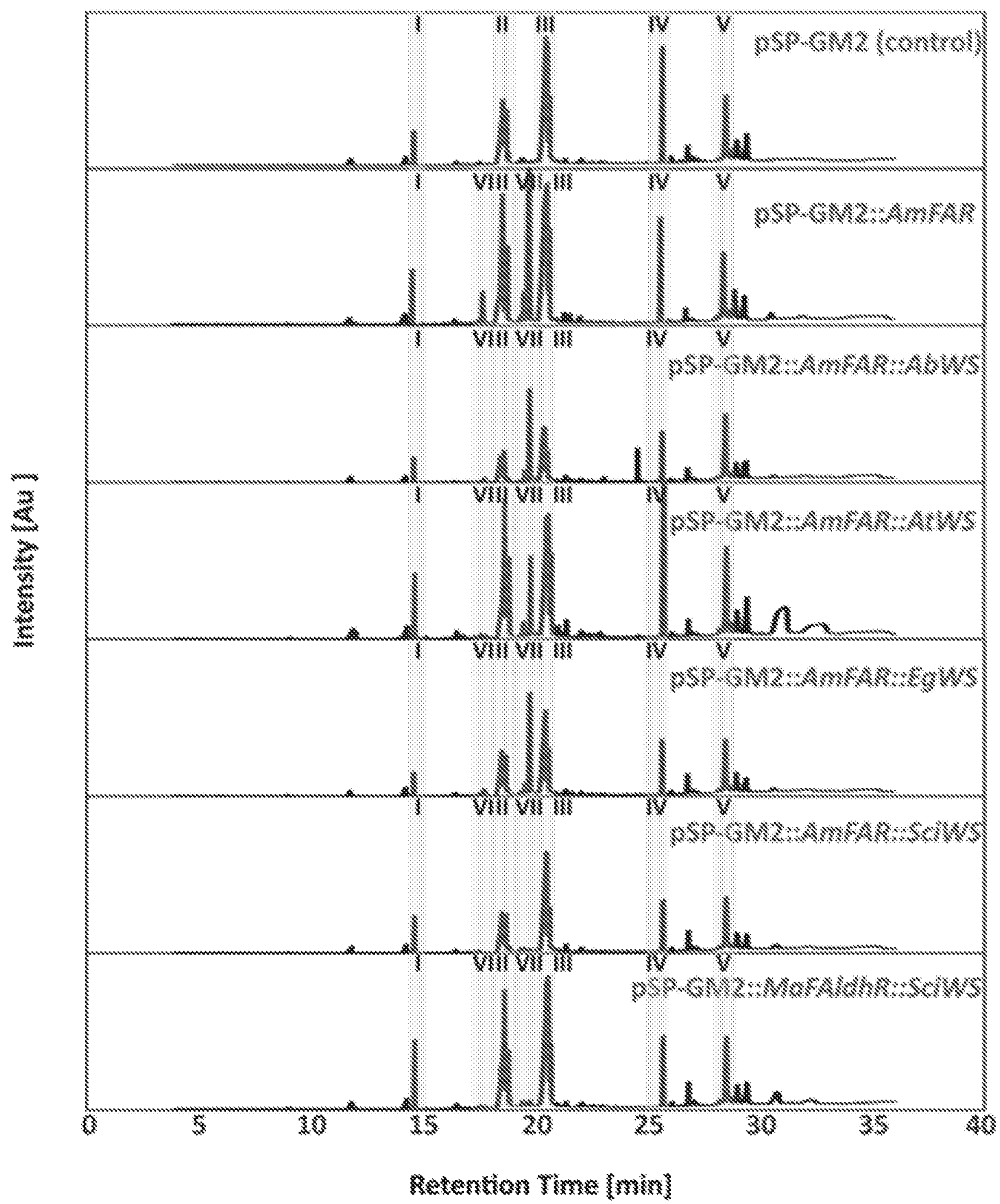
FIG. 3. Shows fatty alcohol and wax ester biosynthesis. Gas chromatograms of shake flask cultures incubated for 48 hours in SD-URA+2% glucose medium. The lines represent *S. cerevisiae* JV03 strains that express *Apis mellifera* (Am) or *Marinobacter aquaeolei* VT8 (MaFAldhR) fatty acyl-CoA reductase (FAR) in combination with the wax synthase (WS) derived from *Acinetobacter baylyi* ADP1 (Ab), *Arabidopsis thaliana* (At), *Euglena gracilis* (Eg) or *Simmondsia chinensis* (Sc). The *S. cerevisiae* control strain, carrying the empty vector pSP-GM2, is also shown. The peaks highlighted by the grey bars labeled with I-X were compared to NIST library standards and predicted to be: I, hexadecane (internal standard); II, palmitoleic acid (C16:1) and palmitic acid (C16:0); III, oleic acid (C18:1) and stearic acid (C18:0); IV, squalene; V, ergosterol; VI, hexadecanol (C16:0); VII, octadecanol (C18:1) and octadecenol (C18:1).
Figure 4:
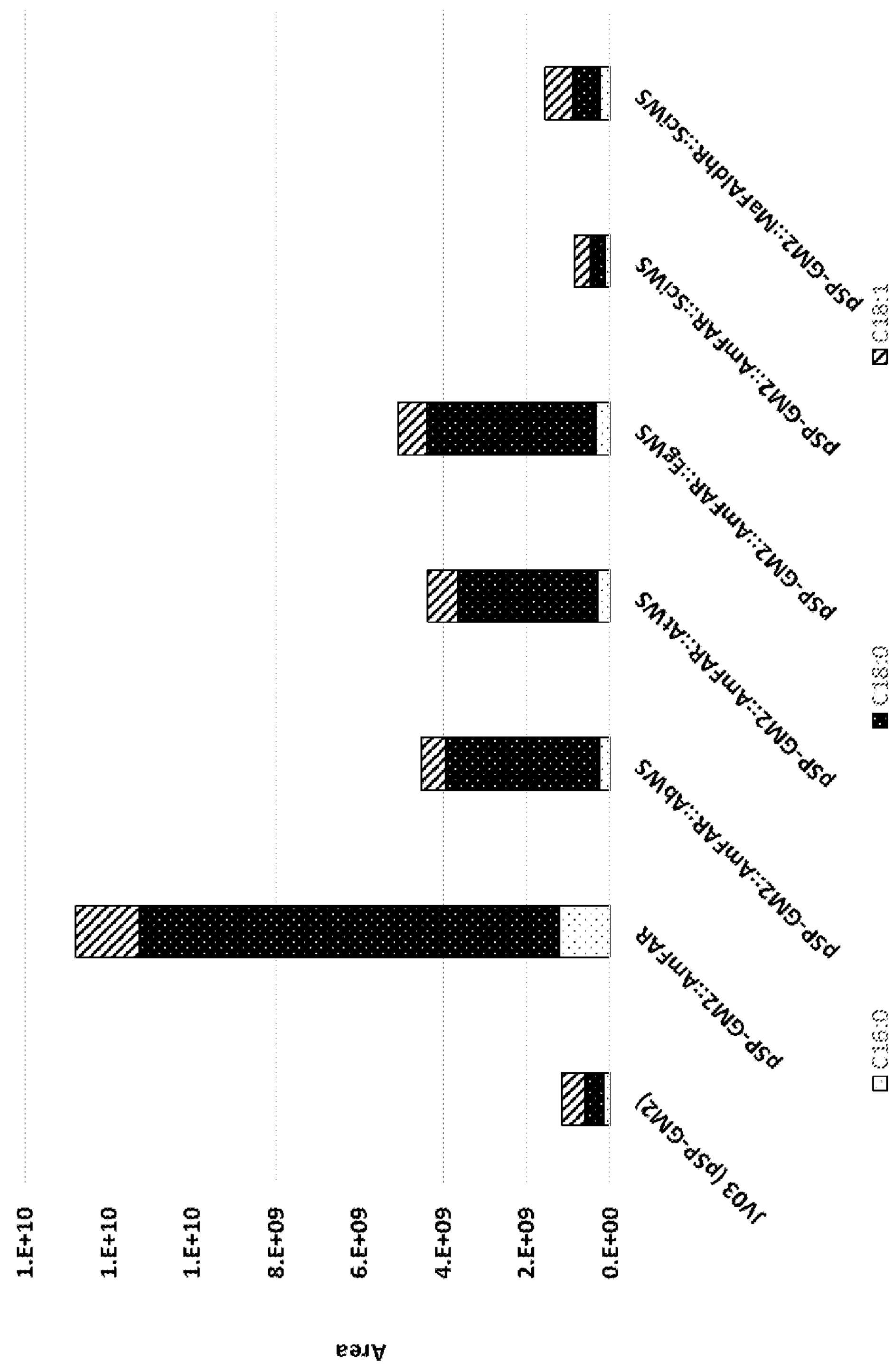
FIG. 4. Quantification of fatty alcohol in the producing strains described in FIG. 3.
Figure 5:
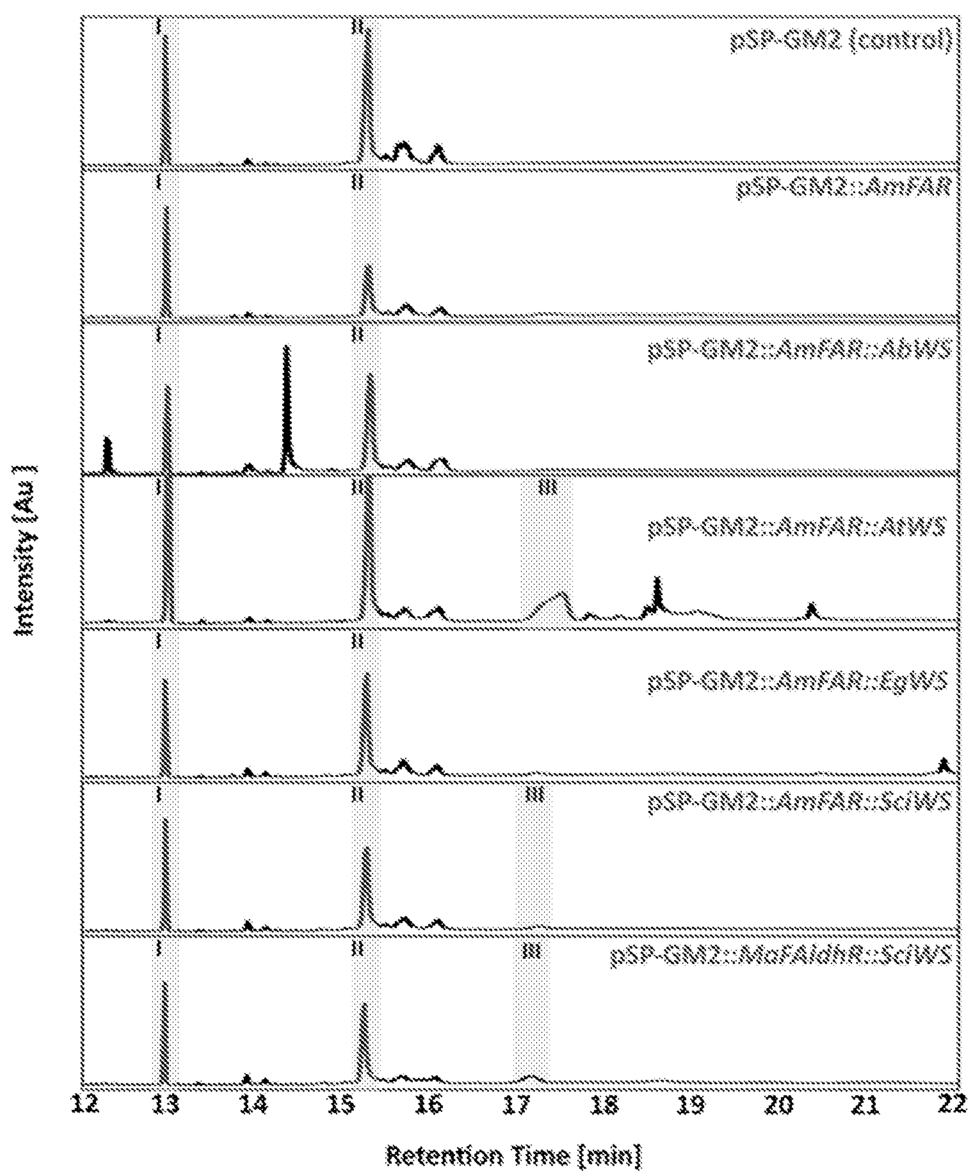
FIG. 5. Shows wax ester biosynthesis. Gas chromatograms of shake flask cultures incubated for 48 hours in SD-URA+2% glucose medium. The lines represent *S. cerevisiae* JV03 strains that express *Apis mellifera* (Am) or *Marinobacter aquaeolei* VT8 (MaFAldhR) fatty acyl-CoA reductase (FAR) in combination with the wax synthase (WS) derived from *Acinetobacter baylyi* ADP1 (Ab), *Arabidopsis thaliana* (At), *Euglena gracilis* (Eg) or *Simmondsia chinensis* (Sc). The *S. cerevisiae* control strain, carrying the empty vector pSP-GM2, is also shown. The peaks highlighted by the grey bars labeled with I-II were compared to NIST library standards and were predicted to be: I, squalene and II, ergosterol. Peak III was identified by comparison of the mass spectrum to those published by Urbanová et al. 2012 and was identified as stearyl palmitate (C18:0-C16:0).

Exemplary gas chromatogram spectra of one independent clone of a control strain (JV03 pSP-GM2) and five producing strains (JV03 pSP-GM2::AmFAR, JV03 pSP-GM2::AmFAR::AbWS, JV03 pSP-GM2::AmFAR::AtWS, JV03 pSP-GM2::AmFAR::EgWS, JV03 pSP-GM2::AmFAR::SciWS, JV03 pSP-GM2::MaFAldhR::SciWS) are shown in FIG. 3 and FIG. 5. Production of long chain fatty alcohols (JV03 pSP-GM2::AmFAR) and consumption of these towards wax esters (JV03 pSP-GM2::AmFAR::AtWS, JV03 pSP-GM2::AmFAR::SciWS, JV03 pSP-GM2::MaFAldhR::SciWS) is indicated in the figure legends. FIG. 4 shows the relative amount of fatty alcohols produced in these strains.

In this example we showed the formation of wax esters and fatty alcohols in strains of *S. cerevisiae* by heterologous expression of different combinations of a fatty acyl-CoA reductase (FAR) and a wax ester synthase (WS). A range of wax esters, e.g. C16:0-C18:0, and fatty alcohols, e.g. C16:0, C18:0, C18:1, were shown to be successfully produced.

Example 2

Heterologous Expression of Various β-Ketoacyl-CoA Synthases (KCS) in *Saccharomyces cerevisiae* to Enhance VLCFA Synthesis and Enable the Synthesis of VLC Fatty Alcohols and Wax Esters In this example heterologously expressed β-ketoacyl-CoA synthase (KCS, FAE) genes are introduced into *S. cerevisiae*. Their gene products catalyze the first step of the elongation of long-chain fatty acids (LCFA) to VLCFA (FIG. 6). *S. cerevisiae* possesses three different intrinsic KCS enzymes: Elo1, Elo2 and Elo3. Elo1 is responsible for the elongation of C14:0 to C16:0, Elo2 for the elongation up to C24 and Elo3 for the elongation from C24 to C26. Since the major fatty acids detected in *S. cerevisiae* are C14:1, C16:1 and C18:1, it is possible to assume that Elo2 and Elo3 are less active in *S. cerevisiae*.

To enhance the pool of VLCFAs, the intrinsic KCS Elo2 from *S. cerevisiae* (accession number NP_009963.1), the KCS from *Simmondsia chinensis* (accession number AAC49186.1) or the FAE1 from *Arabidopsis thaliana* (accession number AAA70154.1) (Trenkamp et al., 2004), the KCS from *Brassica napus* (BnKCS) (accession number AF490459), the KCS from *Crambe abyssinica* (CaKCS) (accession number AY793549), the KCS from *Cardamine graeca* (CgKCS) (accession number ACJ61778.1), the KCS from *Lunaria annua* (LaKCS) (accession number EU871787), or the KCS from *Tropaeolum majus* (TmKCS) (accession number AAL99199.1), which are all able to produce VLCFAs are overexpressed in *S. cerevisiae. Simultaneously, ELO*3 is deleted. Background strains of CEN.PK 113-5D elo3A, CEN.PK113-11Cpox1Δelo3Δ and JV03 (MATa MAL2-8c SUC2 ura3-52 are1Δ dga1Δ are2Δ lro1Δ pox1Δ) elo3Δ are created via using a self-excisable deletion cassette, containing KanMX as a marker, flanked by loxP sites and a cre-recombinase cloned behind the galactose inducible promoter $P_{GAL1}$ (Pan et al., 2011). For gene specific deletion of ELO3 500 bp fragments upstream (SEQ ID NO: 111, SEQ ID NO: 112) and downstream (SEQ ID NO: 113, SEQ ID NO: 114) ELO3 were amplified and fused via Gibson cloning to the particular parts of the deletion cassette.

In particular, for deletion of the elo3 gene, an approach similar to the one described by Agaphonov & Alexandrov 2014. The first linear fragment contained a 502 bp upstream elo3 region and part of the KanMX marker under control of the TEF promoter (deletion cassette 1). The second linear fragment contained part of the KanMX marker, the Cre recombinase under control of the GAL promoter and a 500 bp downstream elo3 region (deletion cassette 2). The KanMX marker and the Cre recombinase were flanked by loxP sites. After integration of the two fragments into the genome of *S. cerevisiae* by homologous recombination at the elo3 locus, the Cre recombinase was induced on galactose medium, leading to its own excision as well as excision of the KanMX marker, only leaving one loxP sequence behind. The oligonucleotides used for amplification of the up- and downstream regions of elo3, amplification of the deletion cassettes are shown in Table 1 (SEQ ID NO: 111-SEQ ID NO: 120). The elo3 deletion cassettes were used to construct the strains CEN.PK 113-5D elo3Δ, CEN.PK113-11C pox1Δ elo3Δ and JV03 elo3Δ.

In addition to the deletion of elo3, the gene coding for the mutated ACC1p** of *S. cerevisiae*, which includes two amino acid substitutions at positions 659 and 1157; S659A and S1157A (SEQ ID NO: 27; accession number NP_014413.1) (Shi et al., 2014), was integrated into the genome of the CEN.PK 113-5D elo3Δ, CEN.PK113-11C pox1Δ elo3Δ and JV03 elo3Δ, leading to CEN.PK 113-5D elo3Δ ACC1, CEN.PK113-11C pox1Δ elo3Δ ACC1 and JV03 elo3Δ ACC1**.

For this integration, a plasmid containing the ACC1 gene under control of the TEF promoter and a KanMX marker for selection was constructed (pCfB353::ACC1) (Plasmid ID 37), based on the plasmid pCfB353 described in Jensen et al., 2014. In this plasmid, the ACC1 gene is flanked by regions guiding the integration of the fragment into the region 194944-195980 of chromosome X. The plasmid was linearized by a NotI digestion and the desired fragment was gel purified and transformed into the desired yeast strain by chemical transformation. The oligonucleotides used for verification of the integration of the ACC1 gene into the genome of *S. cerevisiae* are listed in table 1 (SEQ ID NO: 121-SEQ ID NO: 126).

In addition a background strain overexpressing ELO2 is also constructed by exchanging the natural promoter with a constitutively active TEF1 promoter in the genome of CEN.PK 113-5D elo3Δ, and JV03 elo3Δ creating strain CEN.PK 113-5D elo3Δ::TEF-ELO2, and JV03 elo3Δ::TEF-ELO2. This is done by using the CRISPR/Cas9 system as described in (Jakočiūnas et al., 2015).

The overexpression of KCS gene candidates is done by ordering particular yeast codon optimized genes, cloning these combinations via Gibson cloning under a constitutively active promoter and terminator control on pSP-GM2 in combination with respective reductase/wax ester synthases and desaturases described in Example 1 and Example 3 respectively.

Screening Different Elongases in Combination with Desaturase

To enhance the pool of VLCFAs, the intrinsic KCS Elo2p from *S. cerevisiae* (SEQ ID NO: 16; accession number NP_009963.1), the Fae1p from *Arabidopsis thaliana* (AtFae1p) (codon optimized for *S. cerevisiae*: SEQ ID NO: 17; accession number AAA70154.1), the KCS from *Brassica napus* (BnKCS) (codon optimized for *S. cerevisiae*: SEQ ID NO: 18; accession number AF490459), the KCS from *Crambe abyssinica* (CaKCS) (codon optimized for *S. cerevisiae*: SEQ ID NO: 19; accession number AY793549), the KCS from *Cardamine graeca* (CgKCS) (codon optimized for *S. cerevisiae*: SEQ ID NO: 20; accession number ACJ61778.1), the KCS from *Lunaria annua* (LaKCS) (codon optimized for *S. cerevisiae*: SEQ ID NO: 21; accession number EU871787), the KCS from *Simmondsia chinensis* (SciKCS) (codon optimized for *S. cerevisiae*: SEQ ID NO: 22; accession number AAC49186.1) or the KCS from *Tropaeolum majus* (TmKCS) (codon optimized for *S. cerevisiae*: SEQ ID NO: 23; accession number AAL99199.1), which are all able to produce VLCFAs, were overexpressed in *S. cerevisiae*. The KCS enzymes were combined with the intrinsic Δ9-desaturase of *S. cerevisiae*, Ole1p (SEQ ID NO: 24; accession number EIW10301.1), to increase the amount of monounsaturated, VLCFA. The intrinsic KCS Elo2 from *S. cerevisiae* was additionally combined with the truncated Δ9-desaturase from *Simmondsia chinensis* (SciFAD) (codon optimized for *S. cerevisiae*: SEQ ID NO: 25; accession number AAA33932.1).

The genes coding for Ole1p, SciFAD and the different KCS enzymes were amplified with primers introducing a kozak sequence in front of the ATG start codon and different overhangs at the 5' and 3' end of each gene which are compatible to promoter and terminator sequences, respectively (SEQ ID NO: 77-SEQ ID NO: 90). The primers used to amplify the promoters pTPI, pTDH3, pHXT7, pPGK1 and pTEF1 as well as the terminators pYX212t, FBA1t, CYC1t, TDH2t and ADH1t, are listed in Table 4 (SEQ ID NO: 91-SEQ ID NO: 110).

Plasmids, containing the desired genes, were constructed by using the plasmid backbone pYX212 (SEQ ID NO: 26, Plasmid ID 25) and a modular pathway engineering strategy involving the electroporation of competent yeast cells (Zhou et al., 2012). All plasmids were first assembled in *S. cerevisiae* CEN.PK 113-5D and then extracted by using the Zymoprep Yeast Plasmid Miniprep II kit (Nordic Biolabs) transformed into *E. coli* DHSoli 113-5D. After purification of the plasmid, the plasmids were verified by restriction analysis and sequencing.

The resulting plasmids were: pYX212::Ole1p, pYX212::Elo2, pYX212::Ole1p::Elo2, pYX212::SciFAD::Elo2, pYX212::AtFae1::Ole1, pYX212::BnKCS::Ole1, pYX212::CaKCS::Ole1, pYX212::CgKCS::Ole1, pYX212::LaKCS::Ole1, pYX212::SciKCS::Ole1 and pYX212::TmKCS::Ole1 (Plasmid ID 26-36). Finally, the plasmids were transformed into the desired yeast strains. Yeast competent cells were prepared and transformed with 1 μg of plasmid DNA according to the lithium acetate/single-stranded carrier DNA/polyethylene glycol method (Gietz and Woods, 2002).

Figure 17:
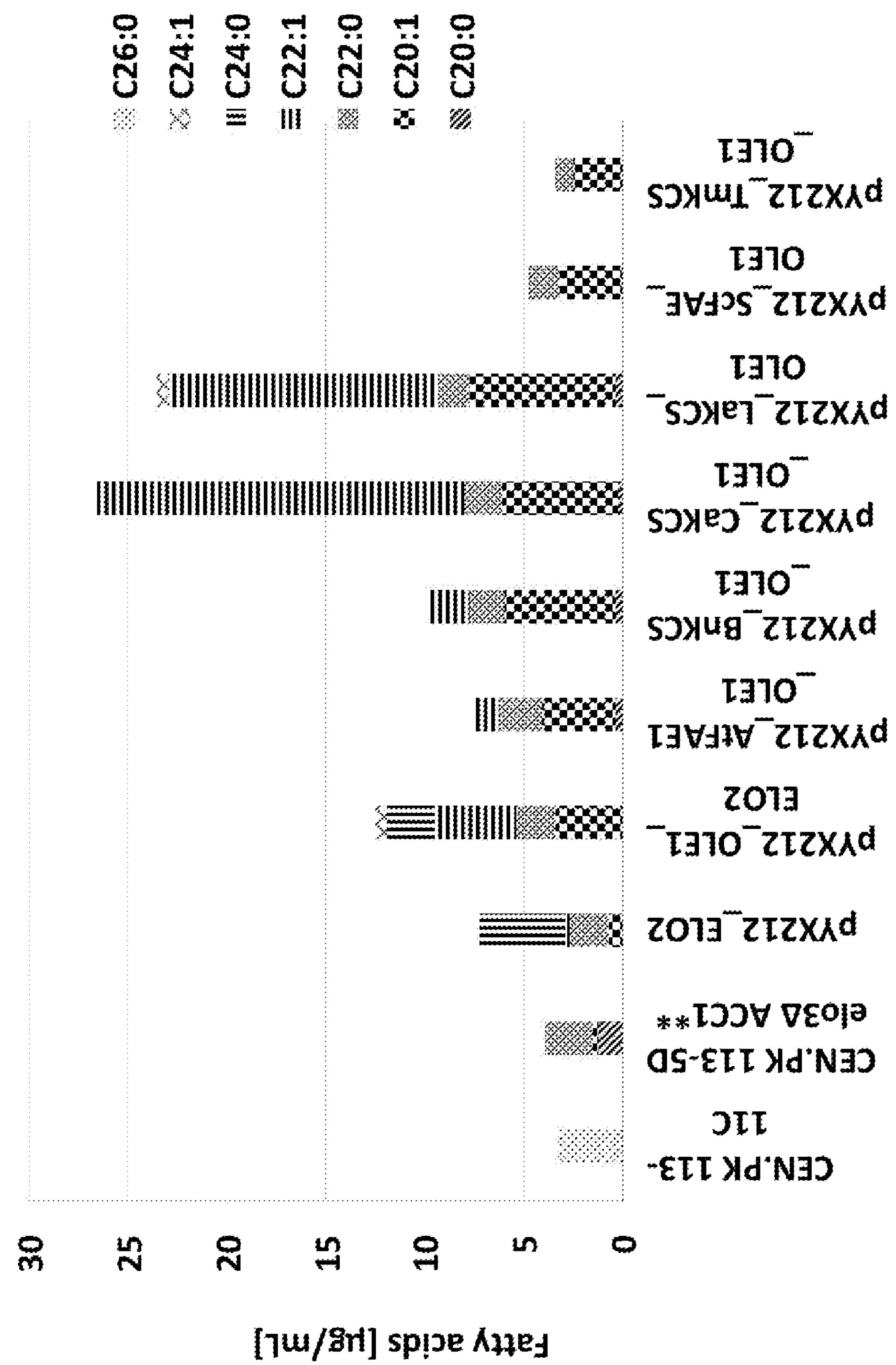
FIG. 17. Shows VLC fatty acid synthesis in *S. cerevisiae* through overexpression of elongase genes ELO2, AtFAE1 (*Arabidopsis thaliana*), BnKCS (*Brassica napus*), CaKCS (*Crambe abyssinica*), LaKCS (*Lunaria annua*), ScFAE (*Simmondsia chinensis*), TmKCS (*Tropaeolum majus*) in combination with overexpression of *S. cerevisiae* derived desaturase OLE1 in the background strain CEN.PK 113-5D Δelo3 ACC1**.

After cultivation, samples were analyzed using the same conditions as described in Example 1. Results are shown in FIG. 17, comparing particular controls with strains overexpressing ELO2, AtFAE1 (*Arabidopsis thaliana*), BnKCS (*Brassica napus*), CaKCS (*Crambe abyssinica*), LaKCS (*Lunaria annua*), ScFAE (*Simmondsia chinensis*), TmKCS (*Tropaeolum majus*), in combination with overexpression of *S. cerevisiae* derived desaturase OLE1 in the strain background CEN.PK 113-5D Δelo3 ACC1**.

We showed the formation of very long chain fatty acids in strains of *S. cerevisiae* by heterologous expression of different combinations of an elongases (KCS) and overexpression of *S. cerevisiae* derived desaturase OLE1. When comparing to the particular control strains (CEN.PK 113-11C, CEN.PK 113-5D Δelo3 ACC1), it becomes clear that the levels of very long chain fatty acids of C20:0, C20:1, C22:0, C22:1, C24:0, C24:1 become detectable and are substantially increased (FIG. 17**).

Production of Docosanol by At5FAR

The FAR tested in this study include those from FAR1 from *Arabidopsis thaliana* (codon optimized for yeast: SEQ ID NO: 42)

Figure 14:
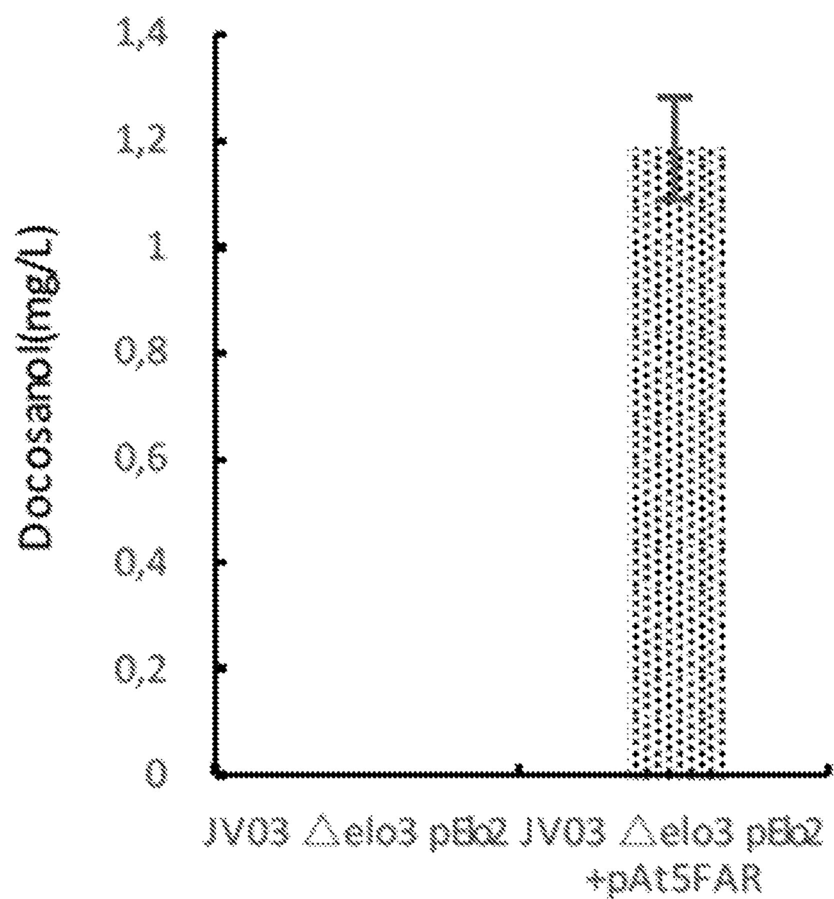
FIG. 14. Shows docosanol production in one independent clone of a control strain (JV03 Δelo3 pELO2) and producing strains (JV03 Δelo3 pELO2 pAt5FAR)

The codon-optimized sequences for the genes At5FAR were obtained from GenScript (860 Centennial Ave., Piscataway, N.J. 08854, U.S.), containing the Kozak sequence AAAAAA directly in front of the start codon ATG, containing 30 bp overhang on each side for subcloning via Gibson cloning with primers (SEQ ID NO: 179-SEQ ID NO: 180) between the TEF1 promoter and CYC1 terminator into pSPGM2-ELO2 creating pSPGM2:At5FAR:ELO2. The plasmid pSPGM2:At5FAR:ELO2 was transformed into the following yeast strains: JV03 Δelo3 strain. Yeast strains were transformed and analyzed by GC-MS using the same conditions as described in Example 1. Docosanol production in one independent clone of a control strain (JV03 Δelo3 pELO2) and producing strains (JV03 Δelo3 pELO2 pAt5FAR) are shown in FIG. 14. Here we show the successful production of Docosanol in yeast strain JV03 Δelo3 pELO2 pAt5FAR up to 1.2 mg/L titer.

High Level Production of Docosanol

Overexpression of ACC1 was performed by integration into the chromosome to replace the gene gal1 in yeast using primers (SEQ ID NO: 204-205) in the IMX581 strain to generate the strain IMX581 pACC1. This was done by using the CRISPR/Cas9 system as described in (Jakočiūnas et al., 2015).

The pathways for high level production of docosanol were assembled in the yeast chromosome using a modular pathway engineering strategy as previously described (Zhou et al., 2012). The whole pathway was divided into three modules of DS1, 2. In more detail, the DS1 module of ELO3(up)+(TDH2t-ELO1-GAL7p)+CYC1t+ELO2 was assembled by fusing the DNA parts of ELO3-up, TDH2t, ELO1, GAL7p, CYC1t and ELO2. The upstream homologous arms ELO3-up (from position −382 to +3) was amplified from CEN.PK113-11C genomic DNA with primer pair (SEQ ID NO: 184-SEQ ID NO: 185). The TDH2t was amplified from yeast genome DNA by using primer pair (SEQ ID NO: 186-SEQ ID NO: 187). The ELO1 was amplified from yeast genome DNA by using primer pair (SEQ ID NO: 188-SEQ ID NO: 189). The GAL7p was amplified from yeast genome DNA by using primer pair (SEQ ID NO: 190-SEQ ID NO: 191). The CYC1t was amplified from yeast genome DNA by using primer pair (SEQ ID NO: 192-SEQ ID NO: 193). The ELO2 was amplified from yeast genome DNA by using primer pair (SEQ ID NO: 194-SEQ ID NO: 195). The DS2 module of ELO2+GAL10p-GAL1p+At5FAR+FBA1+ELO3dw was assembled by fusing the DNA parts of ELO2, GAL10p-GAL1p, At5FAR, FBA1 and ELO3dw. The ELO2 was amplified from yeast genome DNA by using primer pair (SEQ ID NO: 204-SEQ ID NO: 205). The GAL10p-GAL1p was amplified from yeast genome DNA by using primer pair (SEQ ID NO: 196-SEQ ID NO: 197). The At5FAR was amplified from plasmid pSPGM2-At5FAR by using primer pair (SEQ ID NO: 198-SEQ ID NO: 199). The FBA1t was amplified from yeast genome DNA by using primer pair (SEQ ID NO: 200-SEQ ID NO: 201). The ELO3dw was amplified from yeast genome DNA by using primer pair (SEQ ID NO: 202-SEQ ID NO: 203). The double break (DSB) was created by plasmid pROS10-Elo3 using primer (SEQ ID NO: 183).

The pathways for high level docosanol production were integrated into strain IMX581 pACC1 strain to get strain IMX581 pACC1pELO1pELO2pAt5FAR.

Figure 15:
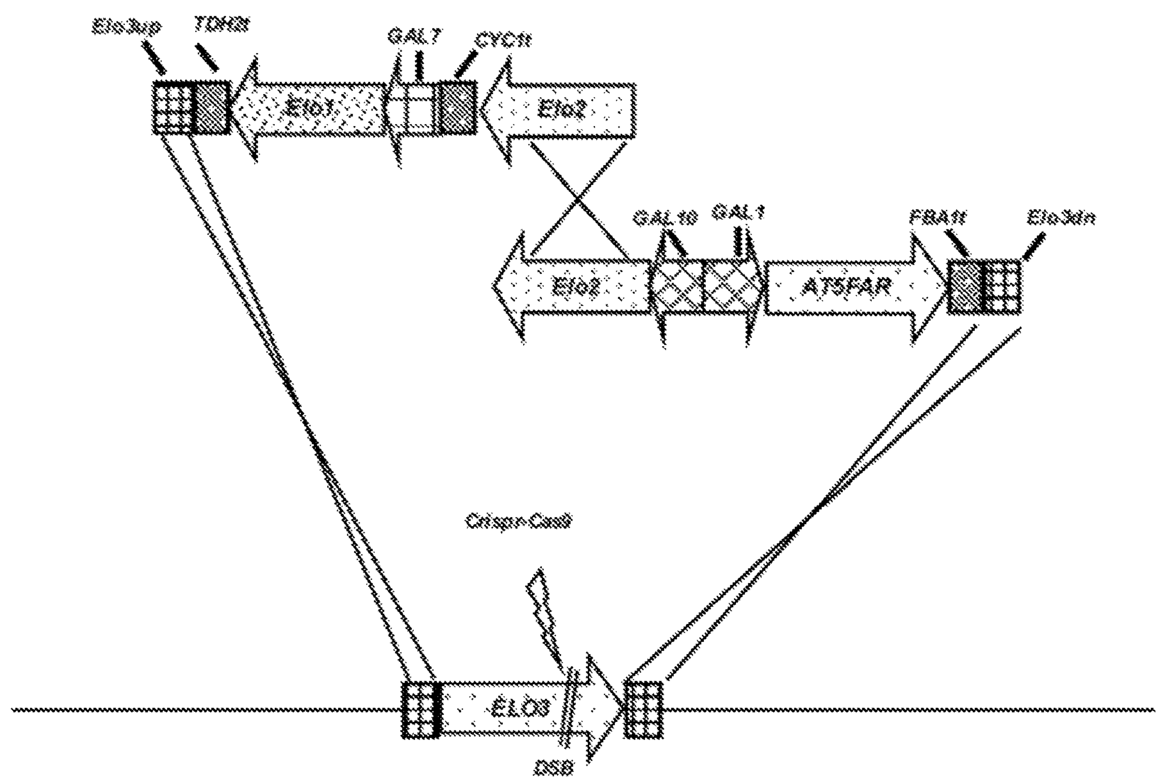
FIG. 15. Shows a schematic illustration of the genome engineering strategy for integrating ELO1, ELO2 and At5FAR overexpression, at the same time as deleting ELO3.

All pathways as described above were integrated according to the genetic arrangement shown in FIG. 15.

Figure 16:
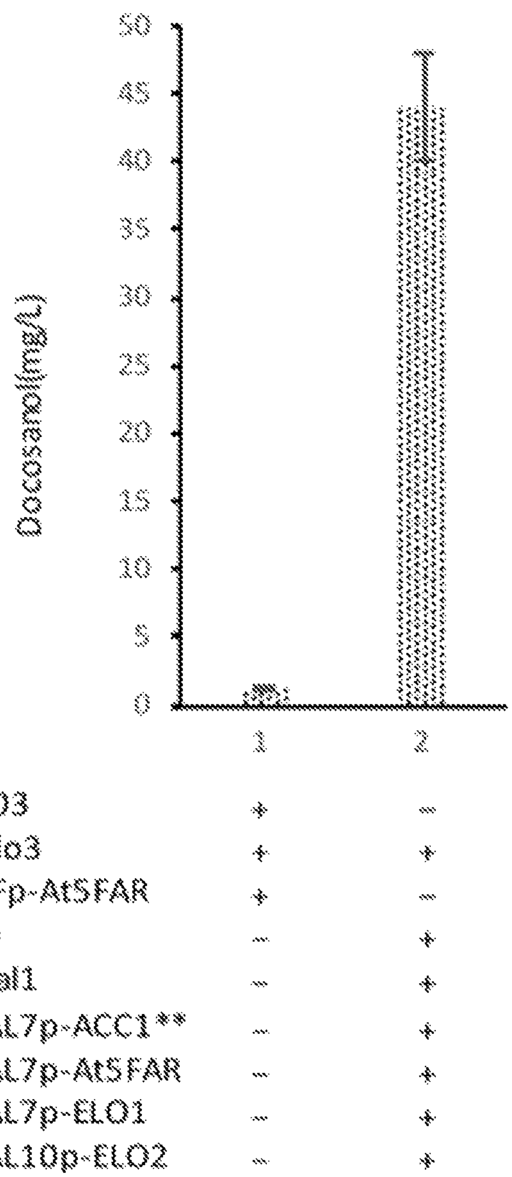
FIG. 16. Shows docosanol production (mg/L) when comparing the two strains JV03 (Δelo3 pELO2 pAt5FAR) and CEN.PK113-5D (Δelo3Δgal1 GAL7p-ACC1** GAL7p-At5FAR GAL7p-ELO1 GAL10p-ELO2).

Production titers of the control strain (JV03 Δelo3 pELO2 pAt5FAR) and the producing strain (IMX581 pACC1pELO1pELO2pAt5FAR) are shown in FIG. 16**. Through the described strategy we accomplished high level production of Docosanol up to 45 mg/L.

Production of Wax Esters by Combining Reductase, Wax Ester Synthase and Elongase Next, the intrinsic elo2 gene was tested in combination with the reductase/wax ester synthases described in Example 1. For this, the genes were amplified with primers introducing a kozak sequence in front of the ATG start codon and different overhangs at the 5' and 3' end of each gene which are compatible with a constitutively active promoter and terminator, respectively (SEQ ID NO: 127-SEQ ID NO: 144). The genes were assembled with the pYX212 plasmid backbone like described previously. The resulting plasmids were: pYX212::AmFAR::Elo2, pYX212: MaFAldhR::Elo2, pYX212::SciFAR::Elo2, pYX212::TaFAR::Elo2, pYX212::AmFAR::AbWS::Elo2, pYX212::AmFAR::AtWS::Elo2, pYX212::AmFAR::EgWS::Elo2, pYX212::AmFAR::SciWS::Elo2, pYX212::MaFAldhR::AbWS::Elo2, pYX212::MaFAldhR::AtWS::Elo2, pYX212::MaFAldhR::EgWS::Elo2, pYX212::MaFAldhR::SciWS::Elo2, pYX212::SciFAR::AbWS::Elo2, pYX212::SciFAR::AtWS::Elo2, pYX212::SciFAR::EgWS::Elo2, pYX212::SciFAR::SciWS::Elo2, pYX212::TaFAR::AbWS::Elo2, pYX212::TaFAR::AtWS::Elo2, pYX212::TaFAR::EgWS::Elo2, pYX212::TaFAR::SciWS::Elo2 (Plasmid ID 38-61).

The plasmids were transformed into CEN.PK 113-5D elo3Δ ACC1**. Yeast competent cells were prepared and transformed with 1 μg of plasmid DNA according to the lithium acetate/single-stranded carrier DNA/polyethylene glycol method (Gietz and Woods, 2002).

Three independent clones were isolated for each of the producer and control strains by streak purification onto fresh SD-Ura 2% glucose plates. Each clone was grown in precultures of 5 mL glucose minimal medium (Verduyn et al., 1992) for 2 days, inoculated to fresh glucose minimal medium at an $OD_{600}$ of 0.05-0.1 in 25 ml in 250 ml shake flasks. The cultures were incubated at 30° C. and 200 rpm. After 48 h, cell pellets were collected by centrifugation for 5 minutes at 1000 rcf and washed twice with 5 ml phosphate buffer (10 mM $KH_2PO_4$, pH 7.5).

To analyze the fatty acid spectrum in strains expressing different KCS genes or a KCS gene in combination with a desaturase, fatty acid methyl esters (FAMEs) were prepared and analyzed according to Khoomrung et al., 2012. Production data of these strains compared to particular control strains (CEN.PK 113-11C and CEN.PK 113-5D elo3Δ ACC1 pYX212) are shown in FIG. 17**.

To analyze the fatty alcohol and wax ester spectrum, extraction of lipids was carried out as previously described with the exception that the final sample was dissolved in hexane (instead of chloroform/methanol) and that heptadecanyl heptadecanoate (wax esters) and heptadecanol (fatty alcohols) were used as internal standards (Khoomrung et al., 2013). Subsequently, 2 μl injections were analyzed by gas chromatography-mass spectrometry (Focus GC ISQ™ single quadrupole GC; Thermo Fisher Scientific) using a ZB-50 column (L=30 m, ID 0.32 mm, df=0.5 μm) (Phenomenex®, Værløse, Denmark). The inlet temperature was set to 375° C., the helium (carrier) gas flow to 1 ml/min splitless. The initial oven temperature was set to 150° C. and held for 10 minutes. Then the temperature was ramped to 350° C. by 7.5° C./min and hold for 10 min. The mass transfer line temperature was set to 250° C., the ion source temperature was set to 250° C. and a full scan for m/z of 50 to 650 was performed. The analytical standards for alcohols and wax esters were purchased from Nu-Check Prep, Inc. (Nu-Check Prep, Inc., Elysian, Minn., USA) with an exact weight amount. They were dissolved in hexane and analyzed using the same protocol and column like for the samples.

Figure 7:
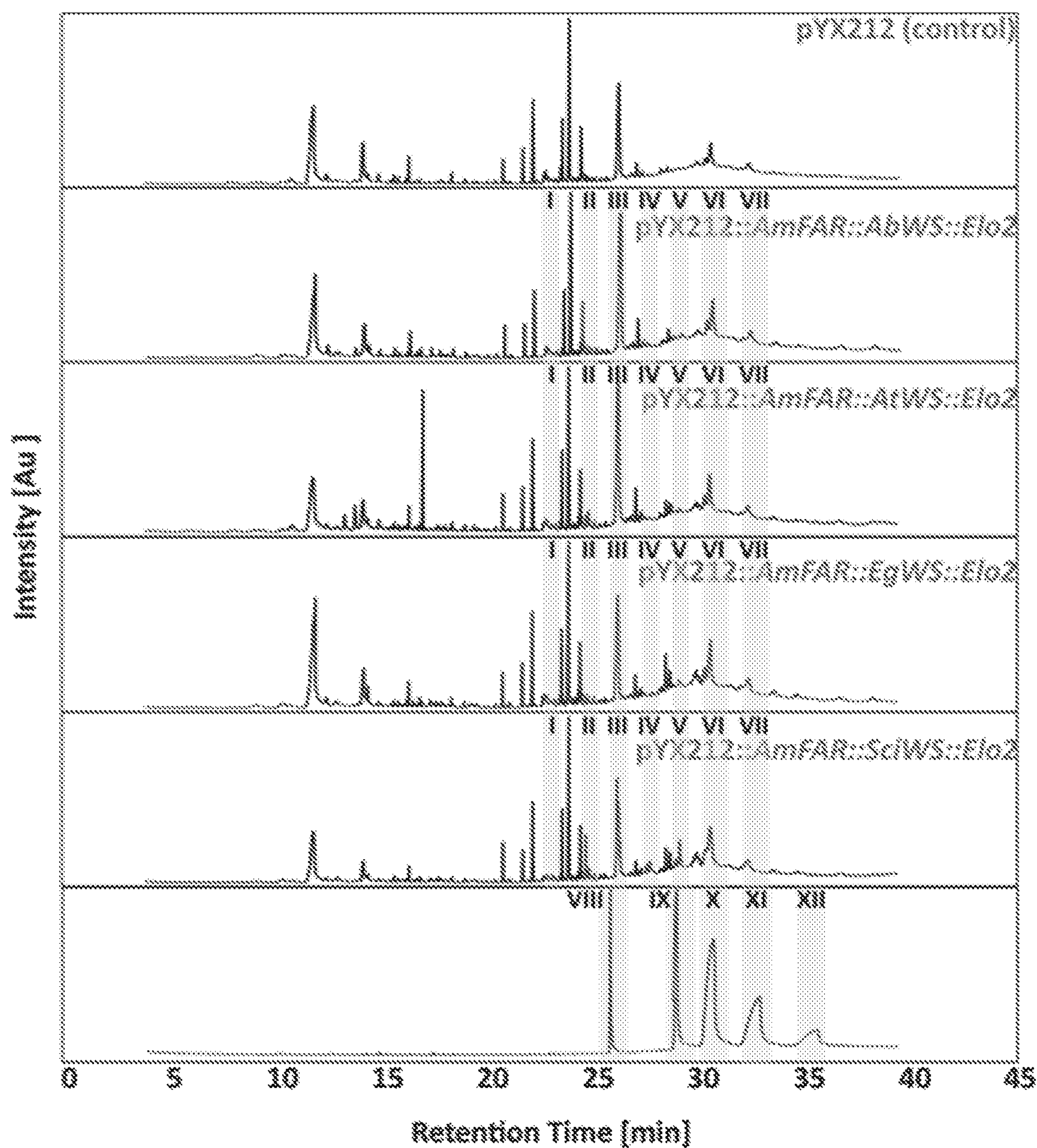
FIG. 7. Shows wax ester biosynthesis. Gas chromatograms of shake flask cultures incubated for 48 hours in Minimal medium+2% glucose medium. The lines represent *S. cerevisiae* CEN.PK113-5D elo3Δ ACC1** strains that express *Apis mellifera* (Am) fatty acyl-CoA reductase (FAR) in combination with the wax synthase (WS) derived from *Acinetobacter baylyi* ADP1 (Ab), *Arabidopsis thaliana* (At), *Euglena gracilis* (Eg) or *Simmondsia chinensis* (Sc). The *S. cerevisiae* control strain, carrying the empty vector pYX212, is also shown. The peaks highlighted by the grey bars labeled with I-VII were identified by comparison of the mass spectrum to those published by Urbanová et al. 2012 and were identified as I, palmityl myristate (C16:0-C14:0); II, palmityl palmitate (C16:0-C16:0), stearyl myristate (C18:0-C14:0), palmityl palmitoleate (C16:0-C16:1) and stearyl myristoleate (C18:0-C14:1); III, stearyl palmitate (C18:0-C16:0); arachidyl myristate (C20:0-C14:0), stearyl palmitoleate (C18:0-C16:1), palmityl oleate (C16:0-C18:1) and oleyl palmitoleate (C18:1-C16:1); IV, arachidyl palmitate (C20:0-C16:0), behenyl myristate (C22:0-C14:0), palmityl arachidate (C16:1-C20:0), stearyl stearate (C18:0-C18:0) and arachidyl palmitoleate (C20:0-C16:1); V, behenyl palmitate (C22:0-C16:0), palmityl behenate (C16:0-C22:0), arachidyl stearate (C20:0-C18:0), stearyl arachidate (C18:0-C20:0), behenyl palmitoleate (C22:0-C16:1) and arachidyl oleate (C20:0-C18:1); VI, behenyl stearate (C22:0-C18:0), arachidyl arachidate (C20:0-C20:0), stearyl behenate (C18:0-C22:0) and behenyl oleate (C22:0-C18:1); VII, arachidyl behenate (C20:0-C22:0) and behenyl arachidate (C22:0-C20:0).
Figure 8:
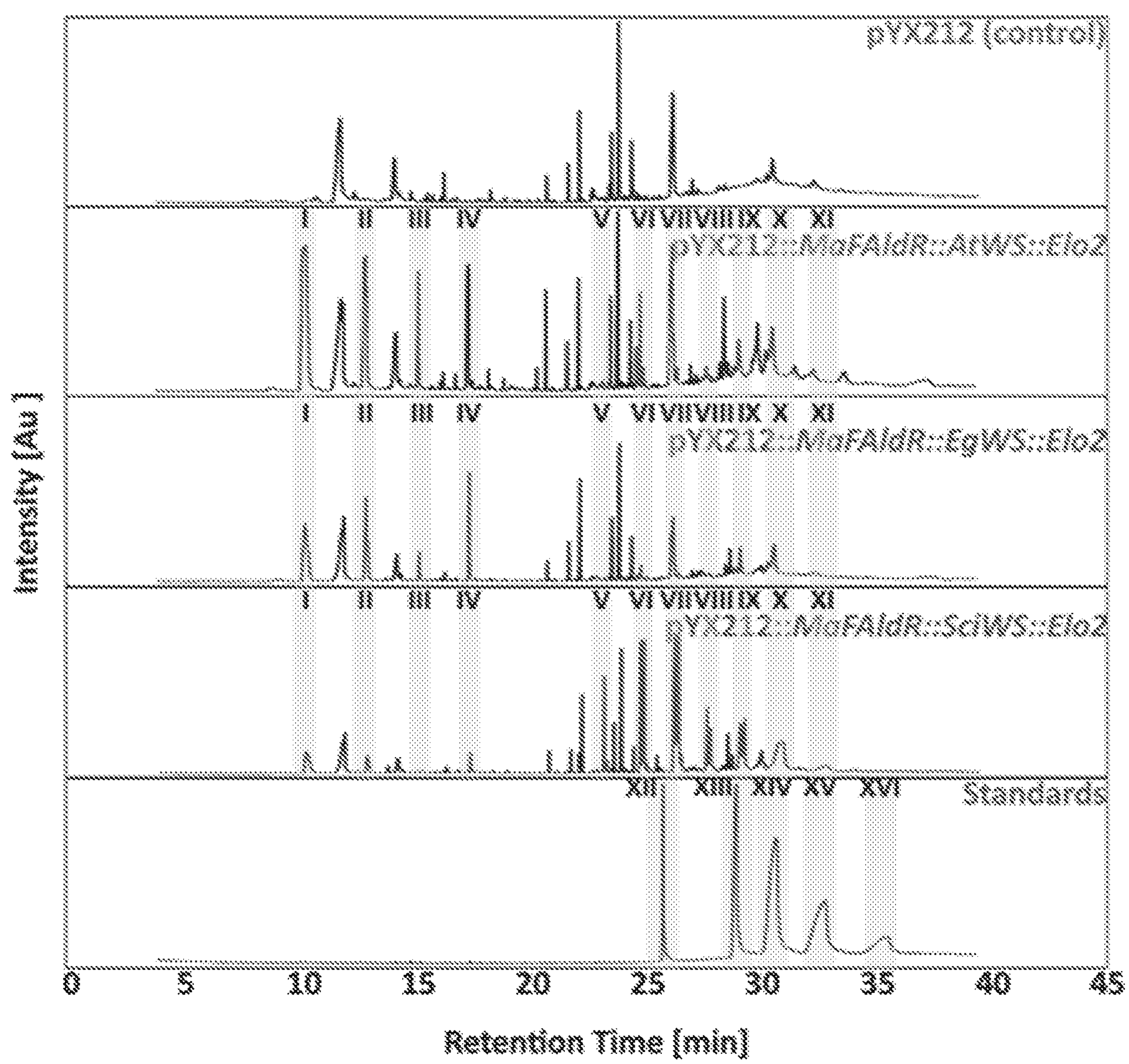
FIG. 8. Shows wax ester biosynthesis. Gas chromatograms of shake flask cultures incubated for 48 hours in Minimal medium+2% glucose medium. The lines represent *S. cerevisiae* CEN.PK113-5D elo3Δ ACC1** strains that express *Marinobacter aquaeolei* VT8 (MaFAldhR) fatty acyl-CoA reductase (FAR) in combination with the wax synthase (WS) derived from *Arabidopsis thaliana* (At), *Euglena gracilis* (Eg) or *Simmondsia chinensis* (Sc). The *S. cerevisiae* control strain, carrying the empty vector pYX212, is also shown. The peaks highlighted by the grey bars labeled with I-VII were identified by comparison of the mass spectrum to those published by Urbanová et al. 2012 and were identified as I, palmityl myristate (C16:0-C14:0) and palmitoleyl myristate (C16:1-C14:0); II, palmityl palmitate (C16:0-C16:0), stearyl myristate (C18:0-C14:0), palmityl palmitoleate (C16:0-C16:1), stearyl myristoleate (C18:0-C14:1) and palmitoleyl palmitoleate (C16:1-C16:1); III, stearyl palmitate (C18:0-C16:0), palmityl stearate (C16:0-C18:0), arachidyl myristate (C20:0-C14:0), stearyl palmitoleate (C18:0-C16:1), palmityl oleate (C16:0-C18:1), oleyl palmitoleate (C18:1-C16:1) and palmitoleyl oleate (C16:1-C18:1); IV, arachidyl palmitate (C20:0-C16:0), behenyl myristate (C22:0-C14:0), palmityl arachidate (C16:0-C20:0), stearyl stearate (C18:0-C18:0) and arachidyl palmitoleate (C20:0-C16:1); V, behenyl palmitate (C22:0-C16:0), palmityl behenate (C16:0-C22:0), arachidyl stearate (C20:0-C18:0), stearyl arachidate (C18:0-C20:0), behenyl palmitoleate (C22:0-C16:1) and arachidyl oleate (C20:0-C18:1); VI, behenyl stearate (C22:0-C18:0), arachidyl arachidate (C20:0-C20:0), stearyl behenate (C18:0-C22:0) and behenyl oleate (C22:0-C18:1); VII, arachidyl behenate (C20:0-C22:0) and behenyl arachidate (C22:0-C20:0).
Figure 9:
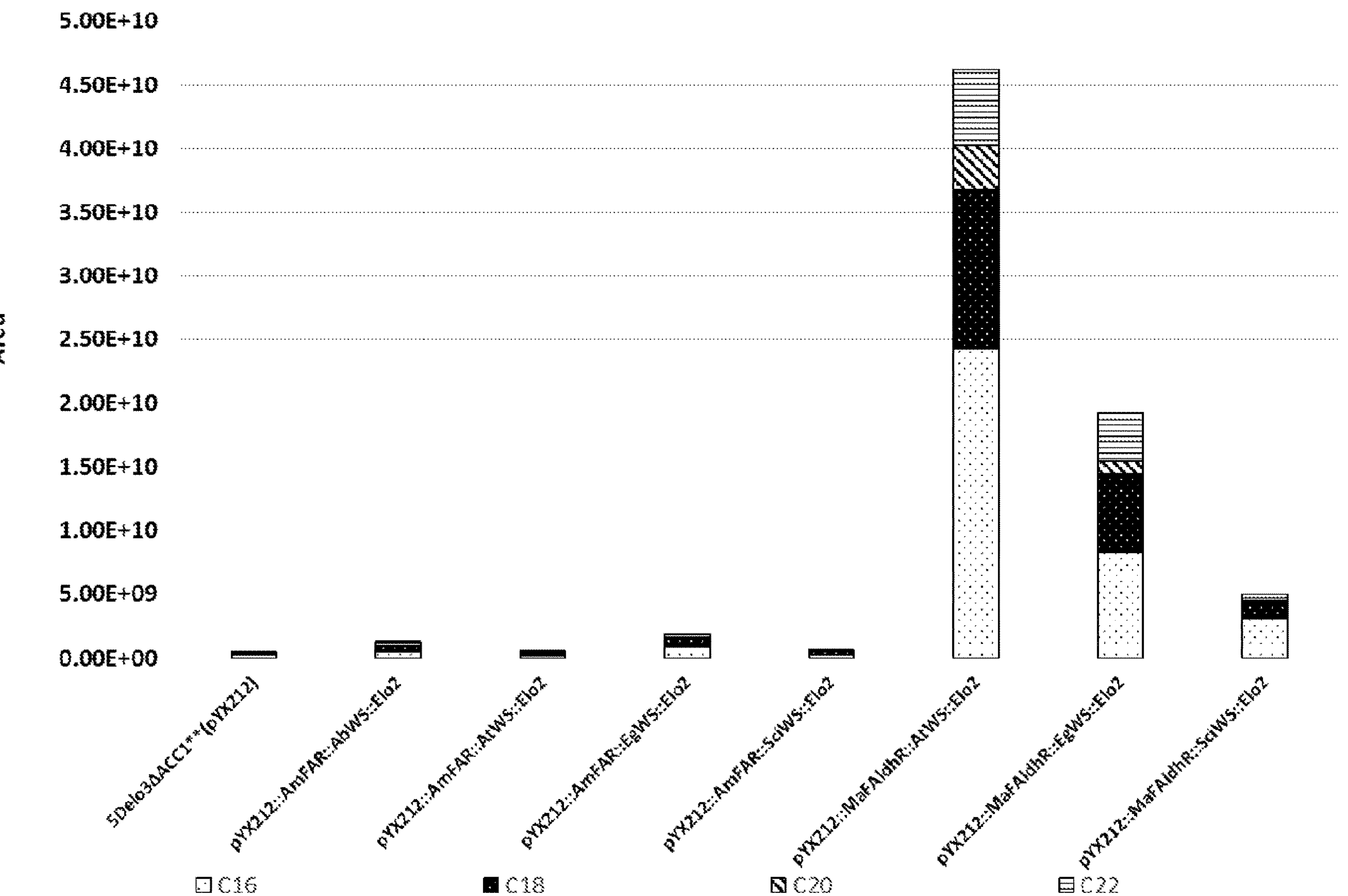
FIG. 9. Quantification of fatty alcohol in the producing strains described in FIGS. 7 and 8.
Figure 10:
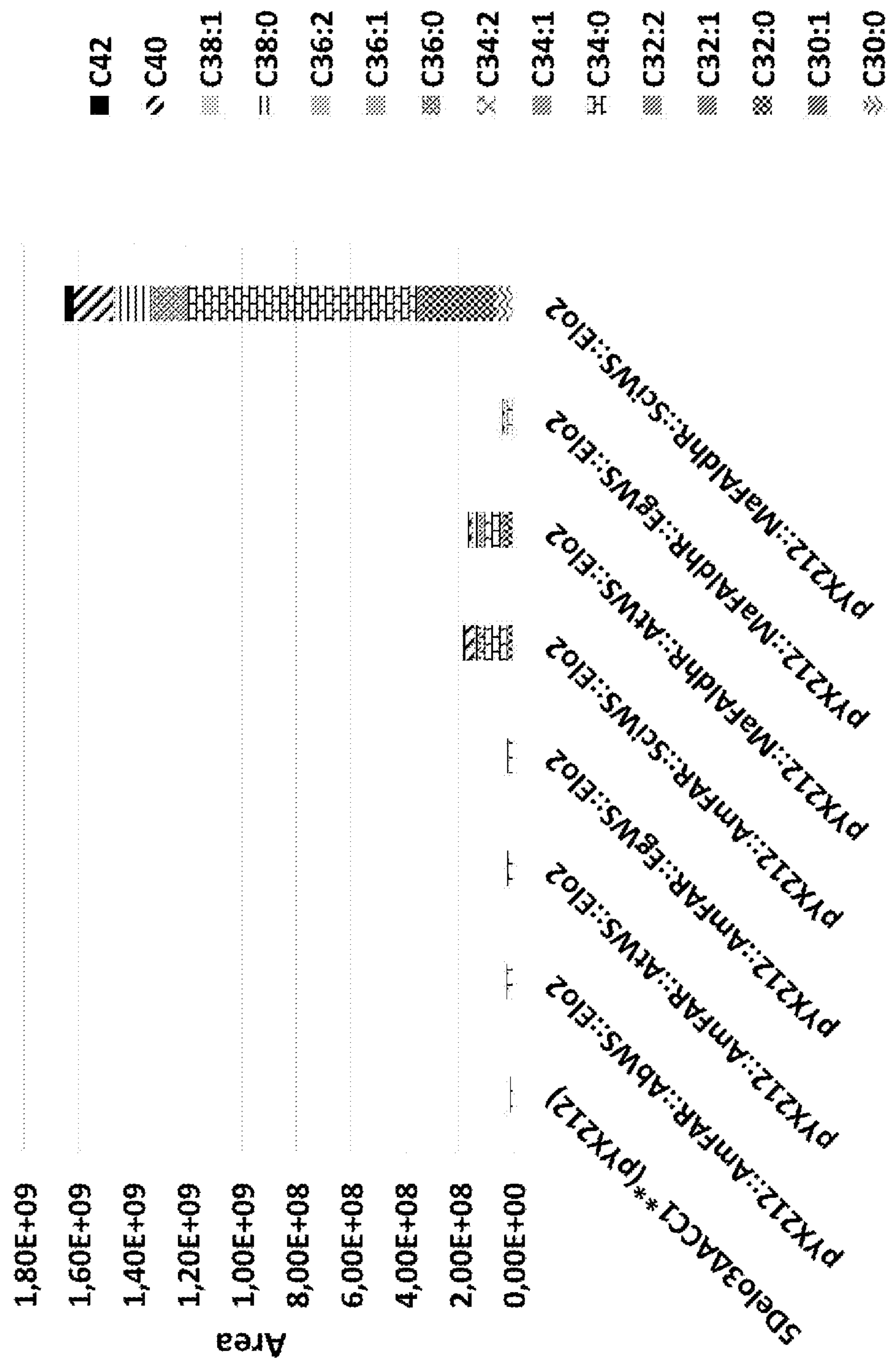
FIG. 10. Quantification of wax esters in the producing strains described in FIGS. 7 and 8.
Figure 11:
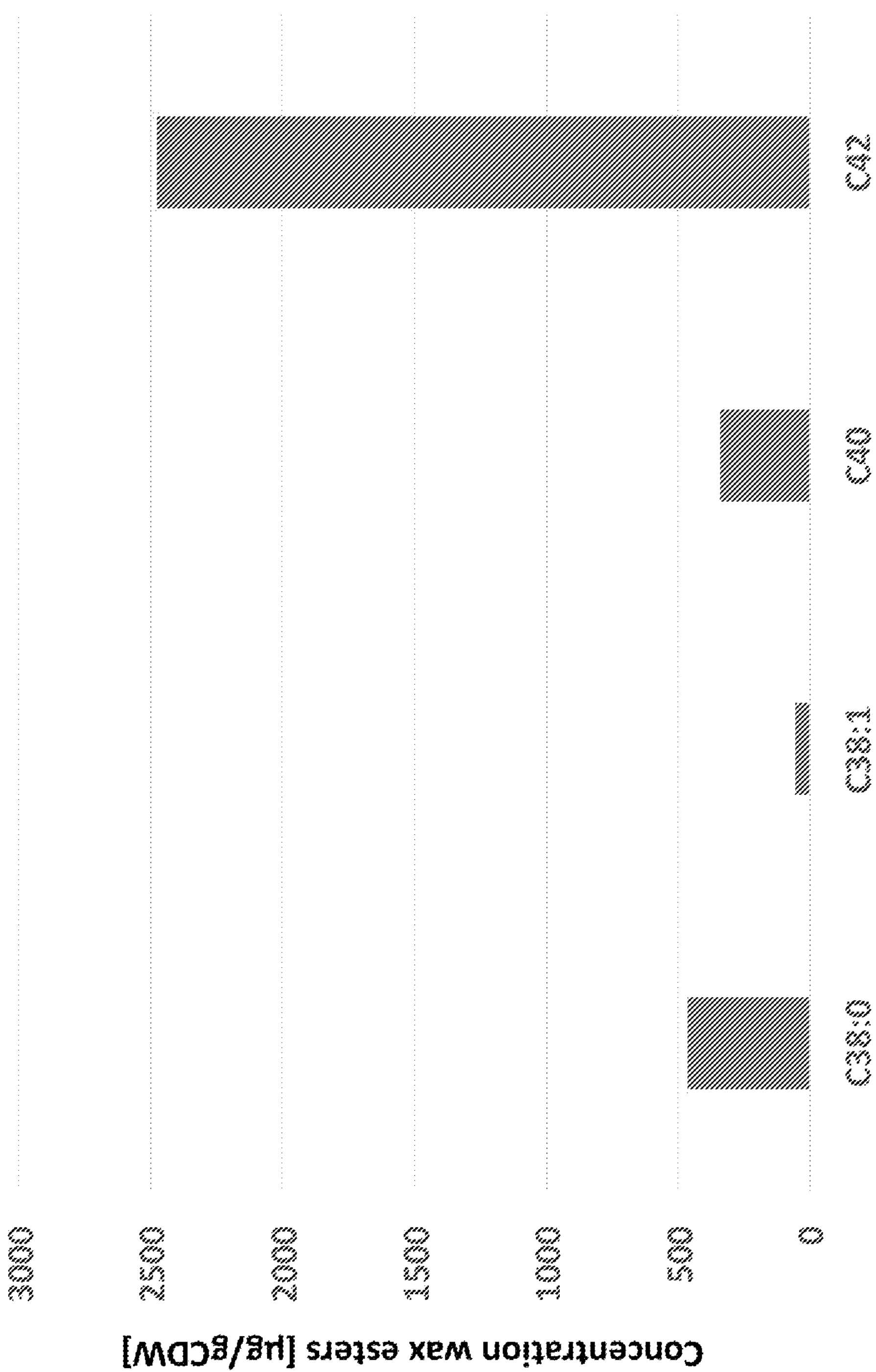
FIG. 11. Shows the concentration of C38 to C42 wax esters in strain 5Delo3ΔACC1** (pYX212::MaFAldhR::SciWS::Elo2).
Figure 12:
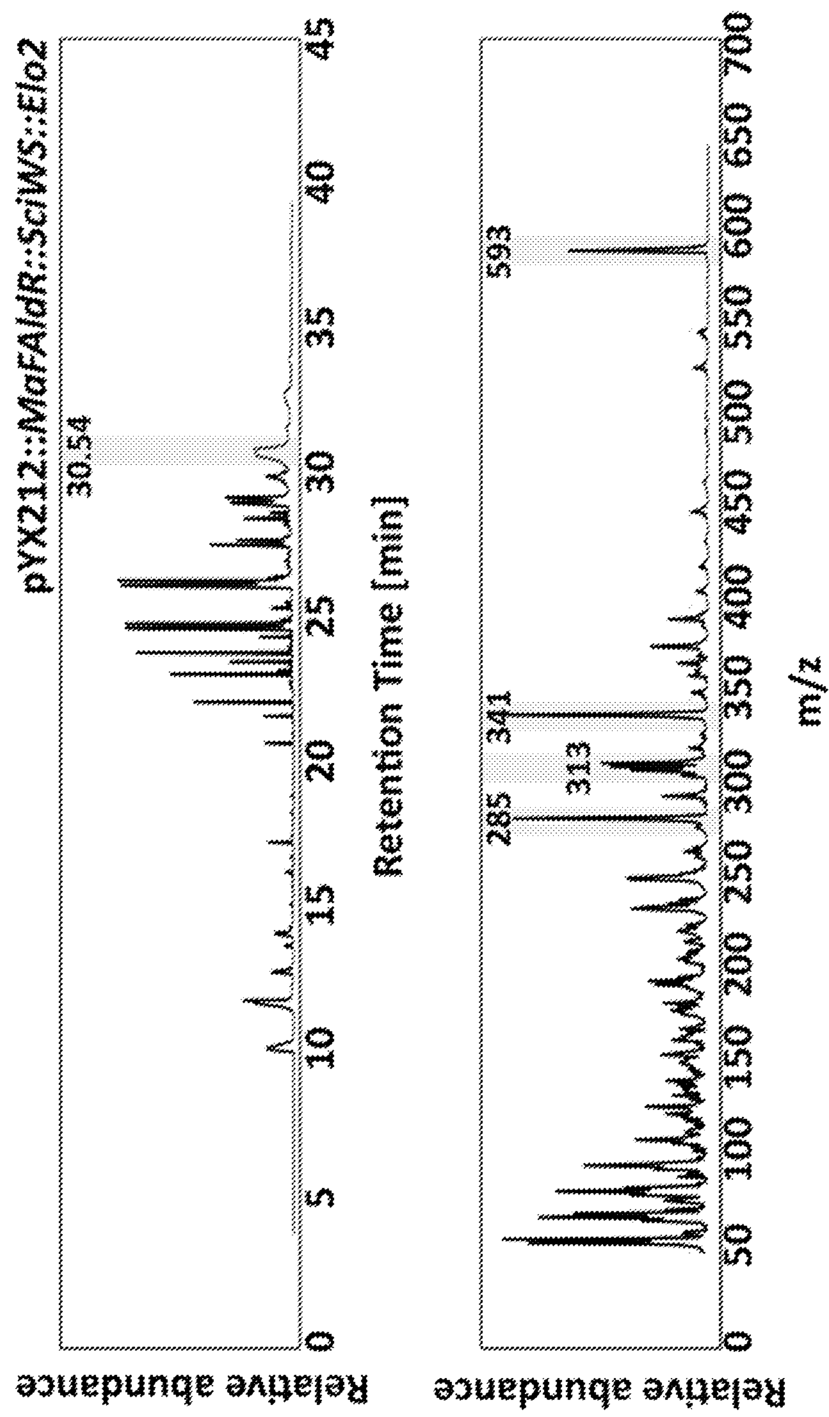
FIG. 12. Shows the specific m/z peaks of C40 wax esters in strain 5Delo3ΔACC1** (pYX212::MaFAldhR::SciWS::Elo2).
Figure 13:
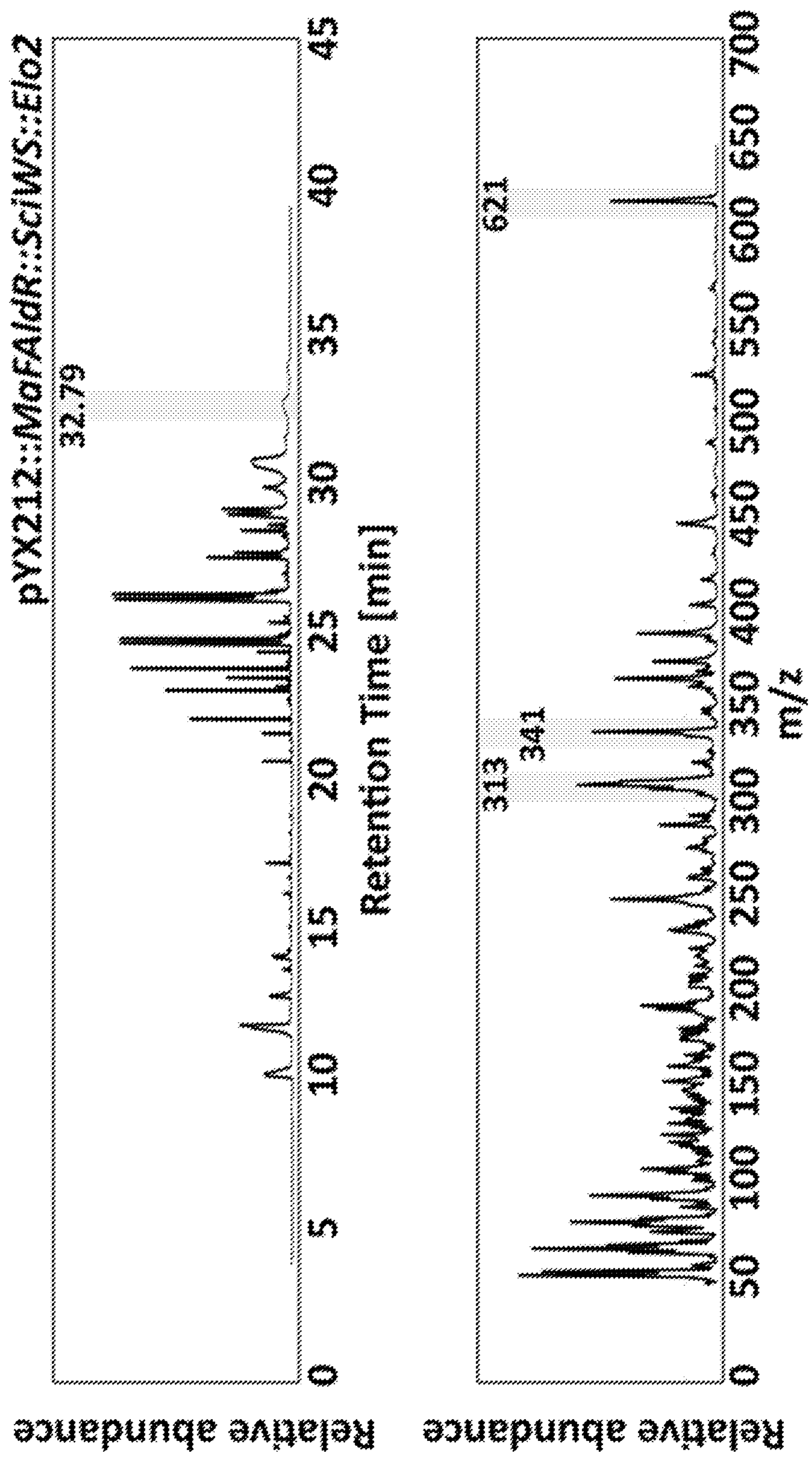
FIG. 13. Shows the specific m/z peaks of C42 wax esters in strain 5Delo3ΔACC1** (pYX212::MaFAldhR::SciWS::Elo2).

Exemplary gas chromatogram spectra of one independent clone of a control strain (CEN.PK 113-5D elo3Δ ACC1 pYX212) and 7 producing strains are shown in FIG. 7, while FIG. 8. FIG. 9, FIG. 10 and FIG. 11 depict the fatty acid, fatty alcohol and wax ester production spectrum in the producing strains, respectively. FIGS. 12 and 13 show the specific m/z peaks of C40 and C42 wax esters detected in the producing strain CEN.PK 113-5D elo3Δ ACC1 (pYX212: MaFAldhR::SciWS::Elo2) and Table 1 lists all wax ester species which could be detected in this strain.

We showed the formation of very long chain fatty alcohols and very long chain wax esters in in strains of *S. cerevisiae* by heterologous expression of different combinations of an elongase, reductases and wax ester synthases. When comparing to the particular control strains (CEN.PK 113-5D Δelo3 ACC1), it becomes clear that long chain and very long chain fatty alcohols of C16, C18, C20, C22 and very long chain wax ester of C30, C32, C34, C36, C38, C40, C42 become detectable and are substantially increased (FIG. 9, FIG. 10, FIG. 11**).

Example 3

Enhancement of Monounsaturated Fatty Acid Synthesis by Overexpression of Various Δ9-Desaturases in *Saccharomyces cerevisiae*

In this example desaturases are overexpressed to increase the production of monounsaturated fatty acids in *S. cerevisiae*. The intrinsic desaturase of *S. cerevisiae* (see Example 2) (accession number EIW10301.1) or heterologously expressed desaturase from *Simmondsia chinensis* (see Example 2) (accession number 1905423A) are overexpressed. The desaturase of *Simmondsia chinensis* is a soluble protein localized in the plastid in its natural host. The codon optimized sequence of the protein was ordered without the predicted signal peptide of the protein which included the first 30 amino acids. Beside these the desaturase ChDes9-1 from *Calanus hyperboreus* (SEQ ID NO: 28) accession number AHL21604.1) is tested and which has a reported substrate range of C20-C26. Yeast codon optimized versions of these genes were ordered and cloned via Gibson cloning (Gibson et al., 2009) in pSP-GM2 under constitutive active promoter and terminator control in combination with respective reductase/wax ester synthase/elongase combinations as described in Example 1 and Example 2.

In particular, the desaturase genes were tested in combination with the reductase/wax ester synthase/elongase genes as described in Example 1 and Example 2. For this, the genes were amplified with primers introducing a kozak sequence in front of the ATG start codon and different overhangs at the 5' and 3' end of each gene which are compatible with a constitutively active promoter and terminator, respectively. The genes were assembled with the pYX212 plasmid backbone as described in Example 2. The resulting plasmids are pYX212::Ole1 (Plasmid ID 26), pYX212::SciFAD (Plasmid ID 63) and pYX212::ChDes9-1 (Plasmid ID 64).

The yeast strains, as described in Example 2, were then transformed and analyzed using the same conditions. To analyze the fatty acid spectrum in strains expressing different desaturases or a desaturase in combination with a KCS and a reductase, fatty acid methyl esters (FAMEs) were prepared and analyzed according to Khoomrung et al., 2012. The analytical standards for FAME were purchased from Sigma Aldrich (Sigma Aldrich, Stockholm, Sweden). They were dissolved in hexane and analyzed using the same protocol and column as the samples.

To analyze the fatty alcohol and wax ester spectrum in strains expressing different reductases in combination with a KCS, a reductase and a wax ester synthase, extraction of lipids was carried out as described in Example 2.

Figure 18:
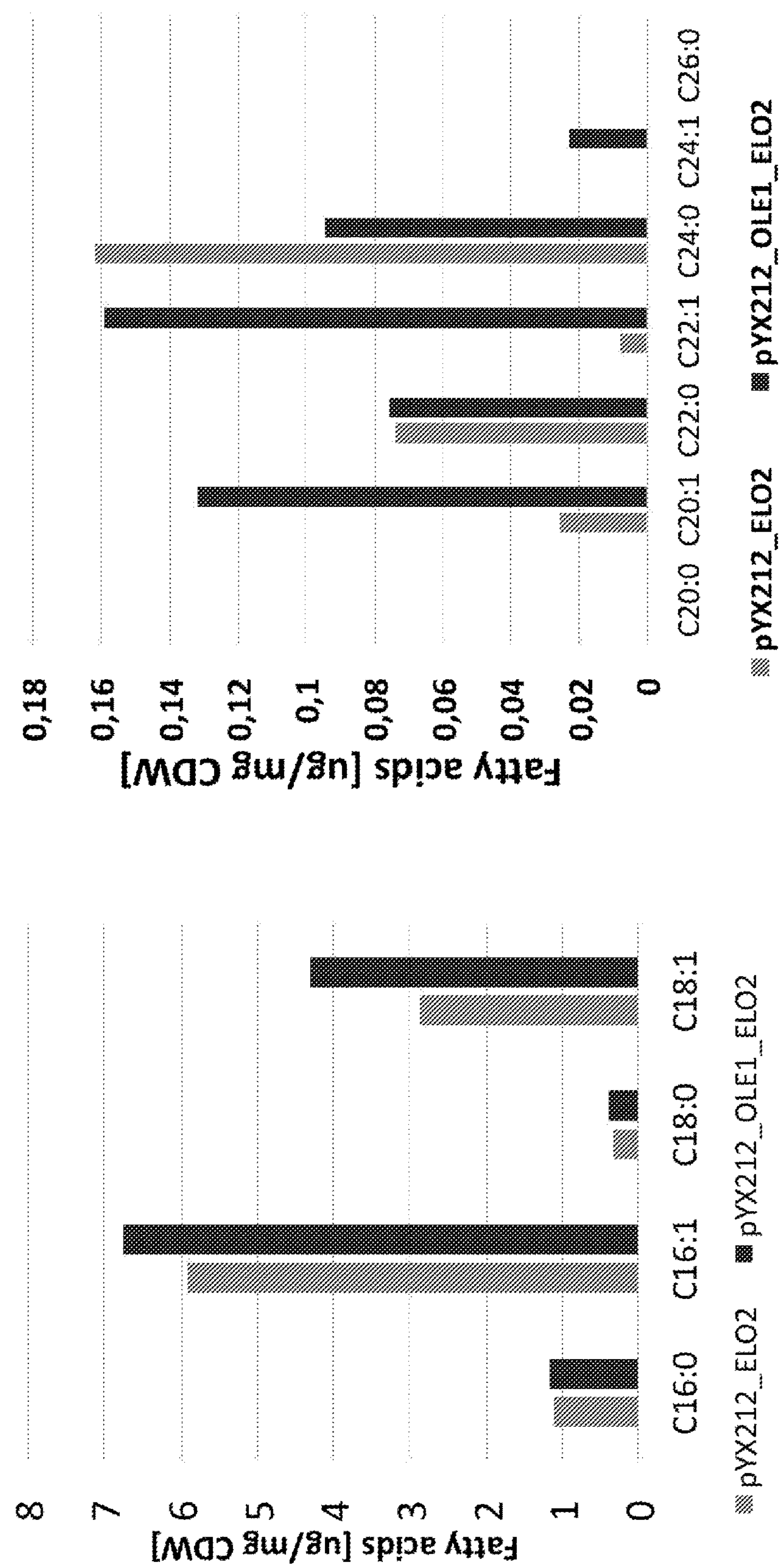
FIG. 18. Shows overexpression of *S. cerevisiae* gene OLE1 in combination with ELO2 and its effect on increasing mono unsaturated fatty acid levels. As a background strain CEN.PK 113-5D Δelo3 ACC1** was used.

Exemplary data of overexpressing the intrinsic desaturase Ole1p and its effect on increasing the mono unsaturated fatty acid content is shown in FIG. 18.

We showed the formation of increased amount of unsaturated fatty acids when overexpressing OLE1 gene in *S. cerevisiae*. In combination with overexpression of the elongase gene ELO2 saturated long chain and very long chain fatty acid levels were shown to decrease and unsaturated fatty acid levels of C16:1, C18:1, C20:1, C22:1 increased (FIG. 18).

Example 4

Increase of Fatty Acyl-CoA Molecules by Overexpression of the Fatty Acyl-CoA Synthase (FAA1)

This example comprises the endogenous overexpression of the fatty acyl-CoA synthase (Faa1) from *S. cerevisiae* (accession number NP_014962.3), catalyzing the formation of fatty acyl-CoA based on free fatty acids. The overexpression of this gene is done by amplification from yeast genomic DNA with respective 30 bp overhangs according to Gibson cloning method followed by cloning on pSP-GM2 under strong constitutive promoter and terminator control, combined with the particular reductase/wax ester synthase/ elongase combinations described in Example 1 and Example 2. Yeast strains as described in Example 1 are transformed and analyzed under the same conditions.

Example 5

Figure 6:
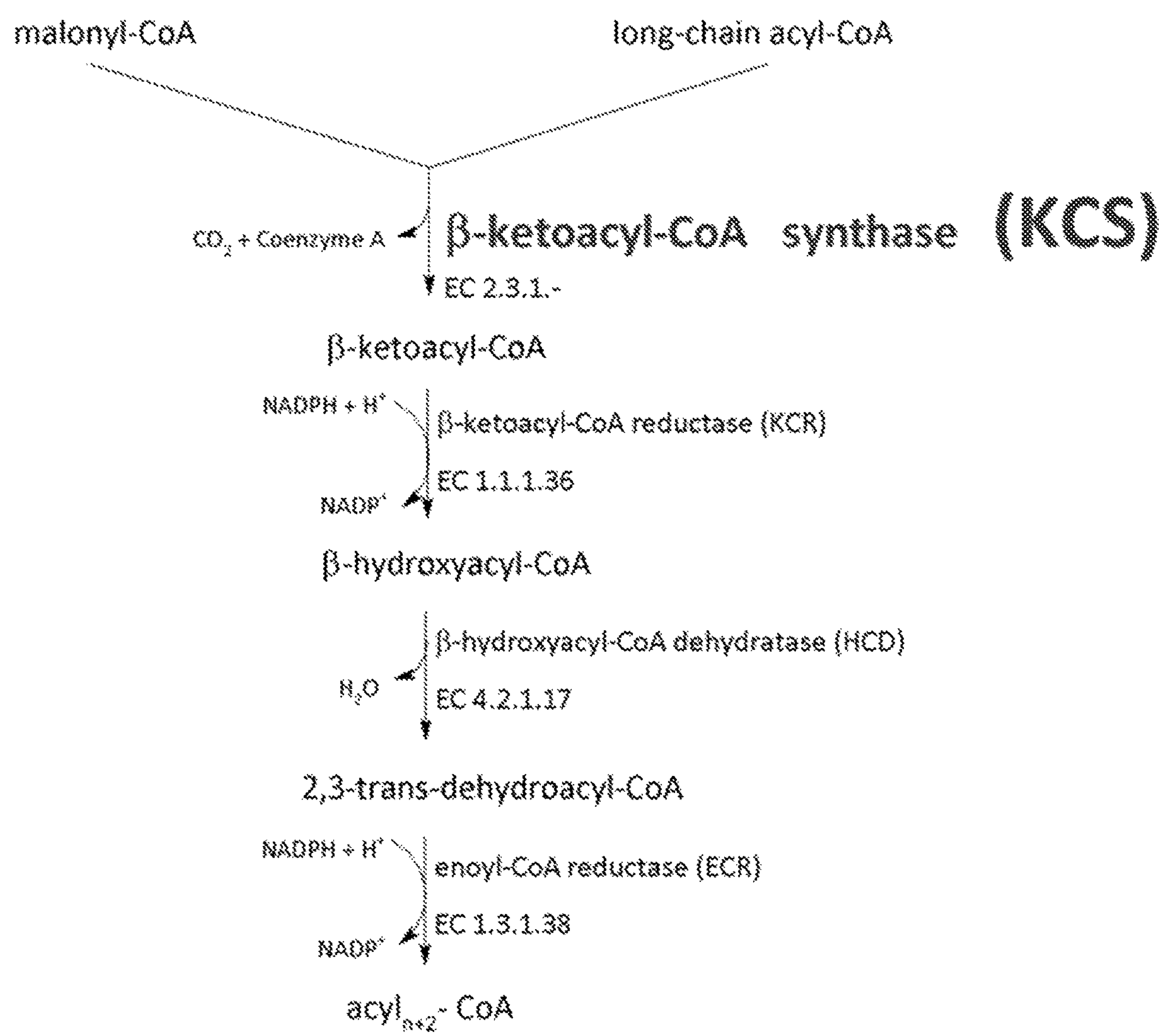
FIG. 6. Shows elongation of fatty acids up to C26 in the endoplasmic reticulum. The first step of the elongation process is catalyzed by a β-ketoacyl-CoA synthase (KCS).

Overexpression of Endogenous Yeast Genes YBR159, PHS1 and TSC13 to Increase VLCFA Synthesis The yeast VLCFA elongation system consists of 4 enzymes: 3-keto acyl-CoA synthase (Elo1, Elo2, Elo3), 3-keto acyl-CoA reductase (YBR159Wp), 3-hydroxy acyl-CoA dehydratase (Phs1) and an enoyl-CoA reductase (Tsc13), see FIG. 6 (Denic and Weissman, 2007). These enzymes are overexpressed in yeast by exchanging their native promoter with a constitutively active strong TEF1 promoter. This is done by using the CRISPR/Cas9 system as previously described (Jakočiūnas et al., 2015).

Example 6

Enhancing VLCFA Synthesis by Coexpressing Plant Derived Elongase Systems

As described in Example 2 elongase enzymes from plants like *Simmondsia chinensis* (accession number AAC49186.1) or the FAE1 from *Arabidopsis thaliana* (accession number AAA70154.1) are overexpressed in *S. cerevisiae*. To improve the elongation cycle for these plant derived enzymes the particular plant derived reductases and dehydrates are co-expressed in *S. cerevisiae*. Here it is exemplified for *Arabidopsis thaliana* genes CER10 (reductase1, Tsc13 ortholog), KCR1 (reductase2, YBR159Wp ortholog), PAS2 (dyhydratase, P1 ortholog) which were codon-optimized for yeast expression and integrated into the genome under constitutively active promoter and terminator control as described elsewhere (Jensen et al., 2014).

Example 7

Expressing *Arabidopsis thaliana* Genes LACS1, LACS2 and LACS3 in Yeast to Improve VLCFA Activation to CoA Form The genetic sequences coding for the long-chain acyl-CoA synthetases LACS1, LACS2 and LACS3 derived from *Arabidopsis thaliana* are codon optimized and heterologously expressed in yeast (Pulsifer et al., 2012). These facilitate an activation of long chain fatty acids with CoA which is important for follow up reactions catalyzed by reductases and wax ester synthases. Yeast codon optimized versions of these genes were ordered and cloned via Gibson cloning in pSP-GM2 under constitutive active promoter and terminator control in combination with respective reductase/wax ester synthase/elongase combinations and tested in particular strains as described in Example 1 and Example 2.

Example 8

Enhancement of VLCFA Synthesis by Evolving the Endogenous Yeast Fatty Acid Synthase For this screening system an appropriate plasmid system is constructed. It is based on the vector backbone of p413TEF (Mumberg et al., 1995) carrying a combination of TEF1 promoter and CYC1 terminator. $P_{KEX2}$ is amplified from the genome with 30 bp overhang and is cloned via Gibson cloning into p413TEF replacing the TEF1 promoter and creating p413KEX2.

For library generation the FAS1 or FAS2 gene from *S. cerevisiae* is mutated by methods of error prone PCR through amplification from *S. cerevisiae* genomic DNA. The primers include 30 bp overhangs respective to the plasmid backbone of p413KEX2 facilitating cloning in between $P_{KEX2}$ and $T_{CYC1}$. The amplified gene library is cloned via Gibson cloning into p413KEX2 creating the libraries lib-Fas1-p413KEX2 or lib-Fas2-p413KEX2 respectively.

An appropriate strain for screening the functionality of the mutated FAS1/FAS2 for VLCFA production is created by gene knockout of ELO2, ELO3 in the yeast genome as described elsewhere (Paul et al., 2006). The method is applied on the strain CEN.PK113-11C (MATa MAL2-8$^c$ SUC2 his3Δ1 ura 3-52). A plasmid, which carries the wildtype ELO3 gene under TEF1 promoter control is constructed (p416TEF-ELO3). This is done by Gibson cloning, amplifying the ELO3 gene from yeast genomic DNA with 30 bp overhang primers for cloning it in between the TEF1 promoter and CYC1 terminator located on p416TEF (Mumberg et al., 1995). This plasmid is used to complement the otherwise lethal phenotype of CEN.PK113-11C, Elo2Δ, Elo3A as described elsewhere (Paul et al., 2006). The library lib-Fas1-p413KEX2 or lib-Fas2-p413KEX2 is transformed into this strain for HIS+prototrophic transformants are selected. These transformants are screened for growth on 5-fluoro-orotic acid (FOA) for negative selection for plasmid loss of p416TEF-ELO3. Only cells carrying a functional FAS system, which is capable of producing VLCFA, compensate for the loss of the elongase system and show growth under these conditions. The screening is done at different temperatures (26° C., 30° C., 33° C., 37° C.) as different cellular needs for VLCFA with different chain length are expected.

The same approach is used on a small library where the linker region between MPT and ACP domain in the Fas2 protein of *S. cerevisiae* is specifically varied. This is done e.g., by error prone PCR or changing linker length in the genome using the CRISPR/Cas9 system as described elsewhere (Jakočiūnas et al., 2015).

Final candidates are subcloned via Gibson cloning into pSP-GM2::AmFAR under TEF1 promoter control and tested in strains JV03 (MATa MAL2-8$^c$ SUC2 ura3-52 are1Δ dga1Δ are2Δ lro1Δ pox1A) and PWY12 (fas1Δ::HIS3fas2Δ::LEU2) (Wenz et al., 2001).

Example 9

Enhancement of VLCFA Synthesis by Heterologous Expression of Fatty Acid Synthases Derived from Mycobacteria Fatty acid synthase gene sequences derived from bacterial hosts like *Mycobacterium vaccae, Mycobacterium diernhoferi* 41002, *Mycobacterium neoaurum* and *Mycobacterium parafortuitum* PA-1, *Mycobacterium intracellulare* were codon optimized for expression in *S. cerevisiae*. For example, the codon-optimized sequences for the gene 3-oxoacyl-ACP synthase [*Mycobacterium vaccae*] (WP_003928293) (SEQ ID NO: 39), was obtained from GenScript (860 Centennial Ave., Piscataway, N.J. 08854, U.S.), containing 30 bp overhang on each side for subcloning via Gibson cloning between the TEF1 promoter and CYC1 terminator into pSP-GM2 and pSP-GM2::AmFAR (Example 1) creating pSP-GM2::MvFas and pSP-GM2::AmFAR::MvFas. Besides, a gene coding for an acyl-carrier protein synthase (AcpS) derived from *Mycobacterium vaccae* (WP_040539704.1) was codon optimized for expression in *S. cerevisiae*, obtained from GenScript and subcloned with previously amplified pTDH3 promoter and tFBA1 terminator sequence via Gibson clone assembly into pSP-GM2::MvFas and pSP-GM2::AmFAR::MvFas. Each plasmid was transformed into the following yeast strains: CEN.PK 113-5D (MATaMAL2-8$^c$ SUC2 ura3-52), JV03 (MATaMAL2-8$^c$ SUC2 ura3-52 are1Δ dga1Δ are2A lro1Δ pox1A) and PWY12 (fas1Δ::HIS3 fas2Δ::LEU2) (Wenz et al., 2001). These plasmids are also transformed into a yeast strain having the FAS1 gene under the control of the $P_{HXT1}$ promoter (CEN.PK 113-5D, $P_{HXT1}$-FAS1). It exhibits a reduced expression of the yeast FAS1 gene under glucose limiting conditions. In this strain, the functionality and selectivity for the production of VLCFA with bacterial FAS systems is tested under glucose limiting conditions, to avoid the competition for Malonyl-CoA supply with the endogenous yeast FAS system. Fatty acid profiles and fatty alcohol profiles are determined as described in Example 1.

In parallel the codon-optimized sequences for the gene 3-oxoacyl-ACP synthase [*Mycobacterium vaccae*] (WP_003928293) (SEQ ID NO: 39) containing 30 bp overhang on each side were subcloned via Gibson cloning between the GPD1 promoter and CYC1 terminator into p415GPD (SEQ ID NO: 41) creating p415GPD::MvFas using primers SEQ ID NO: 173-SEQ ID NO: 178. Besides, a gene coding for an acyl-carrier protein synthase (AcpS) derived from *Mycobacterium vaccae* (WP_040539704.1) (SEQ ID NO: 40) was codon optimized for expression in *S. cerevisiae*, obtained from GenScript and subcloned with previously amplified pTDH3 promoter and tFBA1 terminator sequence (SEQ ID NO: 179-SEQ ID NO: 182) via Gibson clone assembly into p415GPD:MvFas to generate p415 GPD:MvFas::Acps.

The Gibson assembly method (Gibson et al., 2009) was used to construct the plasmids p415GPD:MvFas; p415GPD: MvFas::Acps and pSPGM2::At5FAR.

All plasmids were transformed into *Escherichia coli* DH5α by chemical transformation.

The colonies carrying the desired plasmids were verified by colony PCR.

After isolation of the plasmids and verification of each gene by sequencing (Eurofins Genomics, Ebersberg, Germany). The plasmid p415GPD::MvFas::Acps was transformed into the following yeast strain TDY7005 (Mata lys2 ura3-52 trp1 Δ leu2 Δ elo2::KAN elo3::TRP1/pRS316-ELO3) (Paul et al., 2006) (Example 8) and LEU2 prototrophic transformants were selected. The transformants were screened for growth on FOA and correct clones were confirmed by sequence analysis.

Eight independent clones were isolated and each clone was grown in precultures of 5 mL in SD-leu+2% glucose medium for 2 days, inoculated to fresh SD-leu+2% glucose medium at an $OD_{600}$ of 0.05-0.1 in 25 ml in 250 ml shake flasks. Extraction of lipids was carried out as described before with the exception that the final sample was dissolved in hexane (instead of chloroform/methanol) (Khoomrung et al., 2013). Subsequently, 2 μl injections were analyzed using a gas chromatograph (Focus GC, ThermoScientific) mass spectrometer (DSQII ThermoScientific) equipped with a ZB-5MS Guardian (L=30 m, ID 0.25 mm, df=0.25 μm, Phenomenex) column. The inlet temperature was set to 280° C., the helium (carrier) gas flow to 1 ml/min splitless. The GC program for FAME quantification was as follows: initial temperature of 45° C. hold for 2.5 min; then ramp to 220° C. at a rate of 20° C. per min and hold for 2 min; ramp to 300° C. at a rate of 20° C. per min and hold for 5 min. The temperature of the inlet and detector were kept at 280° C. and 300° C., respectively.

Figure 19:
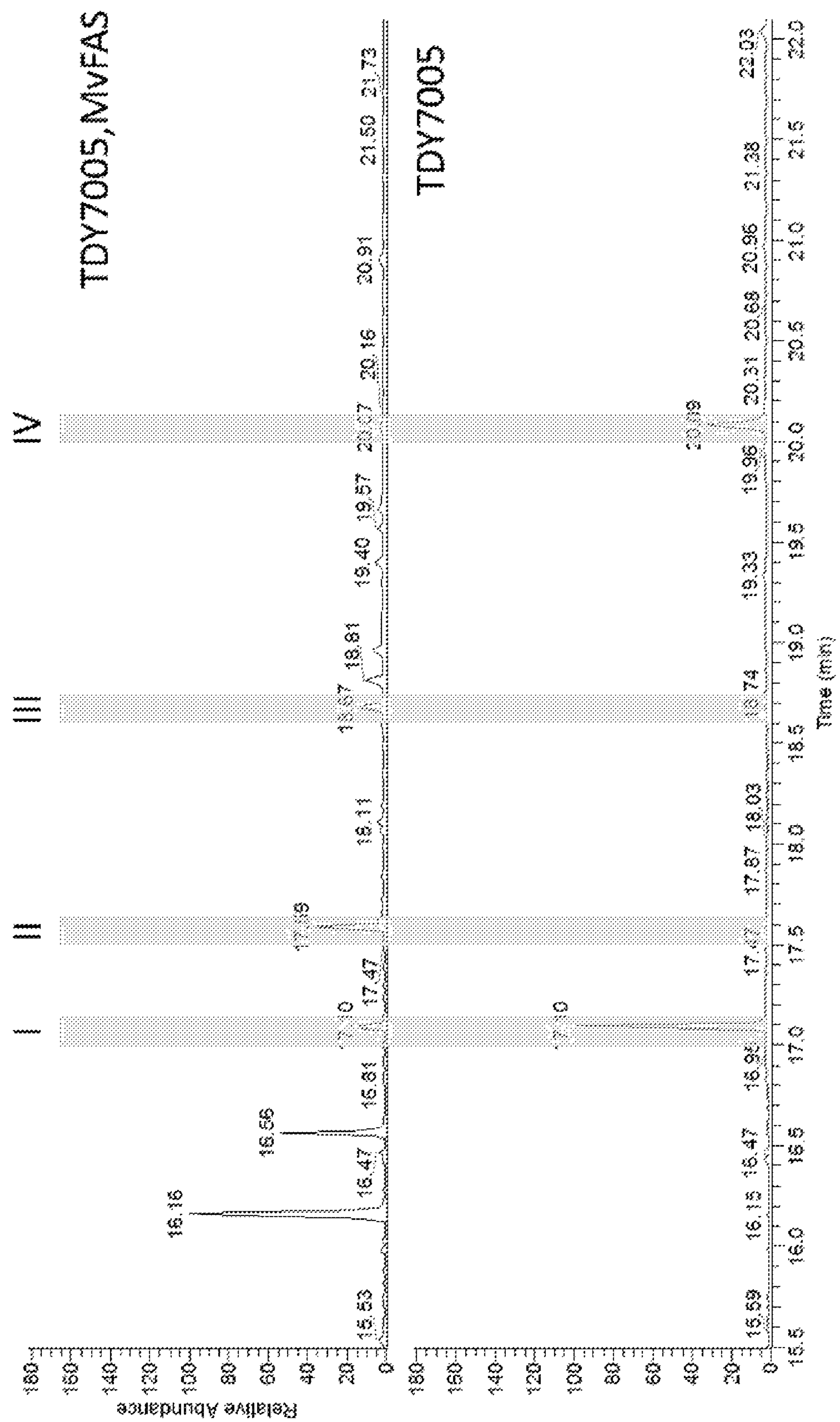
FIG. 19. Shows VLC fatty acid CoA biosynthesis. Gas chromatograms of shake flask cultures incubated for 72 hours in SD-LEU+2% glucose medium. The lines represent *S. cerevisiae* TDY7005 strains that express p415GPD::MvFAS::Acps. The *S. cerevisiae* TDY7005 control strain is also shown. The peaks highlighted by the grey bars labeled with I-X were compared to NIST library standards and predicted to be: I, Heneicosylic acid (internal standard, C21:0); II, Behenic acid (C22:0); III, Tetracosanoic acid (C24:0) and IV, Hexacosanoic Acid (C26:0).
Figure 20:
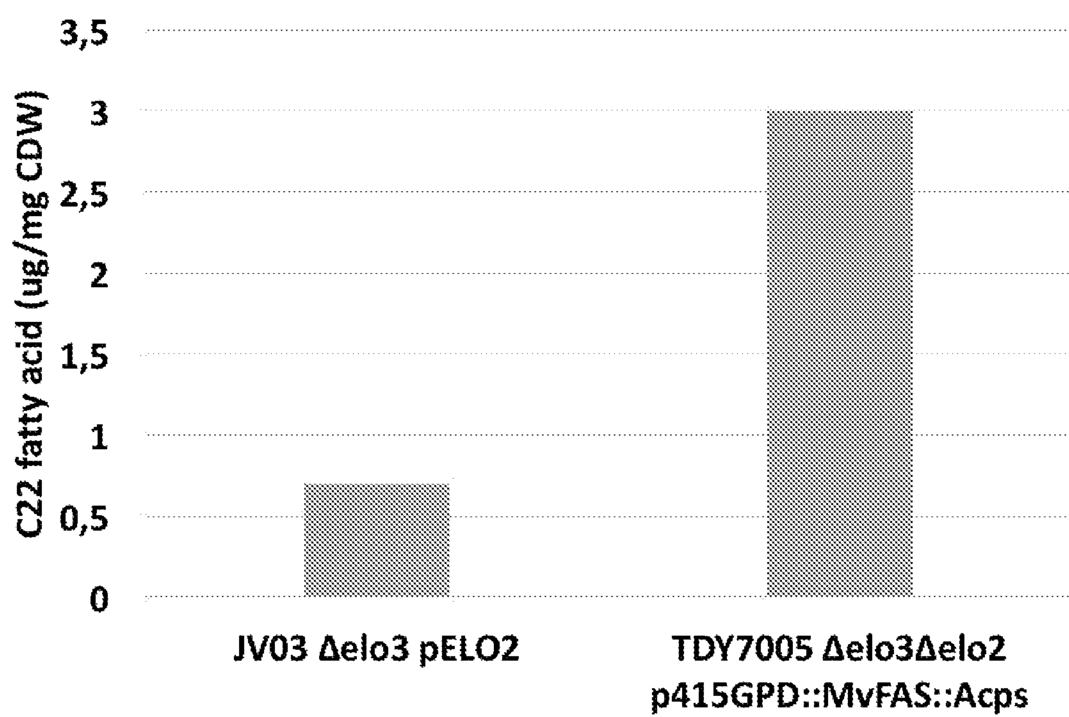
FIG. 20. Shows C22 fatty acid production from two different systems. Comparing the production in JV03 Δelo3 pELO2 and TDY7005 Δelo3Δelo2 p415GPD::MvFAS::Acps.

Gas chromatogram spectra and quantitative data of one independent clone of a control strain (TDY7005) and producing strains (YT01) are shown in FIGS. 19 and 20.

In this example we prove the functional expression of a FAS system derived from Mycobacteria in the yeast *S. cerevisiae* enabling for the specific and high level production of C22 fatty acids up to 3 ug/mg CDW.

Example 10

Enhancement of VLCFA Synthesis by Evolving Yeast Fatty Acid Synthase Through Creation of Chimeric Enzymes (Yeast Origin and Mycobacteria Origin)

Based on the codon optimized gene sequences of bacterial FAS systems derived from mycobacteria as described in Example 9 parts from these are fused to yeast derived FAS1/FAS2 sequences according to the method of DNA shuffling described elsewhere (Crameri et al., 1998). The vector and screening systems used are same to the approach described in Example 8. A library is created through subcloning of chimeras using Gibson cloning into p413KEX2. After the screening, as performed in Example 8, the final candidates are subcloned via Gibson cloning into pSPGM2::AmFAR under TEF1 promoter control and tested in strains JV03 (MATa MAL2-8$^c$ SUC2 ura3-52 are1Δ dga1Δ are2Δ lro1Δ pox1Δ) and PWY12 (fas1Δ::HIS3 fas2Δ:: LEU2).

Example 11

Production of Long Chain Fatty Alcohols and Wax Esters in *Yarrowia lipolytica*

Expression of recombinant genes in accordance with the present invention in *Yarrowia lipolytica* can be accomplished by modification of relevant genetic engineering methods, as discussed herein. *Yarrowia lipolytica* strain PO1f (MATA ura3-302 leu2-270 xpr2-322 axp2-deltaNU49 XPR2::SUC2), a leucine and uracil auxotroph obtained from ATCC (ATCC MYA-2613) is used as a background strain. Genes to be expressed in the strain can be assembled and integrated as previously described (Gao et al., 2014). This method involves the amplification of the genes to be expressed, promoters, terminators, markers, and integration sites. The fragments are then assembled using overlap extension PCR (OE-PCR) into the individual gene expression cassettes and the DNA is then transformed into yeast strains using the Zymogen Frozen EZ yeast transformation kit II (Zymo Research Corporation) as previously reported (Blazeck et al., 2011). Strains are selected on the appropriate dropout media (SD-ura, SD-leu, or SD-ura-leu).

For example, to integrate an elongase (KCS from *Simmondsia chinesis*, accession number: AAC49186.1; codon-optimized for yeast; see Example 2) and reductase (FAR from *Apis mellifera*; accession number: ADJ56408; codon-optimized for yeast; see Example 1) into *Y. lipolytica*, the integration sites (LEU2 locus) promoters (EXP1p and TEF1p), terminators (lip2t and xpr2t), genes (ELO and FAR) and marker gene (URA3) are amplified using primers AKp1-18. The fragments are assembled by OE-PCR into an expression cassettes and transformed into strain PO1f as described above, resulting in strain Y1AK1 (ELO FAR URA3 leu2), capable of producing long-chain alcohols. To create a strain capable of producing wax esters, the gene AtWS (wax ester synthase from *Arabidopsis thaliana*; accession number NP_568547; codon-optimized for yeast) is introduced into strain YIAK1. This is done by amplifying the GPDp promoter, lipltterminator, WES, integration site (URA3 locus) and LEU2 using primers AKp19-30. The resulting fragments are assembled into expression cassettes and transformed into strain YIAK1 to yield strain Y1AK2 (ELO FAR WES URA3 LEU2).

Alternatively, multi-copy integration can be achieved by targeting the genes into rDNA loci as described elsewhere (Gao et al., 2014).

Expression of recombinant genes in accordance with the present invention in *Yarrowia lipolytica* can be accomplished by modification of relevant genetic engineering methods, as discussed herein. In a parallel approach *Y. lipolytica* strain JMY195 (Pol1d MATa, ura3-302, leu2-270, xpr2-322) (Ledall et al., 1994), a leucine and uracil auxotroph, obtained from BIMLip (INRA, UMR1319, MICALIS, Domaine de Vilvert, F-78352 Jouy-en-Josas, France), was used as a background strain. The heterologous genes, coding for various FARs and WSs, which were described in Examples 1 and 2 were synthesized with a codon composition optimized for *Y. lipolytica* (SEQ ID NO: 29-SEQ ID NO: 36). The genes YALI0B20196g (AS 54% identity, 90% query cover to Elo2 of *S. cerevisiae*) (SEQ ID NO: 29) and YALI0C05951p (SEQ ID NO: 30), annotated as a Δ9-desaturase, were amplified with specific, uracil containing primers (SEQ ID NO: 145-SEQ ID NO: 148) based on g-DNA from the *Y. lipolytica* wildtype strain W29 (ATCC® 20460™) (Tharaud et al., 1992). The promoters pTEF, pEXP, pGPAT, pGPD, pPOX2 and pPOT1 as well as the terminator XPR2t were also amplified based on *Y. lipolytica* wildtype g-DNA, using specific primers containing uracil (SEQ ID NO: 149-SEQ ID NO: 150).

Based on the two plasmids JMP62::pTEF::URAex (Plasmid ID 65) and JMP62::pTEF::LEUex (Plasmid ID 66) (Beopoulos et al., 2014), two new plasmids were constructed by circular polymerase extension cloning (CPEC) (Quan et al., 2009; Quan et al., 2011) under use of specific primers (SEQ ID NO: 149-SEQ ID NO: 156), resulting in the plasmids JMP62::URAex(USER) (Plasmid ID 67) and JMP62::LEUex (USER) (Plasmid ID 68). Those plasmids contain a USER site to make them available for USER cloning (Jensen et al., 2014).

The genes coding for various FARs and WSs which were described in Examples 1 and 2 were synthesized with a codon composition optimized for *Y. lipolytica* (SEQ ID NO: 31-SEQ ID NO: 38) and amplified with specific, uracil containing primers (SEQ ID NO: 157-SEQ ID NO: 172).

The plasmids JMP62::URAex(USER) and JMP62::LEUex(USER) were cut with the enzymes Nb.BsmI and AsiSI. The genes of interest were treated with the USER enzyme mix (NEB) before cloning into the cut plasmid backbones. The resulting plasmids were: JMP62::URAex::AmFAR, JMP62::URA3ex::MaFAldhR, JMP62::URA3ex::SciFAR, JMP62::URAex::TaFAR, JMP62::URAex::AmFAR::AbWS, JMP62::URAex::AmFAR::AtWS JMP62::URAex::AmFAR::EgWS, JMP62::URAex::AmFAR::SciWS, JMP62::URAex::MaFAldhR::AbWS, JMP62::URAex::MaFAldhR::AtWS, JMP62::URAex::MaFAldhR::EgWS, JMP62::URAex::MaFAldhR::SciWS, JMP62::URAex::SciFAR::AbWS, JMP62::URAex::SciFAR::AtWS, JMP62::URAex::SciFAR::EgWS, JMP62::URAex::SciFAR::SciWS, JMP62::URAex::TaFAR::AbWS, JMP62::URAex::TaFAR::AtWS, JMP62::URAex::SciFAR::EgWS, JMP62::URAex::TaFAR::SciWS, JMP62::LEUex::YlElo2 JMP62::LEUex::YlOle1 and JMP62::LEUex::YlOle1::YlElo2 (Plasmid ID 69-91).

All USER plasmids were digested with NotI, gel purified and transformed into *Y. lipolytica* JMY195 by chemical transformation, using the one-step transformation protocol by Chen et al., 1997.

Three independent clones were isolated for each of the producer and control strains by streak purification onto fresh SD-Ura/SD-Leu/SD-URA-LEU 2% glucose plates. Each clone was grown in precultures of 5 mL glucose minimal medium (with added Uracil or Leucin where necessary) (Verduyn et al., 1992) for 2 days, inoculated to fresh glucose minimal medium (with added Uracil or Leucin where necessary) at an $OD_{600}$ of 0.05-0.1 in 25 ml in 250 ml shake flasks. The cultures were incubated at 30° C. and 200 rpm. After 48 h, cell pellets were collected by centrifugation for 5 minutes at 1000 rcf and washed twice with 5 ml phosphate buffer (10 mM $KH_2PO_4$, pH 7.5).

To analyze the fatty acid spectrum in strains having integrated the JMP62::LEUex::YlElo2, JMP62::LEUex::YlOle1 or JMP62::LEUex::YlOle1::YlElo2 fragment, fatty acid methyl esters (FAMEs) were prepared and analyzed according to Khoomrung et al., 2012.

The analysis of the fatty alcohols and wax esters in the remaining strains, which have integrated one of the linearized plasmids with the ID 69-88, was carried out as described in Example 2.

Figure 25:
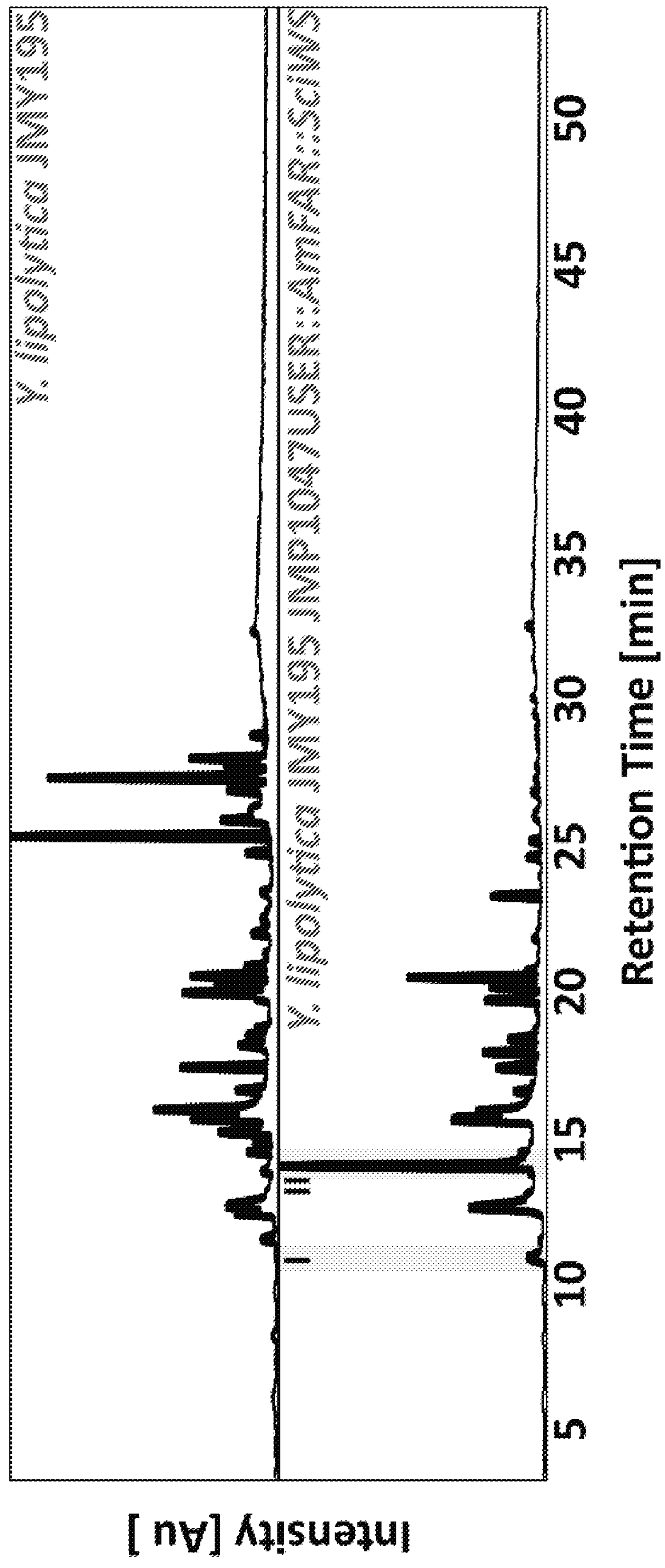
FIG. 25. Shows alcohol biosynthesis in *Y. lipolytica*. Gas chromatograms of shake flask cultures incubated for 48 hours in SD-URA-LEU+2% glucose medium. The upper graph shows the *Y. lipolytica* JMY195 background strain, the lower strain shows the same strain expressing the *Apis mellifera* (Am) fatty acyl-CoA reductase (FAR) in combination with the wax synthase (WS) derived from *Simmondsia chinensis* (Sc). The peaks highlighted by the grey bars labeled with I-II were compared to NIST library standards and predicted to be: I, hexadecanol (C16:0) and II, octadecanol (C18:1).

Exemplary gas chromatogram spectra of one independent clone of a control strain (JMY195 JMP62::URAex(USER)) and producing strain JMY195 JMP1047USER::AmFAR::SciWS are shown in FIG. 25.

Example 12

Production of Long Chain Fatty Alcohols in *Yarrowia lipolytica* Combined with Gene Deletion Flux towards the products of interest can be increased by removing β-oxidation capacity, which can be accomplished by deletion of the gene MFE1. In addition, deletion of the PEX10 gene, which is involved in peroxisomal biogenesis, was done. Therefore, deletion of these genes is combined with the above modifications. To create a strain deleted in PEX10, the ELO-FAR cassettes are targeted to the PEX10 locus instead of the LEU2 locus. These constructs are transformed into strain PO1f, resulting in strain Y1AK3 (Δpex10 ELO FAR URA3 leu2).

Alternatively, to create a strain containing a deletion in the MFE1 gene, the ELO-FAR cassettes are targeted to the MFE0 locus instead of the LEU2 locus. These constructs are transformed into strain PO1f resulting in strain Y1AK4 (Δmfe1 ELO FAR URA3 leu2).

To obtain a strain containing deletion in both genes LEU2 is targeted into the MFE1 locus of strain Y1AK3, resulting in strain Y1AK5 (Δpex10 Δmfe1 ELO FAR URA3 LEU2).

To obtain a wax-ester-producing strain with one of the above deletions, WES is amplified and fused into a LEU2-based expression cassette as described above and targeted to the URA3 locus of strain Y1AK3 or Y1AK4, resulting in strains Y1AK6 (Δpex10 ELO FAR WES URA3 LEU2) and Y1AK7 (Δmfe1 ELO FAR WES URA3 LEU2), respectively. To obtain a wax-ester-producing strain with both deletions, WES is amplified and fused into a LEU2-based expression cassette as described above, and targeted to the MFE1 locus of strain Y1AK3, resulting in strain Y1AK8 (Δpex10 Δmfe1 ELO FAR WES URA3 LEU2).

Flux towards the products of interest can be increased by deletion of genes which consume fatty acids, the precursors for fatty acyl-CoA and fatty alcohol synthesis. Examples of those genes are lro1, dga1 and dga2 whose gene products are responsible for triacylglycerol (TAG) formation in *Y. lipolytica*. The genes pox1-6 are encoding enzymes which are involved in the β-oxidation of fatty acids, thereby reducing the level of free fatty acids. In addition, *Y.*

*lipolytica* possesses an enzyme able to produce diunsaturated fatty acids. Since our products of interest are derived from monounsatured fatty acids, the gene fad2, encoding the Δ-12 desaturase in this organism, is also a target of deletion.

A strain carrying deletions in the before mentioned genes, JMY2159 (Po1d MATA ura3-302 leu2-270 xpr2-322 pox1-6Δdga1Δlro1Δdga2Δfad2Δ) (Beopoulos et al., 2014) was transformed with the plasmids described in Example 11.

To analyze the fatty acid spectrum in strains having integrated the JMP62::LEUex::YlElo2, JMP62::LEUex::YlOle1 or JMP62::LEUex::YlOle1::YlElo2 fragment, fatty acid methyl esters (FAMEs) were prepared and analyzed according to Khoomrung et al., 2012. The analysis of the fatty alcohols and wax esters in the remaining strains, which have integrated one of the linearized plasmids with the ID 69-88, was carried out as described in Example 2.

Example 13

Production of Erucic Acid in *Saccharomyces cerevisiae*

This example demonstrates the production of increased levels of erucic acid (C22:1ω9) in *S. cerevisiae*. Erucic acid is derived from elongation of oleic acid (C18:1). To increase the level of oleic acid, mutations S659A and S1157A (Shi et al., 2014) are introduced into the ACC1 gene using the CRISPR/Cas9 system. In addition, OLE1 encoding fatty acid desaturase was overexpressed. Alternatively, ChDes9-2 was codon-optimised for *S. cerevisiae* and inserted into the yeast genome to replace OLE1 using the CRISPR/Cas system. This is combined with expression of a plant FAE1-like 3-ketoacyl-CoA synthase (KAS) from *Simmondsia chinensis* (accession number AAC49186.1), *Arabidopsis thaliana* (AAA70154.1), *Crambe abyssinica* (AY793549) or *Brassica napus* (AF490459). OLE1 and the respective KAS gene (codon optimized for expression in yeast) are cloned into plasmid pSP-GM2 using Gibson cloning. All listed modifications were implemented in strain CEN.PK 113-5D (ura3-52), JV03 (ura3-52 are1Δ dga1Δ are2Δ lro1Δ pox1Δ), CEN.PK 113-5D elo3Δ, and JV03 elo3Δ.

This example demonstrates the production of increased levels of erucic acid (C22:1ω9) in *S. cerevisiae*. Erucic acid is derived from elongation of oleic acid (C18:1). In particular the gene coding for the double mutated ACC1p ** of *S. cerevisiae* was integrated into the genome of *S. cerevisiae* like described in Example 2.

In addition, OLE1, encoding the *S. cerevisiae* fatty acid desaturase, was overexpressed as described in Examples 2 and 3. Alternatively, the heterologous desaturases ChDes9-1 or SciFAD which are described in Examples 2 and 3 were overexpressed in *S. cerevisiae* to increase the amount of very-long chain, monounsaturated fatty acids.

The expression of a desaturase is combined with the expression of a plant 3-ketoacyl-CoA synthase (KCS) from *Simmondsia chinensis, Arabidopsis thaliana, Crambe abyssinica* or *Brassica napus* which are reported to mainly synthesize erucic acid. The construction of the plasmids harboring those genes was performed like described in Examples 2 and 3.

The plasmids were transformed into the strains CEN.PK 113-5D (ura3-52), JV03 (ura3-52 are1Δ dga1Δ are2Δ lro1Δ pox1Δ), CEN.PK 113-5D elo3Δ, CEN.PK 113-5D elo3Δ ACC1 and JV03 elo3Δ ACC1.

Three independent clones were isolated for each of the producer and control strains by streak purification onto fresh SD-Ura 2% glucose plates. Each clone was grown in pre-cultures of 5 mL glucose minimal medium (Verduyn et al., 1992) for 2 days, inoculated to fresh glucose minimal medium at an $OD_{600}$ of 0.05-0.1 in 25 ml in 250 ml shake flasks. The cultures were incubated at 30° C. and 200 rpm. After 48 h, cell pellets were collected by centrifugation for 5 minutes at 1000 rcf and washed twice with 5 ml phosphate buffer (10 mM $KH_2PO_4$, pH 7.5).

To analyze the fatty acid spectrum in strains expressing a KCS gene in combination with a desaturase, fatty acid methyl esters (FAMEs) were prepared and analyzed according to Khoomrung et al., 2012. The analytical standards for FAME were purchased from Sigma Aldrich (Sigma Aldrich, Stockholm, Sweden). They were dissolved in hexane and analyzed using the same protocol and column like for the samples.

Figure 21:
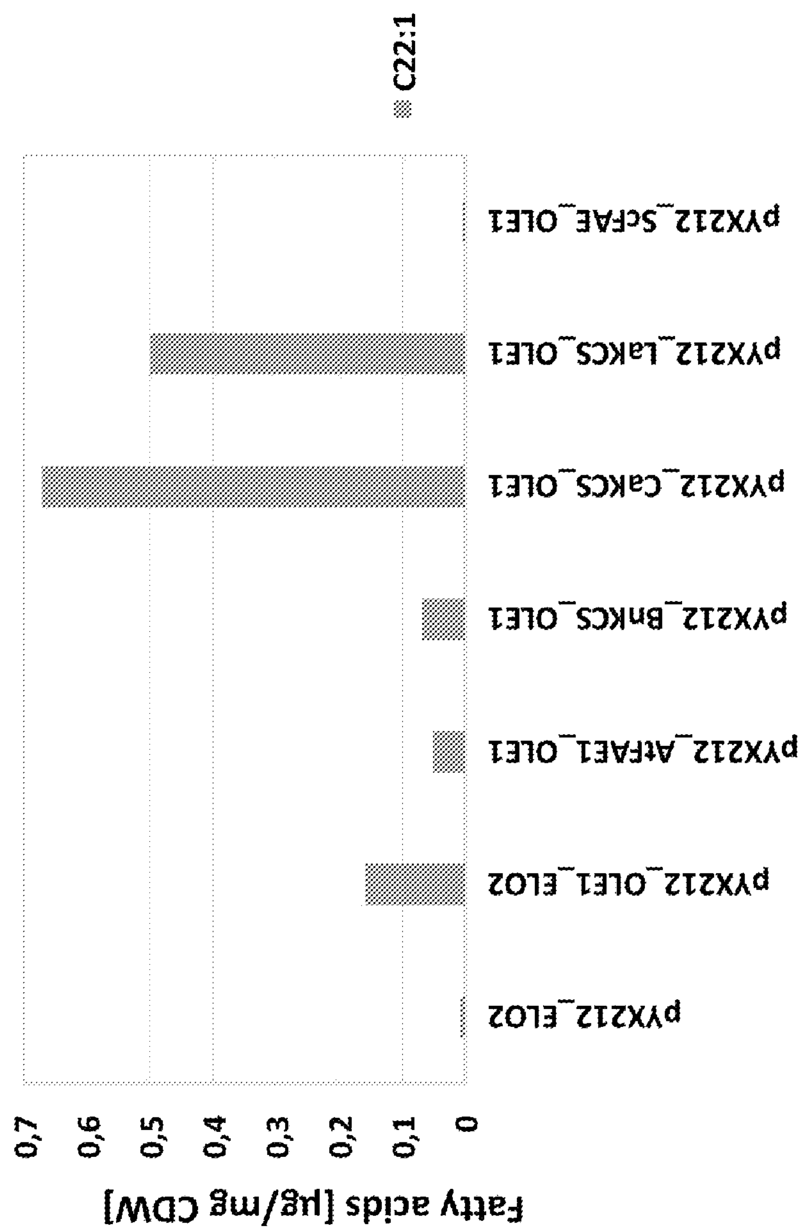
FIG. 21. Shows production of erucic acid in *S. cerevisiae*. Overexpression of *S. cerevisiae* derived desaturase OLE1 and specific elongases in strain background CEN.PK 113-5D Δelo3 ACC1**. Elongases include ELO2 (*S. cerevisiae*), AtFAE1 (*Arabidopsis thaliana*), BnKCS (*Brassica napus*), CaKCS (*Crambe abyssinica*), LaKCS (*Lunaria annua*) and ScFAE (*Simmondsia chinensis*).

Exemplary production data of one independent clone of a control strain (CEN.PK 113-5D elo3Δ ACC1* pYX212) and producing strains are shown in FIG. 21.

Through heterologous expression of KCS elongases in combination with OLE1 overexpression in the particular background strain of CEN.PK 113-5D elo3Δ ACC1* pYX212 we enable yeast for the production of C22:1, erucic acid up to 0.7 ug/mg CDW.

Example 14

Enhancement of Wax Ester Production Through Co-Expression of Specific Transporter Proteins In order to increase the secretion of fatty acid derived products, the promoter of the FAT1 gene encoding a fatty acid transporter is exchanged for the strong constitutive TEF1 promoter using the CRISPR/Cas9 system. To increase the export of wax esters, codon optimized genes encoding *A. thaliana* ABC transporters ABCG11 and ABCG12 are cloned into expression vector pIYC04 (Krivoruchko et al., 2013) under control of the TEF1 and PGK1 promoter, respectively, using Gibson cloning leading to formation of plasmid pTRANS1. Subsequently, codon optimized genes encoding *A. thaliana* lipid transfer proteins LTPG1 and LTPG2 are cloned into pIYC04 in the same way yielding pTRANS2. The LPTG1/LPTG2 expression cassette is then integrated into pTRANS1 to generate pTRANS3. A wax ester and a fatty alcohol producing strain (see Examples 1, 2 and 15) are transformed with plasmids pTRANS1, 2, and 3, respectively, cultivated in shake flasks and intracellular as well as extracellular metabolites are determined.

Example 15

Enhancement of Saturated Fatty Acid Synthesis by Down-regulation of Desaturase OLE1 Gene Expression in *Saccharomyces cerevisiae*

To produce saturated very long chain fatty acids (>C22:0) the endogenous desaturase gene OLE1 from *S. cerevisiae* was downregulated. This is either done by exchanging the natural promoter with a weak yeast promoter like $P_{KEX2}$ or with a glucose concentration dependent promoter like $P_{HXT1}$ using the CRISPR/Cas9 system. These modifications were implemented in strain CEN.PK 113-5D (ura3-52), JV03 (ura3-52 are1Δ dga1Δ are2Δ lro1Δ pox1Δ), CEN.PK 113-5D Elo3Δ, and JV03 Elo3Δ and CEN.PK 113-5D Elo3Δ::TEF-ELO2, JV03 Elo3Δ::TEF-ELO02, respectively.

Example 16

Figure 22:
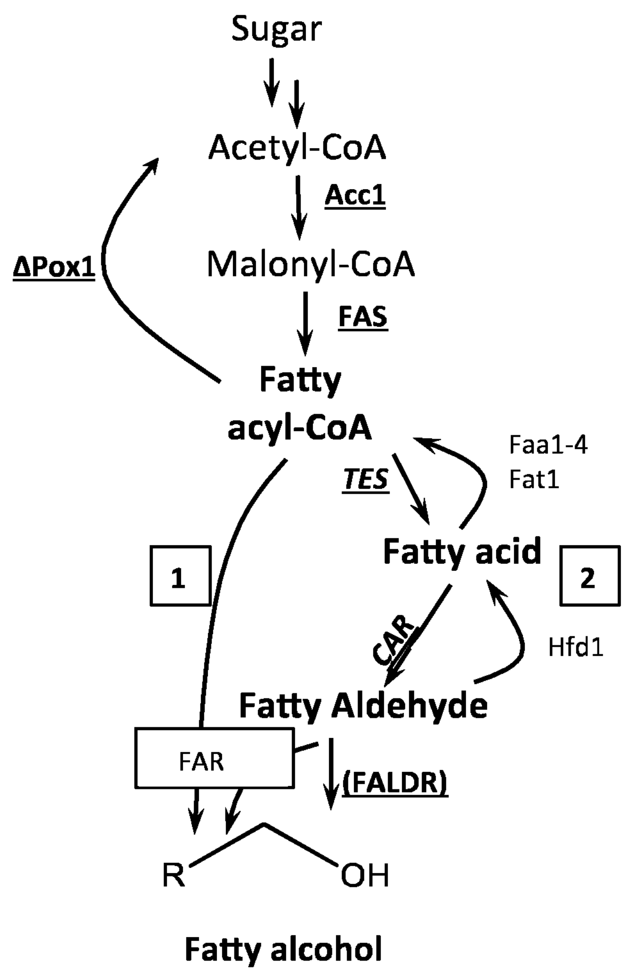
FIG. 22. Shows the metabolic pathways for production of fatty alcohols (i) directly from fatty acyl-CoA or (ii) via free fatty acids and fatty aldehydes.

Very Long Chain Fatty Alcohol Production Derived from Fatty Acyl-CoA Through Free Fatty Acid and Fatty Aldehyde Pathway To evaluate very long chain fatty alcohol production from fatty acyl-CoA through free fatty acids and fatty aldehyde pathway in *S. cerevisiae* (FIG. 22). The following pathways were constructed in *S. cerevisiae* YJZ01 (MATa MAL2-8$^c$ SUC2 his3Δ1 ura3-52 hfd1Δ) (Buijs et al., 2015). A FAR from *Marinobacter aquaeolei* (Willis et al., 2011) was expressed for fatty alcohol production from fatty acyl-CoA. A fatty acid reductase MmCAR from *Mycobacterium marinum* (Akhtar et al., 2013) and the corresponding co-factor phosphopantetheinyl transferase NpgA from *Aspergillus nidulans* were expressed (Mootz et al., 2002) for synthesis of fatty aldehyde, which is then transformed to a fatty alcohol by endogenous aldehyde reductase(s) (Buijs et al., 2015) or by a heterologous long-chain fatty aldehyde reductase from *Marinobacter aquaeolei* (Wahlen et al., 2009) or by any other FAR enzyme as described in Example 1.

The FACoAR encoding gene MaFACoAR, fatty acid reductase encoding gene MmCAR were codon-optimized for yeast from GenScript (Piscataway, N.J., USA). Combinations of these genes were introduced into pYX212 using a modular pathway engineering strategy as previously described (Zhou et al., 2012) resulting in the plasmid pYX212-FaCoAR and pAOHO. After purification of the plasmid, verification by restriction analysis, and sequencing, the plasmids were transformed into hfd1Δ strain *Saccharomyces cerevisiae* YJZ01 (Buijs et al., 2015).

Figure 23:
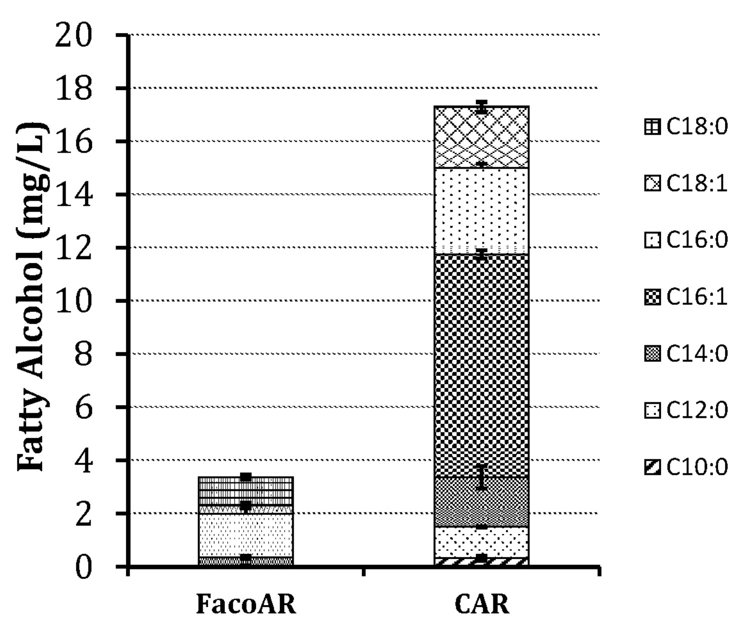
FIG. 23. Shows the quantification of fatty alcohols directly synthesized from (i) fatty acyl-CoA or (ii) via free fatty acids and fatty aldehydes. The fatty alcohols were extracted from 48-h shake flask cultures in glucose minimal medium as previously described (Buijs et al., 2015). FaCoAR represents the Strain YJZ01 (MATa MAL2-8c SUC2 his3Δ1 ura3-52 hfd1Δ) (Buijs et al., 2015) and expresses FAR from *Marinobacter aquaeolei* (Willis et al., 2011), and CAR represents YJZ01 and expresses MmCAR from *Mycobacterium marinum* (Akhtar et al., 2013). The corresponding co-factor phosphopantetheinyl transferase NpgA from *Aspergillus nidulans* was also overexpressed (Mootz et al., 2002).

This approach was also applied on strains producing very long chain fatty acids as mentioned in Example 2 (CEN.PK 113-5D Elo3Δ, and JV03 Elo3Δ, CEN.PK 113-5D Elo3Δ::TEF-ELO2, JV03 Elo3Δ::TEF-ELO02). The strains were analyzed and fatty alcohol profiles were measured as previously described (Buijs et al., 2015). The fatty alcohol production via the pathway through MmCAR from *Mycobacterium marinum* was 6-fold higher when compared to expressing the pathway via FAR from *Marinobacter aquaeolei* (see FIGS. 22 and 23).

Example 17

Figure 24:
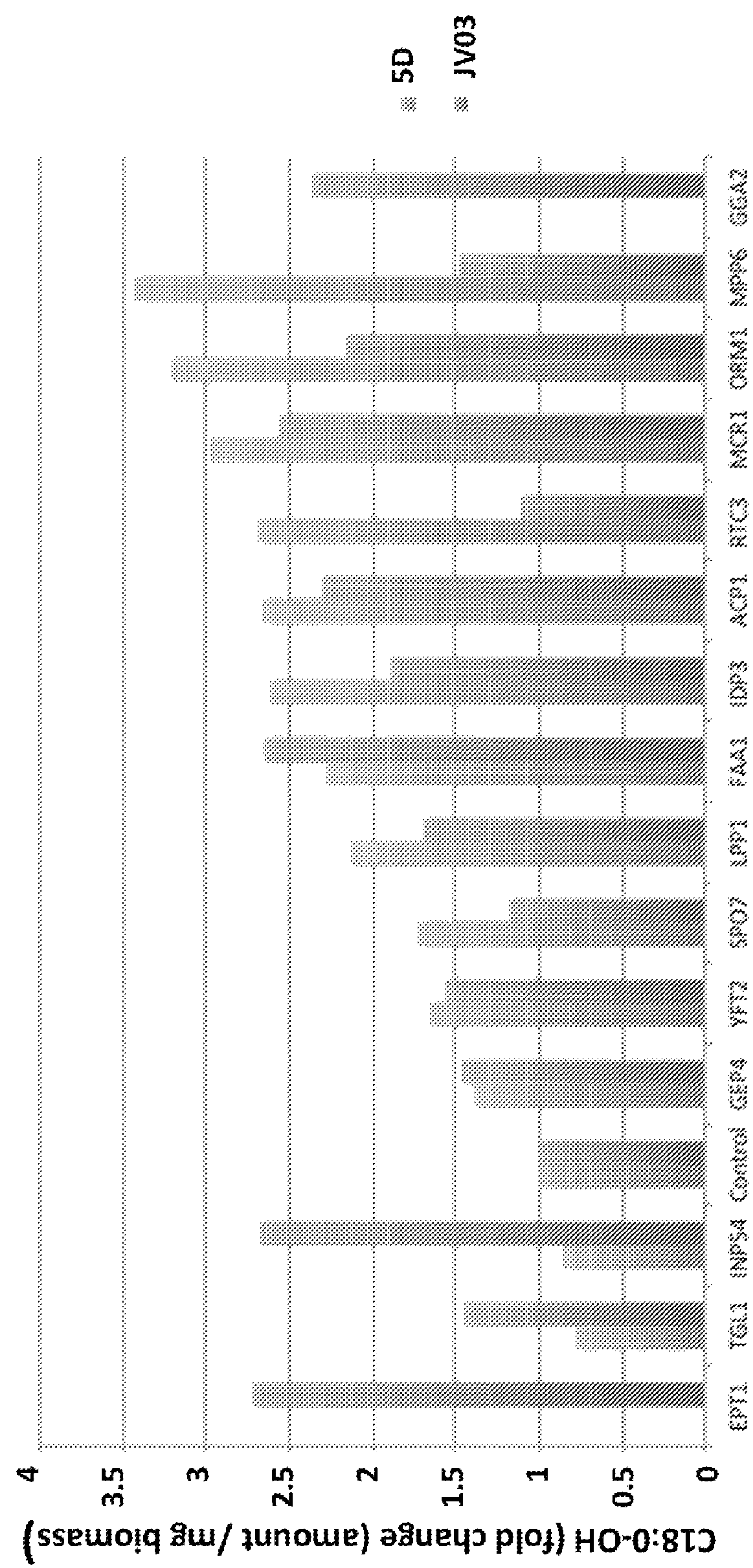
FIG. 24. Show the overexpression of endogenous yeast genes MPP6, ACP1, EPT1, FAA1, GEP4, GGA2, IDP3, INP54, LPP1, MCR1, ORM1, RTC3, SPO7, TGL1, YFT2 using plasmid pSP-GM2::AmFAR (SEQ ID NO: 1, Partow et al. 2010) in yeast strains CEN.PK 113-5D and JV03. Relative quantification of fatty alcohol (C18:1) profiles compared to the particular control strain carrying pSP-GM2::AmFAR without any coexpression.

Overexpression of Endogenous Yeast Genes to Increase Precursor Supply for VLCFA Synthesis Endogenous yeast genes MPP6, ACP1, EPT1, FAA1, GEP4, GGA2, IDP3, INP54, LPP1, MCR1, ORM1, RTC3, SPO7, TGL1, YFT2, FAA3 were amplified from genomic DNA of CEN.PK 113-5D with respective primers flanked by restriction sites for BamHI & SalI and cloned into the expression vector pSP-GM2 (SEQ ID NO: 1) and pSP-GM2::AmFAR. Plasmids were transformed into yeast strains CEN.PK 113-5D and JV03 and fatty acid and fatty alcohol profiles were determined as described in Buijs et al. (2015). Quantification of fatty alcohol production from this screening are shown in FIG. 24.

TABLE 1

Exact wax ester composition in 5Delo3ΔACC1** (pYX212::MaFAldhR::SciWS::Elo2)

| No. | Length | Name | Retention time [min] | Characteristic m/z peaks | Peak intensity |
|---|---|---|---|---|---|
| 1 | C30:0 | Palmityl myristate | 23.19 | 229, 453 | |
| 2 | C30:1 | Palmitoleyl myristate | 23.32 | 222, 229, 451 | |
| 3 | C32:0 | Palmityl palmitate | 24.79 | 224, 257, 481 | 4 = 3 |
| 4 | C32:0 | Stearyl myristate | 24.79 | 211, 229, 481 | |
| 5 | C32:1 | Palmityl palmitoleate | 24.93 | 236, 255, 479 | 5 > 6 |
| 6 | C32:1 | Stearyl myristoleate | 24.98 | 208, 227, 479 | |
| 7 | C32:2 | Palmitoleyl palmitoleate | 25.05 | 222, 237, 477 | |
| 8 | C34:0 | Arachidyl myristate | 26.26 | 229, 509 | 10 > 8 > 9 |
| 9 | C34:0 | Palmityl stearate | 26.26 | 224, 285, 509 | |
| 10 | C34:0 | Stearyl palmitate | 26.26 | 239, 257, 509 | |
| 11 | C34:1 | Stearyl palmitoleate | 26.41 | 236, 255, 507 | 11 > 12 |
| 12 | C34:1 | Palmityl oleate | 26.41 | 264, 283, 507 | |
| 13 | C34:2 | Oleyl palmitoleate | 26.48 | 237, 250, 505 | 13 = 14 |
| 14 | C34:2 | Palmitoleyl oleate | 26.54 | 222, 265, 505 | |
| 15 | C36:0 | Arachidyl palmitate | 27.64 | 257, 537 | 15 > 16 > 18 > 17 |
| 16 | C36:0 | Behenyl myristate | 27.64 | 229, 537 | |
| 17 | C36:0 | Palmityl arachidate | 27.64 | 313, 537 | |
| 18 | C36:0 | Stearyl stearate | 27.64 | 285, 537 | |
| 19 | C36:1 | Arachidyl palmitoelate | 27.79 | 236, 255, 535 | |
| 20 | C36:2 | Eicosenyl palmitoelate | 27.88 | 236, 255, 533 | |
| 21 | C38:0 | Behenyl palmitate | 29.08 | 257, 565 | 21 > 22 > 23 > 24 |
| 22 | C38:0 | Palmityl behenate | 29.08 | 341, 565 | |
| 23 | C38:0 | Arachidyl stearate | 29.08 | 285, 565 | |
| 24 | C38:0 | Stearyl arachidate | 29.08 | 313, 565 | |
| 25 | C38:1 | Behenyl palmitoleate | 29.26 | 236, 255, 563 | 25 > 26 |
| 26 | C38:1 | Arachidyl oleate | 29.26 | 264, 563 | |
| 27 | C40:0 | Behenyl stearate | 30.88 | 285, 593 | 27 = 29 > 28 |
| 28 | C40:0 | Arachidyl arachidate | 30.88 | 313, 593 | |
| 29 | C40:0 | Stearyl behenate | 30.88 | 341, 593 | |
| 30 | C42:0 | Arachidyl behenate | 32.79 | 341, 621 | 30 = 31 |
| 31 | C42:0 | Behenyl arachidate | 32.79 | 313, 621 | |

TABLE 2

| Yeast strains | | |
|---|---|---|
| No: | Strain name | Genotype |
| 1 | CEN.PK 113-5D | (MATa MAL2-8c SUC2 ura3-52) |
| 2 | CEN.PK113-11C | (MATa MAL2-8c SUC2 his3Δ1 ura 3-52)pox1Δ |
| 3 | JV03 | (MATa MAL2-8c SUC2 ura3-52 are1Δ dga1Δ are2Δ lro1Δ pox1Δ) |
| 5 | CEN.PK 113-5D elo3Δ ACC1** | Derived from CEN.PK 113-5D |
| 6 | JV03 elo3Δ | Derived from JV03 |
| 7 | JV03 elo3Δ ACC1** | Derived from JV03 |
| 8 | CEN.PK113-11C pox1Δ elo3Δ | Derived from CEN.PK113-11C |
| 9 | CEN.PK113-11C pox1Δ elo3Δ ACC1** | Derived from CEN.PK113-11C |
| 9 | CEN.PK 113-5D elo3Δ ACC1**:: TEF-ELO2 | Derived from CEN.PK 113-5D |
| 10 | CEN.PK113-11C pox1Δ elo3Δ ACC1**:: TEF-ELO2 | Derived from CEN.PK113-11C |
| 11 | JV03 elo3Δ ACC1**::TEF-ELO2 | Derived from JV03 |
| 12 | *Y. lipolytica* strain W29 (ATCC ® 20460 ™) | Tharaud et al., 1992 |
| 13 | *Y. lipolytica* strain JMY195 (Pol1d MATa, ura3-302, leu2-270, xpr2-322) | Ledall et al., 1994 |
| 14 | *Y. lipolytica* strain JMY2159 (Po1d MATA ura3-302 leu2-270 xpr2-322 pox1-6Δdga1Δlro1Δdga2Δfad2Δ) | Beopoulos et al., 2014 |
| 15 | CEN.PK113-11C elo2Δ, elo3Δ | Derived from CEN.PK113-11C |
| 16 | PWY12 | fas1Δ::HIS3 fas2Δ::LEU2 (Wenz et al., 2001) |
| 17 | CEN.PK 113-5D, $P_{HXT1}$ FAS1 | |
| 18 | YJZ01 | (MATa MAL2-8c SUC2 his3Δ1 ura3-52 hfd1Δ) (Buijs et al., 2015) |
| 21 | TDY7005 | Mata lys2 ura3-52 trp1_leu2_elo2::KAN elo3::TRP1/pARS316-ELO3(http://www.jbc.org/content/281/14/9018.full.pdf+html) |
| 22 | YT01(TDY7005, p415GPD::MvFAS::Acps) | Derived from TDY7005 |
| 23 | YT02(YT01, pSPGM2:At5FAR) | Derived from YT01 |
| 24 | IMX581 | (Mans et al., 2015) |
| 25 | IMX581 pACC1** | Derived from IMX581 |
| 26 | IMX581 pACC1**pELO1pELO2pAt5FAR | Derived from IMX581 |

TABLE 3

| Plasmids | | |
|---|---|---|
| No | Plasmid name | Description |
| 1 | pSP-GM2 | SEQ ID NO: 1, (Partow et al., 2010) |
| 2 | pUC57 | Cloning vector *E. coli*, genscript |
| 3 | pSP-GM2::AmFAR | Derived from pSP-GM2 |
| 4 | pSP-GM2::MaFAldhR | Derived from pSP-GM2 |
| 5 | pSP-GM2::SciFAR | Derived from pSP-GM2 |
| 6 | pSP-GM2::TaFAR | Derived from pSP-GM2::SciFAR |
| 7 | pSPGM2::SciFAR::AtWS | Derived from pSP-GM2::SciFAR |
| 8 | pSPGM2::SciFAR::EgWS | Derived from pSP-GM2::SciFAR |
| 9 | pSPGM2::SciFAR::SciWS | Derived from pSP-GM2::SciFAR |
| 10 | pSPGM2::TaFAR::AtWS | Derived from pSP-GM2::TaFAR |
| 11 | pSPGM2::TaFAR::EgWS | Derived from pSP-GM2::TaFAR |
| 12 | pSPGM2::TaFAR::SciWS | Derived from pSP-GM2::TaFAR |
| 13 | pSPB1 | codon optimized AbWS gene cloned into the HindIII & BamHI restriction sites of pSP-GM2 |
| 14 | pSPB2N | codon optimized MhWS gene cloned into the NotI & SacI restriction sites of pSP-GM2 |
| 15 | pSPGM2::AmFAR::AbWS, | Derived from pSP-GM2::AmFAR |
| 16 | pSPGM2::AmFAR::AtWS, | Derived from pSP-GM2::AmFAR |
| 17 | pSPGM2::AmFAR::EgWS, | Derived from pSP-GM2::AmFAR |
| 18 | pSPGM2::AmFAR::MhWS, | Derived from pSP-GM2::AmFAR |
| 19 | pSPGM2::AmFAR::SciWS, | Derived from pSP-GM2::AmFAR |
| 20 | pSPGM2::MaFAldhR::AbWS, | Derived from pSP-GM2:: MaFAldhR |
| 21 | pSPGM2::MaFAldhR::AtWS, | Derived from pSP-GM2:: MaFAldhR |
| 22 | pSPGM2::MaFAldhR::EgWS, | Derived from pSP-GM2:: MaFAldhR |
| 23 | pSPGM2::MaFAldhR:MhWS | Derived from pSP-GM2:: MaFAldhR |
| 24 | pSPGM2::MaFAldhR::SciWS | Derived from pSP-GM2:: MaFAldhR |

TABLE 3-continued

| No | Plasmid name | Description |
|---|---|---|
| | Plasmids | |
| 25 | pYX212 | R & D Systems |
| 26 | pYX212::Ole1p | Derived from pYX212 |
| 27 | pYX212::Elo2 | Derived from pYX212 |
| 28 | pYX212::Ole1p::Elo2 | Derived from pYX212 |
| 29 | pYX212::SciFAD::Elo2 | Derived from pYX212 |
| 30 | pYX212::AtFae1::Ole1p | Derived from pYX212 |
| 31 | pYX212::BnKCS::Ole1p | Derived from pYX212 |
| 32 | pYX212::CaKCS::Ole1p | Derived from pYX212 |
| 33 | pYX212::CgKCS::Ole1p | Derived from pYX212 |
| 34 | pYX212::LaKCS::Ole1p | Derived from pYX212 |
| 35 | pYX212::ScFAE::Ole1p | Derived from pYX212 |
| 36 | pYX212::TmKCS::Ole1p | Derived from pYX212 |
| 37 | pCfB353::ACC1** | Derived from pCfB353 (Jensen et al., 2014) |
| 38 | pYX212::AmFAR::ELO2 | Derived from pYX212 |
| 39 | pYX212::MaFAldhR::Elo2 | Derived from pYX212 |
| 40 | pYX212::SciFAR::Elo2 | Derived from pYX212 |
| 41 | pYX212::TaFAR::Elo2 | Derived from pYX212 |
| 42 | pYX212::AmFAR::Elo2 | Derived from pYX212 |
| 43 | pYX212::MaFAldhR::Elo2 | Derived from pYX212 |
| 44 | pYX212::SciFAR::Elo2 | Derived from pYX212 |
| 45 | pYX212::TaFAR::Elo2 | Derived from pYX212 |
| 46 | pYX212::AmFAR::AbWS::Elo2 | Derived from pYX212 |
| 47 | pYX212::AmFAR::AtWS::Elo2 | Derived from pYX212 |
| 48 | pYX212::AmFAR::EgWS::Elo2 | Derived from pYX212 |
| 49 | pYX212::AmFAR::ScWS::Elo2 | Derived from pYX212 |
| 50 | pYX212::MaFAldhR::AbWS::Elo2 | Derived from pYX212 |
| 51 | pYX212::MaFAldhR::AtWS::Elo2 | Derived from pYX212 |
| 52 | pYX212::MaFAldhR::EgWS::Elo2 | Derived from pYX212 |
| 53 | pYX212::MaFAldhR::ScWS::ELO2 | Derived from pYX212 |
| 54 | pYX212::ScFAR::AbWS::Elo2 | Derived from pYX212 |
| 55 | pYX212::ScFAR::AtWS::Elo2 | Derived from pYX212 |
| 56 | pYX212::ScFAR::EgWS::Elo2 | Derived from pYX212 |
| 57 | pYX212::ScFAR::ScWS::Elo2 | Derived from pYX212 |
| 58 | pYX212::TaFAR::AbWS::Elo2 | Derived from pYX212 |
| 59 | pYX212::TaFAR::AtWS::Elo2 | Derived from pYX212 |
| 60 | pYX212::TaFAR::EgWS::Elo2 | Derived from pYX212 |
| 61 | pYX212::TaFAR::ScWS::Elo2 | Derived from pYX212 |
| 62 | p413TEF1 | (Mumberg et al., 1995) |
| 63 | pYX212::SciFAD | Derived from pYX212 |
| 64 | pYX212::ChDes9-1 | Derived from pYX212 |
| 65 | J4P62::pTEF::URAex | Beopoulos et al., 2014 |
| 66 | JMP62::pTEF::LEUex | Beopoulos et al., 2014 |
| 67 | JMP62::URAex(USER) | Derived from JMP62::pTEF::URAex |
| 68 | JMP62::LEUex(USER) | Derived from JMP62::pTEF::LEUex |
| 69 | JMP62::URAex::AmFAR | Derived from JMP62::URAex(USER) |
| 70 | JMP62::URAex::MaFAldhR | Derived from JMP62::URAex(USER) |
| 71 | JMP62::URAex::SciFAR | Derived from JMP62::URAex(USER) |
| 72 | JMP62::URAex::TaFAR | Derived from JMP62::URAex(USER) |
| 73 | JMP62::URAex::AmFAR::AbWS | Derived from JMP62::URAex(USER) |
| 74 | JMP62::URAex::AmFAR::AtWS | Derived from JMP62::URAex(USER) |
| 75 | JMP62::URAex::AmFAR::EgWS | Derived from JMP62::URAex(USER) |
| 76 | JMP62::URAex::AmFAR::SciWS | Derived from JMP62::URAex(USER) |
| 77 | JMP62::URAex::MaFAldhR::AbWS | Derived from JMP62::URAex(USER) |
| 78 | JMP62::URAex::MaFAldhR::AtWS | Derived from JMP62::URAex(USER) |
| 79 | JMP62::URAex::MaFAldhR::EgWS | Derived from JMP62::URAex(USER) |
| 80 | JMP62::URAex::MaFAldhR::SciWS | Derived from JMP62::URAex(USER) |
| 81 | JMP62::URAex::SciFAR::AbWS | Derived from JMP62::URAex(USER) |
| 81 | JMP62::URAex::SciFAR::AtWS | Derived from JMP62::URAex(USER) |
| 83 | JMP62::URAex::SciFAR::EgWS | Derived from JMP62::URAex(USER) |
| 84 | JMP62::URAex::SciFAR::SciWS | Derived from JMP62::URAex(USER) |
| 85 | JMP62::URAex::TaFAR::AbWS | Derived from JMP62::URAex(USER) |
| 86 | JMP62::URAex::TaFAR::AtWS | Derived from JMP62::URAex(USER) |
| 87 | JMP62::URAex::TaFAR::EgWS | Derived from JMP62::URAex(USER) |
| 88 | JMP62::URAex::TaFAR::SciWS | Derived from JMP62::URAex(USER) |
| 89 | JMP62::LEUex::YlElo2 | Derived from JMP62::LEUex(USER) |
| 90 | JMP62::LEUex::YlOle1 | Derived from JMP62::LEUex(USER) |
| 91 | JMP62::LEUex::YlElo2::YlOle1 | Derived from JMP62::LEUex(USER) |
| 92 | p413KEX2 | Derived from p413TEF1, replacing $P_{TEF1}$ with $P_{KEX2}$ |
| 93 | lib-Fas1-p413KEX2 | Library based on error prone PCR of Fas1 gene in p413KEX2 |
| 94 | lib-Fas2-p413KEX2 | Library based on error prone PCR of Fas2 gene in p413KEX2 |
| 95 | p416TEF-ELO3 | Based on p416TEF (Mumberg et al., 1995) |
| 96 | pSP-GM2::MvFas | Derived from pSP-GM2 |
| 97 | pSP-GM2::AmFAR::MvFas | Derived from pSP-GM2::AmFAR |

TABLE 3-continued

| Plasmids | | |
|---|---|---|
| No | Plasmid name | Description |
| 98 | pIYC04 | (Krivoruchko et al., 2013) |
| 99 | pTRANS1 | Derived from pIYC04 |
| 100 | pTRANS2 | Derived from pIYC04 |
| 101 | pTRANS3 | Derived from pIYC04 |
| 102 | pYX212-FaCoAR | pYX212 expressing FacoAR |
| 103 | pAOH0 | pYX212 expressing CAR and npgA |
| 104 YT01 | P415GPD:: MvFas | Derived from p415GPD |
| 105 YT02 | P415GPD:: MvFas::Acps | Derived from P415GPD:: MvFas |
| 106 YT03 | pSPGM2:At5FAR | Derived from At5FAR |

TABLE 4

| Nucleotide sequences | |
|---|---|
| SEQ ID NO | Primer name |
| 1 | pSPGM2 |
| 2 | AmFAR optimized for *S. cerevisiae* |
| 3 | MaFAldhR optimized for *S. cerevisiae* |
| 4 | SciFAR optimized for *S. cerevisiae* |
| 5 | TaFAR optimized for *S. cerevisiae* |
| 6 | FAR1 *A. Thaliana* |
| 7 | FAR4 *A. Thaliana* |
| 8 | *M. algicola* DG893 putative reductase |
| 9 | *M. adhaerens* HP15 putative reductase |
| 10 | AbWS optimized for *S. cerevisiae* |
| 11 | AtWS optimized for *S. cerevisiae* |
| 12 | EgWS optimized for *S. cerevisiae* |
| 13 | MhWS optimized for *S. cerevisiae* |
| 14 | SciWS optimized for *S. cerevisiae* |
| 15 | Ma1 *M. Aquaeolei* VT8 |
| 16 | Elo2 *S. cerevisiae* |
| 17 | AtFae1 optimized for *S. cerevisiae* |
| 18 | BnKCS optimized for *S. cerevisiae* |
| 19 | CaKCS optimized for *S. cerevisiae* |
| 20 | CgKCS optimized for *S. cerevisiae* |
| 21 | LaKCS optimized for *S. cerevisiae* |
| 22 | SciKCS optimized for *S. cerevisiae* |
| 23 | TmKCS optimized for *S. cerevisiae* |
| 24 | Ole1p *S. cerevisiae* |
| 25 | SciFAD truncated optimized for *S. cerevisiae* |
| 26 | pXY212 |
| 27 | ACC1**, *S. cerevisiae* |
| 28 | ChDes9-1 optimized for *S. cerevisiae* |
| 29 | Elo2 *Y. lipolytica* |
| 30 | Ole1 *Y. Lipolytica* |
| 31 | AmFAR optimized for *Y. lipolytcia* |
| 32 | MaFAldhR optimized for *Y. lipolytica* |
| 33 | SciFAR optimized for *Y. lipolytica* |
| 34 | TaFAR optimized for *Y. lipolytica* |
| 35 | AbWS optimized for *Y. lipolytica* |
| 36 | AtWS optimized for *Y. lipolytica* |
| 37 | EgWS optimized for *Y. lipolytica* |
| 38 | SciWS optimized for *Y. lipolytcia* |
| 39 | 3-oxoacyl-ACP synthase [*Mycobacterium vaccae*], WP_003928293 (codon optimized for *S. cerevisiae*) |
| 40 | AcpS, WP_040539704, *Mycobacterium vaccae*, (codon optimized for *S. cerevisiae*) |
| 41 | P415GPD |
| 42 | At5FAR (AT5g22500, FAR1 from *Arabidopsis Thaliana* (codon optimized for *S. cerevisiae*) |
| 43 | AbWS fwd BamHI |
| 44 | AbWS rev SaiI |
| 45 | MhWS fwd BamHI |
| 46 | MhWS rev SaiI |
| 47 | AbWS fwd BamHI GA |
| 48 | AbWS rev KpnI GA |
| 49 | AtWS fwd BamHI GA |
| 50 | AtWS rev KpnI GA |
| 51 | EgWS fwd BamHI GA |

TABLE 4-continued

| Nucleotide sequences | |
|---|---|
| SEQ ID NO | Primer name |
| 52 | EgWS rev HindIII GA |
| 53 | MhWS fwd BamHI GA |
| 54 | MhWS rev HindIII GA |
| 55 | SciWS fwd BamHI GA |
| 56 | SciWS rev KpnI GA |
| 57 | pPGK1 |
| 58 | tADH1 |
| 59 | pTEF1 |
| 60 | tCyc1 |
| 61 | AmFAR fwd |
| 62 | AmFAR rev |
| 63 | MaFAldhR fwd |
| 64 | MaFAldhR rev |
| 65 | SciFAR fwd |
| 66 | SciFAR rev |
| 67 | TaFAR fwd |
| 68 | TaFAR rev |
| 69 | AbWS fwd |
| 70 | AbWS rev |
| 71 | AtWS fwd |
| 72 | AtWS rev |
| 73 | EgWS fwd |
| 74 | EgWS rev |
| 75 | SciWS fwd |
| 76 | SciWS rev |
| 77 | pPGK.Ole1 fwd |
| 78 | tADH1.Ole1 rev |
| 79 | pPGK.SciFAD fwd |
| 80 | tADH1.SciFAD rev |
| 81 | pTPI. AtFAE1 fwd |
| 82 | FBA1t. AtFAE1 rev |
| 83 | pTPI. Ca/Bn KCS fwd |
| 84 | FBA1t. Ca/Cg/Bn/La KCS rev |
| 85 | pTPI. CgKCS fwd |
| 86 | pTPI. LaKCS fwd |
| 87 | pTPI. SciKCS fwd |
| 88 | FBA1t. SciKCS rev |
| 89 | pTPI. TmKCS fwd |
| 90 | FBA1t. TmKCS rev |
| 91 | pTPI fwd |
| 92 | pTPI rev |
| 93 | FBA1t fwd |
| 94 | FBA1t rev |
| 95 | CYC1t fwd |
| 96 | CYC1t rev |
| 97 | pTDH3 fwd |
| 98 | pTDH3 rev |
| 99 | pHXT7 fwd |
| 100 | pHXT7 rev |
| 101 | TDH2t fwd |
| 102 | TDH2t rev |
| 103 | ADH1t fwd |
| 104 | ADH1t rev |
| 105 | pPGK1 fwd |

TABLE 4-continued

Nucleotide sequences

| SEQ ID NO | Primer name |
|---|---|
| 106 | pPGK1 rev |
| 107 | pTEF1 fwd |
| 108 | pTEF1 rev |
| 109 | pYX212 fwd |
| 110 | pYX212 rev |
| 111 | Elo3 up fwd |
| 112 | Elo3 up rev |
| 113 | Elo3 down fwd |
| 114 | Elo3 down rev |
| 115 | Chromosome XII in front of Elo3 |
| 116 | Chromosome XII behind Elo3 |
| 117 | Del1 fwd |
| 118 | Del1 rev |
| 119 | Del2 fwd |
| 120 | Del2 rev |
| 121 | X2 up fwd |
| 122 | tADH1-pTEF1 rev |
| 123 | ADH1t-pTEF1 fwd |
| 124 | acc1-CYC1t rev |
| 125 | acc1-CYC1t fwd |
| 126 | X2 down rev |
| 127 | pTDH3.AmFAR fwd |
| 128 | CYC1t.AmFAR rev |
| 129 | pTDH3.MaFAldhR fwd |
| 130 | CYC1t.MaFAldhR rev |
| 131 | pTDH3.SciFAR fwd |
| 132 | CYC1t.SciFAR rev |
| 133 | pTDH3.TaFAR fwd |
| 134 | CYC1t.TaFAR rev |
| 135 | pHXT7.AbWS fwd |
| 136 | TDH2t.AbWS rev |
| 137 | pHXT7.AtWS fwd |
| 138 | TDH2t.AtWS rev |
| 139 | pHXT7t.EgWS fwd |
| 140 | TDH2t.EgWS rev |
| 141 | pHXT7t.SciWS fwd |
| 142 | TDH2t.SciWS rev |
| 143 | pTEF1.Elo2 fwd |
| 144 | pYX212t.Elo2 rev |
| 145 | YlElo2 fwd |
| 146 | YlElo2 rev |
| 147 | YlOle1 fwd |
| 148 | YlOle1 rev |
| 149 | XPR2t rev (JMP62) |
| 150 | XPR2t fwd (USER) |
| 151 | ccdB fwd (XPR2t) |
| 152 | ccdB rev (JMP62) |
| 153 | JMP62 fwd1 (USER) |
| 154 | JMP62 rev1 (JMP62 part 2) |
| 155 | JMP62 fwd2 (J1V1P62 part 1) |
| 156 | JMP62 rev2 (XPR2t) |
| 157 | AmFAR fwd |
| 158 | AmFAR rev |
| 159 | MaFAldhR fwd |
| 160 | MaFAldhR rev |
| 161 | SciFAR fwd |
| 162 | SciFAR rev |
| 163 | TaFAR fwd |
| 164 | TaFAR rev |
| 165 | AbWS fwd |
| 166 | AbWS rev |
| 167 | AtWS fwd |
| 168 | AtWS rev |
| 169 | EgWS fwd |
| 170 | EgWS rev |
| 171 | SciWS fwd |
| 172 | SciWS rev |
| 173 | MvFAS1-F |
| 174 | MvFAS1-R |
| 175 | MvFAS2-F |
| 176 | MvFAS2-R |
| 177 | MvFAS3-F |
| 178 | MvFAS3-R |
| 179 | AT5g22500-F |
| 180 | Primer-AT5g22500-R |
| 181 | TDH3-acps-FBA-F |
| 182 | TDH3-acps-FBA-R |
| 183 | ELO3 target RNA-1 |
| 184 | ELO3up-F |
| 185 | Elo3up-TDH2-R |
| 186 | TDH2t-F |
| 187 | TDH2t-R |
| 188 | Elo1-F |
| 189 | Elo1-R |
| 190 | GAL7-F |
| 191 | GAL7 CYC1-R |
| 192 | CYC1-F |
| 193 | CYC1-R |
| 194 | Elo2-F |
| 195 | Elo2-R |
| 196 | Gal1andGal10-F |
| 197 | Gal1andGal10-R |
| 198 | At5FAR-F |
| 199 | At5FAR-R |
| 200 | FBA1-F |
| 201 | FBA1-R |
| 202 | Elo3updown-F |
| 203 | Elo3down-R |
| 204 | ACC1repair-F |
| 205 | ACC1repair-R |

REFERENCES

Agaphonov, M., Alexandrov, A., 2014. Self-excising integrative yeast plasmid vectors containing an intronated recombinase gene. FEMS Yeast Res. 14, 1048-1054.

Akhtar, M. K., Turner, N.J., Jones, P. R., 2013. Carboxylic acid reductase is a versatile enzyme for the conversion of fatty acids into fuels and chemical commodities. Proc. Natl. Acad. Sci. 110, 87-92.

Beopoulos, A., Verbeke, J., Bordes, F., Guicherd, M., Bressy, M., Marty, A., Nicaud, J.-M., 2014. Metabolic engineering for ricinoleic acid production in the oleaginous yeast *Yarrowia lipolytica*. Appl Microbiol Biotechnol 98, 251-262.

Blazeck, J., Liu, L., Redden, H., Alper, H., 2011. Tuning gene expression in *Yarrowia lipolytica* by a hybrid promoter approach. Appl. Environ. Microbiol. 77, 7905-7914.

Buijs, N. A., Zhou, Y. J., Siewers, V., Nielsen, J., 2015. Long-chain alkane production by the yeast *Saccharomyces cerevisiae*. Biotechnol. Bioeng.

Chen, D. C., Beckerich, J. M., Gaillardin, C., 1997. One-step transformation of the dimorphic yeast *Yarrowia lipolytica*. Appl. Microbiol. Biotechnol. 48, 232-235.

Crameri, A., Raillard, S. A., Bermudez, E., Stemmer, W. P., 1998. DNA shuffling of a family of genes from diverse species accelerates directed evolution. Nature 391, 288-291. doi: 10.1038/34663.

Denic, V., Weissman, J. S., 2007. A Molecular Caliper Mechanism for Determining Very Long-Chain Fatty Acid Length. Cell 130, 663-677. doi:10.1016/j.cell.2007.06.031.

Gao, S., Han, L., Zhu, L., Ge, M., Yang, S., Jiang, Y., Chen, D., 2014. One-step integration of multiple genes into the oleaginous yeast *Yarrowia lipolytica*. Biotechnol. Lett. 36, 2523-2528.

Gibson, D. G., Young, L., Chuang, R.-Y., Venter, J. C., Hutchison, C. A., Smith, H. O., 2009. Enzymatic assembly of DNA molecules up to several hundred kilobases. Nat. Methods 6, 343-345.

Gietz, R. D., Woods, R. A., 2002. Transformation of yeast by lithium acetate/single-stranded carrier DNA/polyethylene glycol method. Methods Enzymol. doi:10.1016/S0076-6879(02)50957-5.

Jakočiūnas, T., Bonde, I., Herrgård, M., Harrison, S. J., Kristensen, M., Pedersen, L. E., Jensen, N. B., Strucko, T., Kildegaard, K. R., David, F., Maury, J., Mortensen, U. H., Forster, J., Nielsen, J., Borodina, I., 2014. EasyClone: Method for iterative chromosomal integration of multiple genes in *Saccharomyces cerevisiae*. FEMS Yeast Res. 14, 238-248. doi:10.1111/1567-1364.12118.

Kalscheuer, R., Stöveken, T., Luftmann, H., Malkus, U., Reichelt, R., Steinbüchel, A., 2006. Neutral lipid biosynthesis in engineered *Escherichia coli*: jojoba oil-like wax esters and fatty acid butyl esters. Appl. Environ. Microbiol. 72, 1373-9. doi:10.1128/AEM.72.2.1373-1379.2006.

Khoomrung, S., Chumnanpuen, P., Jansa-Ard, S., Staišhlman, M., Nookaew, I., Borén, J., Nielsen, J., 2013. Rapid quantification of yeast lipid using microwave-assisted total lipid extraction and HPLC-CAD. Anal. Chem. 85, 4912-4919. doi:10.1021/ac3032405.

Khoomrung S, Chumnanpuen P, Jansa-ard S, Nookaew I, Nielsen J. Appl Microbiol Biotechnol. 2012 June; 94(6): 1637-46. doi: 10.1007/s00253-012-4125-x. Epub 2012 May 9. PMID:22569641.

Krivoruchko, A., Serrano-Amatriain, C., Chen, Y., Siewers, V., Nielsen, J., 2013. Improving biobutanol production in engineered *Saccharomyces cerevisiae* by manipulation of acetyl-CoA metabolism. J. Ind. Microbiol. Biotechnol. 40, 1051-1056. doi:10.1007/s10295-013-1296-0.

Ledall, M. T., Nicaud, J. M., Gaillardin, C., 1994. Multiple copy integration in the yeast *Yarrowia lipolytica*. Curr. Genet. 26,38-44.

Mans, R., van Rossum, H. M., Wijsman, M., Backx, A., Kuijpers, N. G. A., van den Broek, M., Daran-Lapujade, P., Pronk, J. T., van Maris, A. J. A., Daran, J.-M. G., 2015. CRISPR/Cas9: a molecular Swiss army knife for simultaneous introduction of multiple genetic modifications in *Saccharomyces cerevisiae*. FEMS Yeast Res. 15. doi: 10.1093/femsyr/fov004.

Mootz, H. D., Schörgendorfer, K., Marahiel, M. A., 2002. Functional characterization of 4'-phosphopantetheinyl transferase genes of bacterial and fungal origin by complementation of *Saccharomyces cerevisiae* lys5. FEMS Microbiol. Lett. 213, 51-57.

Mumberg, D., Müller, R., Funk, M., 1995. Yeast vectors for the controlled expression of heterologous proteins in different genetic backgrounds. Gene 156, 119-122. doi: 10.1016/0378-1119(95)00037-7.

Pan, R., Zhang, J., Shen, W. L., Tao, Z. Q., Li, S. P., Yan, X., 2011. Sequential deletion of *Pichia pastoris* genes by a self-excisable cassette. FEMS Yeast Res. 11, 292-298. doi: 10.1111/j.1567-1364.2011.00716.x.

Partow, S., Siewers, V., Bjørn, S., Nielsen, J., Maury, J., 2010. Characterization of different promoters for designing a new expression vector in *Saccharomyces cerevisiae*. Yeast 27, 955-964. doi:10.1002/yea.1806.

Paul, S., Gable, K., Beaudoin, F., Cahoon, E., Jaworski, J., Napier, J. A., Dunn, T. M., 2006. Members of the *arabidopsis* FAE1-like 3-ketoacyl-CoA synthase gene family substitute for the elop proteins of *Saccharomyces cerevisiae*. J. Biol. Chem. 281, 9018-9029. doi: 10.1074/jbc.M507723200.

Pulsifer, I. P., Kluge, S., Rowland, O., 2012. *Arabidopsis* LONG-CHAIN ACYL-COA SYNTHETASE 1 (LACS1), LACS2, and LACS3 facilitate fatty acid uptake in yeast. Plant Physiol. Biochem. 51, 31-39. doi:10.1016/j.plaphy.2011.10.003.

Quan, J., Tian, J., 2009. Circular Polymerase Extension Cloning of Complex Gene Libraries and Pathways. PLoS One 4, e6441.

Quan, J., Tian, J., 2011. Circular polymerase extension cloning. *Methods Mol. Biol.* 6, 242-251.

Shi, S., Chen, Y., Siewers, V., Nielsen, J., 2014. Improving production of malonyl coenzyme A-derived metabolites by abolishing Snfl-dependent regulation of Accl. MBio 5. doi: 10.1128/mBio.01130-14.

Teerawanichpan, P., Qiu, X., 2010. Fatty acyl-coA reductase and wax synthase from *euglena gracilis* in the biosynthesis of medium-chain wax esters. Lipids 45, 263-273. doi:10.1007/s11745-010-3395-2.

Tharaud, C., Costes, C., Gaillardin, C., 1992. Secretion of human blood coagulation factor XIIIa by the yeast *Yarrowia lipolytica*. Gene 121, 111-119.

Trenkamp, S., Martin, W., Tietjen, K., 2004. Specific and differential inhibition of very-long-chain fatty acid elongases from *Arabidopsis thaliana* by different herbicides. Proc. Natl. Acad. Sci. U.S.A 101, 11903-11908.

Urbanová, K., Vrkoslav, V., Valterová, I., Háková, M., & Cvac ka, J. (2012). Structural characterization of wax esters by electron ionization mass spectrometry. *Journal of lipid research,* 53(1), 204-213.

Verduyn, C., Postma, E., Scheffers, W. A., Van Dijken, J. P., 1992. Effect of benzoic acid on metabolic fluxes in yeasts: A continuous-culture study on the regulation of respiration and alcoholic fermentation. Yeast 8, 501-517. doi:10.1002/yea.320080703.

Wahlen, B. D., Oswald, W. S., Seefeldt, L. C., Barney, B. M., 2009. Purification, characterization, and potential bacterial Wax production role of an nadph-dependent fatty aldehyde reductase from *Marinobacter aquaeolei* VT8. Appl. Environ. Microbiol. 75, 2758-2764. doi:10.1128/AEM.02578-08.

Wenz, P., Schwank, S., Hoja, U., Schiller, H.-J., 2001. A downstream regulatory element located within the coding sequence mediates autoregulated expression of the yeast fatty acid synthase gene FAS2 by the FAS 1 gene product. Nucleic Acids Res. 29, 4625-4632.

Willis, R. M., Wahlen, B. D., Seefeldt, L. C., Barney, B. M., 2011. Characterization of a fatty acyl-CoA reductase from *Marinobacter aquaeolei* VT8: a bacterial enzyme catalyzing the reduction of fatty acyl-CoA to fatty alcohol. Biochemistry 50, 10550-10558.

Zhou, Y. J., Gao, W., Rong, Q., Jin, G., Chu, H., Liu, W., Yang, W., Zhu, Z., Li, G., Zhu, G., Huang, L., Zhao, Z. K., 2012. Modular pathway engineering of diterpenoid synthases and the mevalonic acid pathway for miltiradiene production. J. Am. Chem. Soc. 134, 3234-41. doi: 10.1021/ja2114486

The invention claimed is:

1. A genetically modified yeast cell capable of producing a very long chain fatty acid (VLCFA) or VLCFA derivative, wherein said genetically modified yeast cell comprises at least one exogenous polynucleotide encoding a *Mycobacterium* fatty acid synthase (FAS), wherein said VLCFA or VLCFA derivative having an acyl chain length of greater than 18 carbons.

2. The genetically modified yeast cell according to claim 1, wherein said at least one polynucleotide encoding said *Mycobacterium* FAS is selected from the group consisting of a polynucleotide encoding a FAS from *Mycobacterium vaccae*, a polynucleotide encoding a FAS from *Mycobacterium diernhoferi* 41002, a polynucleotide encoding a FAS from *Mycobacterium neoaurum*, a polynucleotide encoding a FAS from *Mycobacterium parafortuitum* PA-1, a polynucleotide encoding a FAS from *Mycobacterium intracellulare*, and codon optimized versions thereof.

3. The genetically modified yeast cell according to claim 1, further comprising at least one polynucleotide encoding an elongase, wherein said at least one polynucleotide encoding said elongase is selected from the group consisting of an overexpressed endogenous polynucleotide encoding said elongase, an exogenous polynucleotide encoding said elongase, or a combination thereof.

4. The genetically modified yeast cell according to claim 3, wherein said exogenous polynucleotide encoding said elongase is selected from the group consisting of an elongase from *Arabidopsis thaliana* (Fae1), a β-ketoacyl-CoA synthase (KCS) from *Brassica napus* (BnKCS), a KCS from *Crambe abyssinica* (CaKCS), a KCS from *Cardamine graeca* (CgKCS), a KCS from *Lunaria annua* (LaKCS), a KCS from *Simmondsia chinensis* (SciKCS), a KCS from *Tropaeolum majus* (TmKCS), and codon optimized versions thereof.

5. The genetically modified yeast cell according to claim 3, wherein said yeast cell is a *Saccharomyces cerevisiae* cell and said at least one polynucleotide encoding said elongase comprises an overexpressed endogenous polynucleotide encoding an enzyme from an elongase system selected from the group consisting of a β-ketoacyl-CoA synthase (KCS) (Elo1 and/or Elo2), a β-ketoacyl-CoA reductase (YBR159W), a β-hydroxy acyl-CoA dehydratase (Phs1) and an enoyl-CoA reductase (Tsc13).

6. The genetically modified yeast cell according to claim 1, further comprising at least one exogenous polynucleotide encoding a fatty acyl-CoA reductase (FAR).

7. The genetically modified yeast cell according to claim 6, wherein said at least one exogenous polynucleotide encoding said FAR is selected from the group consisting of a FAR from *Apis mellifera* (AmFAR), a FAR from *Marinobacter aquaeolei*VT8 (MaFA1dhR), a FAR from *Simmondsia chinensis* (SciFAR), a FAR from *Triticum aestivum* (TaFAR), a FAR from *Arabidopsis thaliana* (At5FAR), a FAR from *Marinobacter algicola* DG893, a FAR from *Marinobacter adhaerens* HP15, a FAR from *Taxus baccata*, a FAR from *Euglena gracilis*, a FAR from *Oryza sativa*, a FAR from *Gallus gallus*, a FAR from *Yponomeuta evonymellus*, a FAR from *Mus musculus*, and codon optimized versions thereof.

8. The genetically modified yeast cell according to claim 1, further comprising a polynucleotide encoding a acyl-carrier protein synthase.

9. The genetically modified yeast cell according to claim 1, wherein said yeast cell is a *Saccharomyces cerevisiae* cell genetically modified for reduced expression of and/or knock-out of the gene encoding Elo3.

10. The genetically modified yeast cell according to claim 1, wherein said yeast cell is a *Saccharomyces cerevisiae* cell further comprising at least one overexpressed endogenous polynucleotide encoding a fatty acid synthase selected from the group consisting of fatty acid synthase 1 (Fas1), fatty acid synthase 2 (Fas2) and a combination thereof.

11. The genetically modified yeast cell according to claim 1, further comprising:

an exogenous polynucleotide encoding a fatty acyl-CoA reductase (FAR) from *Arabidopsis thaliana* (At5FAR); and an overexpressed Elo2 polynucleotide encoding a β-ketoacyl-CoA synthase (KCS).

12. The genetically modified yeast cell according to claim 11, wherein said yeast cell is a *Saccharomyces cerevisiae* cell genetically modified for reduced expression of and/or knock-out of the gene encoding Elo3 and further comprising:, an overexpressed endogenous polynucleotide encoding an acetyl-CoA carboxylase (ACC); and an overexpressed Elo1 polynucleotide encoding a KCS, wherein said *S. cerevisiae* cell is genetically modified for knock-out of the gal1 gene encoding a galactokinase.

13. The genetically modified yeast cell according to claim 1, further comprising at least one exogenous polynucleotide encoding a wax synthase (WS).

14. The genetically modified yeast cell according to claim 13, wherein said at least one polynucleotide encoding said WS is selected from the group consisting of a WS from *Acinetobacter baylyi* ADP1 (AbWS), a WS from *Arabidopsis thaliana* (AtWS), a WS from *Euglena gracilis* (EgWS), a WS from *Marinobacter hydrocarbonoclasticus* DSM 8798 (MhWS), a WS from *Simmondsia chinensis* (SciWS), a WS from *Marinobacter aquaeolei* VT8, and codon optimized versions thereof.

15. The genetically modified yeast cell according to claim 1, further comprising at least one polynucleotide encoding a desaturase, wherein said at least one polynucleotide encoding said desaturase is selected from the group consisting of an endogenous polynucleotide overexpressing said desaturase, an exogenous polynucleotide encoding said desaturase, and a combination thereof.

16. The genetically modified yeast cell according to claim 15, wherein said at least one polynucleotide encoding said desaturase comprises an exogenous polynucleotide encoding said desaturase selected from the group consisting of a desaturase from *Simmondsia chinensis* (SciFAD), a desaturase from *Calanus hyperboreus* (ChDes9-1 and/or ChDes9-2), and codon optimized versions thereof.

17. The genetically modified yeast cell according to claim 15, wherein said yeast cell is a *Saccharomyces cerevisiae* cell and said at least one polynucleotide encoding said desaturase comprises an overexpressed endogenous polynucleotide encoding Δ9-desaturase (Ole1).

18. The genetically modified yeast cell according to claim 1, further comprising at least one polynucleotide encoding a thioesterase, wherein said at least one polynucleotide encoding said thioesterase is selected from the group consisting of an overexpressed endogenous polynucleotide encoding said thioesterase, an exogenous polynucleotide encoding said thioesterase and a combination thereof.

19. The genetically modified yeast cell according to claim 18, wherein said at least one polynucleotide encoding said thioesterase comprises an exogenous polynucleotide encoding said desaturase selected from the group consisting of *Homo sapiens* ACOT2, *Homo sapiens* ACOT9, *Rattus norvegicus* ACOT2 and *Rattus norvegicus* ACOT1.

20. The genetically modified yeast cell according to claim 1, wherein said genetically modified yeast cell is a genetically modified yeast cell selected from the group consisting of a genetically modified *Saccharomyces cerevisiae* cell and a genetically modified *Yarrowia lipolytica* cell.

21. A method for the production of a very long chain fatty acid (VLCFA) and/or a VLCFA derivative, said method comprising:

culturing a genetically modified yeast cell according to claim 1 in a culture medium; and isolating said VLCFA and/or said VLCFA derivative from said genetically modified yeast cell and/or from said culture medium.

* * * * *

UNITED STATES PATENT AND TRADEMARK OFFICE

CERTIFICATE OF CORRECTION

PATENT NO. : 10,550,413 B2
APPLICATION NO. : 15/562951
DATED : February 4, 2020
INVENTOR(S) : David et al.

It is certified that error appears in the above-identified patent and that said Letters Patent is hereby corrected as shown below:

On the Title Page

Item (57) Abstract, Line 2: Please correct “very long, chain” to read -- very long chain --

In the Specification

Column 25, Line 3: Please correct “Iro1Δ” to read -- lro1Δ --

Column 30, Line 65: Please correct “DHSoli” to read -- DH5oli --

Column 35, Line 6: Please correct “YBR159” to read -- YBR159W --

Column 38, Line 65: Please correct “lipltterminator” to read -- lip 1 t terminator --

Column 42, Line 67: Please correct “-ELO02” to read -- -ELO2 --

Column 43, Line 28: Please correct “pAOHO” to read -- pAOH0 --

Column 44, Line 7: Please correct “-ELO02” to read -- -ELO2 --

Column 54, Line 28: Please correct “Cvac ka” to read -- Cvacˇka --

Signed and Sealed this
Sixteenth Day of June, 2020

Andrei Iancu
*Director of the United States Patent and Trademark Office*

SEQUENCE LISTING

```
<160> NUMBER OF SEQ ID NOS: 205

<210> SEQ ID NO 1
<211> LENGTH: 7404
<212> TYPE: DNA
```

<213> ORGANISM: Artificial sequence
<220> FEATURE:
<223> OTHER INFORMATION: Episomal expression plasmid

<400> SEQUENCE: 1

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accataccac agcttttcaa ttcaattcat catttttttt ttattctttt ttttgatttc    240
ggtttctttg aaattttttt gattcggtaa tctccgaaca gaaggaagaa cgaaggaagg    300
agcacagact tagattggta tatatacgca tatgtagtgt tgaagaaaca tgaaattgcc    360
cagtattctt aacccaactg cacagaacaa aaacctgcag gaaacgaaga taaatcatgt    420
cgaaagctac atataaggaa cgtgctgcta ctcatcctag tcctgttgct gccaagctat    480
ttaatatcat gcacgaaaag caaacaaact tgtgtgcttc attggatgtt cgtaccacca    540
aggaattact ggagttagtt gaagcattag gtcccaaaat ttgtttacta aaaacacatg    600
tggatatctt gactgatttt tccatggagg gcacagttaa gccgctaaag gcattatccg    660
ccaagtacaa tttttactc ttcgaagaca gaaaatttgc tgacattggt aatacagtca    720
aattgcagta ctctgcgggt gtatacagaa tagcagaatg ggcagacatt acgaatgcac    780
acggtgtggt gggcccaggt attgttagcg gtttgaagca ggcggcagaa gaagtaacaa    840
aggaacctag aggccttttg atgttagcag aattgtcatg caagggctcc ctatctactg    900
gagaatatac taagggtact gttgacattg cgaagagcga caaagatttt gttatcggct    960
ttattgctca aagagacatg ggtggaagag atgaaggtta cgattggttg attatgacac   1020
ccggtgtggg tttagatgac aagggagacg cattgggtca acagtataga accgtggatg   1080
atgtggtctc tacaggatct gacattatta ttgttggaag aggactattt gcaaagggaa   1140
gggatgctaa ggtagagggt gaacgttaca gaaaagcagg ctgggaagca tatttgagaa   1200
gatgcggcca gcaaaactaa aaaactgtat tataagtaaa tgcatgtata ctaaactcac   1260
aaattagagc ttcaatttaa ttatatcagt tattacccta tgcggtgtga aataccgcac   1320
agatgcgtaa ggagaaaata ccgcatcagg aaattgtaaa cgttaatatt ttgttaaaat   1380
tcgcgttaaa tttttgttaa atcagctcat tttttaacca ataggccgaa atcggcaaaa   1440
tcccttataa atcaaaagaa tagaccgaga tagggttgag tgttgttcca gtttggaaca   1500
agagtccact attaaagaac gtggactcca acgtcaaagg gcgaaaaacc gtctatcagg   1560
gcgatggccc actacgtgaa ccatcaccct aatcaagttt tttggggtcg aggtgccgta   1620
aagcactaaa tcggaaccct aaagggagcc cccgatttag agcttgacgg ggaaagccgg   1680
cgaacgtggc gagaaaggaa gggaagaaag cgaaaggagc gggcgctagg gcgctggcaa   1740
gtgtagcggt cacgctgcgc gtaaccacca cacccgccgc gcttaatgcg ccgctacagg   1800
gcgcgtccat tcgccattca ggctgcgcaa ctgttgggaa gggcgatcgg tgcgggcctc   1860
ttcgctatta cgccagctgg ataaaggcgc gccaaacgac ctaggaattg gagcgacctc   1920
atgctatacc tgagaaagca acctgaccta caggaaagag ttactcaaga ataagaattt   1980
tcgttttaaa acctaagagt cactttaaaa tttgtataca cttatttttt ttataactta   2040
tttaataata aaaatcataa atcataagaa attcgcttat ttagaagtgt caacaacgta   2100
tctaccaacg atttgaccct tttccatctt ttcgtaaatt tctggcaagg tagacaagcc   2160
gacaaccttg attggagact tgaccaaacc tctggcgaag aattgttaat taagagctca   2220
```

```
gatcttatcg tcgtcatcct tgtaatccat cgatactagt gcggccgctt gttttatatt   2280
tgttgtaaaa agtagataat tacttccttg atgatctgta aaaaagagaa aaagaaagca   2340
tctaagaact tgaaaaacta cgaattagaa aagaccaaat atgtatttct tgcattgacc   2400
aatttatgca agtttatata tatgtaaatg taagtttcac gaggttctac taaactaaac   2460
cacccccttg gttagaagaa aagagtgtgt gagaacaggc tgttgttgtc acacgattcg   2520
gacaattctg tttgaaagag agagagtaac agtacgatcg aacgaacttt gctctggaga   2580
tcacagtggg catcatagca tgtggtacta aaccctttcc cgccattcca gaaccttcga   2640
ttgcttgtta caaaacctgt gagccgtcgc taggaccttg ttgtgtgacg aaattggaag   2700
ctgcaatcaa taggaagaca ggaagtcgag cgtgtctggg ttttttcagt tttgttcttt   2760
ttgcaaacaa atcacgagcg acggtaattt ctttctcgat aagaggccac gtgctttatg   2820
agggtaacat caattcaaga aggagggaaa cacttccttt ttctggccct gataatagta   2880
tgagggtgaa gccaaaataa aggattcgcg cccaaatcgg catctttaaa tgcaggtatg   2940
cgatagttcc tcactctttc cttactcacg agtaattctt gcaaatgcct attatgcaga   3000
tgttataata tctgtgcgtc ttgagttgaa gtcaggaatc taaaataaaa attaaggtta   3060
ataaaaagag gaaagaaaaa aaaattaatc gatttacaga aacttgcaca ctaaaaatac   3120
acaactaaaa gcaattacag tatgggaagt catcgacgtt atctctacta tagtatatta   3180
tcatttctat tattatcctg ctcagtggta cttgcaaaac aagataagac cccattcttt   3240
gaaggtactt ccaggccggc cgcacacacc atagcttcaa aatgtttcta ctcctttttt   3300
actcttccag attttctcgg actccgcgca tcgccgtacc acttcaaaac acccaagcac   3360
agcatactaa atttcccctc tttcttcctc tagggtgtcg ttaattaccc gtactaaagg   3420
tttggaaaag aaaaaagaga ccgcctcgtt tctttttctt cgtcgaaaaa ggcaataaaa   3480
atttttatca cgtttctttt tcttgaaaat tttttttttt gatttttttc tctttcgatg   3540
acctcccatt gatatttaag ttaataaacg gtcttcaatt tctcaagttt cagtttcatt   3600
tttcttgttc tattacaact tttttactt cttgctcatt agaaagaaag catagcaatc   3660
taatctaagt tttaattaca aggatccgta atacgactca ctatagggcc cgggcgtcga   3720
catggaacag aagttgattt ccgaagaaga cctcgagtaa gcttggtacc gcggctagct   3780
aagatccgct ctaaccgaaa aggaaggagt tagacaacct gaagtctagg tccctattta   3840
tttttttata gttatgttag tattaagaac gttatttata tttcaaattt ttcttttttt   3900
tctgtacaga cgcgtgtacg catgtaacat tatactgaaa accttgcttg agaaggtttt   3960
gggacgctcg aagatcctcc ggatcgtttc gccggcgttt atccagctgc attaatgaat   4020
cggccaacgc gcggggagag gcggtttgcg tattgggcgc tcttccgctt cctcgctcac   4080
tgactcgctg cgctcggtcg ttcggctgcg gcgagcggta tcagctcact caaaggcggt   4140
aatacggtta tccacagaat caggggataa cgcaggaaag aacatgtgag caaaaggcca   4200
gcaaaaggcc aggaaccgta aaaaggccgc gttgctggcg tttttccata ggctccgccc   4260
ccctgacgag catcacaaaa atcgacgctc aagtcagagg tggcgaaacc cgacaggact   4320
ataaagatac caggcgtttc cccctggaag ctccctcgtg cgctctcctg ttccgaccct   4380
gccgcttacc ggatacctgt ccgcctttct cccttcggga agcgtggcgc tttctcatag   4440
ctcacgctgt aggtatctca gttcggtgta ggtcgttcgc tccaagctgg gctgtgtgca   4500
cgaacccccc gttcagcccg accgctgcgc cttatccggt aactatcgtc ttgagtccaa   4560
```

```
cccggtaaga cacgacttat cgccactggc agcagccact ggtaacagga ttagcagagc   4620
gaggtatgta ggcggtgcta cagagttctt gaagtggtgg cctaactacg gctacactag   4680
aaggacagta tttggtatct gcgctctgct gaagccagtt accttcggaa aaagagttgg   4740
tagctcttga tccggcaaac aaaccaccgc tggtagcggt ggtttttttg tttgcaagca   4800
gcagattacg cgcagaaaaa aaggatctca agaagatcct ttgatctttt ctacggggtc   4860
tgacgctcag tggaacgaaa actcacgtta agggattttg gtcatgagat tatcaaaaag   4920
gatcttcacc tagatccttt taaattaaaa atgaagtttt aaatcaatct aaagtatata   4980
tgagtaaact tggtctgaca gttaccaatg cttaatcagt gaggcaccta tctcagcgat   5040
ctgtctattt cgttcatcca tagttgcctg actccccgtc gtgtagataa ctacgatacg   5100
ggagggctta ccatctggcc ccagtgctgc aatgataccg cgagacccac gctcaccggc   5160
tccagattta tcagcaataa accagccagc cggaagggcc gagcgcagaa gtggtcctgc   5220
aactttatcc gcctccatcc agtctattaa ttgttgccgg gaagctagag taagtagttc   5280
gccagttaat agtttgcgca acgttgttgc cattgctaca ggcatcgtgg tgtcacgctc   5340
gtcgtttggt atggcttcat tcagctccgg ttcccaacga tcaaggcgag ttacatgatc   5400
ccccatgttg tgcaaaaaag cggttagctc cttcggtcct ccgatcgttg tcagaagtaa   5460
gttggccgca gtgttatcac tcatggttat ggcagcactg cataattctc ttactgtcat   5520
gccatccgta agatgctttt ctgtgactgg tgagtactca accaagtcat tctgagaata   5580
gtgtatgcgg cgaccgagtt gctcttgccc ggcgtcaata cgggataata ccgcgccaca   5640
tagcagaact ttaaaagtgc tcatcattgg aaaacgttct tcggggcgaa aactctcaag   5700
gatcttaccg ctgttgagat ccagttcgat gtaacccact cgtgcaccca actgatcttc   5760
agcatctttt actttcacca gcgtttctgg gtgagcaaaa acaggaaggc aaaatgccgc   5820
aaaaaaggga ataagggcga cacggaaatg ttgaatactc atactcttcc tttttcaata   5880
ttattgaagc atttatcagg gttattgtct catgagcgga tacatatttg aatgtattta   5940
gaaaaataaa caaatagggg ttccgcgcac atttccccga aaagtgccac ctgaacgaag   6000
catctgtgct tcattttgta gaacaaaaat gcaacgcgag agcgctaatt tttcaaacaa   6060
agaatctgag ctgcattttt acagaacaga aatgcaacgc gaaagcgcta ttttaccaac   6120
gaagaatctg tgcttcattt ttgtaaaaca aaaatgcaac gcgagagcgc taatttttca   6180
aacaaagaat ctgagctgca tttttacaga acagaaatgc aacgcgagag cgctatttta   6240
ccaacaaaga atctatactt cttttttgtt ctacaaaaat gcatcccgag agcgctattt   6300
ttctaacaaa gcatcttaga ttactttttt tctcctttgt gcgctctata atgcagtctc   6360
ttgataactt tttgcactgt aggtccgtta aggttagaag aaggctactt tggtgtctat   6420
tttctcttcc ataaaaaaag cctgactcca cttcccgcgt ttactgatta ctagcgaagc   6480
tgcgggtgca tttttcaag ataaaggcat ccccgattat attctatacc gatgtggatt   6540
gcgcatactt tgtgaacaga aagtgatagc gttgatgatt cttcattggt cagaaaatta   6600
tgaacggttt cttctatttt gtctctatat actacgtata ggaaatgttt acattttcgt   6660
attgttttcg attcactcta tgaatagttc ttactacaat ttttttgtct aaagagtaat   6720
actagagata aacataaaaa atgtagaggt cgagtttaga tgcaagttca aggagcgaaa   6780
ggtggatggg taggttatat agggatatag cacagagata tatagcaaag agatactttt   6840
gagcaatgtt tgtggaagcg gtattcgcaa tattttagta gctcgttaca gtccggtgcg   6900
tttttggttt tttgaaagtg cgtcttcaga gcgcttttgg ttttcaaaag cgctctgaag   6960
```

```
ttcctatact ttctagagaa taggaacttc ggaataggaa cttcaaagcg tttccgaaaa   7020

cgagcgcttc cgaaaatgca acgcgagctg cgcacataca gctcactgtt cacgtcgcac   7080

ctatatctgc gtgttgcctg tatatatata tacatgagaa gaacggcata gtgcgtgttt   7140

atgcttaaat gcgtacttat atgcgtctat ttatgtagga tgaaaggtag tctagtacct   7200

cctgtgatat tatcccattc catgcggggt atcgtatgct tccttcagca ctacccttta   7260

gctgttctat atgctgccac tcctcaattg gattagtctc atccttcaat gctatcattt   7320

cctttgatat tggatcatac taagaaacca ttattatcat gacattaacc tataaaaata   7380

ggcgtatcac gaggcccttt cgtc                                          7404


<210> SEQ ID NO 2
<211> LENGTH: 1571
<212> TYPE: DNA
<213> ORGANISM: Artificial sequence
<220> FEATURE:
<223> OTHER INFORMATION: Synthetic gene codon-optimized for expression
      in Saccharomcyes cerevisiae based on protein-coding sequence from
      Apis mellifera

<400> SEQUENCE: 2

gcggccgcaa aaaaatgtca actatttccg ataatcaatg cacttccgtc agagactttt     60

acaaggacag atccatattc atcactggtg gtacaggttt catgggtaaa gtcttggtag    120

aaaagttgtt aagatcctgt ccaggtatta aaaatatcta tatcttgatg agacctaaaa    180

agagtcaaga tatacaacaa agattgcaaa agttgttgga tgttccattg ttcgacaagt    240

tgagaagaga tacaccagac gaattgttga agatcatccc tattgctggt gacgttaccg    300

aacatgaatt aggtatctct gaagctgatc aaaatgtcat catcagagac gtatctatcg    360

ttttccattc agctgcaact gtaaagttcg atgaaccttt gaaaagatct gttcacatca    420

acatgattgg tacaaagcaa ttgttgaatt tgtgtcatag aatgcacaac ttagaagcct    480

tgattcacgt ttcaaccgct tattgtaatt gcgatagata cgacgtcgca gaagaaatct    540

atccagtatc tgcagaacct gaagaaatca tggccttgac taagttgatg gattcacaaa    600

tgatcgacaa tatcactcca acattgattg gtaatagacc taacacctac acttttacaa    660

aggcattgac agaaagaatg ttgcaatccg aatgcggtca tttgccaatc gctattgtaa    720

gaccttccat tgttttatct tcattcagag aaccagttag tggttgggtc gataatttga    780

acggtcctac aggtattgtt gccgctgcag gtaaaggttt ctttagatct atgttgtgtc    840

aaaagaatat ggttgctgat ttggttccag tcgacatcgt tattaatttg atgatctgca    900

ccgcttggag aaccgcaact aacagaacaa aaaccattcc aatctatcat tgttgcactg    960

gtcaacaaaa tcctattaca tggcaacaat tcgttgaatt aatcttgaag tacaacagaa   1020

tgcatccacc taacgatacc atttggtggc cagacggtaa atgtcacact ttcgcaatcg   1080

tcaacaacgt atgcaagttg ttccaacatt tgttaccagc ccacatcttg gatttcattt   1140

tcagattgag aggtaaacct gctatcatgg tcggtttgca cgaaaagatt gacaaggcag   1200

taaagtgttt ggaatacttc actatgcaac aatggaattt cagagatgac aacgttagac   1260

aattatccgg tgaattgagt ccagaagata gacaaatttt tatgttcgat gttaagcaaa   1320

tcgactggcc ttcttatttg gaacaataca tcttgggtat aagacaattc attattaaag   1380

attctccaga aacattgcct gccgctagat cacatattaa gaaattgtac tggattcaaa   1440

aggttgtcga attcggcatg ttgttagtag ttttgagatt cttgttgttg agaattccaa   1500
```

```
tggcacaatc cgcctgtttc actttgttga gtgctatatt aagaatgtgc agaatgatag   1560

tttaaactag t                                                        1571


<210> SEQ ID NO 3
<211> LENGTH: 1562
<212> TYPE: DNA
<213> ORGANISM: Artificial sequence
<220> FEATURE:
<223> OTHER INFORMATION: Synthetic gene codon-optimized for expression
      in Saccharomcyes cerevisiae based on protein-coding sequence from
      Marinobacter aquaeolei VT8

<400> SEQUENCE: 3

gcggccgcaa aaaaatggca atccaacaag ttcaccacgc agacacaagt tcatccaagg     60

tattaggtca attaagaggt aaaagagtat tgataacagg tactacaggt ttcttgggta    120

aagttgtctt agaaagattg atcagagctg ttccagatat cggtgcaata tatttgttga    180

tcagaggtaa taagagacat cctgatgcta gatccagatt cttggaagaa atcgcaacat    240

cttcagtttt cgatagattg agagaagccg atagtgaagg ttttgacgct ttcttggaag    300

aaagaataca ctgtgttact ggtgaagtca cagaagctgg tttcggtatc ggtcaagaag    360

attatagaaa attggccact gaattagacg ctgtaattaa ttccgctgca agtgttaact    420

tcagagaaga attggataag gcattagcca ttaatacatt gtgtttaaga aacatagccg    480

gtatggtaga tttgaatcca aagttagcag tcttgcaagt atccacatgc tacgttaatg    540

gtatgaactc tggtcaagta accgaatcag ttattaaacc tgccggtgaa gctgttccaa    600

gatctcctga tggtttctac gaaatagaag aattagttag attgttacaa gataagatag    660

aagacgtcca agctagatac tctggtaaag ttttggaaag aaagttagtc gatttgggta    720

ttagagaagc aaatagatat ggttggtcag acacatacac ctttactaaa tggttgggtg    780

aacaattgtt aatgaaggct ttaaacggta gaacattgac catcttgaga ccatctatca    840

tcgaatcagc attggaagaa ccagcccctg gttggataga aggtgtaaaa gttgctgatg    900

caatcatttt ggcctacgct agagaaaaag ttaccttatt cccaggtaaa agatctggta    960

taatcgatgt tatccctgtc gacttagtag ctaactccat aatcttgagt ttagcagaag   1020

ccttgggtga accaggtaga agaagaatct atcaatgttg ctctggtggt ggtaatccta   1080

tcagtttggg tgaattcatt gatcatttga tggcagaatc taaagccaac tatgccgctt   1140

acgaccactt gttttacaga caaccatcaa agcctttctt agctgtcaac agagcattat   1200

ttgatttggt catttctggt gtaagattgc cattgtcatt gactgacaga gttttgaagt   1260

tgttgggtaa ctccagagat ttgaagatgt tgagaaactt agacaccact caaagtttgg   1320

caaccatatt tggtttctat actgccccag attacatctt cagaaatgac gaattgatgg   1380

ctttagcaaa cagaatgggt gaagtcgata aaggtttgtt tcctgtagat gctagattga   1440

tcgactggga attatatttg agaaagatcc atttggcagg tttgaacaga tacgcattga   1500

aagaaagaaa agtctactca ttgaaaaccg caagacaaag aaagaaagca gcataaacta   1560

gt                                                                  1562


<210> SEQ ID NO 4
<211> LENGTH: 1502
<212> TYPE: DNA
<213> ORGANISM: Artificial sequence
<220> FEATURE:
<223> OTHER INFORMATION: Synthetic sequence codon-optimized for
      expression in Saccharomcyes cerevisiae based on protein sequence
      from Simmondsia chinensis
```

<400> SEQUENCE: 4

```
gcggccgcaa aaaaatggaa gaaatgggtt caatcttgga attcttggac aataaggcta     60
tcttggtcac aggtgcaaca ggtagtttgg ctaaaatctt tgttgaaaaa gtcttgagat    120
cacaacctaa cgttaaaaag ttgtatttgt tgttgagagc taccgatgac gaaactgctg    180
cattgagatt gcaaaacgaa gttttcggta aagaattgtt taaagtcttg aagcaaaatt    240
tgggtgcaaa cttttactct ttcgtatcag aaaaggttac cgttgtccca ggtgacataa    300
ctggtgaaga cttgtgtttg aaggatgtta atttgaagga agaaatgtgg agagaaattg    360
atgtagttgt caacttagcc gctaccatta atttcatcga aagatacgac gtatccttgt    420
tgattaacac ttacggtgca aagtacgttt tggatttcgc caaaaagtgc aataagttga    480
agatcttcgt ccatgtatct actgcttacg tttcaggtga aaagaatggt ttgatcttgg    540
aaaagcctta ttacatgggt gaatctttga acggtagatt gggtttggat atcaacgtcg    600
aaaagaaatt ggttgaagcc aagattaatg aattgcaagc agccggtgct acagaaaaat    660
ccattaagag taccatgaag gatatgggta tagaaagagc aagacactgg ggttggccaa    720
atgtttatgt ctttaccaaa gccttgggtg aaatgttatt gatgcaatac aagggtgaca    780
ttcctttgac aataatcaga ccaaccatca tcacttctac attcaaagaa ccattccctg    840
gttgggtaga aggtgttaga acaatagata acgtacctgt ttactacggt aaaggtagat    900
tgagatgtat gttatgcggt ccttcaacta taatcgactt aatcccagct gatatggtag    960
ttaacgctac aattgtcgca atggtagcac atgccaatca aagatatgtt gaaccagtca   1020
cttaccacgt tggttcttca gctgcaaatc ctatgaaatt atccgccttg ccagaaatgg   1080
ctcatagata cttcacaaag aatccatgga taaaccctga tagaaatcca gtccatgtag   1140
gtagagctat ggtcttttcc agtttcagta ctttccactt gtatttgaca ttgaactttt   1200
tattgccatt gaaggttttg gaaatcgcaa acacaatttt ctgtcaatgg ttcaagggta   1260
aatacatgga cttgaagaga aagaccagat tgttgttgag attggttgat atctataaac   1320
cttacttatt tttccaaggt atcttcgatg acatgaacac agaaaagtta agaatagccg   1380
ctaaggaatc tatcgttgaa gctgacatgt tttatttcga tccaagagca attaactggg   1440
aagattattt cttaaaaact cactttcctg gtgtcgttga acatgtattg aactaaacta   1500
gt                                                                  1502
```

<210> SEQ ID NO 5
<211> LENGTH: 1544
<212> TYPE: DNA
<213> ORGANISM: Artificial sequence
<220> FEATURE:
<223> OTHER INFORMATION: Synthetic sequence codon-optimized for expression in Saccharomcyes cerevisiae based on protein sequence from Triticum aestivum

<400> SEQUENCE: 5

```
gcggccgcaa aaaaatggtt gatacattgt ctgaagaaaa cataattggt tactttaaaa     60
ataagtccat cttgattact ggttccacag gtttcttggg caagattttg gttgaaaaga    120
tattgagagt acaaccagat gttaagaaaa tatatttgcc tgtcagagca gtagacgctg    180
cagccgctaa acatagagtt gaaactgaag ttgtcggtaa agaattgttc ggtttgttga    240
gagaaaagca cggtggtaga ttccaatcat tcatatggga aaagatcgtc ccattagctg    300
gtgacgtaat gagagaagat ttcggtgtag actctgaaac attaagagaa ttgagagtta    360
```

```
cccaagaatt agatgttatt gtcaatggtg cagccactac aaacttttat gaaagatacg    420

atgtcgcatt ggacgtaaac gttatgggtg taaagcatat gtgtaacttc gccaaaaagt    480

gcccaaactt gaaggtcttg ttacacgtat ctaccgcata tgtagccggt gaaaaacaag    540

gtttagttca agaaagacct tttaagaatg gtgaaacctt gttagaaggt actagattgg    600

atatagacac agaattgaag ttggctaagg atttgaaaaa gcaattagaa gcagatgttg    660

actcttcacc aaaagctgaa agaaaagcaa tgaaggactt aggtttgaca agagcaagac    720

attttagatg gcctaatact tacgttttca caaagagtat gggtgaaatg gtcttatctc    780

aattgcaatg tgatgtacca gtagttatag ttagacctag tatcatcact tctgttcaaa    840

acgatccatt gcctggttgg atcgaaggta ccagaactat tgacacaatc gttatcggtt    900

acgccaagca aaatttgact tactttttag ctgatttgaa cttgacaatg gatgtcatgc    960

caggtgacat ggtcgtaaat gccatgatgg ctgcaatcgt tgctcattcc agttcttcat   1020

tagaaaagac taagtcacat ccaaagcaac acgcccctgc tgtttaccac gtctccagtt   1080

ctttgagaaa tccagcacct tataacgttt tacatgaagc cggttttaga tacttcacag   1140

aacacccaag agttggtcct gatggtagaa cagtcagaac ccataaaatg accttttttgt   1200

catccatggc ttcattccac ttgttcatga tgttgagata cagattgttg ttggaattgt   1260

tgcatttgtt gtccatcttg tgttgcggtt tgttcggttt ggatacattg taccatgacc   1320

aagctagaaa gtacagattc gttatgcact tggttgattt gtacggtcca tttgcattgt   1380

tcaaaggttg cttcgatgac gttaatttga acaagttgag attggctatg acctcaaatc   1440

atggttcctt gtttaacttc gatcctaaaa ctatagattg ggacgaatac ttctacagag   1500

tccacatacc aggtgtcata aaatacatgt tgaaataaac tagt                    1544
```

<210> SEQ ID NO 6
<211> LENGTH: 1476
<212> TYPE: DNA
<213> ORGANISM: Arabidopsis thaliana

<400> SEQUENCE: 6

```
atggaatcca attgtgttca atttctcggt aacaagacca ttctcatcac aggagctcct     60

ggttttcttg ccaaggtttt ggtagagaaa atactaaggt tgcaaccaaa tgtgaagaag    120

atataccttc tgttgagagc tcccgacgaa aaatcagcca tgcaacgcct acgtagtgag    180

gttatggaga tcgacctttt taaagtgttg aggaacaatc taggagaaga caatttgaat    240

gccttgatgc gggaaaaaat tgtgccggtt ccaggtgata tatcgatcga taatttggga    300

ttgaaagaca ctgatctcat acaacgtatg tggagtgaga ttgatatcat aatcaacata    360

gcagccacaa caaatttcga tgaaagatat gatattggtc ttggcatcaa cacatttgga    420

gccctgaatg ttctcaactt cgccaaaaag tgtgttaaag gacaattgct tctccatgtc    480

tcaaccgcgt atataagcgg tgaacaacct ggattgttac tagagaaacc attcaagatg    540

ggggagactc tcagcgggga tcgggaacta gacatcaata tagaacatga tctaatgaaa    600

caaaaattga aagagcttca agattgttct gatgaagaga tctcgcaaac aatgaaagat    660

tttggaatgg caagggcaaa gcttcatgga tggccaaata catatgtatt caccaaagca    720

atgggagaga tgctaatggg aaaatacaga gaaaatttgc cacttgttat catacgtcca    780

acaatgatta ctagtactat tgccgaacca ttccccggtt ggattgaagg gttgaaaaca    840

ttagacagtg tgattgttgc atatggtaaa ggaaggctta aatgttttct tgcggattca    900

aactcagtct ttgaccttat accggcagac atggtagtaa atgcgatggt tgcagccgcg    960
```

```
acagctcatt cgggagacac cgggattcag gcaatatatc atgttggttc gtcttgtaag   1020

aatccagtca cgtttggaca acttcacgat ttcacggctc gttacttcgc taaacgtcct   1080

ttgattggtc ggaatggctc gccaatcata gtggtcaaag gaaccattct gtccactatg   1140

gctcaattca gcctctacat gacccttcgt tacaagcttc ctctacagat acttcgattg   1200

atcaatatag tttatccatg gagtcacgga gataactaca gtgacctaag ccgcaaaatc   1260

aagctagcta tgcgactagt tgagctttac cagccttact tactcttcaa gggcatattt   1320

gatgatttaa ataccgaaag actgcgaatg aaaagaaagg agaatatcaa agagttagat   1380

ggatcgttcg agttcgatcc caagtccatt gattgggaca attatatcac aaacacccac   1440

attcctggcc tcatcaccca tgtgcttaaa caataa                             1476
```

<210> SEQ ID NO 7
<211> LENGTH: 1482
<212> TYPE: DNA
<213> ORGANISM: Arabidopsis thaliana

<400> SEQUENCE: 7

```
atggactcca attgcattca gttcctccat gacaagacga ttctcgtcac cggtgttccc     60

ggtttcctcg ccaaagtgtt tgtggagaaa atattgagga ttcaaccaaa ggtaaagaag    120

cttttccttc ttttgagagc agcagacaat gaatcagcca tgcaacggtt tcacagtgag    180

gttttggaga aagatctttt tagagtgttg aaaaacgctt taggtgatga gaatctgaaa    240

gctttcataa cagaaaaagt cgtacctatt cccggtgata tatccgttga taatttggga    300

gtgaagggtt ctgatctctt acaacatatg tggaatgaga ttgatatcat tgtcaatgta    360

gccgccacaa cgaactttga tgaaagatat gatgttggtc ttagcgtcaa cacatttgga    420

ccgctcaatg tcctcaactt tgccaagaag tgtgttaaag gacagttgct tcttcatgtt    480

tcaaccgcgt atgtgcgcgg agagaagtct ggacttttac atgagaaaac atttcacatg    540

ggggagacat tgaacggaca tagaaaatta gtcattgaga ccgaaatgga gctaatgaaa    600

caaaaactga aagagctaca gaaacaaaat tgttcagaag aagagatttc acagtctatg    660

aaagatcttg gaatgtcaag ggcaaagctt catggatggc caaacacata tgtgtttacc    720

aaatcaatgg gagagatgct tcttggtaat tatagagaaa accttcccat cgttatcatc    780

cgtcccacaa tgatcactag cactttttca gaaccatttc ccggttggat cgaagggtta    840

agaaccatag acagtgtgat tgttgcatat ggcaaaggaa ggcttaaatg ttttcttgca    900

gatccaaact cagtccttga tcttatacct gtggacatgg tcgcaaacgc aatggtcacg    960

gctgcggcaa tacacgcagg gaagctaggt tcccagaccg tgtaccatgt cggatcatct   1020

tgtaaaaacc cgatcacatt cgaacagatt catgatctcg cggctagcta cttcacgaaa   1080

aaccctcttg ttagacgcga tggttcatct atactagtct ccaaaggaac tatcttgtcc   1140

acaatggctc agttcagttt ctacatgacc cttcgttaca agctaccttt gcagatgttg   1200

cgattgatat atgtaattta tccttggtgg aatggtaata aatataaaga cattgaccgc   1260

aagattaagc tggcgatgcg gttggtcgac ctctacagac cttatgtctt gtttaagggc   1320

atatttgacg atacgaatac tgagaaactg cggttgaaaa gaaaggagat taataaagaa   1380

atgtatggtt tgtttgaatt tgatccaaag tctattgatt gggaggatta tatgacgacc   1440

attcatattc ccggcctcat cacctatgta ctcaaaaaat aa                      1482
```

<210> SEQ ID NO 8

```
<211> LENGTH: 1539
<212> TYPE: DNA
<213> ORGANISM: Artificial sequence
<220> FEATURE:
<223> OTHER INFORMATION: Synthetic sequence codon-optimized for
      expression in Saccharomcyes cerevisiae based on protein sequence
      from Marinobacter algicola DG893

<400> SEQUENCE: 8

atggcaacac agcagcaaca aaacggagcg tcagcgtccg gtgttcttga gcaactacgt     60

ggtaaacacg tgctgatcac cggcaccacc gggtttcttg gtaaggtggt actggaaaaa    120

ttgattcgca cggtgccgga tattggcggg atccatcttc ttatccgtgg taacaaaagg    180

catcctgcag cacgggaacg attcctcaac gagatcgcca gttcttccgt gttcgaacgc    240

cttcggcacg atgacaacga ggcgtttgaa acctttcttg aggaacgcgt tcactgcatc    300

accggcgaag tgacagagtc gcgtttcggg ctcacgccgg agcggttccg tgcacttgcc    360

gggcaggtcg atgcgtttat aaattccgca gccagtgtga acttccggga ggaactcgac    420

aaggcgctga agattaacac cctgtgcctg gagaacgttg ccgctctggc ggagctcaat    480

agcgccatgg cggttatcca ggtgtccacc tgctacgtca atggcaagaa ttccggccag    540

atcacggagt ccgtcatcaa gccggcgggc gagtctattc cccgcagcac cgacggctac    600

tatgaaatcg aagagcttgt gcatttgctg caggacaaaa tttccgacgt gaaagcccga    660

tactccggca aagtacttga aaaaaagctg gtggacctgg ggattcgaga ggccaacaac    720

tacggctgga gtgacaccta cacgtttacc aaatggctgg gtgagcaact cctgatgaaa    780

gccctttccg ggcgttcact tacgattgtt cgcccttcca tcattgaaag tgcactggaa    840

gagccttcgc caggatggat tgaaggtgtg aaggtggcag acgccattat ccttgcctat    900

gcccgtgaga aggtctccct gttcccaggc aagcgtagcg gcattatcga tgtgatcccg    960

gtggacctgg tggccaacag tatcatcttg tccctggcag aagccctttc cgggtcaggg   1020

cagcgccgca tctatcaatg ctgcagtggc ggttctaatc cgatttcgct gggcaagttc   1080

attgactacc tgatggccga agccaagacc aactatgcag cgtatgacca gttgttctac   1140

cgacggccca cgaaaccgtt tgtggcggtc aatcgcaagc tgtttgatgt tgtggttggc   1200

ggcatgcgcg tgccgttgtc gattgctggc aaggcaatga ggctggctgg ccagaaccgt   1260

gagctcaagg ttctcaaaaa cctcgatacc acgcgttcac tggccaccat ctttggtttc   1320

tacacggcac cggattacat cttccgtaac gattcgctga tggccctggc ttcgcgcatg   1380

ggtgaactgg accgtgtcct gttcccggtg gatgcgcgtc agattgactg gcagctgtac   1440

ttgtgcaaga tccacctggg aggtctcaac cgctacgctc tgaaggagcg aaaactgtac   1500

agcctgcggg ccgccgacac ccgcaaaaaa gccgcctga                          1539


<210> SEQ ID NO 9
<211> LENGTH: 1536
<212> TYPE: DNA
<213> ORGANISM: Marinobacter adhaerens HP15

<400> SEQUENCE: 9

atggcaacac agcagctgaa tcccgatgca tcatcaaaag tacttgagcg gctccggggc     60

aagcacgttc tgattaccgg caccacgggc tttctcggca aggtggttct ggaaaagctc    120

attcgcgccg ttccggacat aggcggcatt catctgctga tccgtggaaa caaacgtcac    180

cccgatgcgc gggatcgttt ttttgaggag atcgccacgt cgtcagtctt cgatcgtctg    240

cgccaggacg ataacgaggc ttttgaaacc ttcattgaag atcgtgtgca ttgcgtaacc    300
```

```
ggggaagtga ccgagccttt gtttggtctg tccgctgacc gtttccgcaa gctggctggc    360

ggcatcgatg tggttgtcaa ctccgcagcc agtgtgaact tccgggaaga gcttgataaa    420

gcgcttgcca tcaatacccg ttgcctcgac aacgtggccg agcttgcgcg acagaacaag    480

tcgctggcgg tgctgcaggt ttccacctgc tatgtaaacg gcatgaattc cggacagatc    540

acggagaccg tgatcaagcc ggcaggtgag gccataccccc ggagcactga aggttactat    600

gagatcgaag aacttgtccg gctgctggag gacaagatag cggacgtgcg ttcccgctac    660

tccggcaagg cactggaaaa gaagctggtg gaccttggca tccgtgaagc caaccattat    720

ggctggagcg atacctatac ctttaccaaa tggctcggtg agcaactcct gctcaaggcc    780

ctgtccgggc gggcactgac cattgtgcgc ccatccatta ttgaaagtgc actcgaggaa    840

cccgcgccag gctggattga aggtgtgaag gtggcggatg ccattatcct tgcgtatgcc    900

cgcgagaagg tcacgctctt ccctggcaaa cgcgctggcg tcatcgatgt tattcccgtg    960

gatctggtgg ccaatgccat catcctggcg gcggctgaag ccgttgctga ttcgccacgt   1020

caccggattt accagtgttg cagtggcagc tccaacccgg tttctctcgg gcagtttatt   1080

gaccacctca tggcggaatc caaagccaac ttcgccgaat acgatcagct gttctaccga   1140

cagccgacca aacccttcat tgcagtcaac cgccggctgt tcgatgccgt cgtaggcggg   1200

gtgcgcattc cactgagcat taccgggaag gttttgcgca tgctgggcca aaatcgcgag   1260

ttgaaagtgc tccggaatct ggacacgaca cgctcgctgg cgaccatttt cggtttctac   1320

accgcgccag actatatctt ccggaatgat gatctgctgg ccctggcatc gaggatgggt   1380

gagctggaca aggtgctgtt cccggtagat gcccgccaga ttgactggtc ggtctatctg   1440

cgcaagatcc acctggcagg cctgaaccga tacgccctca aggagcgcaa ggtatacagc   1500

ctgcgctctg ccaaggcccg aaaaaaggca gcgtga                              1536
```

```
<210> SEQ ID NO 10
<211> LENGTH: 1377
<212> TYPE: DNA
<213> ORGANISM: Artificial sequence
<220> FEATURE:
<223> OTHER INFORMATION: Synthetic sequence codon-optimized for
      expression in Saccharomcyes cerevisiae based on protein sequence
      from Acinetobacter baylyi ADP1

<400> SEQUENCE: 10
```

```
atgcgtccat tacatccaat tgatttcatc ttcctatctt tagaaaagag acagcaacca     60

atgcatgtag gcgggctttt tctcttccaa attcctgaca atgctccaga cacattcatc    120

caagacttgg ttaatgatat cagaatttcc aagtcaatac ctgttccacc tttcaataac    180

aaactcaacg gcttgttctg ggacgaggat gaagagttcg atctggatca tcactttcga    240

catatcgcat taccacaccc tggtagaatc agggagttac tcatctacat ttcccaagag    300

cattcaacat tacttgatag agccaagcca ttgtggacat gcaacataat cgaaggtata    360

gaaggcaata gatttgccat gtacttcaag atacatcacg ctatggttga tggagtcgct    420

ggaatgagac taatcgagaa gagcctttct cacgatgtta cagaaaagtc aattgtacca    480

ccttggtgtg tagaaggtaa acgagctaag cgtttacgtg aaccaaaaac cggaaagatc    540

aaaaagatta tgtctggtat caaatctcaa cttcaagcca cgcctactgt cattcaagag    600

ttgtctcaaa cagtgttcaa agacattggt agaaacccag atcacgtgtc ctcatttcaa    660

gcgccatgtt ctattctgaa ccaaagagta tccagtagta gaagatttgc agcacagtct    720
```

```
tttgatcttg ataggttcag aaacattgca aagtctctga acgtcaccat aaacgacgtg    780

gttctagctg tttgctctgg ggcactgaga gcttatctaa tgtcacataa cagcttgcca    840

tcaaaaccat tgattgcgat ggttcctgcc tctatacgta atgatgattc agatgtcagt    900

aacagaataa caatgatcct tgccaaccta gctactcata aggatgatcc tttgcagaga    960

ttagaaatca ttagaagatc agtgcaaaac tcaaagcaga gattcaaaag gatgaccagt   1020

gatcaaatct tgaattactc tgcagtggta tacggtccag ctggtctgaa tatcatatca   1080

ggaatgatgc caaaaagaca agcctttaac ttagttatct ccaatgtacc tggtccacga   1140

gaacctctct actggaacgg agctaagttg gatgcacttt acccagcctc tatcgtttta   1200

gatggtcagg ctttgaacat tacaatgact agttatctag acaagctaga agttgggttg   1260

attgcgtgta gaaatgccct acctagaatg cagaatttgc tgactcactt agaagaggag   1320

attcaactct ttgaaggcgt catcgcaaaa caagaggata tcaaaactgc aaactaa      1377
```

```
<210> SEQ ID NO 11
<211> LENGTH: 1464
<212> TYPE: DNA
<213> ORGANISM: Artificial sequence
<220> FEATURE:
<223> OTHER INFORMATION: Synthetic sequence codon-optimized for
      expression in Saccharomcyes cerevisiae based on protein sequence
      from Arabidopsis thaliana

<400> SEQUENCE: 11

ggatccaaaa aaatgaaagc cgaaaaagtt atggaaagag aaattgaaac cacacctatt     60

gaaccattgt cacctatgtc ccacatgttg tcctcaccaa atttctttat cgttatcaca    120

ttcggtttta aaaccagatg taacagatca gccttcgtcg atggtataaa taacacttta    180

atcaatgctc caagattttc ttcaaagatg gaaattaatt acaaaaagaa aggtgaacca    240

gtctggattc cagtaaagtt gagagttgat gaccatatca tcgtaccaga tttggaatac    300

tctaacatac aaaaccctga tcaattcgtt gaagactaca cttctaacat agctaacatc    360

ccaatggata tgtcaaaacc tttgtgggaa ttccacttgt tgaacatgaa gacatccaag    420

gcagaaagtt tagccatcgt taaaattcat cactctatcg gtgacggcat gtctttgatg    480

tcattgttat tggcatgttc tagaaagata tcagatccag acgcattagt ttctaatact    540

acagccacta agaaacctgc tgattcaatg gcatggtggt tgtttgttgg tttctggttc    600

atgataagag taacattcac cactatcgtt gaattttcca agttgatgtt gactgtttgc    660

tttttagaag atacaaagaa tccattgatg ggtaaccctt ctgacggttt ccaatcatgg    720

aaggttgtcc atagaatcat ctctttcgaa gatgttaagt taattaagga cacaatgaac    780

atgaaggtaa acgatgtttt gttgggtatg acccaagcag gtttatccag atatttgtcc    840

agtaaatacg atggtagtac agccgaaaag aaaaagattt tggaaaagtt gagagtcaga    900

ggtgctgtag ctattaattt gagaccagct accaaaattg aagatttggc cgacatgatg    960

gctaaaggtt ccaagtgtag atggggtaac ttcatcggta cagtcatttt cccattgtgg   1020

gtaaagagtg aaaaagatcc attggaatac attagaagag ccaaagctac tatggacaga   1080

aagaaaattt cattggaagc atttttcttt tatggtataa tcaaattcac attgaagttc   1140

tttggtggta aagctgttga agcattcggt aaaagaattt ttggtcatac ctccttagct   1200

ttttctaatg tcaaaggtcc agatgaagaa atatctttct ttcatcaccc tatctcctat   1260

atcgccggta gtgctttagt tggtgcacaa gccttgaaca tacacttcat ctcatacgtt   1320

gataagatcg tcatcaattt ggctgtcgat acaaccacta ttcaagaccc taacagatta   1380
```

```
tgcgatgaca tggtagaagc tttggaaatt attaagtctg caacccaagg tgaaattttt   1440

cataagactg aagtttaagt cgac                                          1464


<210> SEQ ID NO 12
<211> LENGTH: 1038
<212> TYPE: DNA
<213> ORGANISM: Artificial sequence
<220> FEATURE:
<223> OTHER INFORMATION: Synthetic sequence codon-optimized for
      expression in Saccharomcyes cerevisiae based on protein sequence
      from Euglena gracilis

<400> SEQUENCE: 12

ggatccaaaa aaatgttcac cattccaaga agagtcaagg caggtagaaa gagattttta     60

ttatgctcac cagtattatt attaaacatt atgcaaccat atattttctt ttggaccgtt    120

ggtagacatt actgtaactt catccctttg tacgctgcat tttgcacttg gtggacagca    180

ttcaaggtta tggcctttgg tatcggtaga ggtccattgt gtcaattttc tgctttccac    240

aaatttgcag ttgtcatgtt gttaccaatt ttacctcatg gtgacactaa tcacggtgtt    300

aaggacgaaa gatcaggttc ttcatggtcc agtcctactt acttagaaat gttcgctaag    360

ttctgtggtt tgggtttatg cacatatggt atttcccaat tgagtcatga tggtttccca    420

gttttgtaca acgtcttttt gtccttgatc atgtatttgc acatatgcgt tcaatacacc    480

ggttccaatt tggctacttc taaggtattg caagttcctt tatctgatgg tatgaaccaa    540

ccatacttca gtacatcttt gtcaaacttc tggggtagaa gatggaactt ggttgcatct    600

tcatccttaa gacatgtagt ttacgaccct attagagaag gtagattggt cccaaaaggt    660

caccctgaag aaaaaccagg tggtggtaaa gaagtatcta gaaaggtttt gggttcattg    720

atggcatttt tagtttccgg tatcatgcat gaatatatct tgtggttagc caccggtttc    780

tggagtggtc aaatgttgtt atttttcgtc gtacatggtg ttgccgtcgc cgctgaaaga    840

gtcgctaagg tagcatgggc cagacacggt ttgccagcca taccttgtgc tgtttctatt    900

ccaatgacaa taggtttctt gttcggtacc gctgaattgt tattctaccc acctattttc    960

tctgctaact gggcagaaca tggtgtcgca gacttaagaa gacaattcag atctttgggt   1020

ttatcagtat aagtcgac                                                 1038


<210> SEQ ID NO 13
<211> LENGTH: 1422
<212> TYPE: DNA
<213> ORGANISM: Artificial sequence
<220> FEATURE:
<223> OTHER INFORMATION: Synthetic sequence codon-optimized for
      expression in Saccharomcyes cerevisiae based on protein sequence
      from Marinobacter hydrocarbonoclasticus DSM 8798

<400> SEQUENCE: 13

atgaagagat taggtactct agacgctagt tggcttgcag tcgaatccga agatacgcca     60

atgcacgtgg gcactctcca aatcttctca ttaccagaag gtgctccaga gacatttcta    120

cgtgatatgg ttacaaggat gaaagaggca ggagatgttg ccccaccatg ggggttacaag   180

ctcgcatggt ccggtttcct tggcagggtt attgctcctg cctggaaggt agacaaagat    240

atcgatttgg attatcatgt ccgacatagt gcattgccaa gaccaggtgg tgaaagagag    300

ctagggatac ttgtttctag attacactcc aaccctttag atttctctag accactatgg    360

gaatgccatg tcattgaagg tcttgaaaac aacagatttg cactgtatac taagatgcat    420
```

```
cactctatga ttgatgggat atctggagta agattgatgc aaagagtatt gaccactgac    480

ccagagagat gtaacatgcc tcctccatgg acagttagac ctcaccagag aagaggagct    540

aaaacagata aagaggcttc tgtgcctgct gcggtttctc aagcaatgga cgccttgaag    600

ctccaagcgg atatggcccc tagactatgg caagctggca atcgtctagt acattctgtc    660

agacaccctg aggatggctt aacagctcca ttcaccggtc cagtgtctgt ccttaaccat    720

agagttacag cgcagagaag attcgctact caacactacc aactagatag attgaaaaac    780

ttagcgcatg ccagtggtgg ttcactgaat gatatagtgc tttacttatg tggtactgcc    840

ttgagaaggt tttggctgga gcagaataac ttgcctgaca cacctttaac ggcaggaatt    900

ccagtgaata tcagaccagc tgatgacgaa ggcaccggaa cacaaatctc attcatgatt    960

gctagtttgg ctactgacga agctgatcct ctcaatagat tacaacagat caaaacctca   1020

acacgaaggg cgaaggagca tctccaaaag ttgcctaagt cagcactaac acaatacaca   1080

atgctgctga tgtcacctta catcttacaa ttgatgagcg gattgggagg tagaatgagg   1140

ccagttttca atgttactat aagcaatgtc cctgggcctg aggggacatt gtattacgaa   1200

ggagctagat tggaagccat gtacccagtt tcccttatcg cccacggtgg tgccttgaac   1260

atcacatgcc tgtcttacgc tggctccctt aactttgggt ttaccggttg tcgtgatact   1320

ttaccatcaa tgcaaaagtt agcagtctat actggtgaag cattggatga actcgaatct   1380

ctaattctgc caccaaagaa gcgtgcccgt actagaaagt aa                      1422
```

<210> SEQ ID NO 14
<211> LENGTH: 1077
<212> TYPE: DNA
<213> ORGANISM: Artificial sequence
<220> FEATURE:
<223> OTHER INFORMATION: Synthetic sequence codon-optimized for expression in Saccharomcyes cerevisiae based on protein sequence from Simmondsia chinensis

<400> SEQUENCE: 14

```
ggatccaaaa aaatggaagt agaaaaagaa ttgaaaacct ttagtgaagt ctggataagt     60

gccattgccg ccgcttgcta ttgtagattt gtacctgctg ttgctccaca tggtggtgca    120

ttgagattat tgttgttgtt gccagttgtc ttgttgttta ttttcttgcc tttgagattg    180

tcttcattcc acttgggtgg tcctactgca ttatatttgg tttggttagc caacttcaag    240

ttgttgttgt tcgctttcca tttgggtcca ttatccaacc cttccttaag tttgttacac    300

ttcatcagta ctacattgtt gccaattaag tttagagatg acccttctaa cgatcatgaa    360

aagaataaga gaacattgtc attcgaatgg agaaaagtag ttttgtttgt tgccaagtta    420

gtctttttcg ctggtatttt aaagatatac gaattcagaa aggatttgcc acatttcgta    480

atctccgttt tgtactgttt ccacttctac ttgggtacag aaataacctt agctgcatct    540

gcagttatcg ccagagctac tttaggtttg gacttatatc cacaattcaa tgaaccttac    600

ttggccacat ccttacaaga tttttggggt agaagatgga acttgatggt tagtgacata    660

ttgggtttaa ccacttatca accagtcaga agagtattgt caagatgggt tagattaaga    720

tgggaagttg caggtgccat gttggtagcc tttaccgttt ctggtttgat gcatgaagtt    780

ttctttttct atttgaccag agctagacct tcatgggaag ttactggttt ctttgtctta    840

cacggtgtat gcacagctgt tgaaatggtc gttaagaaag cagtctctgg taaagtaaga    900

ttgagaagag aagtctcagg tgcattaact gttggtttcg ttatggtcac aggtggttgg    960

ttgtttttac cacaattggt tagacatggt gttgatttga agacaatcga cgaataccct   1020
```

```
gttatgttca actacaccca aaagaaattg atgggtttgt taggttggta agtcgac      1077


<210> SEQ ID NO 15
<211> LENGTH: 1368
<212> TYPE: DNA
<213> ORGANISM: Marinobacter aquaeolei VT8

<400> SEQUENCE: 15

gtgacgcccc tgaatcccac tgaccagctc tttctctggc tggaaaaacg ccagcagccc     60

atgcatgtgg gcggcctcca gctgttttcc ttccccgaag gcgcgccgga cgactatgtc    120

gcgcagctgg cagaccagct tcggcagaag acggaggtga ccgccccctt taaccagcgc    180

ctgagctatc gcctgggcca gccggtatgg gtggaggatg agcacctgga ccttgagcat    240

catttccgct tcgaggcgct gcccacaccc gggcgtattc gggagctgct gtcgttcgta    300

tcggcggagc attcgcacct gatggaccgg gagcgcccca tgtgggaggt gcacctgatc    360

gagggcctga aagaccggca gtttgcgctc tacaccaagg ttcaccattc cctggtggac    420

ggtgtctcgg ccatgcgcat ggccacccgg atgctgagtg aaaacccgga cgaacacggc    480

atgccgccaa tctgggatct gccttgcctg tcacgggata ggggtgagtc ggacggacac    540

tccctctggc gcagtgtcac ccatttgctg ggcgctttcgg gccgccagct cggcaccatt    600

cccactgtgg caaaggagct actgaaaacc atcaatcagg cccggaagga tccggcctac    660

gactccattt tccatgcccc gcgctgcatg ctgaaccaga aaatcaccgg ttcccgtcgt    720

ttcgccgccc agtcctggtg cctgaaacgg attcgcgccg tgtgcgaggc ctatggcacc    780

acggtcaacg atgtcgtaac tgccatgtgc gcagcggctc tgcgtaccta tctgatgaat    840

caggatgcct tgccggagaa accactggtg gcctttgtgc cggtgtcact acgccgggac    900

gacagctccg gggcaacca ggtaggcgtc atcctggcga gccttcacac cgatgtgcag    960

gaggccggcg aacgactgtt aaaaatccac catggcatgg aagaggccaa gcagcgctac   1020

cggcatatga gcccggagga aatcgtcaac tacacggccc tgaccctggc gccggccgcc   1080

ttccacctgc tgaccgggct ggcgcccaag tggcagacgt tcaatgtggt gatttccaat   1140

gtccccgggc catccaggcc cctgtactgg aacggggcga aactggaagg catgtatccg   1200

gtgtctatcg atatggacag actggccctg aacatgacac tgaccagcta taacgaccag   1260

gtggagttcg gcctgattgg ctgtcgccgg accctgccca gcctgcaacg gatgctggac   1320

tacctggaac agggtctggc agagctggag ctcaacgccg gtctgtaa                1368


<210> SEQ ID NO 16
<211> LENGTH: 1044
<212> TYPE: DNA
<213> ORGANISM: Saccharomyces cerevisiae

<400> SEQUENCE: 16

atgaattcac tcgttactca atatgctgct ccgttgttcg agcgttatcc ccaacttcat     60

gactatttac caactttgga gcgaccattt tttaatattt cgttgtggga acatttcgat    120

gatgtcgtca ctcgtgtaac taacggtaga tttgttccaa gcgaattcca attcattgca    180

ggtgaattac cattaagcac tttgcccccct gtgctatacg ccatcactgc ctattacgtt    240

attatttttg gtggcaggtt tttgttaagt aagtcgaaac catttaaatt aaatggcctt    300

ttccaattgc ataatttggt tttaacttca ctttcattga cgcttttatt gcttatggtt    360

gaacaattag tgccaattat tgttcagcac gggttatact tcgctatctg taatattggt    420
```

```
gcttggactc aaccgctcgt tacattatat tacatgaatt acattgtcaa gtttattgaa    480

tttatagaca ccttttctt ggtgctaaaa cataaaaaat tgacattttt gcatacttat    540

caccatggcg ctactgcctt attatgttac acccaattga tgggcaccac atctatttct    600

tgggtcccta tttcattgaa ccttggtgtt cacgtggtta tgtattggta ctatttcttg    660

gctgccagag gcatcagggt ctggtggaag gaatgggtta ccagatttca aattatccaa    720

tttgttttgg atatcggttt catatatttt gctgtctacc aaaaagcagt tcacttgtat    780

ttcccaattt tgccacattg tggtgactgt gtgggttcaa caactgccac ctttgcaggt    840

tgtgccatta tttcttcata tttggtacta tttatttcat tttacattaa cgtttataaa    900

cgtaaaggca ccaaaaccag tagagtggta aagcgtgccc acggcggtgt tgccgcaaag    960

gttaatgagt atgttaacgt tgacttgaaa aacgttccta ctccatctcc atcaccaaaa   1020

cctcaacaca gaagaaaaag gtaa                                          1044
```

<210> SEQ ID NO 17
<211> LENGTH: 1527
<212> TYPE: DNA
<213> ORGANISM: Artificial sequence
<220> FEATURE:
<223> OTHER INFORMATION: Synthetic sequence codon-optimized for expression in Saccharomcyes cerevisiae based on protein sequence from Arabidopsis thaliana

<400> SEQUENCE: 17

```
aaaaaaatga cttccgtaaa cgtaaaatta ttgtatagat atgtattgac caacttcttc     60

aacttgtgct tattcccatt aacagccttc ttggctggta aagctagtag attgactatc    120

aatgatttgc ataacttttt atcatatttg caacacaact taatcaccgt tactttgttg    180

ttcgctttca ccgtattcgg tttggttttg tacatcgtca ctagacctaa tccagtctac    240

ttggtagatt attcttgtta cttaccacct ccacatttga aggtttccgt cagtaaagtt    300

atggatattt tctatcaaat cagaaaggct gacacttctt caagaaatgt tgcatgcgat    360

gacccttcca gtttagattt cttgagaaag atccaagaaa gatcaggttt gggtgacgaa    420

acatactcac cagaaggttt gatccatgtt cctccaagaa agacttttgc tgcatcaaga    480

gaagaaacag aaaaagttat tatcggtgca ttagaaaatt tgttcgaaaa cacaaaggtc    540

aatccaagag aaatcggtat tttagttgtc aactcttcaa tgttcaatcc tacaccatct    600

ttgtcagcta tggtagttaa cacctttaag ttaagatcca acatcaaaag tttcaatttg    660

ggtggtatgg gttgttctgc cggtgtaata gctattgatt tggcaaagga cttgttacat    720

gttcacaaaa acacttatgc attggtcgta tctactgaaa atatcacaca aggtatctat    780

gccggtgaaa acagatcaat gatggtatca aattgcttgt ttagagttgg tggtgccgct    840

attttgttat ccaataagag tggtgacaga agaagatcaa agtacaagtt ggttcataca    900

gtcagaacac acaccggtgc tgatgacaaa tcttttagat gtgttcaaca agaagatgac    960

gaatccggta aaatcggtgt ttgcttgagt aaggatatca ccaacgtcgc cggtactaca   1020

ttgaccaaga atatcgctac tttgggtcct ttgatcttgc cattgtcaga aaagttcttg   1080

tttttcgcca cattcgttgc taaaaagttg ttgaaggata agattaaaca ttactacgtc   1140

cctgatttta agttagcagt agaccatttc tgtattcacg caggtggtag agccgttata   1200

gatgaattgg aaaagaattt gggtttgtct ccaatagacg ttgaagctag tagatcaact   1260

ttacacagat ttggtaatac ctccagttct tcaatttggt atgaattggc ttacatagaa   1320

gcaaagggta gaatgaaaaa gggtaacaaa gcctggcaaa ttgctttagg ttccggtttc   1380
```

```
aagtgtaata gtgcagtatg ggttgccttg agaaacgtta aagcatctgc caattcacct   1440

tggcaacatt gcatcgatag atacccagtc aagatagatt ccgacttatc taagtcaaag   1500

actcacgtac aaaacggtcg ttcttaa                                       1527


<210> SEQ ID NO 18
<211> LENGTH: 1521
<212> TYPE: DNA
<213> ORGANISM: Artificial sequence
<220> FEATURE:
<223> OTHER INFORMATION: Synthetic sequence codon-optimized for
      expression in Saccharomcyes cerevisiae based on protein sequence
      from Brassica napus

<400> SEQUENCE: 18

atgacatcta ttaatgttaa attgttgtac cattacgtta ttactaattt gtttaatttg     60

tgtttctttc cattgacagc aattgttgct ggtaaagcat atagattgac tatcgatgat    120

ttgcatcatt tgtactactc ttacttacaa cataatttga tcactatcgc tccattattc    180

gcttttactg ttttcggttc agttttgtac atcgcaacaa gaccaaagcc agtttactta    240

gttgaatact cttgttactt gccaccaact cattgtagat catctatctc aaaagttatg    300

gatattttct atcaagttag aaaggctgat ccatcaagaa atggtacatg taacgattct    360

tcatggttgg atttcttgag aaagatccaa gaaagatcag gtttgggtga cgaaactcat    420

ggtccagaag gtttgttaca agttccacca agaaaaactt ttgctgctgc tagagaagaa    480

acagaacaag ttattattgg tgcattagaa aatttgttta aaaacacaaa cgttaatcca    540

aaagatattg gtattttagt tgttaattct tcaatgttca acccaactcc atctttgtca    600

gctatggttg ttaacacttt taaattgaga tcaaacgtta gatcctttaa tttgggtggt    660

atgggttgtt ctgctggtgt tattgcaatt gatttggcta aagatttgtt gcatgttcat    720

aagaacactt atgcattggt tgtttcaact gaaaacatca catacaacat ctatgctggt    780

gacaacagat caatgatggt ttcaaactgt ttgtttagag ttggtggtgc agctatcttg    840

ttgtctaata agccaagaga tagaagaaga tcaaagtacg aattggttca tacagttaga    900

actcatacag gtgctgatga taaatctttt agatgtgttc aacaaggtga cgatgaaaac    960

ggtaaaactg gtgtttcttt atcaaaggat atcactgatg ttgcaggtag aacagttaag   1020

aaaaatatcg ctacattggg tccattgatc ttgccattgt ctgaaaaatt gttgtttttc   1080

gttactttta tgggtaaaaa gttgtttaaa gataagatta aacattacta cgttccagat   1140

ttcaaattgg ctatcgatca tttctgtatt catgcaggtg gtaaagctgt tattgatgtt   1200

ttggaaaaga atttgggttt ggcaccaatt gatgttgaag ctagtagatc aactttgcat   1260

agattcggta acacatcttc atcttcaatt tggtacgaat tggcatacat tgaagctaaa   1320

ggtagaatga agaaaggtaa taaggtttgg caaatcgcat tgggttctgg ttttaaatgt   1380

aattcagcag tttgggttgc tttgaacaac gttaaagcat ctactaattc tccttgggaa   1440

cattgtatcg aaagatatcc agttaagatc gattctgatt ctggtaaatc tgaaactaga   1500

gcacaaaatg gtagatcata a                                             1521


<210> SEQ ID NO 19
<211> LENGTH: 1521
<212> TYPE: DNA
<213> ORGANISM: Artificial sequence
<220> FEATURE:
<223> OTHER INFORMATION: Synthetic sequence codon-optimized for
      expression in Saccharomcyes cerevisiae based on protein sequence
```

from Crambe abyssinica

<400> SEQUENCE: 19

```
atgacatcta ttaatgttaa attgttgtac cattacgtta ttactaattt gtttaatttg     60

tgtttctttc cattgacagc aattgttgct ggtaaagcta gtagattgac tatcgatgat    120

ttgcatcatt tgtactactc atatttgcaa cataacgtta tcactatcgc tccattgttc    180

gcttttactg ttttcggttc tatcttgtac attgttacaa gaccaaagcc agtttactta    240

gttgaatact cttgttactt gccaccaact caatgtagat catctatctc aaaagttatg    300

gatattttct atcaagttag aaaggctgat ccttttagaa atggtacatg tgatgattct    360

tcatggttgg atttcttgag aaagatccaa gaaagatcag gtttgggtga cgaaactcat    420

ggtccagaag gtttgttaca agttccacca agaaaaactt ttgctgctgc tagagaagaa    480

acagaacaag ttattgttgg tgctttgaaa aatttgttcg aaaacacaaa ggttaaccca    540

aaagatattg gtattttggt tgttaattct tcaatgttca acccaactcc atctttatca    600

gctatggttg ttaacacttt taaattgaga tcaaacgtta gatcctttaa tttgggtggt    660

atgggttgtt ctgctggtgt tattgcaatt gatttggcta aagatttgtt gcatgttcat    720

aaaaatactt atgcattagt tgtttcaact gaaaacatca catacaacat ctatgctggt    780

gacaacagat caatgatggt ttcaaactgt ttgtttagag ttggtggtgc agctatcttg    840

ttgtctaata agccaagaga tagaagaaga tcaaagtacg aattagttca tacagttaga    900

actcatacag gtgctgatga taaatctttt agatgtgttc aacaaggtga cgatgaaaat    960

ggtaaaactg gtgtttcttt gtcaaaggat atcactgaag ttgcaggtag aacagttaag   1020

aaaaatatcg ctacattggg tccattgatc ttgccattgt cagaaaaatt gttgtttttc   1080

gttactttta tggctaagaa attgtttaaa gataaggtta agcattacta cgttccagat   1140

ttcaaattgg ctatcgatca tttctgtatt catgcaggtg gtagagctgt tattgatgtt   1200

ttggaaaaga atttgggttt ggcaccaatt gatgttgaag ctagtagatc aactttgcat   1260

agattcggta acacatcttc atcttcaatt tggtacgaat tagcatacat cgaagctaaa   1320

ggtagaatga agaaaggtaa taaggtttgg caaattgcat tgggttctgg ttttaaatgt   1380

aattcagcag tttgggttgc tttgtctaac gttaaagcat ctactaattc tccttgggaa   1440

cattgtatcg atagatatcc agttaagatc gattctgatt cagcaaagtc tgaaactaga   1500

gcacaaaatg gtagatcata a                                              1521
```

<210> SEQ ID NO 20
<211> LENGTH: 1521
<212> TYPE: DNA
<213> ORGANISM: Artificial sequence
<220> FEATURE:
<223> OTHER INFORMATION: Synthetic sequence codon-optimized for expression in Saccharomcyes cerevisiae based on protein sequence from Cardamine graeca

<400> SEQUENCE: 20

```
atgacttcta ttaatgttaa attgttgtac cattacgttt tgactaattt ctttaatttg     60

tgtttatttc cattaacagc atttccagct ggtaaagcat ctcaattgac tacaaacgat    120

ttgcatcatt tgtattcata cttacatcat aatttgatta ctgttacatt gttatttgct    180

tttactgttt tcggttctat cttgtacatt gttacaagac caaaaccagt ttacttggtt    240

gattactcat gttacttacc accaagacat ttgtcttgtg gtatttcaag agttatggaa    300

attttctatg aaatcagaaa gtctgatcca tcaagagaag ttccattcga tgatccatct    360
```

```
tcattagaat ttttgagaaa gatccaagaa agatcaggtt taggtgacga aacatacggt    420

ccacaaggtt tggttcatga tatgccattg agaatgaact tcgctgctgc tagagaagaa    480

actgaacaag ttattaatgg tgcattagaa aaattgttcg aaaacacaaa ggttaatcca    540

agagaaattg gtattttagt tgttaattct tcaatgttca acccaactcc atctttgtca    600

gctatggttg ttaacacttt taaattgaga tcaaacatca aatctttttc attaggtggt    660

atgggttgtt cagctggtat catcgcaatt gatttggcta aagatttgtt acatgttcat    720

aagaacactt atgcattggt tgtttctact gaaaacatca cacattcaac ttacacaggt    780

gacaatagat caatgatggt ttcaaactgt ttgtttagaa tgggtggtgc agctattttg    840

ttatctaata aggctggtga cagaagaaga tcaaagtaca aattggcaca tacagttaga    900

actcatacag gtgctgatga tcaatctttt agatgtgtta gacaagaaga tgatgataga    960

ggtaaaatcg gtgtttgttt gtctaaggat atcactgctg ttgctggtaa aactgttact   1020

aaaaatatcg ctacattggg tccattggtt ttaccattgt ctgaaaagtt cttgtacgtt   1080

gtttcattga tggctaagaa attgtttaaa aataagatta aacatactta cgttccagat   1140

ttcaaattgg ctatcgatca tttctgtatt catgcaggtg gtagagctgt tattgatgtt   1200

ttggaaaaga atttggcatt gtctccagtt gatgttgaag ctagtagatc aactttgcat   1260

agattcggta acacatcttc atcttcaatt tggtacgaat tggcatacat tgaagctaaa   1320

ggtagaatga agaaaggtaa taaggtttgg caaatcgcaa tcggttctgg ttttaaatgt   1380

aattcagcag tttgggttgc tttgtgtaac gttaagccat ctgttaattc accttgggaa   1440

cattgtatcg atagatatcc agttgaaatt aattacggtt cttcaaagtc tgaaactaga   1500

gcacaaaatg gtagatcata a                                              1521
```

```
<210> SEQ ID NO 21
<211> LENGTH: 1518
<212> TYPE: DNA
<213> ORGANISM: Artificial sequence
<220> FEATURE:
<223> OTHER INFORMATION: Synthetic sequence codon-optimized for
      expression in Saccharomcyes cerevisiae based on protein sequence
      from Lunaria annua

<400> SEQUENCE: 21

atgacttcta ttaatgttaa attgttgtac cattacgtta ttactaattt ctttaatttg     60

tgtttctttc cattgacagc tattttggct ggtaaagcta gtagattgac tacaaacgat    120

ttgcatcatt tctactctta cttgcaacat aatttgatta ctttgacatt gttgttcgct    180

tttactgttt tcggttcagt tttgtacttc gttacaagac caaaaccagt ttacttggtt    240

gattactctt gttacttacc accacaacat ttgtcagctg gtatctctaa gactatggaa    300

attttctatc aaattagaaa gtctgatcca ttgagaaacg ttgcattgga tgattcttct    360

tctttggatt tcttgagaaa gatccaagaa agatcaggtt tgggtgacga aacatacggt    420

ccagaaggtt tgttcgaaat tccaccaaga aagaatttgg cttctgcaag agaagaaact    480

gaacaagtta ttaatggtgc tttgaaaaat ttgttcgaaa acacaaaggt taacccaaaa    540

gaaattggta ttttagttgt taattcatct atgttcaacc caactccatc attgtctgca    600

atggttgtta acacttttaa attgagatca aacatcaaat cttttaattt gggtggtatg    660

ggttgttcag caggtgttat tgctattgat ttggcaaaag atttgttgca tgttcataag    720

aacacttatg ctttggttgt ttctactgaa aacatcacac aaaacatcta tacaggtgac    780
```

aacagatcaa tgatggtttc taactgtttg tttagagttg gtggtgctgc aattttgtta 840
tcaaataagc caggtgacag aagaagatca aaatatagat tggctcatac tgttagaact 900
catacaggtg cagatgataa atcatttggt tgtgttagac aagaagaaga tgattctggt 960
aaaacaggtg tttcattatc taaggatatc actggtgttg ctggtatcac agttcaaaag 1020
aatatcacta cattgggtcc attggttttg ccattgtcag aaaagatttt gttcgttgtt 1080
acttttgttg ctaagaaatt gttgaaggat aagattaaac attactacgt tccagatttc 1140
aaattggcag ttgatcattt ctgtattcat gctggtggta gagcagttat tgatgttttg 1200
gaaaagaatt tgggtttgtc tccaattgat gttgaagcta gtagatcaac tttgcataga 1260
ttcggtaaca catcatcttc atctatttgg tacgaattgg cttacattga agcaaaaggt 1320
agaatgaaga aaggtaataa ggcttggcaa attgcagttg gttcaggttt taaatgtaat 1380
tctgctgttt gggttgcatt gagaaatgtt aaagcatctg caaattctcc ttgggaacat 1440
tgtatccata agtacccagt tcaaatgtac tcaggttcat ctaaatctga aactagagca 1500
caaaatggta gatcataa 1518

<210> SEQ ID NO 22
<211> LENGTH: 1566
<212> TYPE: DNA
<213> ORGANISM: Artificial sequence
<220> FEATURE:
<223> OTHER INFORMATION: Synthetic sequence codon-optimized for expression in Saccharomcyes cerevisiae based on protein sequence from Simmondsia chinensis

<400> SEQUENCE: 22
atgaaagcaa aaacaataac aaatcctgaa atacaagtct caaccactat gaccaccacc 60
actaccacag caaccttacc aaacttcaaa tcttcaatta atttgcatca cgtcaagtta 120
ggttatcatt acttgatatc caacgctttg tttttagtat tcatcccatt gttgggtttg 180
gcaagtgccc atttgtccag tttttctgca cacgatttgt ctttgttgtt cgacttgttg 240
agaagaaatt tgttacctgt tgtcgtttgt tcatttttgt tcgttttgtt ggcaactttg 300
cactttttaa caagaccaag aaacgtctat ttggtagatt tcgcctgcta caaaccacat 360
cctaacttga ttacctctca cgaaatgttt atggacagaa cttcaagagc tggttccttt 420
agtaaggaaa acatcgaatt tcaaagaaag attttagaaa gagctggtat gggtagagaa 480
acttatgttc ctaaatccgt taccaaggtc ccacctgaac caagtattgc tgctgctaga 540
gctgaagcag aagaagttat gtacggtgct atagatgaag ttttggaaaa gactggtgta 600
aaaccaaagc aaatcggtat tttagttgtc aattgttcct tgtttaaccc aacacctagt 660
ttatcttcaa tgatcgttaa ccattacaaa ttgcgtggta acatcttgtc atacaactta 720
ggtggtatgg gttgctccgc cggtttaata agtatcgatt tggctaagga cttgttacaa 780
gtttacagaa acacttacgt cttggtagtt tctacagaaa acatgacctt gaactggtac 840
tggggtaacg atagatcaat gttgatcaca aactgtttgt tcagaatggg tggtgctgca 900
ataatcttgt ctaacagatg gagagataga agaagatcaa agtaccaatt gttgcatacc 960
gtaagaactc acaaaggtgc tgatgacaag tcctacagat gcgttttgca acaagaagat 1020
gaaaacaaca aagttggtgt cgctttgtca aaggacttaa tggccgttgc tggtgaagca 1080
ttaaaggcca atattactac attgggtcca ttggtcttgc ctatgtcaga acaattgtta 1140
tttttcgcca cattggtagc tagaaaggtt tttaagatga ccaacgttaa gccatacatc 1200
cctgatttca aattggccgc taagcatttc tgtatccacg ctggtggtaa agccgttttg 1260

```
gacgaattag aaaccaattt ggaattaact ccttggcatt tggaaccatc aagaatgact   1320

ttgtacagat tcggtaacac atccagttct tcattgtggt atgaattagc atacgccgaa   1380

gctaaaggta gaattagaaa gggtgacaga acttggatga taggttttgg ttctggtttc   1440

aaatgtaatt cagtcgtatg gagagcttta agatcagtta atcctgctag agaaaagaat   1500

ccttggatgg atgaaattga aaactttcca gtacatgttc ctaagattgc tccaatagca   1560

tcttaa                                                              1566


<210> SEQ ID NO 23
<211> LENGTH: 1512
<212> TYPE: DNA
<213> ORGANISM: Artificial sequence
<220> FEATURE:
<223> OTHER INFORMATION: Synthetic sequence codon-optimized for
      expression in Saccharomcyes cerevisiae based on protein sequence
      from Tropaeolum majus

<400> SEQUENCE: 23

atgtctggta ctaaagctac atctgtttca gttccattgc cagatttcaa gcaatctgtt     60

aatttgaagt atgttaaatt gggttatcat tactcaatca ctcatgctat gtacttgttt    120

ttaacaccat tgttgttgat catgtcagca caaatttcta ctttttcaat ccaagatttt    180

catcatttgt acaaccattt gatcttgcat aatttgtctt ctttgatttt atgtattgct    240

ttattgttat ttgttttgac attatacttt ttaactagac caacaccagt ttatttgttg    300

aacttctctt gttacaagcc agatgcaatc cataagtgtg atagaagaag attcatggat    360

actattcgtg gtatgggtac ttatacagaa gaaaacatcg aatttcaaag aaaggttttg    420

gaaagatcag gtattggtga atcttcatat ttgccaccaa cagtttttaa aattccacca    480

agagtttacg atgctgaaga aagagctgaa gcagaaatgt tgatgtttgg tgcagttgat    540

ggtttgttcg aaaagatttc tgttaagcca aaccaaatcg gtgttttggt tgttaactgt    600

ggtttgttta atccaatccc atctttgtct tcaatgatcg ttaacagata caaaatgcgt    660

ggtaatgttt tctcttacaa tttgggtggt atgggttgtt ctgctggtgt tatttcaatt    720

gatttggcaa aagatttgtt acaagttaga ccaaattctt atgctttggt tgtttcttta    780

gaatgtatct ctaaaaattt gtacttaggt gaacaaagat caatgttggt ttcaaactgt    840

ttgtttagaa tgggtggtgc tgcaatcttg ttgtctaata agatgtcaga tagatggaga    900

tcaaagtaca gattggttca tactgttaga acacataagg gtactgaaga taactgtttc    960

tcttgtgtta caagaaagga agattcagat ggtaaaatcg gtatttcttt gtctaaaaat   1020

ttgatggctg ttgcaggtga cgctttgaag actaacatca ctacattggg tccattggtt   1080

ttgccaatgt ctgaacaatt gttgtttttc gctacattgg ttggtaaaaa ggtttttaaa   1140

atgaaattgc aaccatatat tccagatttc aaattggcat tcgaacattt ctgtattcat   1200

gctggtggta gagcagtttt ggatgaattg gaaaagaatt tgaaattatc ttcatggcac   1260

atggaaccat caagaatgtc attgtacaga tttggtaata cttcttcatc ttcattgtgg   1320

tatgaattag cttactctga agcaaaaggt agaattaaga aaggtgacag agtttggcaa   1380

atcgctttcg gttctggttt taaatgtaat tcagctgttt ggaaagcatt aagaaacgtt   1440

aacccagcag aagaaaagaa tccttggatg gatgaaattc atttgtttcc agttgaagtt   1500

ccattaaatt aa                                                       1512


<210> SEQ ID NO 24
```

<211> LENGTH: 1533
<212> TYPE: DNA
<213> ORGANISM: Saccharomyces cerevisiae

<400> SEQUENCE: 24

```
atgccaactt ctggaactac tattgaattg attgacgacc aatttccaaa ggatgactct     60
gccagcagtg gcattgtcga cgaagtcgac ttaacggaag ctaatatttt ggctactggt    120
ttgaataaga aagcaccaag aattgtcaac ggttttggtt ctttaatggg ctccaaggaa    180
atggtttccg tggaattcga caagaaggga aacgaaaaga agtccaattt ggatcgtctg    240
ctagaaaagg acaaccaaga aaaagaagaa gctaaaacta aaattcacat ctccgaacaa    300
ccatggactt tgaataactg gcaccaacat ttgaactggt tgaacatggt tcttgtttgt    360
ggtatgccaa tgattggttg gtactttgct ctctctggta aagtgccttt gcatttaaac    420
gttttccttt tctccgtttt ctactacgct gtcggtggtg tttctattac tgccggttac    480
catagattat ggtctcacag atcttactcc gctcactggc cattgagatt attctacgct    540
atcttcggtt gtgcttccgt tgaagggtcc gctaaatggt ggggccactc tcacagaatt    600
caccatcgtt acactgatac cttgagagat ccttatgacg ctcgtagagg tctatggtac    660
tcccacatgg gatggatgct tttgaagcca aatccaaaat acaaggctag agctgatatt    720
accgatatga ctgatgattg gaccattaga ttccaacaca gacactacat cttgttgatg    780
ttgttaaccg ctttcgtcat tccaactctt atctgtggtt actttttcaa cgactatatg    840
ggtggtttga tctatgccgg ttttattcgt gtctttgtca ttcaacaagc taccttttgc    900
attaactcct tggctcatta catcggtacc caaccattcg atgacagaag aacccctcgt    960
gacaactgga ttactgccat tgttactttc ggtgaaggtt accataactt ccaccacgaa   1020
ttcccaactg attacagaaa cgctattaag tggtaccaat acgacccaac taaggttatc   1080
atctatttga cttctttagt tggtctagca tacgacttga agaaattctc tcaaaatgct   1140
attgaagaag ccttgattca acaagaacaa aagaagatca ataaaaagaa ggctaagatt   1200
aactggggtc cagttttgac tgatttgcca atgtgggaca aacaaacctt cttggctaag   1260
tctaaggaaa acaagggttt ggttatcatt tctggtattg ttcacgacgt atctggttat   1320
atctctgaac atccaggtgg tgaaacttta attaaaactg cattaggtaa ggacgctacc   1380
aaggctttca gtggtggtgt ctaccgtcac tcaaatgccg ctcaaaatgt cttggctgat   1440
atgagagtgg ctgttatcaa ggaaagtaag aactctgcta ttagaatggc tagtaagaga   1500
ggtgaaatct acgaaactgg taagttcttt taa                                1533
```

<210> SEQ ID NO 25
<211> LENGTH: 1113
<212> TYPE: DNA
<213> ORGANISM: Artificial sequence
<220> FEATURE:
<223> OTHER INFORMATION: Synthetic sequence codon-optimized for expression in Saccharomcyes cerevisiae based on truncated protein sequence from Simmondsia chinensis

<400> SEQUENCE: 25

```
aaaaaaatgg tattcatggc ctcatcaact atcggtatta catcaaaaga aatccctaac     60
gcaaagaaac ctcacatgcc tccaagagaa gcccatgtcc aaaagactca ctccatgcca    120
ccacaaaaga ttgaaatttt taagagtttg gaaggttggg ccgaagaaaa tgtattggtt    180
catttgaaac cagttgaaaa gtgttggcaa cctcaagatt tcttgccaga ccctgcatcc    240
gaaggtttca tggatcaagt taaggaatta agagaaagaa ctaaggaaat cccagatgaa    300
```

```
tatttggttg tcttagtcgg tgacatgatt acagaagaag cattgcctac ttaccaaaca    360

atgttgaaca ccttagatgg tgttagagac gaaactggtg cttccttaac aagttgggca    420

atttggacaa gagcttggac cgcagaagaa aacagacatg gtgacttgtt gaacaaatat    480

ttgtacttaa ccggtagagt tgacatgaag caaatcgaaa agactatcca atatttgatt    540

ggttccggta tggacccaag aagtgaaaac aacccttatt tgggttttat atatacctct    600

ttccaagaaa gagcaacttt tatatcacat ggtaacacag ccagattggc taaagatcac    660

ggtgacttcc aattagcaca agtatgtggt attatagctg ctgatgaaaa gagacatgaa    720

accgcctaca ctaagatcgt tgaaaagttg ttcgaaatcg atccagacgg tgctgtcttg    780

gccttagctg atatgatgag aaagaaagtt tctatgcctg cacacttgat gtatgatggt    840

aaagatgaca atttgttcga aaactactca gcagtagccc aacaaatcgg tgtttataca    900

gcaaaggatt acgccgacat tttggaacat ttggttaaca gatggaaggt cgaaaacttg    960

atgggtttat ctggtgaagg tcacaaggcc caagattttg tttgcggttt ggctccaaga   1020

attagaaaat tgggtgaaag agcacaatct ttgtcaaagc cagtctcttt agtacctttt   1080

tcatggattt ttaataagga attaaaggtt taa                                1113
```

<210> SEQ ID NO 26
<211> LENGTH: 8338
<212> TYPE: DNA
<213> ORGANISM: Artificial sequence
<220> FEATURE:
<223> OTHER INFORMATION: Expression plasmid

<400> SEQUENCE: 26

```
gaattcacca tggatcctag ggcccacaag cttacgcgtc gacccgggta tccgtatgat     60

gtgcctgact acgcatgata tctcgagctc agctagctaa ctgaataagg aacaatgaac    120

gtttttcctt tctcttgttc ctagtattaa tgactgaccg atacatccct tttttttttg    180

tctttgtcta gctccaattc gccctatagt gagtcgtatt acaattcact ggccgtcgtt    240

ttacaacgtc gtgactggga aaaccctggc gttacccaac ttaatcgcct tgcagcacat    300

ccccctttcg ccagctggcg taatagcgaa gaggcccgca ccgatcgccc ttcccaacag    360

ttgcgcagcc tgaatggcga atggacgcgc cctgtagcgg cgcattaagc gcggcgggtg    420

tggtggttac gcgcagcgtg accgctacac ttgccagcgc cctagcgccc gctcctttcg    480

ctttcttccc ttcctttctc gccacgttcg ccggctttcc ccgtcaagct ctaaatcggg    540

ggctcccttt agggttccga tttagtggtt tacggcacct cgaccccaaa aaacttgatt    600

agggtgatgg ttcacgtagt gggccatcgc cctgatagac ggtttttcgc cctttgacgt    660

tggagtccac gttctttaat agtggactct tgttccaaac tggaacaaca ctcaacccta    720

tctcggtcta ttcttttgat ttataaggga ttttgccgat ttcggcctat tggttaaaaa    780

atgagctgat ttaacaaaaa tttaacgcga attttaacaa aatattaacg cttacaattt    840

cctgatgcgg tattttctcc ttacgcatct gtgcggtatt tcacaccgca tagggtaata    900

actgatataa ttaaattgaa gctctaattt gtgagtttag tatacatgca tttacttata    960

atacagtttt ttagttttgc tggccgcatc ttctcaaata tgcttcccag cctgcttttc   1020

tgtaacgttc accctctacc ttagcatccc ttccctttgc aaatagtcct cttccaacaa   1080

taataatgtc agatcctgta gagaccacat catccacggt tctatactgt tgacccaatg   1140

cgtctccctt gtcatctaaa cccacaccgg gtgtcataat caaccaatcg taaccttcat   1200
```

```
ctcttccacc catgtctctt tgagcaataa agccgataac aaaatctttg tcgctcttcg   1260
caatgtcaac agtaccctta gtatattctc cagtagatag ggagcccttg catgacaatt   1320
ctgctaacat caaaaggcct ctaggttcct ttgttacttc ttctgccgcc tgcttcaaac   1380
cgctaacaat acctggcccc accacaccgt gtgcattcgt aatgtctgcc cattctgcta   1440
ttctgtatac acccgcagag tactgcaatt tgactgtatt accaatgtca gcaaattttc   1500
tgtcttcgaa gagtaaaaaa ttgtacttgg cggataatgc ctttagcggc ttaactgtgc   1560
cctccatcga aaaatcagtc aatatatcca catgtgtttt tagtaaacaa attttgggac   1620
ctaatgcttc aactaactcc agtaattcct tggtggtacg aacatccaat gaagcacaca   1680
agtttgtttg cttttcgtgc atgatattaa atagcttggc agcaacagga ctaggatgag   1740
tagcagcacg ttccttatat gtagctttcg acatgattta tcttcgtttc ctgcaggttt   1800
ttgttctgtg cagttgggtt aagaatactg ggcaatttca tgtttcttca acactacata   1860
tgcgtatata taccaatcta agtctgtgct ccttccttcg ttcttccttc tgttcggaga   1920
ttaccgaatc aaaaaaattt caaggaaacc gaaatcaaaa aaaagaataa aaaaaaaatg   1980
atgaattgaa aaggtggtat ggtgcactct cagtacaatc tgctctgatg ccgcatagtt   2040
aagccagccc cgacacccgc caacacccgc tgacgcgccc tgacgggctt gtctgctccc   2100
ggcatccgct tacagacaag ctgtgaccgt ctccgggagc tgcatgtgtc agaggttttc   2160
accgtcatca ccgaaacgcg cgagacgaaa gggcctcgtg atacgcctat ttttataggt   2220
taatgtcatg ataataatgg tttcttagac gtgcggccgc tctagaacta gtggatcaat   2280
tccacggact atagactata ctagtatact ccgtctactg tacgatacac ttccgctcag   2340
gtccttgtcc tttaacgagg ccttaccact cttttgttac tctattgatc cagctcagca   2400
aaggcagtgt gatctaagat tctatcttcg cgatgtagta aaactagcta gaccgagaaa   2460
gagactagaa atgcaaaagg cacttctaca atggctgcca tcattattat ccgatgtgac   2520
gctgcagctt ctcaatgata ttcgaatacg ctttgaggag atacagccta atatccgaca   2580
aactgtttta cagatttacg atcgtacttg ttacccatca ttgaattttg aacatccgaa   2640
cctgggagtt ttccctgaaa cagatagtat atttgaacct gtataataat atatagtcta   2700
gcgctttacg gaagacaatg tatgtatttc ggttcctgga gaaactattg catctattgc   2760
ataggtaatc ttgcacgtcg catccccggt tcattttctg cgtttccatc ttgcacttca   2820
atagcatatc tttgttaacg aagcatctgt gcttcatttt gtagaacaaa aatgcaacgc   2880
gagagcgcta atttttcaaa caaagaatct gagctgcatt tttacagaac agaaatgcaa   2940
cgcgaaagcg ctattttacc aacgaagaat ctgtgcttca tttttgtaaa acaaaaatgc   3000
aacgcgagag cgctaatttt tcaaacaaag aatctgagct gcatttttac agaacagaaa   3060
tgcaacgcga gagcgctatt ttaccaacaa agaatctata cttctttttt gttctacaaa   3120
aatgcatccc gagagcgcta tttttctaac aaagcatctt agattacttt ttttctcctt   3180
tgtgcgctct ataatgcagt ctcttgataa ctttttgcac tgtaggtccg ttaaggttag   3240
aagaaggcta ctttggtgtc tattttctct tccataaaaa aagcctgact ccacttcccg   3300
cgtttactga ttactagcga agctgcgggt gcattttttc aagataaagg catccccgat   3360
tatattctat accgatgtgg attgcgcata ctttgtgaac agaaagtgat agcgttgatg   3420
attcttcatt ggtcagaaaa ttatgaacgg tttcttctat tttgtctcta tatactacgt   3480
ataggaaatg tttacatttt cgtattgttt tcgattcact ctatgaatag ttcttactac   3540
aatttttttg tctaaagagt aatactagag ataaacataa aaaatgtaga ggtcgagttt   3600
```

```
agatgcaagt tcaaggagcg aaaggtggat gggtaggtta tatagggata tagcacagag   3660
atatatagca aagagatact tttgagcaat gtttgtggaa gcggtattcg caatatttta   3720
gtagctcgtt acagtccggt gcgtttttgg ttttttgaaa gtgcgtcttc agagcgcttt   3780
tggttttcaa aagcgctctg aagttcctat actttctaga gaataggaac ttcggaatag   3840
gaacttcaaa gcgtttccga aaacgagcgc ttccgaaaat gcaacgcgag ctgcgcacat   3900
acagctcact gttcacgtcg cacctatatc tgcgtgttgc ctgtatatat atatacatga   3960
gaagaacggc atagtgcgtg tttatgctta aatgcgtact tatatgcgtc tatttatgta   4020
ggatgaaagg tagtctagta cctcctgtga tattatccca ttccatgcgg ggtatcgtat   4080
gcttccttca gcactaccct ttagctgttc tatatgctgc cactcctcaa ttggattagt   4140
ctcatccttc aatgctatca tttcctttga tattggatca tatgcatagt accgagaaac   4200
tagtgcgaag tagtgatcag gtattgctgt tatctgatga gtatacgttg tcctggccac   4260
ggcagaagca cgcttatcgc tccaatttcc cacaacatta gtcaactccg ttaggccctt   4320
cattgaaaga aatgaggtca tcaaatgtct tccaatgtga gattttgggc catttttat   4380
agcaaagatt gaataaggcg catttttctt caaagctgcg gccgcactct cactagtacg   4440
tcaggtggca cttttcgggg aaatgtgcgc ggaaccccta tttgtttatt tttctaaata   4500
cattcaaata tgtatccgct catgagacaa taaccgtgat aaatgcttca ataatattga   4560
aaaaggaaga gtatgagtat tcaacatttc cgtgtcgccc ttattccctt ttttgcggca   4620
ttttgccttc ctgtttttgc tcacccagaa acgctggtga aagtaaaaga tgctgaagat   4680
cagttgggtg cacgagtggg ttacatcgaa ctggatctca acagcggtaa gatccttgag   4740
agttttcgcc ccgaagaacg ttttccaatg atgagcactt ttaaagttct gctatgtggc   4800
gcggtattat cccgtattga cgccgggcaa gagcaactcg ctcgccgcat acactattct   4860
cagaatgact tggttgagta ctcaccagtc acagaaaagc atcttacgga tggcatgaca   4920
gtaagagaat tatgcagtgc tgccataacc atgagtgata acactgcggc caacttactt   4980
ctgacaacga tcggaggacc gaaggagcta accgcttttt tggacaacat gggggatcat   5040
gtaactcgcc ttgatcgttg ggaaccggag ctgaatgaag ccataccaaa cgacgagcgt   5100
gacaccacga tgcctgtagc aatggcaaca acgttgcgca aactattaac tggcgaacta   5160
cttactctag cttcccggca acaattaata gactggatgg aggcggataa agttgcagga   5220
ccacttctgc gctcggccct tccggctggc tggtttattg ctgataaatc tggagccggt   5280
gagcgtgggt ctcgcggtat cattgcagca ctggggccag atggtaagcc ctcccgtatc   5340
gtagttatct acacgacggg gagtcaggca actatggatg aacgaaatag acagatcgct   5400
gagataggtg cctcactgat taagcattgg taactgtcag accaagttta ctcatatata   5460
ctttagattg atttaaaact tcatttttaa tttaaaagga tctaggtgaa gatccttttt   5520
gataatctca tgaccaaaat cccttaacgt gagttttcgt tccactgagc gtcagacccc   5580
gtagaaaaga tcaaaggatc ttcttgagat cctttttttc tgcgcgtaat ctgctgcttg   5640
caaacaaaaa aaccaccgct accagcggtg gtttgtttgc cggatcaaga gctaccaact   5700
ctttttccga aggtaactgg cttcagcaga gcgcagatac caaatactgt ccttctagtg   5760
tagccgtagt taggccacca cttcaagaac tctgtagcac cgcctacata cctcgctctg   5820
ctaatcctgt taccagtggc tgctgccagt ggcgataagt cgtgtcttac cgggttggac   5880
tcaagacgat agttaccgga taaggcgcag cggtcgggct gaacgggggg ttcgtgcaca   5940
```

```
cagcccagct tggagcgaac gacctacacc gaactgagat acctacagcg tgagctatga   6000
gaaagcgcca cgcttcccga agggagaaag gcggacaggt atccggtaag cggcagggtc   6060
ggaacaggag agcgcacgag ggagcttcca gggggaaacg cctggtatct ttatagtcct   6120
gtcgggtttc gccacctctg acttgagcgt cgatttttgt gatgctcgtc aggggggcgg   6180
agcctatgga aaaacgccag caacgcggcc tttttacggt tcctggcctt ttgctggcct   6240
tttgctcaca tgttctttcc tgcgttatcc cctgattctg tggataaccg tattaccgcc   6300
tttgagtgag ctgataccgg tcgccgcagc cgaacgaccg agcgcagcga gtcagtgagc   6360
gaggaagcgg aagagcgccc aatacgcaaa ccgcctctcc ccgcgcgttg gccgattcat   6420
taatgcagct ggcacgacag gtttcccgac tggaaagcgg gcagtgagcg caacgcaatt   6480
aatgtgagtt acctcactca ttaggcaccc caggctttac actttatgct tccggctcct   6540
atgttgtgtg gaattgtgag cggataacaa tttcacacag gaaacagcta tgaccatgat   6600
tacgccaagc tcgaaatacg actcactata gggcgaattg ggtaccgggc cggccgtcga   6660
gcttgatggc atcgtggtgt cacgctcgtc gtttggtatg gcttcattca gctccggttc   6720
ccaacgatca aggcgagtta catgatcccc catgttgtga aaaaaagcgg ttagctcttc   6780
ggtcctccga tcgttgtcag aagtaagttg gccgcagtgt tatcactcat ggttatggca   6840
ggaactgcat aattctctta ctgtcatgcc atccgtaaga tgcttttctg tgactggtgt   6900
actcaaccaa gtcattctga gaatagtgta tgcggcgacc gagttgctct tgcccggcgt   6960
caacacggga taataccgcg ccacatagca gaactttaaa agtgctcatc attggaaaac   7020
gttcttcggg gcgaaaactc tcaaggatct taccgctgtt gagatccagt tcgatgtaac   7080
ccactcgtgc acccaactga tcttcagcat cttttacttt caccagcgtt tctgggtgag   7140
caaaaacagg aaggcaaaat gccgcaaaaa agggaataag ggcgacacgg aaatgttgaa   7200
tactcatact cttccttttt caatattatt gaagcattta tcagggttat tgtctcatga   7260
gcgatacata tttgaatgta tttagaaaaa taaacaaata ggggttccgc gcacatttcc   7320
ccgaaaagtg ccacctgacg tctaagaaac cattattatc atgacattaa cctataaaaa   7380
taggcgtatc acgaggccct ttcgtcttca agaattgggg atctacgtat ggtcattctt   7440
cttcagattc cctcatggag aagtgcggca gatgtatatg acagagtcgc cagtttccaa   7500
gagactttat tcaggcactt ccatgatagg caagagagaa gacccagaga tgttgttgtc   7560
ctagttacac atggtattta ttccagagta ttcctgatga aatggtttag atggacatac   7620
gaagagtttg aatcgtttac caatgttcct aacgggagcg taatggtgat ggaactggac   7680
gaatccatca atagatacgt cctgaggacc gtgctaccca aatggactga ttgtgaggga   7740
gacctaacta catagtgttt aaagattacg gatatttaac ttacttagaa taatgccatt   7800
tttttgagtt ataataatcc tacgttagtg tgagcgggat ttaaactgtg aggaccttaa   7860
tacattcaga cacttctgcg gtatcaccct acttattccc ttcgagatta tatctaggaa   7920
cccatcaggt tggtggaaga ttacccgttc taagactttt cagcttcctc tattgatgtt   7980
acacctggac accccttttc tggcatccag tttttaatct tcagtggcat gtgagattct   8040
ccgaaattaa ttaaagcaat cacacaattc tctcggatac cacctcggtt gaaactgaca   8100
ggtggtttgt tacgcatgct aatgcaaagg agcctatata cctttggctc ggctgctgta   8160
acagggaata taaagggcag cataatttag gagtttagtg aacttgcaac atttactatt   8220
ttcccttctt acgtaaatat ttttcttttt aattctaaat caatcttttt caattttttg   8280
tttgtattct tttcttgctt aaatctataa ctacaaaaaa cacatacata aactaaaa     8338
```

<210> SEQ ID NO 27
<211> LENGTH: 6702
<212> TYPE: DNA
<213> ORGANISM: Artificial sequence
<220> FEATURE:
<223> OTHER INFORMATION: Mutated form of the ACC1 gene from
Saccharomyces cerevisiae

<400> SEQUENCE: 27
atgagcgaag aaagcttatt cgagtcttct ccacagaaga tggagtacga aattacaaac 60
tactcagaaa gacatacaga acttccaggt catttcattg gcctcaatac agtagataaa 120
ctagaggagt ccccgttaag ggactttgtt aagagtcacg gtggtcacac ggtcatatcc 180
aagatcctga tagcaaataa tggtattgcc gccgtgaaag aaattagatc cgtcagaaaa 240
tgggcatacg agacgttcgg cgatgacaga accgtccaat tcgtcgccat ggccacccca 300
gaagatctgg aggccaacgc agaatatatc cgtatggccg atcaatacat tgaagtgcca 360
ggtggtacta ataataacaa ctacgctaac gtagacttga tcgtagacat cgccgaaaga 420
gcagacgtag acgccgtatg ggctggctgg ggtcacgcct ccgagaatcc actattgcct 480
gaaaaattgt cccagtctaa gaggaaagtc atctttattg ggcctccagg taacgccatg 540
aggtctttag gtgataaaat ctcctctacc attgtcgctc aaagtgctaa agtcccatgt 600
attccatggt ctggtaccgg tgttgacacc gttcacgtgg acgagaaaac cggtctggtc 660
tctgtcgacg atgacatcta tcaaaagggt tgttgtacct ctcctgaaga tggtttacaa 720
aaggccaagc gtattggttt tcctgtcatg attaaggcat ccgaaggtgg tggtggtaaa 780
ggtatcagac aagttgaacg tgaagaagat ttcatcgctt tataccacca ggcagccaac 840
gaaattccag gctcccccat tttcatcatg aagttggccg gtagagcgcg tcacttggaa 900
gttcaactgc tagcagatca gtacggtaca aatatttcct tgttcggtag agactgttcc 960
gttcagagac gtcatcaaaa aattatcgaa gaagcaccag ttacaattgc caaggctgaa 1020
acatttcacg agatggaaaa ggctgccgtc agactgggga aactagtcgg ttatgtctct 1080
gccggtaccg tggagtatct atattctcat gatgatggaa aattctactt tttagaattg 1140
aacccaagat tacaagtcga gcatccaaca acggaaatgg tctccggtgt taacttacct 1200
gcagctcaat tacaaatcgc tatgggtatc cctatgcata gaataagtga cattagaact 1260
ttatatggta tgaatcctca ttctgcctca gaaatcgatt tcgaattcaa aactcaagat 1320
gccaccaaga aacaaagaag acctattcca aagggtcatt gtaccgcttg tcgtatcaca 1380
tcagaagatc caaacgatgg attcaagcca tcgggtggta ctttgcatga actaaacttc 1440
cgttcttcct ctaatgtttg ggggttactt c tccgtgggta acaatggtaa tattcactcc 1500
ttttcggact ctcagttcgg ccatattttt gcttttggtg aaaatagaca agcttccagg 1560
aaacacatgg ttgttgccct gaaggaattg tccattaggg gtgatttcag aactactgtg 1620
gaatacttga tcaaactttt ggaaactgaa gatttcgagg ataacactat taccaccggt 1680
tggttggacg atttgattac tcataaaatg accgctgaaa agcctgatcc aactcttgcc 1740
gtcatttgcg gtgccgctac aaaggctttc ttagcatctg aagaagcccg ccacaagtat 1800
atcgaatcct tacaaaaggg acaagttcta tctaaagacc tactgcaaac tatgttccct 1860
gtagatttta tccatgaggg taaaagatac aagttcaccg tagctaaatc cggtaatgac 1920
cgttacacat tatttatcaa tggttctaaa tgtgatatca tactgcgtca actagctgat 1980
ggtggtcttt tgattgccat aggcggtaaa tcgcatacca tctattggaa agaagaagtt 2040

-continued

```
gctgctacaa gattatccgt tgactctatg actactttgt tggaagttga aaacgatcca   2100
acccagttgc gtactccatc ccctggtaaa ttggttaaat tcttggtgga aaatggtgaa   2160
cacattatca agggccaacc atatgcagaa attgaagtta tgaaaatgca aatgcctttg   2220
gtttctcaag aaaatggtat cgtccagtta ttaaagcaac ctggttctac cattgttgca   2280
ggtgatatca tggctattat gactcttgac gatccatcca aggtcaagca cgctctacca   2340
tttgaaggta tgctgccaga ttttggttct ccagttatcg aaggaaccaa acctgcctat   2400
aaattcaagt cattagtgtc tactttggaa aacattttga agggttatga caaccaagtt   2460
attatgaacg cttccttgca acaattgata gaggttttga gaaatccaaa actgccttac   2520
tcagaatgga aactacacat ctctgcttta cattcaagat tgcctgctaa gctagatgaa   2580
caaatggaag agttagttgc acgttctttg agacgtggtg ctgttttccc agctagacaa   2640
ttaagtaaat tgattgatat ggccgtgaag aatcctgaat acaaccccga caaattgctg   2700
ggcgccgtcg tggaaccatt ggcggatatt gctcataagt actctaacgg gttagaagcc   2760
catgaacatt ctatatttgt ccatttcttg gaagaatatt acgaagttga aaagttattc   2820
aatggtccaa atgttcgtga ggaaaatatc attctgaaat tgcgtgatga aaaccctaaa   2880
gatctagata aagttgcgct aactgttttg tctcattcga aagtttcagc gaagaataac   2940
ctgatcctag ctatcttgaa acattatcaa ccattgtgca agttatcttc taaagtttct   3000
gccattttct ctactcctct acaacatatt gttgaactag aatctaaggc taccgctaag   3060
gtcgctctac aagcaagaga aattttgatt caaggcgctt taccttcggt caaggaaaga   3120
actgaacaaa ttgaacatat cttaaaatcc tctgttgtga aggttgccta tggctcatcc   3180
aatccaaagc gctctgaacc agatttgaat atcttgaagg acttgatcga ttctaattac   3240
gttgtgttcg atgttttact tcaattccta acccatcaag acccagttgt gactgctgca   3300
gctgctcaag tctatattcg tcgtgcttat cgtgcttaca ccataggaga tattagagtt   3360
cacgaaggtg tcacagttcc aattgttgaa tggaaattcc aactaccttc agctgcgttc   3420
tccacctttc caactgttaa atctaaaatg ggtatgaaca gggctgttgc tgtttcagat   3480
ttgtcatatg ttgcaaacag tcagtcatct ccgttaagag aaggtatttt gatggctgtg   3540
gatcatttag atgatgttga tgaaattttg tcacaaagtt tggaagttat tcctcgtcac   3600
caatcttctt ctaacggacc tgctcctgat cgttctggta gctccgcatc gttgagtaat   3660
gttgctaatg tttgtgttgc ttctacagaa ggtttcgaat ctgaagagga aattttggta   3720
aggttgagag aaattttgga tttgaataag caggaattaa tcaatgcttc tatccgtcgt   3780
atcacattta tgttcggttt taaagatggg tcttatccaa agtattatac ttttaacggt   3840
ccaaattata acgaaaatga aacaattcgt cacattgagc cggctttggc cttccaactg   3900
gaattaggaa gattgtccaa cttcaacatt aaaccaattt tcactgataa tagaaacatc   3960
catgtctacg aagctgttag taagacttct ccattggata agagattctt tacaagaggt   4020
attattagaa cgggtcatat ccgtgatgac atttctattc aagaatatct gacttctgaa   4080
gctaacagat tgatgagtga tatattggat aatttagaag tcaccgacac ttcaaattct   4140
gatttgaatc atatcttcat caacttcatt gcggtgtttg atatctctcc agaagatgtc   4200
gaagccgcct tcggtggttt cttagaaaga tttggtaaga gattgttgag attgcgtgtt   4260
tcttctgccg aaattagaat catcatcaaa gatcctcaaa caggtgcccc agtaccattg   4320
cgtgccttga tcaataacgt ttctggttat gttatcaaaa cagaaatgta caccgaagtc   4380
```

-continued

```
aagaacgcaa aaggtgaatg ggtatttaag tctttgggta aacctggatc catgcattta   4440
agacctattg ctactcctta ccctgttaag gaatggttgc aaccaaaacg ttataaggca   4500
cacttgatgg gtaccacata tgtctatgac ttcccagaat tattccgcca agcatcgtca   4560
tcccaatgga aaaatttctc tgcagatgtt aagttaacag atgatttctt tatttccaac   4620
gagttgattg aagatgaaaa cggcgaatta actgaggtgg aaagagaacc tggtgccaac   4680
gctattggta tggttgcctt taagattact gtaaagactc ctgaatatcc aagaggccgt   4740
caatttgttg ttgttgctaa cgatatcaca ttcaagatcg gttcctttgg tccacaagaa   4800
gacgaattct tcaataaggt tactgaatat gctagaaagc gtggtatccc aagaatttac   4860
ttggctgcaa actcaggtgc cagaattggt atggctgaag agattgttcc actatttcaa   4920
gttgcatgga atgatgctgc caatccggac aagggcttcc aatacttata cttaacaagt   4980
gaaggtatgg aaactttaaa gaaatttgac aaagaaaatt ctgttctcac tgaacgtact   5040
gttataaacg gtgaagaaag atttgtcatc aagacaatta ttggttctga agatgggtta   5100
ggtgtcgaat gtctacgtgg atctggttta attgctggtg caacgtcaag ggcttaccac   5160
gatatcttca ctatcacctt agtcacttgt agatccgtcg gtatcggtgc ttatttggtt   5220
cgtttgggtc aaagagctat tcaggtcgaa ggccagccaa ttattttaac tggtgctcct   5280
gcaatcaaca aaatgctggg tagagaagtt tatacttcta acttacaatt gggtggtact   5340
caaatcatgt ataacaacgg tgtttcacat ttgactgctg ttgacgattt agctggtgta   5400
gagaagattg ttgaatggat gtcttatgtt ccagccaagc gtaatatgcc agttcctatc   5460
ttggaaacta aagacacatg ggatagacca gttgatttca ctccaactaa tgatgaaact   5520
tacgatgtaa gatggatgat tgaaggtcgt gagactgaaa gtggatttga atatggtttg   5580
tttgataaag ggtctttctt tgaaactttg tcaggatggg ccaaaggtgt tgtcgttggt   5640
agagcccgtc ttggtggtat tccactgggt gttattggtg ttgaaacaag aactgtcgag   5700
aacttgattc ctgctgatcc agctaatcca aatagtgctg aaacattaat tcaagaacct   5760
ggtcaagttt ggcatccaaa ctccgccttc aagactgctc aagctatcaa tgactttaac   5820
aacggtgaac aattgccaat gatgattttg gccaactgga gaggtttctc tggtggtcaa   5880
cgtgatatgt tcaacgaagt cttgaagtat ggttcgttta ttgttgacgc attggtggat   5940
tacaaacaac caattattat ctatatccca cctaccggtg aactaagagg tggttcatgg   6000
gttgttgtcg atccaactat caacgctgac caaatggaaa tgtatgccga cgtcaacgct   6060
agagctggtg ttttggaacc acaaggtatg gttggtatca agttccgtag agaaaaattg   6120
ctggacacca tgaacagatt ggatgacaag tacagagaat tgagatctca attatccaac   6180
aagagtttgg ctccagaagt acatcagcaa atatccaagc aattagctga tcgtgagaga   6240
gaactattgc caatttacgg acaaatcagt cttcaatttg ctgatttgca cgataggtct   6300
tcacgtatgg tggccaaggg tgttatttct aaggaactgg aatggaccga ggcacgtcgt   6360
ttcttcttct ggagattgag aagaagattg aacgaagaat atttgattaa aaggttgagc   6420
catcaggtag gcgaagcatc aagattagaa aagatcgcaa gaattagatc gtggtaccct   6480
gcttcagtgg accatgaaga tgataggcaa gtcgcaacat ggattgaaga aaactacaaa   6540
actttggacg ataaactaaa gggtttgaaa ttagagtcat tcgctcaaga cttagctaaa   6600
aagatcagaa gcgaccatga caatgctatt gatggattat ctgaagttat caagatgtta   6660
tctaccgatg ataaagaaaa attgttgaag actttgaaat aa                       6702
```

```
<210> SEQ ID NO 28
<211> LENGTH: 1032
<212> TYPE: DNA
<213> ORGANISM: Artificial sequence
<220> FEATURE:
<223> OTHER INFORMATION: Synthetic sequence codon-optimized for
      expression in Saccharomcyes cerevisiae based on protein sequence
      from Calanus hyperboreus

<400> SEQUENCE: 28

atggaagaaa tcaacatcaa gcctcaagac ggtttaaaag aaatggaaac agaaggtgac      60

agtggtcatg cctcagacgc ctccgacgaa gttttggaat acgctaaaaa tgttgaatca     120

gtcgaattag aaccatacga aactgatata gtatggcaaa acgttgccaa gttcgtcata     180

atccatgctt tgtttttcta tggtgcaaca tacttgcctt ctatgtcatt gaacatgtgg     240

atttttatgt tgatatctac tcaaatctca ggtttaggta ttacaatggg tgcacataga     300

ttatgggccc acaagacata caaggctaag ttgccattga gaatattctt gaccttcgct     360

aattccttag caggtcaaaa ctccatatac atctggagta gagatcatag aacccatcac     420

aaatgtagtg aaaagatggg tgacccacac aatgccaaga gaggtttctt tttcgctcac     480

atgggttggt tgatggttag aaaacaccct gaagtcacaa gagcaggtaa aaccgtaaac     540

atgactgatt tggaaaacga caaattggtt atgttacaac ataagtacta catcacctcc     600

ttcttgttat gtggtttcgt aatcccaact gttttgcctt atttgttgtg gggtgaatgc     660

ttatatactg cctacttcat ggctattttt agatacgtca tcacattgca tgtcacctgg     720

ttggtaaatt ctgctgcaca cttctttggt tacaagccat acgataagac tataggtcct     780

acagaaaaca tgttggtttc attgttggct atgggtgaag gtttccataa ctatcatcac     840

acatttcctt atgactactc cacaagtgaa tggggttaca cctttaacac tacttcaaga     900

atcattgatg ctatggcttc aataggtcaa gcctatgatt tgagaaccgc atctaaagcc     960

actatcgaag ccagaagtgt cagaacaggt ttaccagaat taacagcaat ctatcaaaag    1020

aaagcattat aa                                                        1032


<210> SEQ ID NO 29
<211> LENGTH: 1604
<212> TYPE: DNA
<213> ORGANISM: Yarrowia lipolytica

<400> SEQUENCE: 29

atgagtgagt atttcccaca aaacaaatgc ccccagcagc gaacacgccc cgacaccgat      60

acacgcagca gcgcggaggt gacacaaatg cctcggattt gcacctgtga tcatgaacac     120

gttacgtcga catgggacac acgtcctgtg taatcgacca ttcagtcaac gaaacagatg     180

ttttaggagg acacctcgag ccagaagatg atcgaccggg gatactaccg gtagttgtgt     240

caccaacact cagctcaagc gctgttatcg tcgtcgcggg gtgatttgac ccctgatcta     300

cgcgtcgcgt acaacaaaac gtggcagatt tggggtttaa tcgccggaca acagaaacga     360

atacgcagag acagtaacgg atggataata caaatcctac ctcgcccctt gatctatcta     420

cgtctctcac atgtcgcatg atccatatcg ttacttccga tctcatgttt gacaaaatcc     480

atacaaggcg aagtgaggca aaccccgaac atatacgtga caacaagcct cgtgtcacta     540

ctatgtggtg gccgccacaa cactgacgtg acgtcctttt tgggacacga cctctgtcac     600

acctttacta tccgctctat actaactcag gcgccgtccc tattgaattc aacgtcccct     660

ccgtggaccg accctttggt atctacctct gggccatctt tgaccaggcc tgggagaagc     720
```

-continued

```
ttttcggctg gcccgcgtcc tctttcattt tcgtgcgaaa tgaccccaac atcccctttt    780

cctctacccc tcccgtgatc attgccatca ttgtgtacta cattgtcatc tttggcggcc    840

gagaggtgat gcgaaacctg tctcccatcc gactcaactg gctcttccag atccacaaca    900

tcttcctcac ccttctgtcc ggtatgctcc tcctcctcct cgttgagcag ctcttcccca    960

tcattgtccg acagggtatc ctctacgcca tctgcgacta cggatcttgg actcagccca   1020

ttgtcttctg ctactacctc aactacctga ccaagtactt tgagctgatc gacaccgttt   1080

tccttgtgct gcgaaagaag aagctgactt tcctccacac ctaccaccat ggtgccactg   1140

ctcttctgtg ctacacccag ctcattggta agacctcggt ctcttgggtc cccatcaccc   1200

ttaacctgtt tgtccacgtt gtcatgtact tctactactt cctggctgcg cgaggtatcc   1260

gagtgtggtg gaaggagtgg gtcacccggc tccagatcat ccagttcgtt atcgatcttg   1320

gatttgtcta ctttgcctct tacacctact tcacctctac ctactggccc tggatgccca   1380

acatgggctc ttgtgccggc gaggagtttg ctgctattta cggctgtggt ctgctgacct   1440

cttacctctt cctcttcatc gccttctaca tcaactctta ccgaaagccc tcttccaagg   1500

gaccttccaa gcctgttgtt gctgtcgatg gccctgttgg cggcgtcaac gcccagactg   1560

gtgcttctcg aggccagacc actacccgat ctcgacgagc ataa                     1604
```

<210> SEQ ID NO 30
<211> LENGTH: 1449
<212> TYPE: DNA
<213> ORGANISM: Yarrowia lipolytica

<400> SEQUENCE: 30

```
atggtgaaaa acgtggacca agtggatctc tcgcaggtcg acaccattgc ctccggccga     60

gatgtcaact acaaggtcaa gtacacctcc ggcgttaaga tgagccaggg cgcctacgac    120

gacaagggcc gccacatttc cgagcagccc ttcacctggg ccaactggca ccagcacatc    180

aactggctca acttcattct ggtgattgcg ctgcctctgt cgtcctttgc tgccgctccc    240

ttcgtctcct tcaactggaa gaccgccgcg tttgctgtcg gctattacat gtgcaccggt    300

ctcggtatca ccgccggcta ccaccgaatg tgggcccatc gagcctacaa ggccgctctg    360

cccgttcgaa tcatccttgc tctgtttgga ggaggagctg tcgagggctc catccgatgg    420

tgggcctcgt ctcaccgagt ccaccaccga tggaccgact ccaacaagga cccttacgac    480

gcccgaaagg gattctggtt ctcccacttt ggctggatgc tgcttgtgcc caaccccaag    540

aacaagggcc gaactgacat ttctgacctc aacaacgact gggttgtccg actccagcac    600

aagtactacg tttacgttct cgtcttcatg gccattgttc tgcccaccct cgtctgtggc    660

tttggctggg gcgactggaa gggaggtctt gtctacgccg gtatcatgcg atacaccttt    720

gtgcagcagg tgactttctg tgtcaactcc cttgcccact ggattggaga gcagcccttc    780

gacgaccgac gaactccccg agaccacgct cttaccgccc tggtcacctt tggagagggc    840

taccacaact tccaccacga gttcccctcg gactaccgaa acgccctcat ctggtaccag    900

tacgacccca ccaagtggct catctggacc ctcaagcagg ttggtctcgc ctgggacctc    960

cagaccttct cccagaacgc catcgagcag ggtctcgtgc agcagcgaca gaagaagctg   1020

gacaagtggc gaaacaacct caactggggt atccccattg agcagctgcc tgtcattgag   1080

tttgaggagt tccaagagca ggccaagacc cgagatctgg ttctcatttc tggcattgtc   1140

cacgacgtgt ctgcctttgt cgagcaccac cctggtggaa aggccctcat tatgagcgcc   1200

gtcggcaagg acggtaccgc tgtcttcaac ggaggtgtct accgacactc caacgctggc   1260
```

```
cacaacctgc ttgccaccat gcgagtttcg gtcattcgag gcggcatgga ggttgaggtg   1320

tggaagactg cccagaacga aaagaaggac cagaacattg tctccgatga gagtggaaac   1380

cgaatccacc gagctggtct ccaggccacc cgggtcgaga accccggtat gtctggcatg   1440

gctgcttag                                                            1449
```

```
<210> SEQ ID NO 31
<211> LENGTH: 1551
<212> TYPE: DNA
<213> ORGANISM: Artificial sequence
<220> FEATURE:
<223> OTHER INFORMATION: Synthetic sequence codon-optimized for
      expression in Yarrowia lipolytica based on protein sequence from
      Apis mellifera

<400> SEQUENCE: 31

atgtctacta tttccgataa ccagtgtact tctgttcgag acttctacaa ggaccgatcc     60

atcttcatca ccggcggcac cggcttcatg ggaaaggtcc tggtggagaa gctgctccga    120

tcctgccccg gcatcaagaa catctacatt ctgatgcgac ccaagaagtc tcaggacatt    180

cagcagcgac tccagaagct gctcgacgtc cccctcttcg acaagctgcg acgagacacc    240

cccgacgagc tgctcaagat cattcccatt gctggcgacg tcaccgagca cgagctgggt    300

atttccgagg ccgaccagaa cgtgatcatt cgagacgtct ccatcgtgtt ccactctgcc    360

gctaccgtca agttcgacga gcccctgaag cgatccgtgc acatcaacat gattggaacc    420

aagcagctgc tcaacctctg ccaccgaatg cacaacctgg aggccctgat tcacgtgtct    480

accgcctact gcaactgtga ccgatacgac gtcgctgagg aaatctaccc cgtgtccgct    540

gagcccgagg agattatggc cctcaccaag ctgatggact ctcagatgat cgacaacatt    600

acccccaccc tgatcggtaa ccgacccaac acctacacct tcaccaaggc tctcaccgag    660

cgaatgctcc agtccgagtg tggacacctg cccatcgcca ttgtccgacc ctccatcgtg    720

ctctcctctt tccgagagcc cgtctctggc tgggtggaca acctgaacgg acctaccgga    780

attgtggccg ctgccggcaa gggtttcttc cgatctatgc tctgccagaa gaacatggtc    840

gccgacctgg tccccgtgga catcgtgatt aacctcatga tctgtaccgc ttggcgaacc    900

gccaccaacc gaaccaagac catccccatc taccactgct gtaccggcca gcagaacccc    960

atcacctggc agcagttcgt ggagctgatt ctgaagtaca accgaatgca ccctcccaac   1020

gacaccatct ggtggcccga cggcaagtgc cacaccttcg ctattgtcaa caacgtgtgt   1080

aagctgttcc agcacctgct ccccgcccac atcctcgact tcattttccg actgcgaggc   1140

aagcccgcta tcatggtcgg actgcacgag aagattgaca aggccgtgaa gtgcctggag   1200

tacttcacca tgcagcagtg gaacttccga gacgacaacg tccgacagct gtctggagag   1260

ctgtctcccg aggaccgaca gattttcatg ttcgacgtga agcagattga ctggccctct   1320

tacctggagc agtacatcct gggcatccga cagttcatca ttaaggactc ccctgagacc   1380

ctgcccgctg cccgatctca catcaagaag ctctactgga ttcagaaggt cgtggagttc   1440

ggcatgctgc tcgtcgtgct gcgattcctg ctcctgcgaa tccctatggc ccagtccgcc   1500

tgtttcaccc tgctctctgc catcctccga atgtgccgaa tgattgtgta a             1551
```

```
<210> SEQ ID NO 32
<211> LENGTH: 1542
<212> TYPE: DNA
<213> ORGANISM: Artificial sequence
<220> FEATURE:
```

<223> OTHER INFORMATION: Synthetic sequence codon-optimized for expression in Yarrowia lipolytica based on protein sequence from Marinobacter aquaeolei VT8

<400> SEQUENCE: 32

```
atggccatcc agcaggtgca ccacgctgac acctcctctt ccaaggtgct cggacagctg     60

cgaggcaagc gagtcctgat taccggcacc accggtttcc tcggaaaggt cgtcctggag    120

cgactgatcc gagccgtgcc cgacatcggc gctatctacc tgctcattcg aggaaacaag    180

cgacaccccg acgcccgatc tcgattcctg gaggagatcg ctacctcttc cgtcttcgac    240

cgactccgag aggctgactc tgagggattc gacgctttcc tggaggagcg aatccactgt    300

gtgaccggtg aagtcaccga ggctggcttc ggtattggac aggaagacta ccgaaagctg    360

gccaccgagc tggacgctgt gatcaactct gccgcttccg tcaacttccg agaggagctg    420

gacaaggccc tcgctatcaa caccctgtgc ctccgaaaca ttgccggaat ggtggacctg    480

aaccccaagc tcgctgtcct ccaggtctcc acctgttacg tcaacggtat gaactctgga    540

caggtgaccg agtccgtcat caagcccgcc ggtgaagctg tgccccgatc cccgacgga    600

ttctacgaga tcgaggagct ggtgcgactg ctccaggaca agattgagga cgtccaggcc    660

cgatactctg gcaaggtgct ggagcgaaag ctcgtggacc tgggcatccg agaggctaac    720

cgatacggct ggtccgacac ctacaccttc accaagtggc tgggcgagca gctgctcatg    780

aaggccctca acggtcgaac cctcaccatc ctgcgaccct ctatcattga gtctgccctg    840

gaggagcctg ctcctggatg gattgagggt gtcaaggtgg ccgacgctat cattctggcc    900

tacgcccgag agaaggtcac cctcttcccc ggaaagcgat ctggcatcat tgacgtcatc    960

cccgtggacc tcgtcgccaa ctctatcatt ctgtccctcg ctgaggctct gggtgaacct   1020

ggccgacgac gaatctacca gtgctgttct ggcggtggaa accccatctc cctgggagag   1080

ttcattgacc acctcatggc cgagtctaag gctaactacg ccgcttacga ccacctgttc   1140

taccgacagc cctccaagcc cttcctcgcc gtgaaccgag ccctgttcga cctggtcatc   1200

tctggtgtcc gactgcccct ctccctgacc gaccgagtcc tgaagctgct cggcaactcc   1260

cgagacctga agatgctgcg aaacctcgac accacccagt ccctggccac catcttcggc   1320

ttctacaccg ctcccgacta cattttccga aacgacgagc tgatggccct cgctaaccga   1380

atgggagagg tggacaaggg actgttcccc gtggacgccc gactcatcga ctgggagctg   1440

tacctgcgaa agattcacct ggccggtctc aaccgatacg ctctgaagga gcgaaaggtc   1500

tactccctca agaccgcccg acagcgaaag aaggccgctt aa                      1542
```

<210> SEQ ID NO 33
<211> LENGTH: 1482
<212> TYPE: DNA
<213> ORGANISM: Artificial sequence
<220> FEATURE:
<223> OTHER INFORMATION: Synthetic sequence codon-optimized for expression in Yarrowia lipolytica based on protein sequence from Simmondsia chinensis

<400> SEQUENCE: 33

```
atggaggaga tgggctccat cctggagttc ctggacaaca aggccattct cgtgaccgga     60

gctaccggct ccctcgctaa gattttcgtg gagaaggtcc tgcgatctca gcccaacgtc    120

aagaagctct acctgctgct ccgagctacc gacgacgaga ccgccgctct gcgactccag    180

aacgaggtgt tcggcaagga gctgttcaag gtcctgaagc agaacctcgg agctaacttc    240

tactccttcg tgtctgagaa ggtcaccgtc gtgcccggcg acatcaccgg agaggacctg    300
```

```
tgcctcaagg acgtcaacct gaaggaagag atgtggcgag agattgacgt cgtggtcaac    360

ctcgccgcta ccatcaactt cattgagcga tacgacgtgt ccctcctgat caacacctac    420

ggtgccaagt acgtcctgga cttcgctaag aagtgtaaca agctcaagat tttcgtgcac    480

gtctccaccg cctacgtgtc tggagagaag aacggcctga tcctggagaa gccctactac    540

atgggagagt ctctgaacgg ccgactggga ctcgacatca acgtggagaa gaagctggtc    600

gaggccaaga ttaacgagct tcaggccgct ggcgctaccg agaagtccat caagtctacc    660

atgaaggaca tgggcattga gcgagcccga cactggggtt ggcccaacgt gtacgtcttc    720

accaaggctc tgggagagat gctcctgatg cagtacaagg gcgacatccc cctgaccatc    780

attcgaccca ccatcattac ctccaccttc aaggagcctt tccctggttg ggtggaggga    840

gtccgaacca ttgacaacgt gcccgtctac tacggcaagg gccgactgcg atgcatgctc    900

tgtggaccct ctaccatcat tgacctgatc cccgccgaca tggtggtcaa cgccaccatt    960

gtggctatgg tcgcccacgc taaccagcga tacgtggagc ccgtcaccta ccacgtcggt   1020

tcctctgccg ctaaccccat gaagctctct gctctgcctg agatggctca ccgatacttc   1080

accaagaacc cctggatcaa ccctgaccga aaccctgtgc acgtgggacg agctatggtc   1140

ttctcctcct tctccacctt ccacctgtac ctcaccctga acttcctcct gcccctcaag   1200

gtcctggaga tcgctaacac cattttctgc cagtggttca agggcaagta catggacctg   1260

aagcgaaaga cccgactcct gctccgactg gtggacatct acaagcccta cctcttcttc   1320

cagggtattt tcgacgacat gaacaccgag aagctgcgaa tcgccgctaa ggagtctatt   1380

gtcgaggccg acatgttcta cttcgacccc cgagctatta actgggagga ctacttcctg   1440

aagacccact tccccggtgt ggtcgagcac gtgctcaact aa                      1482
```

<210> SEQ ID NO 34
<211> LENGTH: 1524
<212> TYPE: DNA
<213> ORGANISM: Artificial sequence
<220> FEATURE:
<223> OTHER INFORMATION: Synthetic sequence codon-optimized for expression in Yarrowia lipolytica based on protein sequence from Triticum aestivum

<400> SEQUENCE: 34

```
atggtggaca ccctgtctga ggagaacatc attggatact tcaagaacaa gtctatcctc     60

attaccggct ccaccggctt cctgggcaag atcctggtcg agaagattct gcgagtccag    120

cccgacgtca agaaaatcta cctgcccgtc cgagctgtgg acgccgctgc cgctaagcac    180

cgagtggaga ccgaggtcgt gggcaaggag ctgttcggac tgctccgaga gaagcacggc    240

ggtcgattcc agtctttcat ctgggagaag attgtccccc tggccggtga cgtgatgcga    300

gaggacttcg gagtggactc cgagaccctc cgagagctgc gagtgaccca ggagctggac    360

gtcatcgtga acggcgccgc taccaccaac ttctacgagc gatacgacgt cgccctggac    420

gtcaacgtga tgggtgtgaa gcacatgtgc aacttcgcta agaagtgtcc caacctgaag    480

gtcctgctcc acgtgtccac cgcctacgtc gctggcgaga agcagggtct cgtgcaggag    540

cgacccttca agaacggtga aaccctgctg gagggcaccc gactggacat tgacaccgag    600

ctgaagctgg ccaaggacct gaagaagcag ctggaggctg acgtggactc ctcccccaag    660

gccgagcgaa aggctatgaa ggacctcgga ctgacccgag cccgacactt ccgatggccc    720

aacacctacg tcttcaccaa gtctatgggc gagatggtgc tctcccagct ccagtgcgac    780
```

-continued

```
gtccccgtcg tgatcgtgcg accctctatc attacctccg tccagaacga ccctctgcct    840

ggatggattg agggcacccg aaccattgac accatcgtga ttggttacgc caagcagaac    900

ctgacctact tcctcgctga cctcaacctg actatggacg tcatgcccgg agacatggtc    960

gtgaacgcca tgatggccgc tattgtggct cactcctctt cctctctgga gaagaccaag   1020

tctcacccca agcagcacgc cccgctgtc taccacgtgt cctcttccct gcgaaaccct   1080

gctccttaca acgtcctcca cgaggctggc ttccgatact tcaccgagca cccccgagtc   1140

ggacctgacg gacgaaccgt gcgaacccac aagatgacct tcctgtcctc tatggcctcc   1200

ttccacctgt tcatgatgct ccgataccga ctgctgctgg agctgctgca cctcctgtcc   1260

atcctgtgct gtggtctctt cggactggac accctctacc acgaccaggc ccgaaagtac   1320

cgattcgtca tgcacctggt ggacctctac ggacccttcg ctctgttcaa gggctgtttc   1380

gacgacgtga acctcaacaa gctccgactg gccatgacct ctaaccacgg ctccctgttc   1440

aacttcgacc ccaagaccat tgactgggac gagtacttct accgagtcca catccccggt   1500

gtgattaagt acatgctgaa gtaa                                          1524
```

<210> SEQ ID NO 35
<211> LENGTH: 1377
<212> TYPE: DNA
<213> ORGANISM: Artificial sequence
<220> FEATURE:
<223> OTHER INFORMATION: Synthetic sequence codon-optimized for expression in Yarrowia lipolytica based on protein sequence from Acinetobacter baylyi ADP1

<400> SEQUENCE: 35

```
atgcgacccc tgcaccccat cgacttcatc ttcctgtccc tggagaagcg acagcagccc     60

atgcacgtcg gcggtctgtt cctcttccag atccccgaca acgcccccga caccttcatt    120

caggacctgg tcaacgacat ccgaatttct aagtccatcc ccgtccctcc cttcaacaac    180

aagctgaacg gactcttctg ggacgaggac gaggagttcg acctggacca ccacttccga    240

cacattgctc tccctcaccc tggacgaatc cgagagctgc tcatctacat ttcccaggag    300

cactctaccc tgctcgaccg agctaagccc ctgtggacct gcaacatcat tgagggaatc    360

gagggcaacc gattcgccat gtacttcaag attcaccacg ctatggtgga cggtgtggcc    420

ggaatgcgac tgattgagaa gtctctctcc cacgacgtga ccgagaagtc tatcgtccct    480

ccctggtgtg tggagggcaa gcgagctaag cgactgcgag agcccaagac cggaaagatc    540

aagaagatta tgtccggcat caagtctcag ctccaggcca cccccaccgt cattcaggag    600

ctgtcccaga ccgtgttcaa ggacatcgga cgaaaccccg accacgtctc ctctttccag    660

gccccctgct ctatcctgaa ccagcgagtg tcctcttccc gacgattcgc cgctcagtcc    720

ttcgacctcg accgattccg aaacatcgct aagtctctga acgtcaccat taacgacgtg    780

gttctggctg tgtgttccgg agccctgcga gcttacctca tgtctcacaa ctccctgccc    840

tctaagcccc tcatcgctat ggtccccgct tctattcgaa acgacgactc cgacgtgtct    900

aaccgaatca ccatgattct ggccaacctc gctacccaca aggacgaccc cctccagcga    960

ctggagatca ttcgacgatc cgtccagaac tctaagcagc gattcaagcg aatgacctcc   1020

gaccagattc tgaactactc tgctgtcgtg tacggccccg ccggtctcaa catcatttcc   1080

ggcatgatgc ccaagcgaca ggctttcaac ctggtcatct ctaacgtgcc tggtccccga   1140

gagcctctct actggaacgg agccaagctg gacgctctct accctgcttc cattgtcctg   1200

gacggacagg ccctcaacat taccatgacc tcttacctgg acaagctgga ggtcggtctg   1260
```

attgcttgcc gaaacgccct cccccgaatg cagaacctgc tcacccacct ggaggaagag 1320
atccagctct tcgagggtgt gatcgctaag caggaagaca ttaagaccgc caactaa 1377

<210> SEQ ID NO 36
<211> LENGTH: 1446
<212> TYPE: DNA
<213> ORGANISM: Artificial sequence
<220> FEATURE:
<223> OTHER INFORMATION: Synthetic sequence codon-optimized for expression in Yarrowia lipolytica based on protein sequence from Arabidopsis thaliana

<400> SEQUENCE: 36
atgaaggccg agaaggtcat ggagcgagag atcgagacca cccccattga gcccctctcc 60
cccatgtctc acatgctgtc ctctcccaac ttcttcatcg tgattacctt cggattcaag 120
acccgatgca accgatccgc cttcgtggac ggcatcaaca acaccctgat taacgctccc 180
cgattctcct ctaagatgga gatcaactac aagaagaagg gagagcccgt ctggattccc 240
gtgaagctcc gagtggacga ccacatcatt gtgcccgacc tggagtactc taacatccag 300
aaccccgacc agttcgtcga ggactacacc tccaacatcg ccaacattcc tatggacatg 360
tctaagcccc tgtgggagtt ccacctgctc aacatgaaga cctccaaggc cgagtctctc 420
gctatcgtca agattcacca ctccatcgga gacggcatgt ccctgatgtc tctgctcctg 480
gcttgctccc gaaagatttc tgaccccgac gctctcgtgt ccaacaccac cgctaccaag 540
aagcccgccg actctatggc ttggtggctg ttcgtcggct tctggttcat gatccgagtg 600
accttcacca ccattgtcga gttctccaag ctcatgctga ccgtgtgctt cctggaggac 660
accaagaacc ccctgatggg caacccctcc gacggtttcc agtcttggaa ggtcgtgcac 720
cgaatcattt ctttcgagga cgtcaagctg atcaaggaca ccatgaacat gaaggtcaac 780
gacgtgctgc tcggaatgac ccaggctgga ctctcccgat acctgtcctc taagtacgac 840
ggctccaccg ccgagaagaa gaagatcctg gagaagctgc gagtgcgagg agccgtcgct 900
atcaacctcc gacccgccac caagattgag gacctggccg acatgatggc taagggttcc 960
aagtgccgat ggggtaactt catcggaacc gtgattttcc ccctctgggt caagtctgag 1020
aaggaccccc tggagtacat ccgacgagct aaggctacta tggaccgaaa gaagatttcc 1080
ctggaggcct tcttcttcta cggcatcatt aagttcaccc tgaagttctt cggcggcaag 1140
gccgtggagg ctttcggcaa gcgaatcttc ggacacacct ccctcgcttt ctctaacgtc 1200
aagggtcccg acgaggagat ttccttcttc caccacccca tctcctacat tgctggctct 1260
gctctggtgg gtgcccaggc tctgaacatc cacttcattt cttacgtgga caagatcgtc 1320
attaacctgg ccgtggacac caccaccatc caggaccccca accgactctg tgacgacatg 1380
gtcgaggccc tggagatcat taagtccgct acccagggag agattttcca caagaccgag 1440
gtctaa 1446

<210> SEQ ID NO 37
<211> LENGTH: 1020
<212> TYPE: DNA
<213> ORGANISM: Artificial sequence
<220> FEATURE:
<223> OTHER INFORMATION: Synthetic sequence codon-optimized for expression in Yarrowia lipolytica based on protein sequence from Euglena gracilis

<400> SEQUENCE: 37

```
atgttcacca tcccccgacg agtcaaggcc ggacgaaagc gattcctgct ctgctccccc     60

gtgctgctcc tgaacatcat gcagccctac attttcttct ggaccgtcgg ccgacactac    120

tgcaacttca tcccccctcta cgccgctttc tgtacctggt ggaccgcctt caaggtcatg    180

gctttcggca ttggtcgagg acccctctgt cagttctccg ccttccacaa gttcgctgtc    240

gtgatgctgc tgcctatcct gccccacggc gacaccaacc acggtgtcaa ggacgagcga    300

tctggctcct cttggtcctc tcccacctac ctggagatgt tcgccaagtt ctgcggcctc    360

ggtctgtgta cctacggtat ttcccagctc tctcacgacg gattccccgt cctgtacaac    420

gtgttcctct ccctgatcat gtacctccac atttgcgtgc agtacaccgg ttccaacctg    480

gccacctcta aggtcctcca ggtgcccctg tctgacggta tgaaccagcc ctacttctct    540

acctccctgt ctaacttctg gggacgacga tggaacctcg tcgcttcctc ttccctgcga    600

cacgtcgtgt acgaccccat tcgagaggga cgactcgtgc ccaagggaca ccctgaggag    660

aagcccggcg gcggcaagga agtctcccga aaggtgctcg gctctctgat ggccttcctg    720

gtctccggta tcatgcacga gtacattctc tggctggcta ccggattctg gtctggccag    780

atgctcctgt tcttcgtggt gcacggcgtg gctgtggccg ctgagcgagt cgctaaggtg    840

gcttgggctc gacacggtct ccctgccatc ccctgtgctg tgtccatccc catgaccatt    900

ggtttcctgt tcggcaccgc cgagctgctg ttctaccctc ccattttctc tgccaactgg    960

gctgagcacg gagtcgctga cctgcgacga cagttccgat ccctcggcct gtctgtgtaa   1020
```

```
<210> SEQ ID NO 38
<211> LENGTH: 1059
<212> TYPE: DNA
<213> ORGANISM: Artificial sequence
<220> FEATURE:
<223> OTHER INFORMATION: Synthetic sequence codon-optimized for
      expression in Yarrowia lipolytica based on protein sequence from
      Simmondsia chinensis

<400> SEQUENCE: 38

atggaggtgg agaaggagct gaagaccttc tccgaggtct ggatctctgc tattgccgct     60

gcctgctact gtcgattcgt ccccgctgtg gctccccacg gcggcgccct gcgactgctc    120

ctgctcctgc ccgtcgtgct cctgttcatc ttcctgcccc tccgactgtc ctctttccac    180

ctgggaggcc ccaccgctct ctacctggtg tggctcgcca acttcaagct cctgctcttc    240

gccttccacc tgggacccct ctccaacccc tccctgtctc tgctccactt catctctacc    300

accctgctcc ccattaagtt ccgagacgac ccctccaacg accacgagaa gaacaagcga    360

accctgtctt tcgagtggcg aaaggtcgtg ctgttcgtcg ctaagctcgt gttcttcgcc    420

ggtatcctca aaatctacga gttccgaaag gacctgcccc atttcgtcat ctccgtgctc    480

tactgcttcc acttctacct gggcaccgag atcaccctcg ctgcctctgc tgtgattgcc    540

cgagccaccc tcggactgga cctctacccc cagttcaacg agccctacct ggccacctcc    600

ctccaggact tctggggacg acgatggaac ctgatggtct ctgacattct gggactcacc    660

acctaccagc ccgtccgacg agtgctgtcc cgatgggtgc gactccgatg ggaggtggct    720

ggagccatgc tggtcgcttt caccgtgtcc ggtctcatgc acgaggtctt cttcttctac    780

ctgacccgag cccgaccttc ttgggaggtc accggtttct tcgtcctcca cggagtgtgt    840

accgctgtcg agatggtcgt gaagaaggcc gtgtccggca aggtccgact gcgacgagag    900

gtgtctggag ccctcaccgt cggcttcgtc atggtgaccg gtggatggct gttcctcccc    960

cagctggtgc gacacggtgt ggacctgaag accattgacg agtaccccgt catgttcaac   1020
```

```
tacacccaga agaagctgat gggcctgctc ggttggtaa                        1059


<210> SEQ ID NO 39
<211> LENGTH: 9266
<212> TYPE: DNA
<213> ORGANISM: Artificial sequence
<220> FEATURE:
<223> OTHER INFORMATION: Synthetic sequence codon-optimized for
      expression in Saccharomcyes cerevisiae based on protein sequence
      from Mycobacterium vaccae

<400> SEQUENCE: 39

atgacaatca acgatcaaca tagagccgcc gctggtagtg actcaagaac tggtcaagac     60

ttcgaacctt tatctggtac acacgccttg gtagatagat tacatgctgg tgaaccatac    120

gctgtcgcat ttggtggtca aggtggtcct tggttagaaa atttggaaga attagttaac    180

tcagctggta tcgaatctga aatttcacaa ttggtagccg aagctgaatt aatgttggaa    240

ccattggcta gagaattagt tgtagtcaga ccaattggtt tcgaacctat gaagtggata    300

agagcattag ctgctgatga accattgcct gccgctaaag atttgactac agcagccata    360

tctggtccag gtatcttgtt aacacaaatg gctgcacaaa gagctttgaa gagacaaggt    420

ttagatttgg acgcacaccc acctgttgca attgccggtc attcacaagg tgtaactgct    480

gtcgaatcct taaaagccgg tggtgctaga gatgttgaat tgttagcaat aggtcaattg    540

atcggtgccg ctggttcctt agttagtaga agatgtggta tggttggtag aggtgacaga    600

tcccctatgg ttagtgtatt gaatgttgac ccagcaagaa tggccgaatt gttagacgaa    660

tttgctcaag atgttagaac tgtattgcca cctgcattat caatcagaaa cggtagaaga    720

tccgttgtaa ttactggtac accagaacaa ttagctagat tcgaattgta ttgcgaaaag    780

attaccgaaa aggaagaagc tgaaagaaag aataagacta gaggtggtgc aatttttaga    840

ccaatattca atcaattgaa cgtcgaagtt ggttttcata cacctagatt ggctggtggt    900

attgatttgg ttaacgaatg ggcagccaga actggtttgg atagagaatt aactagagaa    960

ttgaccgaaa ctatcttcgt caagccagtt gattgggtat cagaagtcga aggtttggct   1020

gctgctggtg ctaaatggat tgttgactta ggtccatccg atacagtcac cagattgact   1080

gcacctgtta taagaggttt aggtattggt atagttgctg ctgctacaag agctggtcaa   1140

agatcattgt ttactgtagg tgcagaacca gctgtcgcac ctgcctggtc ttcttatgct   1200

ccaaagcctg tagccttgcc agatggttct gtcaaagcat ctactaagtt cactagatta   1260

acaggtagat cacctatctt gttagctggt atgacaccaa ccactgtcga tgctaaaatt   1320

gttgctgctg ctgctaatgc aggtcactgg gctgaattgg ctggtggtgg tcaagttacc   1380

gaagaaattt ttgatgccag aatcgctgaa ttaactcaat tgttagaacc aggtagagct   1440

gttcaattca atagtttgtt tttagatcca tacttgtgga agttacaatt gggtggtaaa   1500

agattagttc aaaaggctag acaatctggt gcaccaatag atggtgtcgt tgtaactgct   1560

ggtatccctg acttagaaga agcagttgat ttgatcgaag aattgcatac agtaggtata   1620

tcaaacgtcg tttttaaacc aggtactgtt gatcaaatta aatccgtaat caagattgca   1680

gccgaagttc ctggtagaga tgtaatagtc cacgttgaag gtggtagagc tggtggtcat   1740

cactcttggg aagatttgga tgacttgtta ttgtctactt atggtgactt gagaaagcat   1800

tccaacataa ctatctgtgt tggtggtggt ataggtacac cagaaagagc tgctgaatat   1860

ttgtctggtg actgggccaa aacttacggt tttccagcta tgcctgtaga tggtatcttg   1920
```

```
gtcggtactg ctgctatggc tactttagaa gccacaacct ctccagctgt taagcaatta   1980
ttggtagaca ctacaggtac tgatacatgg gttggtgctg gtaaagccat ttctggtatg   2040
gcttctggta gatcacaatt aggtgcagac atccatgaaa ttgataatac tgcttccaga   2100
tgcggtagat tattggatga agttgcaggt gacgctgacg cagtagccga aagaagagac   2160
gaaattatag cagctatggc tgatactgca aaaccatact ttggtgacgt cgctgatatg   2220
acatatttgc aatggttaca aagatacgtt gaattggcta ttggtgacgg tgacagtacc   2280
gcagatactg ctgcaccagg ttctccttgg ttagctgata catggagaga aagatttgaa   2340
gaaatgttga ccagagctga agcaagatta catgaaaagg atagtggtcc tatcgaatct   2400
ttgttcgccg ctggtccaga atcacaagca ttgttggata atcctgatac agcaattgca   2460
gccttattgg ccagatatcc agatgctgaa acagttaaat tgcacccagc tgacgtccca   2520
tttttcgtta ccttatgtaa aaagccaggt aaacctgtaa actttgtacc agtcattgat   2580
aaggacgtca gaagatggtg gagatcagat tcattatggc aagcccatga cgctagatac   2640
actgctgatc aagtctgcat cattccaggt acacaagccg ttgctggtat taccagagta   2700
gacgaacctg tcggtgaatt attggataga ttcgaacaag aaatcgttga cagaattttg   2760
gcaacaggtg ccgaaccagt acctgtagtc agtagaagac aagcaagagc cgatgtagct   2820
ggtcctttag cagttgtatt ggactctcca gatgttttat gggccggtag aactgctgtt   2880
aatcctgtac acagaattgg tgctccaggc gaatggcaag tcaatgatgt tccaggtaaa   2940
ccttctgcaa cacatccaaa caccggtgca agattagaat tggccggtga cggttccgtt   3000
accttaagtg tacctttgtc tgacatttgg atagatatca gattcacttt gccagcaacc   3060
actgttgatg gtggtgcccc tatcgttaca gtagaagacg cttcaaccgc aatgagagcc   3120
gtcttggcta ttgctgctgg tgttgacggt ccagatgcat tacctgccgt tgaaaattca   3180
accgctactg tctccgttga atgggaccca gaaaaggtcg ctgatcatac aggtgttaca   3240
gcaacctttg gtgctccatt ggcacctggt ttaaccttgg tcccagatgc tttggttggt   3300
ttatgttggc cagctgtttt tgccgctgtt ggttcagctt taactgatga cggtttccca   3360
gtcgttgaag gtttattgtc cttggttcat ttggatcacg cagcccattt gttggcaact   3420
atgcctgcca caaaatctga attgaccgtt tcagctactg catctgctgc tgttgataca   3480
gaagtcggta gagtagtccc agtagacgtc accatcgctg attctgaagg tacagttttg   3540
gccaccttag gtgaaagatt tgctattaga ggtagaactg gtgcagttga attaacagat   3600
ccacctagag ccggtggtgc tattacagac aatgctactg atactccaag aagaagaaga   3660
agagatgttg tagtcaacgc acctgttgac atgtcagcct tcgctgttgt atccggtgac   3720
cacaatccaa tacatactga tagagccgct gcattattgg ctggtttgaa aatgcctatc   3780
gttcacggta tgtggttatc tgccgctgca caacatgcag ttaccgccac tgatggtaga   3840
gctaccccac ctgcaagatt ggttggttgg acttcaagat ttttgggtat ggtattgcca   3900
ggtgacgaaa ttgagtttag agtagacaga gttggtatcg atagaggtgc tgaaattgtt   3960
gaagtagccg ctaaagtagg tggtgaattg gtcatgtctg caactgccca attagcagcc   4020
cctaaaacag tttatgcttt tccaggtcaa ggtattcaat caaagggtat gggtatggat   4080
gtcagagcaa gatccaaggc tgcaagagct gtttgggaca cagcagataa gtttactaga   4140
gaaaccttag gtttctctgt tttgcacgtc gttagagata acccaactag tttaatagct   4200
tctggtgtcc attatcatca ccctgaaggt gttttatact tgactcaatt cactcaagtt   4260
gctatggcaa cagtagccgc tgcacaagtc gccgaaatga gagaacaagg tgctttcgta   4320
```

```
gaaggtgcca ttgcttgtgg tcatagtgtc ggtgaatata ctgcattggc ctgcgtttct   4380
ggtgtatacg aattaccagc tttattggaa gtagtctttc acagaggttc taagatgcat   4440
gacattgttc caagagatgc tcaaggtaga tcaaattata gattggccgc tatcagacct   4500
tcccaaattg atttggatga cgcagacgtt aaagatttca tagccgaaat cagtgataga   4560
actggtgaat ttttggaaat cgttaacttc aacttaagag gttctcaata cgctatcgca   4620
ggtactgttg ctggtttgga agcattggaa gcagaagtag aaaagagaag agaattgtct   4680
ggtggtaaaa gatcctttat tttagttcca ggtatcgatg tacctttcca ttccagtgtt   4740
ttgagagtcg gtgttgccga ttttagaaga gctttagaaa gagttatgcc agatcctaat   4800
gatccagact tattagtagg tagatatatt cctaacttgg tcccaagacc ttttacatta   4860
gatagagact tcgtacaaga aattagagat ttggtcccag cagaaccttt agacgaaata   4920
ttggctgatt acgacacttg gagaaacgaa agaccaaacg aattatgtag aaaattggta   4980
atagaattat tggcctggca atttgcttct cctgtcagat ggatcgaaac tcaagatttg   5040
ttgtttatcg aagaagcagc cggtggtttg ggtgttgaaa gattcgtaga aattggtgtc   5100
aagaatgcac caaccgttgc cggtttagct gcaaacactt tgaaattgcc tgaatactct   5160
cataacacaa ccgaagtatt gaacgctgaa agagatgccg ctgtcttatt tgcaacagat   5220
accgacccag aacctgattt ggacgaacca gctggtgact ctgcaccagc tgctgaagct   5280
gcaccagccg aagctgttcc agccgctcca gctgctccag ctccagctgc tgctccatca   5340
ggtggtccaa gacctgatga cattactttc gacgccagtg atgctacaat ggcattgatc   5400
gccttgtctg ctaagatcag aatcgaccaa atcgaaccat tagattccat agaaagtata   5460
actgatggtg cttcttcaag aagaaaccaa atgttggttg atttgggttc agaattaaac   5520
ttgggtgcaa ttgacggtgc tgctgaagca gatttggccg gtttaaaagc acaagttaca   5580
aagttggcca gaacctataa accatttggc ctgttttaag tgacgctata aatgatcaag   5640
tcagaacagt tttcggtcca tctggtaaaa gacctgcata catcggtgaa agagtcaaaa   5700
agacttggga attgggtgaa ggttgggtta aacacgtaac cgtcgaagtt gctttaggta   5760
ctagagaagg ttccagtgtt agaggtggtg cattgggtgg tttacatgac ggtgcattag   5820
ccgatgctgc tgctgttgat aaagctattg atgctgctgt ttctgctgtt gcagccagaa   5880
gaggtgtagc tgtctctttg ccatctgctg ctggtgccgc tggtggtgtt gtagatagtg   5940
cagccttggg tgaatttgct gaacaagtaa ccggtcctga tggtgtcttg gcatctgctg   6000
caagaactat attagatcaa ttgggtttgg gtgctccatt cgttacacct gacgctagtg   6060
cagatgccga attgattgat ttggttaccg cagaattggg ttctgactgg ccaagattag   6120
ttgcacctgt attcgatggt agaaaggctg ttttattgga tgacagatgg gcttcagcta   6180
gagaagattt ggttagaatt tggttgatgg acgaaggtga catagaagct gattgggtta   6240
gattgtccga aagattcgaa ggtgcaggtc atgtcgttgg tactcaagcc acttattggc   6300
agggtaaagc attggccgct ggtagaaatg ttcacgcctc tttatatgct agagcagccg   6360
ctggtgcaga aaacccagcc actggtagat accatgatga agttgcagta gtcacaggtg   6420
cctccaaagg tagtattgca gcctcagttg tagctcaatt attggatggt ggtgctactg   6480
tcgttgcaac tacatccaag ttagatgacg ctagattggc attctacaga gaattataca   6540
gagataacgc cagattcggt gctaaattgt gggttttacc agccaatatg gcttcataca   6600
acgatattga cgctttggtc gaatgggttg gtacagaaca aaccgaatca ttaggtccaa   6660
```

```
aatccataca tttgaaggat gctttgactc ctacattatt gtttccattc gctgcaccta   6720
gagttggtgg tgacttgtca gatgctggtt ccagaagtga aatggaaatg aaagtcttat   6780
tgtgggcagt tcaaagatta ataggtggtt tgtctcacat ctcttcagat agagacattg   6840
ccgctagatt acatgtagtc ttgccaggtt cacctaatag aggcatgttt ggtggtgacg   6900
gtgcttatgg tgaatccaag gcagccttag atgcagttgt agccagatgg aaagctgaaa   6960
caagttgggc acaaagagtt tctttagccc acgctttgat aggttggact agaggtacag   7020
gtttgatggg tcataacgac gttatcgtag atgcagtaga agaagccggt gtcaccactt   7080
actcaactga acaaatggct tccatgttat tggacttatg tgatgttgaa actaaggtag   7140
ctgctgctag agaaccagtt caagctgatt tgacaggtgg tttggcagaa gccgaattag   7200
atttgagtgc tttggcaaca aaagctagag aagatgcaac ctctgcccca gctgatgacg   7260
ctgaagatga cgaagctgct gatcatttga ttgccgcttt gccatcacca cctagacctg   7320
ctgttacagc accagcccct gaatgggcag atttggacgt tgatccagcc gatatggtcg   7380
ttatagtagg tggtgctgaa ttaggtcctt atggttccag tagaactaga tacgaaatgg   7440
aagtcgataa tgaattgtct gctgctggtg ttttagaatt ggcttggaca accggtttga   7500
ttaaatggga agatgaccca agacctggtt ggtatgactc tgattctggt gaattgatag   7560
atgaatcaga aatcgttgaa agataccacg acgaagtagt ctccagatgc ggtattagag   7620
aatttgttga tgacggtgct atagacccag atcatgcaag tcctttattg gtctctgttt   7680
tcttagacaa ggattttaga ttcgttgtat cttcagaagc tgatgcaaga gcctttgttg   7740
aatttgaccc agaacataca gctgcaagac caatccctga ctctggtgac tgggaagtca   7800
taagaaaagc tggtactgaa atcagagttc caagaaaaac taagttgtcc agaacagtag   7860
gtgcacaaat tccaaccggt tttgatccta ctgtttgggg tatcagtcct gacatggcta   7920
cttctattga tagagttgca ttgtggaata tagtagccac agtcgatgca tttttgtctt   7980
ctggtttcac cccaactgaa ttattgagat gggttcaccc ttcacaagta gcttccaccc   8040
aaggtactgg tatgggtggt atgactagta tgcaaacaat gtatcatggt aatttgttgg   8100
gtagatcaaa gccaaacgat atcttacaag aagttttgcc taacgtcgtt gccgctcacg   8160
tcatgcaaag ttatgttggt ggttacggtg ctatggttca tccagtagca gcctgtgcta   8220
ctgtagcagt ctctgttgaa gaaggtgttg ataagatcag attgggtaaa gccgaatttg   8280
tagtcgctgg tggtttcgat gacttaacct tggaagctat aatcggtttt ggtgacatgg   8340
ctgcaactgc cgatacagaa accatgagag caaaaggtat ctccgattca agattttcaa   8400
gagctaatga cagaagaaga ttgggtttct tagaagctca aggtggtggt actattttat   8460
tggcaaacgg tgctttagca ttgcaaatgg gtttgccagt tttagctgtt gtaggttacg   8520
cacaaagttt tgccgatggt gttcatactt ctataccagc acctggtttg ggtggtttag   8580
gtgctggcag aggtggtaga gaatctcaat tggctagatc cttggcaaag ttaggtgttg   8640
gtgccgatga catcgctgtc gttagtaaac acgacacttc tacattagct aatgatccaa   8700
acgaaacaga attacatgaa agattggccg atgctttagg tagagcacca ggtaatcctt   8760
tgttcgtagt ctctcaaaaa tcattaactg gtcactctaa gggtggtgcc gctgcattcc   8820
aattgatggg tttatgtcaa atgttaagag atggtgtcat tccacctaac agatcattgg   8880
actgcgttga tgacgaatta gccacttccg ctcattttgt ttggccaaga gaaacattaa   8940
gattgggtga caaatatcct ttgaaggctg gtttagttac aagtttgggt tttggtcacg   9000
tttctggttt gattgcctta gtacatccac aagcattttt ggccgcttta gcacctgaac   9060
```

```
aaagagcagc ctacactgca caagcccaag aaagagcttt ggcaggtcaa agaagattag   9120

cctctgctat tgcaggtggt agaccaatgt ttgaaagacc tgctgataga agattcgacg   9180

gtgaccaacc agaaaagact caagaagctg ctatgttatt ggaccctgcc tcaagattag   9240

gtgaaaatgg tgtttacaga agatga                                         9266
```

<210> SEQ ID NO 40
<211> LENGTH: 402
<212> TYPE: DNA
<213> ORGANISM: Artificial sequnce
<220> FEATURE:
<223> OTHER INFORMATION: Synthetic sequence codon-optimized for expression in Saccharomcyes cerevisiae based on protein sequence from Mycobacterium vaccae

<400> SEQUENCE: 40

```
atgttgccag tcggtatagt tggtattggt attgatttgg tttctatccc agaatttgca     60

gaacaagtag acagacctgg tactgtcttt gctgaaactt tcacacctgg tgaaagaaga    120

gatgctgctg ataaatcttc atccgccgct agacatttgg cagccagatg ggctgcaaaa    180

gaagcagtaa ttaaggcctg gagtggttca agattcgcca agagaccagt cttacctgaa    240

gctatccata gagatatcga agttattaca gacatgtggg gtagaccaag agttagattg    300

tcaggtgccg tagctgaaca cttaaaggaa gttaccatcc atttgtcctt aacccacgaa    360

gctgatactg ctgctgctgt tgcagtattg gaagaaagat aa                       402
```

<210> SEQ ID NO 41
<211> LENGTH: 6902
<212> TYPE: DNA
<213> ORGANISM: Artificial sequence
<220> FEATURE:
<223> OTHER INFORMATION: Expression vector

<400> SEQUENCE: 41

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatcga ctacgtcgta aggccgtttc tgacagagta aaattcttga gggaactttc    240

accattatgg gaaatggttc aagaaggtat tgacttaaac tccatcaaat ggtcaggtca    300

ttgagtgttt tttatttgtt gtattttttt tttttagag aaaatcctcc aatatcaaat    360

taggaatcgt agtttcatga ttttctgtta cacctaactt tttgtgtggt gccctcctcc    420

ttgtcaatat taatgttaaa gtgcaattct tttccttat cacgttgagc cattagtatc    480

aatttgctta cctgtattcc tttactatcc tcctttttct ccttcttgat aaatgtatgt    540

agattgcgta tatagtttcg tctaccctat gaacatattc cattttgtaa tttcgtgtcg    600

tttctattat gaatttcatt tataaagttt atgtacaaat atcataaaaa aagagaatct    660

ttttaagcaa ggattttctt aacttcttcg gcgacagcat caccgacttc ggtggtactg    720

ttggaaccac ctaaatcacc agttctgata cctgcatcca aaaccttttt aactgcatct    780

tcaatggcct taccttcttc aggcaagttc aatgacaatt tcaacatcat tgcagcagac    840

aagatagtgg cgatagggtc aaccttattc tttggcaaat ctggagcaga accgtggcat    900

ggttcgtaca aaccaaatgc ggtgttcttg tctggcaaag aggccaagga cgcagatggc    960

aacaaaccca aggaacctgg gataacggag gcttcatcgg agatgatatc accaaacatg   1020
```

-continued

```
ttgctggtga ttataatacc atttaggtgg gttgggttct taactaggat catggcggca   1080
gaatcaatca attgatgttg aaccttcaat gtagggaatt cgttcttgat ggtttcctcc   1140
acagtttttc tccataatct tgaagaggcc aaaacattag ctttatccaa ggaccaaata   1200
ggcaatggtg gctcatgttg tagggccatg aaagcggcca ttcttgtgat tctttgcact   1260
tctggaacgg tgtattgttc actatcccaa gcgacaccat caccatcgtc ttcctttctc   1320
ttaccaaagt aaatacctcc cactaattct ctgacaacaa cgaagtcagt acctttagca   1380
aattgtggct tgattggaga taagtctaaa agagagtcgg atgcaaagtt acatggtctt   1440
aagttggcgt acaattgaag ttctttacgg atttttagta aaccttgttc aggtctaaca   1500
ctaccggtac cccatttagg accacccaca gcacctaaca aaacggcatc aaccttcttg   1560
gaggcttcca gcgcctcatc tggaagtggg acacctgtag catcgatagc agcaccacca   1620
attaaatgat tttcgaaatc gaacttgaca ttggaacgaa catcagaaat agctttaaga   1680
accttaatgg cttcggctgt gatttcttga ccaacgtggt cacctggcaa aacgacgatc   1740
ttcttagggg cagacatagg ggcagacatt agaatggtat atccttgaaa tatatatata   1800
tattgctgaa atgtaaaagg taagaaaagt tagaaagtaa gacgattgct aaccacctat   1860
tggaaaaaac aataggtcct taaataatat tgtcaacttc aagtattgtg atgcaagcat   1920
ttagtcatga acgcttctct attctatatg aaaagccggt tccggcctct cacctttcct   1980
ttttctccca atttttcagt tgaaaaaggt atatgcgtca ggcgacctct gaaattaaca   2040
aaaaatttcc agtcatcgaa tttgattctg tgcgatagcg cccctgtgtg ttctcgttat   2100
gttgaggaaa aaaataatgg ttgctaagag attcgaactc ttgcatctta cgatacctga   2160
gtattcccac agttaactgc ggtcaagata tttcttgaat caggcgcctt agaccgctcg   2220
gccaaacaac caattacttg ttgagaaata gagtataatt atcctataaa tataacgttt   2280
ttgaacacac atgaacaagg aagtacagga caattgattt tgaagagaat gtggattttg   2340
atgtaattgt tgggattcca tttttaataa ggcaataata ttaggtatgt ggatatacta   2400
gaagttctcc tcgaccgtcg atatgcggtg tgaaataccg cacagatgcg taaggagaaa   2460
ataccgcatc aggaaattgt aaacgttaat attttgttaa aattcgcgtt aaatttttgt   2520
taaatcagct cattttttaa ccaataggcc gaaatcggca aaatccctta taaatcaaaa   2580
gaatagaccg agatagggtt gagtgttgtt ccagtttgga acaagagtcc actattaaag   2640
aacgtggact ccaacgtcaa agggcgaaaa accgtctatc agggcgatgg cccactacgt   2700
gaaccatcac cctaatcaag ttttttgggg tcgaggtgcc gtaaagcact aaatcggaac   2760
cctaaaggga gcccccgatt tagagcttga cggggaaagc cggcgaacgt ggcgagaaag   2820
gaagggaaga aagcgaaagg agcgggcgct agggcgctgg caagtgtagc ggtcacgctg   2880
cgcgtaacca ccacacccgc cgcgcttaat gcgccgctac agggcgcgtc gcgccattcg   2940
ccattcaggc tgcgcaactg ttgggaaggg cgatcggtgc gggcctcttc gctattacgc   3000
cagctggcga aagggggatg tgctgcaagg cgattaagtt gggtaacgcc agggttttcc   3060
cagtcacgac gttgtaaaac gacggccagt gagcgcgcgt aatacgactc actatagggc   3120
gaattgggta ccggccgcaa attaaagcct tcgagcgtcc caaaaccttc tcaagcaagg   3180
ttttcagtat aatgttacat gcgtacacgc gtctgtacag aaaaaaaaga aaaatttgaa   3240
atataaataa cgttcttaat actaacataa ctataaaaaa ataaataggg acctagactt   3300
caggttgtct aactccttcc ttttcggtta gagcggatgt ggggggaggg cgtgaatgta   3360
agcgtgacat aactaattac atgactcgag gtcgacggta tcgataagct tgatatcgaa   3420
```

```
ttcctgcagc ccgggggatc cactagttct agatccgtcg aaactaagtt cttggtgttt   3480
taaaactaaa aaaaagacta actataaaag tagaatttaa gaagtttaag aaatagattt   3540
acagaattac aatcaatacc taccgtcttt atatacttat tagtcaagta ggggaataat   3600
ttcagggaac tggtttaaac cttttttttc agctttttcc aaatcagaga gagcagaagg   3660
taatagaagg tgtaagaaaa tgagatagat acatgcgtgg gtcaattgcc ttgtgtcatc   3720
atttactcca ggcaggttgc atcactccat tgaggttgtg cccgtttttt gcctgtttgt   3780
gccctgttct ctgtagttgc gctaagagaa tggacctatg aactgatggt tggtgaagaa   3840
aacaatattt tggtgctggg attctttttt tttctggatg ccagcttaaa aagcgggctc   3900
cattatattt agtggatgcc aggaataaac ctgttcaccc aagcaccatc agtgttatat   3960
attctgtgta acccgccccc tattttggca tgtacgggtt acagcagaat taaaaggcta   4020
attttttgac taaataaagt taggaaaatc actactatta attatttacg tattctttga   4080
aatggcagta ttgataatga taaactcgag agctccagct tttgttccct ttagtgaggg   4140
ttaattgcgc gcttggcgta atcatggtca tagctgtttc ctgtgtgaaa ttgttatccg   4200
ctcacaattc cacacaacat aggagccgga agcataaagt gtaaagcctg gggtgcctaa   4260
tgagtgaggt aactcacatt aattgcgttg cgctcactgc ccgctttcca gtcgggaaac   4320
ctgtcgtgcc agctgcatta atgaatcggc caacgcgcgg ggagaggcgg tttgcgtatt   4380
gggcgctctt ccgcttcctc gctcactgac tcgctgcgct cggtcgttcg gctgcggcga   4440
gcggtatcag ctcactcaaa ggcggtaata cggttatcca cagaatcagg ggataacgca   4500
ggaaagaaca tgtgagcaaa aggccagcaa aaggccagga accgtaaaaa ggccgcgttg   4560
ctggcgtttt tccataggct ccgcccccct gacgagcatc acaaaaatcg acgctcaagt   4620
cagaggtggc gaaacccgac aggactataa agataccagg cgtttccccc tggaagctcc   4680
ctcgtgcgct ctcctgttcc gaccctgccg cttaccggat acctgtccgc ctttctccct   4740
tcgggaagcg tggcgctttc tcatagctca cgctgtaggt atctcagttc ggtgtaggtc   4800
gttcgctcca agctgggctg tgtgcacgaa ccccccgttc agcccgaccg ctgcgcctta   4860
tccggtaact atcgtcttga gtccaacccg gtaagacacg acttatcgcc actggcagca   4920
gccactggta acaggattag cagagcgagg tatgtaggcg gtgctacaga gttcttgaag   4980
tggtggccta actacggcta cactagaagg acagtatttg gtatctgcgc tctgctgaag   5040
ccagttacct tcggaaaaag agttggtagc tcttgatccg gcaaacaaac caccgctggt   5100
agcggtggtt tttttgtttg caagcagcag attacgcgca gaaaaaaagg atctcaagaa   5160
gatcctttga tcttttctac ggggtctgac gctcagtgga acgaaaactc acgttaaggg   5220
attttggtca tgagattatc aaaaaggatc ttcacctaga tccttttaaa ttaaaaatga   5280
agttttaaat caatctaaag tatatatgag taaacttggt ctgacagtta ccaatgctta   5340
atcagtgagg cacctatctc agcgatctgt ctatttcgtt catccatagt tgcctgactc   5400
cccgtcgtgt agataactac gatacgggag ggcttaccat ctggccccag tgctgcaatg   5460
ataccgcgag acccacgctc accggctcca gatttatcag caataaacca gccagccgga   5520
agggccgagc gcagaagtgg tcctgcaact ttatccgcct ccatccagtc tattaattgt   5580
tgccgggaag ctagagtaag tagttcgcca gttaatagtt tgcgcaacgt tgttgccatt   5640
gctacaggca tcgtggtgtc acgctcgtcg tttggtatgg cttcattcag ctccggttcc   5700
caacgatcaa ggcgagttac atgatccccc atgttgtgca aaaaagcggt tagctccttc   5760
```

```
ggtcctccga tcgttgtcag aagtaagttg gccgcagtgt tatcactcat ggttatggca   5820
gcactgcata attctcttac tgtcatgcca tccgtaagat gcttttctgt gactggtgag   5880
tactcaacca agtcattctg agaatagtgt atgcggcgac cgagttgctc ttgcccggcg   5940
tcaatacggg ataataccgc gccacatagc agaactttaa aagtgctcat cattggaaaa   6000
cgttcttcgg ggcgaaaact ctcaaggatc ttaccgctgt tgagatccag ttcgatgtaa   6060
cccactcgtg cacccaactg atcttcagca tcttttactt tcaccagcgt ttctgggtga   6120
gcaaaaacag gaaggcaaaa tgccgcaaaa aagggaataa gggcgacacg gaaatgttga   6180
atactcatac tcttcctttt tcaatattat tgaagcattt atcagggtta ttgtctcatg   6240
agcggataca tatttgaatg tatttagaaa aataaacaaa taggggttcc gcgcacattt   6300
ccccgaaaag tgccacctgg gtccttttca tcacgtgcta taaaaataat tataatttaa   6360
atttttaat ataaatatat aaattaaaaa tagaaagtaa aaaaagaaat taaagaaaaa   6420
atagttttg ttttccgaag atgtaaaaga ctctaggggg atcgccaaca aatactacct   6480
tttatcttgc tcttcctgct ctcaggtatt aatgccgaat tgtttcatct tgtctgtgta   6540
gaagaccaca cacgaaaatc ctgtgatttt acattttact tatcgttaat cgaatgtata   6600
tctatttaat ctgcttttct tgtctaataa atatatatgt aaagtacgct ttttgttgaa   6660
attttttaaa cctttgttta tttttttttc ttcattccgt aactcttcta ccttctttat   6720
ttactttcta aaatccaaat acaaaacata aaaataaata aacacagagt aaattcccaa   6780
attattccat cattaaaaga tacgaggcgc gtgtaagtta caggcaagcg atccgtccta   6840
agaaaccatt attatcatga cattaaccta taaaaatagg cgtatcacga ggccctttcg   6900
tc                                                                  6902
```

<210> SEQ ID NO 42
<211> LENGTH: 1476
<212> TYPE: DNA
<213> ORGANISM: Artificial seuqnece
<220> FEATURE:
<223> OTHER INFORMATION: Synthetic sequence codon-optimized for expression in Saccharomcyes cerevisiae based on protein sequence from Arabidopsis Thaliana

<400> SEQUENCE: 42

```
atggaatcta attgtgttca attcttgggt aataagacta tcttgatcac aggtgcacca     60
ggtttcttgg ctaaggtttt ggttgaaaag attttgagat tgcaaccaaa tgttaagaaa    120
atatatttgt tgttgagagc accagatgaa aaatctgcta tgcaaagatt gagatcagaa    180
gttatggaaa ttgatttgtt taaagttttg agaaacaatt tgggtgaaga taatttgaac    240
gctttgatga gagaaaagat tgttccagtt ccaggtgaca tctctatcga taatttgggt    300
ttgaaggata ctgatttgat ccaaagaatg tggtcagaaa tcgatatcat tattaacatt    360
gctgcaacta caaacttcga tgaaagatac gatattggtt taggtattaa tacattcggt    420
gcattaaacg ttttgaactt cgctaagaaa tgtgttaagg gtcaattgtt gttgcatgtt    480
tctactgctt acatttcagg tgaacaacca ggtttgttat tggaaaagcc ttttaaaatg    540
ggtgaaacat tgtctggtga cagagaatta gatatcaaca tcgaacatga tttgatgaaa    600
caaaaattga aagaattgca agattgttct gatgaagaaa tttcacaaac tatgaaggat    660
tttggtatgg caagagctaa attgcatggt tggccaaaca cttatgtttt tacaaaggca    720
atgggtgaaa tgttgatggg taaatacaga gaaaatttgc cattggttat tatcagacca    780
actatgatca cttctacaat tgctgaacca tttccaggtt ggatcgaagg tttgaagaca    840
```

```
ttggattcag ttattgttgc ttatggtaaa ggtagattga agtgtttctt ggctgattct    900

aattcagttt tcgatttgat cccagcagat atggttgtta atgctatggt tgctgctgct    960

actgcacatt caggtgacac aggtattcaa gctatctatc atgttggttc ttcatgcaag   1020

aacccagtta ctttcggtca attgcatgat ttcacagcaa gatacttcgc taaaagacca   1080

ttaatcggta gaaacggttc tccaatcatc gttgttaagg gtactatctt atctacaatg   1140

gcacaatttt cattgtacat gacattgaga tacaaattgc cattgcaaat tttaagattg   1200

attaatatcg tttacccttg gtctcatggt gacaactact ctgatttgtc aagaaaaatt   1260

aaattggcta tgagattggt tgaattgtac caaccatact tattgtttaa aggtattttt   1320

gatgatttga atactgaaag attgagaatg aagagaaagg aaaacatcaa agaattggat   1380

ggttcttttg aatttgatcc aaagtcaatc gattgggata actacatcac taacacacat   1440

atcccaggtt tgatcacaca tgttttgaaa caataa                             1476
```

<210> SEQ ID NO 43
<211> LENGTH: 32
<212> TYPE: DNA
<213> ORGANISM: Artificial sequence
<220> FEATURE:
<223> OTHER INFORMATION: PCR Primer

<400> SEQUENCE: 43

```
aggggatcc aaaaaaatgc gtccattaca tc                                  32
```

<210> SEQ ID NO 44
<211> LENGTH: 33
<212> TYPE: DNA
<213> ORGANISM: Artificial sequence
<220> FEATURE:
<223> OTHER INFORMATION: PCR primer

<400> SEQUENCE: 44

```
agggtcgact tagtttgcag ttttgatatc ctc                                33
```

<210> SEQ ID NO 45
<211> LENGTH: 30
<212> TYPE: DNA
<213> ORGANISM: Artificial sequence
<220> FEATURE:
<223> OTHER INFORMATION: PCR primer

<400> SEQUENCE: 45

```
aggggatcc aaaaaaatga agagattagg                                     30
```

<210> SEQ ID NO 46
<211> LENGTH: 27
<212> TYPE: DNA
<213> ORGANISM: Artificial sequence
<220> FEATURE:
<223> OTHER INFORMATION: PCR primer

<400> SEQUENCE: 46

```
aaggtcgact tactttctag tacgggc                                       27
```

<210> SEQ ID NO 47
<211> LENGTH: 50
<212> TYPE: DNA
<213> ORGANISM: Artificial sequence
<220> FEATURE:
<223> OTHER INFORMATION: PCR primer

<400> SEQUENCE: 47
taagttttaa ttacaaggat ccaaaaaaat gcgtccatta catccaattg 50

<210> SEQ ID NO 48
<211> LENGTH: 54
<212> TYPE: DNA
<213> ORGANISM: Artificial sequence
<220> FEATURE:
<223> OTHER INFORMATION: PCR primer

<400> SEQUENCE: 48
tcttagctag ccgcggtacc ttagtttgca gttttgatat cctcttgttt tgcg 54

<210> SEQ ID NO 49
<211> LENGTH: 50
<212> TYPE: DNA
<213> ORGANISM: Artificial sequence
<220> FEATURE:
<223> OTHER INFORMATION: PCR primer

<400> SEQUENCE: 49
taagttttaa ttacaaggat ccaaaaaaat gaaagccgaa aaagttatgg 50

<210> SEQ ID NO 50
<211> LENGTH: 55
<212> TYPE: DNA
<213> ORGANISM: Artificial sequence
<220> FEATURE:
<223> OTHER INFORMATION: PCR primer

<400> SEQUENCE: 50
tcttagctag ccgcggtacc ttaaacttca gtcttatgaa aaatttcacc ttggg 55

<210> SEQ ID NO 51
<211> LENGTH: 50
<212> TYPE: DNA
<213> ORGANISM: Artificial Sequence
<220> FEATURE:
<223> OTHER INFORMATION: PCR primer

<400> SEQUENCE: 51
taagttttaa ttacaaggat ccaaaaaaat gttcaccatt ccaagaagag 50

<210> SEQ ID NO 52
<211> LENGTH: 60
<212> TYPE: DNA
<213> ORGANISM: Artificial sequence
<220> FEATURE:
<223> OTHER INFORMATION: PCR primer

<400> SEQUENCE: 52
cttagctagc cgcggtacca agcttttata ctgataaacc caaagatctg aattgtcttc 60

<210> SEQ ID NO 53
<211> LENGTH: 50
<212> TYPE: DNA
<213> ORGANISM: Artificial sequence
<220> FEATURE:
<223> OTHER INFORMATION: PCR primer

<400> SEQUENCE: 53
taagttttaa ttacaaggat ccaaaaaaat gaagagatta ggtactctag 50

<210> SEQ ID NO 54
<211> LENGTH: 49

<212> TYPE: DNA
<213> ORGANISM: Artificial sequence
<220> FEATURE:
<223> OTHER INFORMATION: Artificial sequence

<400> SEQUENCE: 54
tcttagctag ccgcggtacc ttactttcta gtacgggcac gcttctttg 49

<210> SEQ ID NO 55
<211> LENGTH: 55
<212> TYPE: DNA
<213> ORGANISM: Artificial sequence
<220> FEATURE:
<223> OTHER INFORMATION: Artificial sequence

<400> SEQUENCE: 55
taagttttaa ttacaaggat ccaaaaaaat ggaagtagaa aaagaattga aaacc 55

<210> SEQ ID NO 56
<211> LENGTH: 54
<212> TYPE: DNA
<213> ORGANISM: Artificial sequence
<220> FEATURE:
<223> OTHER INFORMATION: Artificial sequence

<400> SEQUENCE: 56
tcttagctag ccgcggtacc ttaccaacct aacaaaccca tcaatttctt ttgg 54

<210> SEQ ID NO 57
<211> LENGTH: 22
<212> TYPE: DNA
<213> ORGANISM: Artificial sequence
<220> FEATURE:
<223> OTHER INFORMATION: Artificial sequence

<400> SEQUENCE: 57
ggggtggttt agtttagtag aa 22

<210> SEQ ID NO 58
<211> LENGTH: 22
<212> TYPE: DNA
<213> ORGANISM: Artificial sequences
<220> FEATURE:
<223> OTHER INFORMATION: PCR primer

<400> SEQUENCE: 58
gcaacctgac ctacaggaaa ga 22

<210> SEQ ID NO 59
<211> LENGTH: 24
<212> TYPE: DNA
<213> ORGANISM: Artificial sequence
<220> FEATURE:
<223> OTHER INFORMATION: Artificial sequence

<400> SEQUENCE: 59
ttttacttct tgctcattag aaag 24

<210> SEQ ID NO 60
<211> LENGTH: 21
<212> TYPE: DNA
<213> ORGANISM: Artificial sequence
<220> FEATURE:
<223> OTHER INFORMATION: PCR primer

<400> SEQUENCE: 60
ggacctagac ttcaggttgt c 21

<210> SEQ ID NO 61
<211> LENGTH: 21
<212> TYPE: DNA
<213> ORGANISM: Artificial sequence
<220> FEATURE:
<223> OTHER INFORMATION: PCR primer

<400> SEQUENCE: 61
tctggccacc aaatggtatc g 21

<210> SEQ ID NO 62
<211> LENGTH: 25
<212> TYPE: DNA
<213> ORGANISM: Artificial sequence
<220> FEATURE:
<223> OTHER INFORMATION: PCR primer

<400> SEQUENCE: 62
tcgcagaaga aatctatcca gtatc 25

<210> SEQ ID NO 63
<211> LENGTH: 25
<212> TYPE: DNA
<213> ORGANISM: Artificial sequence
<220> FEATURE:
<223> OTHER INFORMATION: PCR primer

<400> SEQUENCE: 63
tagattcttc ttctacctgg ttcac 25

<210> SEQ ID NO 64
<211> LENGTH: 25
<212> TYPE: DNA
<213> ORGANISM: Artificial sequence
<220> FEATURE:
<223> OTHER INFORMATION: Artificial sequence

<400> SEQUENCE: 64
tgctacgtta atggtatgaa ctctg 25

<210> SEQ ID NO 65
<211> LENGTH: 23
<212> TYPE: DNA
<213> ORGANISM: Artificial sequence
<220> FEATURE:
<223> OTHER INFORMATION: PCR primer

<400> SEQUENCE: 65
tgattggcat gtgctaccat tgc 23

<210> SEQ ID NO 66
<211> LENGTH: 26
<212> TYPE: DNA
<213> ORGANISM: Artificial sequence
<220> FEATURE:
<223> OTHER INFORMATION: PCR primer

<400> SEQUENCE: 66
tgcttacgtt tcaggtgaaa agaatg 26

<210> SEQ ID NO 67
<211> LENGTH: 23
<212> TYPE: DNA
<213> ORGANISM: Artificial sequence
<220> FEATURE:
<223> OTHER INFORMATION: PCR primer

<400> SEQUENCE: 67
agaactggag acgtggtaaa cag 23

<210> SEQ ID NO 68
<211> LENGTH: 23
<212> TYPE: DNA
<213> ORGANISM: Artificial sequence
<220> FEATURE:
<223> OTHER INFORMATION: PCR primer

<400> SEQUENCE: 68
acgtatctac cgcatatgta gcc 23

<210> SEQ ID NO 69
<211> LENGTH: 26
<212> TYPE: DNA
<213> ORGANISM: Artificial sequence
<220> FEATURE:
<223> OTHER INFORMATION: PCR primer

<400> SEQUENCE: 69
acagaaaagt caattgtacc accttg 26

<210> SEQ ID NO 70
<211> LENGTH: 25
<212> TYPE: DNA
<213> ORGANISM: Artificial sequence
<220> FEATURE:
<223> OTHER INFORMATION: PCR primer

<400> SEQUENCE: 70
atctctgcaa aggatcatcc ttatg 25

<210> SEQ ID NO 71
<211> LENGTH: 27
<212> TYPE: DNA
<213> ORGANISM: Artificial sequence
<220> FEATURE:
<223> OTHER INFORMATION: PCR primer

<400> SEQUENCE: 71
tggcatgttc tagaaagata tcagatc 27

<210> SEQ ID NO 72
<211> LENGTH: 21
<212> TYPE: DNA
<213> ORGANISM: Artificial sequence
<220> FEATURE:
<223> OTHER INFORMATION: PCR primer

<400> SEQUENCE: 72
accccatcta cacttggaac c 21

<210> SEQ ID NO 73
<211> LENGTH: 24
<212> TYPE: DNA
<213> ORGANISM: Artificial sequence
<220> FEATURE:
<223> OTHER INFORMATION: PCR primer

<400> SEQUENCE: 73
accaatttta cctcatggtg acac 24

<210> SEQ ID NO 74
<211> LENGTH: 20
<212> TYPE: DNA
<213> ORGANISM: Artificial sequence
<220> FEATURE:
<223> OTHER INFORMATION: PCR primer

<400> SEQUENCE: 74
tccagaaacc ggtggctaac 20

<210> SEQ ID NO 75
<211> LENGTH: 25
<212> TYPE: DNA
<213> ORGANISM: Artificial sequence
<220> FEATURE:
<223> OTHER INFORMATION: PCR primer

<400> SEQUENCE: 75
tccaaccctt ccttaagttt gttac 25

<210> SEQ ID NO 76
<211> LENGTH: 25
<212> TYPE: DNA
<213> ORGANISM: Artificial sequence
<220> FEATURE:
<223> OTHER INFORMATION: PCR primer

<400> SEQUENCE: 76
atgcatcaaa ccagaaacgg taaag 25

<210> SEQ ID NO 77
<211> LENGTH: 63
<212> TYPE: DNA
<213> ORGANISM: Artificial sequence
<220> FEATURE:
<223> OTHER INFORMATION: PCR primer

<400> SEQUENCE: 77
ttatctactt tttacaacaa atataacaaa aaaatgccaa cttctggaac tactattgaa 60
ttg 63

<210> SEQ ID NO 78
<211> LENGTH: 62
<212> TYPE: DNA
<213> ORGANISM: Artificial sequence
<220> FEATURE:
<223> OTHER INFORMATION: PCR primer

<400> SEQUENCE: 78
aataaaaatc ataaatcata agaaattcgc ttaaaagaac ttaccagttt cgtagatttc 60
ac 62

<210> SEQ ID NO 79
<211> LENGTH: 56
<212> TYPE: DNA
<213> ORGANISM: Artificial sequence
<220> FEATURE:
<223> OTHER INFORMATION: PCR primer

<400> SEQUENCE: 79
ttatctactt tttacaacaa atataacaaa aaaatggtat tcatggcctc atcaac 56

<210> SEQ ID NO 80
<211> LENGTH: 62

<212> TYPE: DNA
<213> ORGANISM: Artificial sequence
<220> FEATURE:
<223> OTHER INFORMATION: PCR primer

<400> SEQUENCE: 80
aataaaaatc ataaatcata agaaattcgc ttaaaccttt aattccttat taaaaatcca 60
tg 62

<210> SEQ ID NO 81
<211> LENGTH: 64
<212> TYPE: DNA
<213> ORGANISM: Artificial sequence
<220> FEATURE:
<223> OTHER INFORMATION: PCR primer

<400> SEQUENCE: 81
aactacaaaa aacacataca taaactaaaa aaatgacttc cgtaaacgta aaattattgt 60
atag 64

<210> SEQ ID NO 82
<211> LENGTH: 56
<212> TYPE: DNA
<213> ORGANISM: Artificial sequence
<220> FEATURE:
<223> OTHER INFORMATION: PCR primer

<400> SEQUENCE: 82
aaaaaactat atcaattaat ttgaattaac ttaagaacga ccgttttgta cgtgag 56

<210> SEQ ID NO 83
<211> LENGTH: 60
<212> TYPE: DNA
<213> ORGANISM: Artificial sequence
<220> FEATURE:
<223> OTHER INFORMATION: PCR primer

<400> SEQUENCE: 83
tacaaaaaac acatacataa actaaaaaaa tgacatctat taatgttaaa ttgttgtacc 60

<210> SEQ ID NO 84
<211> LENGTH: 60
<212> TYPE: DNA
<213> ORGANISM: Artificial sequence
<220> FEATURE:
<223> OTHER INFORMATION: PCR primer

<400> SEQUENCE: 84
aaaaaactat atcaattaat ttgaattaac ttatgatcta ccattttgtg ctctagtttc 60

<210> SEQ ID NO 85
<211> LENGTH: 60
<212> TYPE: DNA
<213> ORGANISM: Artificial sequence
<220> FEATURE:
<223> OTHER INFORMATION: PCR primer

<400> SEQUENCE: 85
tacaaaaaac acatacataa actaaaaaaa tgacttctat taatgttaaa ttgttgtacc 60

<210> SEQ ID NO 86
<211> LENGTH: 60
<212> TYPE: DNA
<213> ORGANISM: Artificial sequence
<220> FEATURE:

<223> OTHER INFORMATION: PCR primer

<400> SEQUENCE: 86
tacaaaaaac acatacataa actaaaaaaa tgacttctat taatgttaaa ttgttgtacc 60

<210> SEQ ID NO 87
<211> LENGTH: 60
<212> TYPE: DNA
<213> ORGANISM: Artificial sequence
<220> FEATURE:
<223> OTHER INFORMATION: PCR primer

<400> SEQUENCE: 87
aactacaaaa aacacataca taaactaaaa aaatgaaagc aaaaacaata acaaatcctg 60

<210> SEQ ID NO 88
<211> LENGTH: 57
<212> TYPE: DNA
<213> ORGANISM: Artificial sequence
<220> FEATURE:
<223> OTHER INFORMATION: PCR primer

<400> SEQUENCE: 88
aaaaaactat atcaattaat ttgaattaac ttaagatgct attggagcaa tcttagg 57

<210> SEQ ID NO 89
<211> LENGTH: 56
<212> TYPE: DNA
<213> ORGANISM: Artificial sequence
<220> FEATURE:
<223> OTHER INFORMATION: PCR primer

<400> SEQUENCE: 89
actacaaaaa acacatacat aaactaaaaa aatgtctggt actaaagcta catctg 56

<210> SEQ ID NO 90
<211> LENGTH: 58
<212> TYPE: DNA
<213> ORGANISM: Artificial sequence
<220> FEATURE:
<223> OTHER INFORMATION: PCR primer

<400> SEQUENCE: 90
aaaaaactat atcaattaat ttgaattaac ttaatttaat ggaacttcaa ctggaaac 58

<210> SEQ ID NO 91
<211> LENGTH: 39
<212> TYPE: DNA
<213> ORGANISM: Artificial sequence
<220> FEATURE:
<223> OTHER INFORMATION: PCR primer

<400> SEQUENCE: 91
gtttaaagat tacggatatt taacttactt agaataatg 39

<210> SEQ ID NO 92
<211> LENGTH: 30
<212> TYPE: DNA
<213> ORGANISM: Artificial sequence
<220> FEATURE:
<223> OTHER INFORMATION: PCR primer

<400> SEQUENCE: 92
cattttagtt tatgtatgtg ttttttgtag 30

<210> SEQ ID NO 93
<211> LENGTH: 36
<212> TYPE: DNA
<213> ORGANISM: Artificial sequence
<220> FEATURE:
<223> OTHER INFORMATION: PCR primer

<400> SEQUENCE: 93
gttaattcaa attaattgat atagtttttt aatgag 36

<210> SEQ ID NO 94
<211> LENGTH: 32
<212> TYPE: DNA
<213> ORGANISM: Artificial sequence
<220> FEATURE:
<223> OTHER INFORMATION: PCR primer

<400> SEQUENCE: 94
agtaagctac tatgaaagac tttacaaaga ac 32

<210> SEQ ID NO 95
<211> LENGTH: 37
<212> TYPE: DNA
<213> ORGANISM: Artificial sequnce
<220> FEATURE:
<223> OTHER INFORMATION: PCR primer

<400> SEQUENCE: 95
gataccgtcg acctcgagtc atgtaattag ttatgtc 37

<210> SEQ ID NO 96
<211> LENGTH: 35
<212> TYPE: DNA
<213> ORGANISM: Artificial sequence
<220> FEATURE:
<223> OTHER INFORMATION: PCR primer

<400> SEQUENCE: 96
gggtaccggc cgcaaattaa agccttcgag cgtcc 35

<210> SEQ ID NO 97
<211> LENGTH: 32
<212> TYPE: DNA
<213> ORGANISM: Artificial sequence
<220> FEATURE:
<223> OTHER INFORMATION: PCR primer

<400> SEQUENCE: 97
ctcgagttta tcattatcaa tactgccatt tc 32

<210> SEQ ID NO 98
<211> LENGTH: 40
<212> TYPE: DNA
<213> ORGANISM: Artificial sequence
<220> FEATURE:
<223> OTHER INFORMATION: PCR primer

<400> SEQUENCE: 98
gtttgtttat gtgtgtttat tcgaaactaa gttcttggtg 40

<210> SEQ ID NO 99
<211> LENGTH: 59
<212> TYPE: DNA
<213> ORGANISM: Artificial sequence
<220> FEATURE:
<223> OTHER INFORMATION: PCR primer

<400> SEQUENCE: 99
gtattctttg aaatggcagt attgataatg ataaactcga gctcgtagga acaatttcg 59

<210> SEQ ID NO 100
<211> LENGTH: 40
<212> TYPE: DNA
<213> ORGANISM: Artificial sequence
<220> FEATURE:
<223> OTHER INFORMATION: PCR primer

<400> SEQUENCE: 100 catttttga ttaaaattaa aaaaactttt tgtttttgtg 40

<210> SEQ ID NO 101
<211> LENGTH: 38
<212> TYPE: DNA
<213> ORGANISM: Artificial sequence
<220> FEATURE:
<223> OTHER INFORMATION: PCR primer

<400> SEQUENCE: 101
atttaactcc ttaagttact ttaatgattt agtttta 38

<210> SEQ ID NO 102
<211> LENGTH: 24
<212> TYPE: DNA
<213> ORGANISM: Artificial sequence
<220> FEATURE:
<223> OTHER INFORMATION: PCR primer

<400> SEQUENCE: 102
gcgaaaagcc aattagtgtg atac 24

<210> SEQ ID NO 103
<211> LENGTH: 40
<212> TYPE: DNA
<213> ORGANISM: Artificial sequence
<220> FEATURE:
<223> OTHER INFORMATION: PCR primer

<400> SEQUENCE: 103
gcgaatttct tatgatttat gatttttatt attaaataag 40

<210> SEQ ID NO 104
<211> LENGTH: 36
<212> TYPE: DNA
<213> ORGANISM: Artificial sequence
<220> FEATURE:
<223> OTHER INFORMATION: PCR primer

<400> SEQUENCE: 104
gcatatctac aattgggtga aatggggagc gatttg 36

<210> SEQ ID NO 105
<211> LENGTH: 31
<212> TYPE: DNA
<213> ORGANISM: Artificial sequence
<220> FEATURE:
<223> OTHER INFORMATION: PCR primer

<400> SEQUENCE: 105
cgcacagata ttataacatc tgcacaatag g 31

<210> SEQ ID NO 106
<211> LENGTH: 37

<212> TYPE: DNA
<213> ORGANISM: Artificial sequence
<220> FEATURE:
<223> OTHER INFORMATION: PCR primer

<400> SEQUENCE: 106
cattttgtta tatttgttgt aaaaagtaga taattac 37

<210> SEQ ID NO 107
<211> LENGTH: 34
<212> TYPE: DNA
<213> ORGANISM: Artificial sequence
<220> FEATURE:
<223> OTHER INFORMATION: PCR primer

<400> SEQUENCE: 107
atagcttcaa aatgtttcta ctcctttttt actc 34

<210> SEQ ID NO 108
<211> LENGTH: 33
<212> TYPE: DNA
<213> ORGANISM: Artificial sequence
<220> FEATURE:
<223> OTHER INFORMATION: PCR primer

<400> SEQUENCE: 108
tttgtaatta aaacttagat tagattgcta tgc 33

<210> SEQ ID NO 109
<211> LENGTH: 36
<212> TYPE: DNA
<213> ORGANISM: Artificial sequence
<220> FEATURE:
<223> OTHER INFORMATION: PCR primer

<400> SEQUENCE: 109
tagggcccac aagcttacgc gtcgacccgg gtatcc 36

<210> SEQ ID NO 110
<211> LENGTH: 31
<212> TYPE: DNA
<213> ORGANISM: Artificial sequence
<220> FEATURE:
<223> OTHER INFORMATION: PCR primer

<400> SEQUENCE: 110
gccgtaaacc actaaatcgg aaccctaaag g 31

<210> SEQ ID NO 111
<211> LENGTH: 36
<212> TYPE: DNA
<213> ORGANISM: Artificial sequence
<220> FEATURE:
<223> OTHER INFORMATION: PCR primer

<400> SEQUENCE: 111
agcagaatta tgaataataa acattgatga caatag 36

<210> SEQ ID NO 112
<211> LENGTH: 57
<212> TYPE: DNA
<213> ORGANISM: Artificial sequence
<220> FEATURE:
<223> OTHER INFORMATION: PCR primer

<400> SEQUENCE: 112
acattatacg aacggtaatt aagggttgtc gactgtttat gtttcgtaaa caaacgg 57

<210> SEQ ID NO 113
<211> LENGTH: 56
<212> TYPE: DNA
<213> ORGANISM: Artificial sequence
<220> FEATURE:
<223> OTHER INFORMATION: PCR primer

<400> SEQUENCE: 113
tgtatgctat acgaacggta tatcagatcc ataggaagcg agaatttttg acagcg 56

<210> SEQ ID NO 114
<211> LENGTH: 28
<212> TYPE: DNA
<213> ORGANISM: Artificial sequence
<220> FEATURE:
<223> OTHER INFORMATION: PCR primer

<400> SEQUENCE: 114
tagataatga tgctgggccg ataattag 28

<210> SEQ ID NO 115
<211> LENGTH: 34
<212> TYPE: DNA
<213> ORGANISM: Artificial sequence
<220> FEATURE:
<223> OTHER INFORMATION: PCR primer

<400> SEQUENCE: 115
tgcgtcgtta gatttctggg gttaagatag caac 34

<210> SEQ ID NO 116
<211> LENGTH: 39
<212> TYPE: DNA
<213> ORGANISM: Artificial sequence
<220> FEATURE:
<223> OTHER INFORMATION: PCR primer

<400> SEQUENCE: 116
tattggagag ctagaacaac caatgaactt cattgaaga 39

<210> SEQ ID NO 117
<211> LENGTH: 29
<212> TYPE: DNA
<213> ORGANISM: Artificial sequence
<220> FEATURE:
<223> OTHER INFORMATION: PCR primer

<400> SEQUENCE: 117
gacaaccctt aattaccgtt cgtataatg 29

<210> SEQ ID NO 118
<211> LENGTH: 24
<212> TYPE: DNA
<213> ORGANISM: Artificial sequence
<220> FEATURE:
<223> OTHER INFORMATION: PCR primer

<400> SEQUENCE: 118
caacctatta atttcccctc gtca 24

<210> SEQ ID NO 119
<211> LENGTH: 20
<212> TYPE: DNA
<213> ORGANISM: Artificial sequence
<220> FEATURE:
<223> OTHER INFORMATION: PCR primer

<400> SEQUENCE: 119
ggcaaaacag cattccaggt 20

<210> SEQ ID NO 120
<211> LENGTH: 25
<212> TYPE: DNA
<213> ORGANISM: Artificial sequence
<220> FEATURE:
<223> OTHER INFORMATION: PCR primer

<400> SEQUENCE: 120
ggatctgata taccgttcgt atagc 25

<210> SEQ ID NO 121
<211> LENGTH: 30
<212> TYPE: DNA
<213> ORGANISM: Artificial sequence
<220> FEATURE:
<223> OTHER INFORMATION: PCR primer

<400> SEQUENCE: 121
gaaattttca ttatgtgtta gagagagacg 30

<210> SEQ ID NO 122
<211> LENGTH: 34
<212> TYPE: DNA
<213> ORGANISM: Artificial sequence
<220> FEATURE:
<223> OTHER INFORMATION: PCR primer

<400> SEQUENCE: 122
ctatggtgtg tgcgttggta gatacgttgt tgac 34

<210> SEQ ID NO 123
<211> LENGTH: 32
<212> TYPE: DNA
<213> ORGANISM: Artificial sequence
<220> FEATURE:
<223> OTHER INFORMATION: PCR primer

<400> SEQUENCE: 123
gtatctacca acgcacacac catagcttca aa 32

<210> SEQ ID NO 124
<211> LENGTH: 48
<212> TYPE: DNA
<213> ORGANISM: Artificial sequence
<220> FEATURE:
<223> OTHER INFORMATION: PCR primer

<400> SEQUENCE: 124
gataaagaaa aattgttgaa gactttgaaa taaatccgct ctaaccga 48

<210> SEQ ID NO 125
<211> LENGTH: 33
<212> TYPE: DNA
<213> ORGANISM: Artificial sequence
<220> FEATURE:
<223> OTHER INFORMATION: PCR primer

<400> SEQUENCE: 125
gactttgaaa taaatccgct ctaaccgaaa agg 33

<210> SEQ ID NO 126
<211> LENGTH: 28
<212> TYPE: DNA
<213> ORGANISM: Artificial sequence
<220> FEATURE:
<223> OTHER INFORMATION: PCR primer

<400> SEQUENCE: 126
ctttgtagaa cagctctctc ttaaacac 28

<210> SEQ ID NO 127
<211> LENGTH: 60
<212> TYPE: DNA
<213> ORGANISM: Artificial sequence
<220> FEATURE:
<223> OTHER INFORMATION: PCR primer

<400> SEQUENCE: 127
gtttcgaata aacacacata aacaaacaaa aaaatgtcaa ctatttccga taatcaatgc 60

<210> SEQ ID NO 128
<211> LENGTH: 63
<212> TYPE: DNA
<213> ORGANISM: Artificial sequence
<220> FEATURE:
<223> OTHER INFORMATION: PCR primer

<400> SEQUENCE: 128
ctaattacat gactcgaggt cgacggtatc ttaaactatc attctgcaca ttcttaatat 60
agc 63

<210> SEQ ID NO 129
<211> LENGTH: 57
<212> TYPE: DNA
<213> ORGANISM: Artificial sequence
<220> FEATURE:
<223> OTHER INFORMATION: PCR primer

<400> SEQUENCE: 129
gtttcgaata aacacacata aacaaacaaa aaaatggcaa tccaacaagt tcaccac 57

<210> SEQ ID NO 130
<211> LENGTH: 58
<212> TYPE: DNA
<213> ORGANISM: Artificial sequence
<220> FEATURE:
<223> OTHER INFORMATION: PCR primer

<400> SEQUENCE: 130
ctaattacat gactcgaggt cgacggtatc ttatgctgct ttctttcttt gtcttgcg 58

<210> SEQ ID NO 131
<211> LENGTH: 63
<212> TYPE: DNA
<213> ORGANISM: Artificial sequence
<220> FEATURE:
<223> OTHER INFORMATION: PCR primer

<400> SEQUENCE: 131
gtttcgaata aacacacata aacaaacaaa aaaatggaag aaatgggttc aatcttggaa 60
ttc 63

<210> SEQ ID NO 132
<211> LENGTH: 59

<212> TYPE: DNA
<213> ORGANISM: Artificial sequence
<220> FEATURE:
<223> OTHER INFORMATION: PCR primer

<400> SEQUENCE: 132
ctaattacat gactcgaggt cgacggtatc ttagttcaat acatgttcaa cgacaccag 59

<210> SEQ ID NO 133
<211> LENGTH: 60
<212> TYPE: DNA
<213> ORGANISM: Artificial sequence
<220> FEATURE:
<223> OTHER INFORMATION: PCR primer

<400> SEQUENCE: 133
gtttcgaata aacacacata aacaaacaaa aaaatggttg atacattgtc tgaagaaaac 60

<210> SEQ ID NO 134
<211> LENGTH: 60
<212> TYPE: DNA
<213> ORGANISM: Artificial sequence
<220> FEATURE:
<223> OTHER INFORMATION: PCR primer

<400> SEQUENCE: 134
ctaattacat gactcgaggt cgacggtatc ttatttcaac atgtatttta tgacacctgg 60

<210> SEQ ID NO 135
<211> LENGTH: 58
<212> TYPE: DNA
<213> ORGANISM: Artificial sequence
<220> FEATURE:
<223> OTHER INFORMATION: PCR primer

<400> SEQUENCE: 135
acaaaaagtt tttttaattt taatcaaaaa aatgcgtcca ttacatccaa ttgatttc 58

<210> SEQ ID NO 136
<211> LENGTH: 62
<212> TYPE: DNA
<213> ORGANISM: Artificial sequence
<220> FEATURE:
<223> OTHER INFORMATION: PCR primer

<400> SEQUENCE: 136
aaatcattaa agtaacttaa ggagttaaat ttagtttgca gttttgatat cctcttgttt 60
tg 62

<210> SEQ ID NO 137
<211> LENGTH: 59
<212> TYPE: DNA
<213> ORGANISM: Artificial sequence
<220> FEATURE:
<223> OTHER INFORMATION: PCR primer

<400> SEQUENCE: 137
acaaaaagtt tttttaattt taatcaaaaa aatgaaagcc gaaaaagtta tggaaagag 59

<210> SEQ ID NO 138
<211> LENGTH: 63
<212> TYPE: DNA
<213> ORGANISM: Artificial sequence
<220> FEATURE:
<223> OTHER INFORMATION: PCR primer

<400> SEQUENCE: 138
aaatcattaa agtaacttaa ggagttaaat ttaaacttca gtcttatgaa aaatttcacc 60
ttg 63

<210> SEQ ID NO 139
<211> LENGTH: 58
<212> TYPE: DNA
<213> ORGANISM: Artificial sequence
<220> FEATURE:
<223> OTHER INFORMATION: PCR primer

<400> SEQUENCE: 139
acaaaaagtt tttttaattt taatcaaaaa aatgttcacc attccaagaa gagtcaag 58

<210> SEQ ID NO 140
<211> LENGTH: 62
<212> TYPE: DNA
<213> ORGANISM: Artificial sequence
<220> FEATURE:
<223> OTHER INFORMATION: PCR primer

<400> SEQUENCE: 140
aaatcattaa agtaacttaa ggagttaaat ttatactgat aaacccaaag atctgaattg 60
tc 62

<210> SEQ ID NO 141
<211> LENGTH: 63
<212> TYPE: DNA
<213> ORGANISM: Artificial sequence
<220> FEATURE:
<223> OTHER INFORMATION: PCR primer

<400> SEQUENCE: 141
acaaaaagtt tttttaattt taatcaaaaa aatggaagta gaaaaagaat tgaaaacctt 60
tag 63

<210> SEQ ID NO 142
<211> LENGTH: 58
<212> TYPE: DNA
<213> ORGANISM: Artificial sequence
<220> FEATURE:
<223> OTHER INFORMATION: PCR primer

<400> SEQUENCE: 142
aaatcattaa agtaacttaa ggagttaaat ttaccaacct aacaaaccca tcaatttc 58

<210> SEQ ID NO 143
<211> LENGTH: 61
<212> TYPE: DNA
<213> ORGANISM: Artificial sequence
<220> FEATURE:
<223> OTHER INFORMATION: PCR primer

<400> SEQUENCE: 143
tagcaatcta atctaagttt taattacaaa atgaattcac tcgttactca atatgctgct 60
c 61

<210> SEQ ID NO 144
<211> LENGTH: 60
<212> TYPE: DNA
<213> ORGANISM: Artificial sequence
<220> FEATURE:
<223> OTHER INFORMATION: PCR primer

<400> SEQUENCE: 144
gggtcgacgc gtaagcttgt gggccctatt accttttttct tctgtgttga ggttttggtg 60

<210> SEQ ID NO 145
<211> LENGTH: 28
<212> TYPE: DNA
<213> ORGANISM: Artificial sequence
<220> FEATURE:
<223> OTHER INFORMATION: PCR primer
<220> FEATURE:
<221> NAME/KEY: modified_base
<222> LOCATION: (9)..(9)
<223> OTHER INFORMATION: deoxyuracil
<220> FEATURE:
<221> NAME/KEY: misc_feature
<222> LOCATION: (9)..(9)
<223> OTHER INFORMATION: n is a, c, g, or t

<400> SEQUENCE: 145
agtgcaggna tgagtgagta tttcccac 28

<210> SEQ ID NO 146
<211> LENGTH: 28
<212> TYPE: DNA
<213> ORGANISM: Artificial sequence
<220> FEATURE:
<223> OTHER INFORMATION: PCR primer
<220> FEATURE:
<221> NAME/KEY: modified_base
<222> LOCATION: (8)..(8)
<223> OTHER INFORMATION: deoxyuracil
<220> FEATURE:
<221> NAME/KEY: misc_feature
<222> LOCATION: (8)..(8)
<223> OTHER INFORMATION: n is a, c, g, or t

<400> SEQUENCE: 146
cgtgcgantt atgctcgtcg agatcggg 28

<210> SEQ ID NO 147
<211> LENGTH: 31
<212> TYPE: DNA
<213> ORGANISM: Artificial sequence
<220> FEATURE:
<223> OTHER INFORMATION: PCR primer
<220> FEATURE:
<221> NAME/KEY: modified_base
<222> LOCATION: (9)..(9)
<223> OTHER INFORMATION: deoxyuracil
<220> FEATURE:
<221> NAME/KEY: misc_feature
<222> LOCATION: (9)..(9)
<223> OTHER INFORMATION: n is a, c, g, or t

<400> SEQUENCE: 147
atctgtcana tggtgaaaaa cgtggaccaa g 31

<210> SEQ ID NO 148
<211> LENGTH: 23
<212> TYPE: DNA
<213> ORGANISM: Artificial sequence
<220> FEATURE:
<223> OTHER INFORMATION: PCR primer

<400> SEQUENCE: 148
ctaagcagcc atgccagaca tac 23

<210> SEQ ID NO 149

<211> LENGTH: 60
<212> TYPE: DNA
<213> ORGANISM: Artificial sequence
<220> FEATURE:
<223> OTHER INFORMATION: PCR primer

<400> SEQUENCE: 149
aagcgataat taccctgtta tccctagaat cgatgataag ctgtcaaaca tgagaattcg 60

<210> SEQ ID NO 150
<211> LENGTH: 36
<212> TYPE: DNA
<213> ORGANISM: Artificial sequence
<220> FEATURE:
<223> OTHER INFORMATION: PCR primer

<400> SEQUENCE: 150
tgcgatcgca cgcattcccc cacgttgccg gtcttg 36

<210> SEQ ID NO 151
<211> LENGTH: 41
<212> TYPE: DNA
<213> ORGANISM: Artificial sequence
<220> FEATURE:
<223> OTHER INFORMATION: PCR primer

<400> SEQUENCE: 151
aagaccggca acgtggggga atgcgtgcga tcgcagccta c 41

<210> SEQ ID NO 152
<211> LENGTH: 42
<212> TYPE: DNA
<213> ORGANISM: Artificial sequence
<220> FEATURE:
<223> OTHER INFORMATION: PCR primer

<400> SEQUENCE: 152
tagcttagat accacagaca cgaatgcacg cgatcgctgc gc 42

<210> SEQ ID NO 153
<211> LENGTH: 51
<212> TYPE: DNA
<213> ORGANISM: Artificial sequence
<220> FEATURE:
<223> OTHER INFORMATION: PCR primer

<400> SEQUENCE: 153
tcggcgcagc gatcgcgtgc attcgtgtct gtggtatcta agctatttat c 51

<210> SEQ ID NO 154
<211> LENGTH: 44
<212> TYPE: DNA
<213> ORGANISM: Artificial sequence
<220> FEATURE:
<223> OTHER INFORMATION: PCR primer

<400> SEQUENCE: 154
tgtagcaccg cctacatacc tcgctctgct aatcctgtta ccag 44

<210> SEQ ID NO 155
<211> LENGTH: 43
<212> TYPE: DNA
<213> ORGANISM: Artificial sequence
<220> FEATURE:
<223> OTHER INFORMATION: PCR primer

<400> SEQUENCE: 155
agcgaggtat gtaggcggtg ctacagagtt cttgaagtgg tgg 43

<210> SEQ ID NO 156
<211> LENGTH: 56
<212> TYPE: DNA
<213> ORGANISM: Artificial sequence
<220> FEATURE:
<223> OTHER INFORMATION: PCR primer

<400> SEQUENCE: 156
tgcccgtgtc cgaattctca tgtttgacag cttatcatcg attctaggga taacag 56

<210> SEQ ID NO 157
<211> LENGTH: 30
<212> TYPE: DNA
<213> ORGANISM: Artificial sequence
<220> FEATURE:
<223> OTHER INFORMATION: PCR primer
<220> FEATURE:
<221> NAME/KEY: modified_base
<222> LOCATION: (9)..(9)
<223> OTHER INFORMATION: deoxyuracil
<220> FEATURE:
<221> NAME/KEY: misc_feature
<222> LOCATION: (9)..(9)
<223> OTHER INFORMATION: n is a, c, g, or t

<400> SEQUENCE: 157
agtgcaggna tgtctactat ttccgataac 30

<210> SEQ ID NO 158
<211> LENGTH: 27
<212> TYPE: DNA
<213> ORGANISM: Artificial sequence
<220> FEATURE:
<223> OTHER INFORMATION: PCR primer
<220> FEATURE:
<221> NAME/KEY: modified_base
<222> LOCATION: (8)..(8)
<223> OTHER INFORMATION: deoxyuracil
<220> FEATURE:
<221> NAME/KEY: misc_feature
<222> LOCATION: (8)..(8)
<223> OTHER INFORMATION: n is a, c, g, or t

<400> SEQUENCE: 158
cgtgcgantt acacaatcat tcggcac 27

<210> SEQ ID NO 159
<211> LENGTH: 28
<212> TYPE: DNA
<213> ORGANISM: Artificial sequence
<220> FEATURE:
<223> OTHER INFORMATION: PCR primer
<220> FEATURE:
<221> NAME/KEY: modified_base
<222> LOCATION: (9)..(9)
<223> OTHER INFORMATION: deoxyuracil
<220> FEATURE:
<221> NAME/KEY: misc_feature
<222> LOCATION: (9)..(9)
<223> OTHER INFORMATION: n is a, c, g, or t

<400> SEQUENCE: 159
agtgcaggna tggccatcca gcaggtgc 28

<210> SEQ ID NO 160
<211> LENGTH: 29
<212> TYPE: DNA

<213> ORGANISM: Artificial sequence
<220> FEATURE:
<223> OTHER INFORMATION: PCR primer
<220> FEATURE:
<221> NAME/KEY: modified_base
<222> LOCATION: (8)..(8)
<223> OTHER INFORMATION: deoxyuracil
<220> FEATURE:
<221> NAME/KEY: misc_feature
<222> LOCATION: (8)..(8)
<223> OTHER INFORMATION: n is a, c, g, or t

<400> SEQUENCE: 160
cgtgcgantt aagcggcctt ctttcgctg 29

<210> SEQ ID NO 161
<211> LENGTH: 30
<212> TYPE: DNA
<213> ORGANISM: Artificial sequence
<220> FEATURE:
<223> OTHER INFORMATION: PCR primer
<220> FEATURE:
<221> NAME/KEY: modified_base
<222> LOCATION: (9)..(9)
<223> OTHER INFORMATION: deoxyuracil
<220> FEATURE:
<221> NAME/KEY: misc_feature
<222> LOCATION: (9)..(9)
<223> OTHER INFORMATION: n is a, c, g, or t

<400> SEQUENCE: 161
agtgcaggna tggaggagat gggctccatc 30

<210> SEQ ID NO 162
<211> LENGTH: 29
<212> TYPE: DNA
<213> ORGANISM: Artificial sequence
<220> FEATURE:
<223> OTHER INFORMATION: PCR primer
<220> FEATURE:
<221> NAME/KEY: modified_base
<222> LOCATION: (8)..(8)
<223> OTHER INFORMATION: deoxyuracil
<220> FEATURE:
<221> NAME/KEY: misc_feature
<222> LOCATION: (8)..(8)
<223> OTHER INFORMATION: n is a, c, g, or t

<400> SEQUENCE: 162
cgtgcgantt agttgagcac gtgctcgac 29

<210> SEQ ID NO 163
<211> LENGTH: 28
<212> TYPE: DNA
<213> ORGANISM: Artificial sequence
<220> FEATURE:
<223> OTHER INFORMATION: PCR primer
<220> FEATURE:
<221> NAME/KEY: modified_base
<222> LOCATION: (9)..(9)
<223> OTHER INFORMATION: deoxyuracil
<220> FEATURE:
<221> NAME/KEY: misc_feature
<222> LOCATION: (9)..(9)
<223> OTHER INFORMATION: n is a, c, g, or t

<400> SEQUENCE: 163
agtgcaggna tggtggacac cctgtctg 28

<210> SEQ ID NO 164
<211> LENGTH: 34

<212> TYPE: DNA
<213> ORGANISM: Artificial sequence
<220> FEATURE:
<223> OTHER INFORMATION: PCR primer
<220> FEATURE:
<221> NAME/KEY: modified_base
<222> LOCATION: (8)..(8)
<223> OTHER INFORMATION: deoxyuracil
<220> FEATURE:
<221> NAME/KEY: misc_feature
<222> LOCATION: (8)..(8)
<223> OTHER INFORMATION: n is a, c, g, or t

<400> SEQUENCE: 164
cgtgcgantt acttcagcat gtacttaatc acac 34

<210> SEQ ID NO 165
<211> LENGTH: 30
<212> TYPE: DNA
<213> ORGANISM: Artificial sequence
<220> FEATURE:
<223> OTHER INFORMATION: PCR primer
<220> FEATURE:
<221> NAME/KEY: modified_base
<222> LOCATION: (9)..(9)
<223> OTHER INFORMATION: deoxyuracil
<220> FEATURE:
<221> NAME/KEY: misc_feature
<222> LOCATION: (9)..(9)
<223> OTHER INFORMATION: n is a, c, g, or t

<400> SEQUENCE: 165
atctgtcana tgcgacccct gcaccccatc 30

<210> SEQ ID NO 166
<211> LENGTH: 36
<212> TYPE: DNA
<213> ORGANISM: Artificial sequence
<220> FEATURE:
<223> OTHER INFORMATION: PCR primer
<220> FEATURE:
<221> NAME/KEY: modified_base
<222> LOCATION: (8)..(8)
<223> OTHER INFORMATION: deoxyuracil
<220> FEATURE:
<221> NAME/KEY: misc_feature
<222> LOCATION: (8)..(8)
<223> OTHER INFORMATION: n is a, c, g, or t

<400> SEQUENCE: 166
cacgcgantt agttggcggt cttaatgtct tcctgc 36

<210> SEQ ID NO 167
<211> LENGTH: 30
<212> TYPE: DNA
<213> ORGANISM: Artificial sequence
<220> FEATURE:
<223> OTHER INFORMATION: PCR primer
<220> FEATURE:
<221> NAME/KEY: modified_base
<222> LOCATION: (9)..(9)
<223> OTHER INFORMATION: deoxyuracil
<220> FEATURE:
<221> NAME/KEY: misc_feature
<222> LOCATION: (9)..(9)
<223> OTHER INFORMATION: n is a, c, g, or t

<400> SEQUENCE: 167
atctgtcana tgaaggccga gaaggtcatg 30

<210> SEQ ID NO 168

<211> LENGTH: 33
<212> TYPE: DNA
<213> ORGANISM: Artificial sequence
<220> FEATURE:
<223> OTHER INFORMATION: PCR primer
<220> FEATURE:
<221> NAME/KEY: modified_base
<222> LOCATION: (8)..(8)
<223> OTHER INFORMATION: deoxyuracil
<220> FEATURE:
<221> NAME/KEY: misc_feature
<222> LOCATION: (8)..(8)
<223> OTHER INFORMATION: n is a, c, g, or t

<400> SEQUENCE: 168
cacgcgantt agacctcggt cttgtggaaa atc 33

<210> SEQ ID NO 169
<211> LENGTH: 29
<212> TYPE: DNA
<213> ORGANISM: Artificial sequence
<220> FEATURE:
<223> OTHER INFORMATION: PCR primer
<220> FEATURE:
<221> NAME/KEY: modified_base
<222> LOCATION: (9)..(9)
<223> OTHER INFORMATION: deoxyuracil
<220> FEATURE:
<221> NAME/KEY: misc_feature
<222> LOCATION: (9)..(9)
<223> OTHER INFORMATION: n is a, c, g, or t

<400> SEQUENCE: 169
atctgtcana tgttcaccat cccccgacg 29

<210> SEQ ID NO 170
<211> LENGTH: 28
<212> TYPE: DNA
<213> ORGANISM: Artificial sequence
<220> FEATURE:
<223> OTHER INFORMATION: PCR primer
<220> FEATURE:
<221> NAME/KEY: modified_base
<222> LOCATION: (8)..(8)
<223> OTHER INFORMATION: deoxyuracil
<220> FEATURE:
<221> NAME/KEY: misc_feature
<222> LOCATION: (8)..(8)
<223> OTHER INFORMATION: n is a, c, g, or t

<400> SEQUENCE: 170
cacgcgantt acacagacag gccgaggg 28

<210> SEQ ID NO 171
<211> LENGTH: 30
<212> TYPE: DNA
<213> ORGANISM: Artificial sequence
<220> FEATURE:
<223> OTHER INFORMATION: PCR primer
<220> FEATURE:
<221> NAME/KEY: modified_base
<222> LOCATION: (9)..(9)
<223> OTHER INFORMATION: deoxyuracil
<220> FEATURE:
<221> NAME/KEY: misc_feature
<222> LOCATION: (9)..(9)
<223> OTHER INFORMATION: n is a, c, g, or t

<400> SEQUENCE: 171
atctgtcana tggaggtgga gaaggagctg 30

<210> SEQ ID NO 172
<211> LENGTH: 27
<212> TYPE: DNA
<213> ORGANISM: Artificial sequence
<220> FEATURE:
<223> OTHER INFORMATION: PCR primer
<220> FEATURE:
<221> NAME/KEY: modified_base
<222> LOCATION: (8)..(8)
<223> OTHER INFORMATION: deoxyuracil
<220> FEATURE:
<221> NAME/KEY: misc_feature
<222> LOCATION: (8)..(8)
<223> OTHER INFORMATION: n is a, c, g, or t

<400> SEQUENCE: 172
cacgcgantt accaaccgag caggccc 27

<210> SEQ ID NO 173
<211> LENGTH: 21
<212> TYPE: DNA
<213> ORGANISM: Artificial sequence
<220> FEATURE:
<223> OTHER INFORMATION: PCR primer

<400> SEQUENCE: 173
aaaaagagac cgcctcgttt c 21

<210> SEQ ID NO 174
<211> LENGTH: 20
<212> TYPE: DNA
<213> ORGANISM: Artificial sequence
<220> FEATURE:
<223> OTHER INFORMATION: PCR primer

<400> SEQUENCE: 174
tgggtcccat tcaacggaga 20

<210> SEQ ID NO 175
<211> LENGTH: 20
<212> TYPE: DNA
<213> ORGANISM: Artificial sequence
<220> FEATURE:
<223> OTHER INFORMATION: PCR primer

<400> SEQUENCE: 175
catccaaaca ccggtgcaag 20

<210> SEQ ID NO 176
<211> LENGTH: 21
<212> TYPE: DNA
<213> ORGANISM: Artificial sequence
<220> FEATURE:
<223> OTHER INFORMATION: PCR primer

<400> SEQUENCE: 176
acctgtgact actgcaactt c 21

<210> SEQ ID NO 177
<211> LENGTH: 21
<212> TYPE: DNA
<213> ORGANISM: Artificial sequence
<220> FEATURE:
<223> OTHER INFORMATION: PCR primer

<400> SEQUENCE: 177
ggcttcagct agagaagatt t 21

<210> SEQ ID NO 178
<211> LENGTH: 22
<212> TYPE: DNA
<213> ORGANISM: Artificial sequence
<220> FEATURE:
<223> OTHER INFORMATION: PCR primer

<400> SEQUENCE: 178
agtataatgt tacatgcgta ca 22

<210> SEQ ID NO 179
<211> LENGTH: 63
<212> TYPE: DNA
<213> ORGANISM: Artificial sequence
<220> FEATURE:
<223> OTHER INFORMATION: PCR primer

<400> SEQUENCE: 179
atcttatcgt cgtcatcctt gtaatccatc gatactagtt tattgtttca aaacatgtgt 60
gat 63

<210> SEQ ID NO 180
<211> LENGTH: 66
<212> TYPE: DNA
<213> ORGANISM: Artificial sequence
<220> FEATURE:
<223> OTHER INFORMATION: PCR primer

<400> SEQUENCE: 180
tctacttttt acaacaaata taaaacaagc ggccgcaaaa caatggaatc taattgtgtt 60
caattc 66

<210> SEQ ID NO 181
<211> LENGTH: 62
<212> TYPE: DNA
<213> ORGANISM: Artificial sequence
<220> FEATURE:
<223> OTHER INFORMATION: PCR primer

<400> SEQUENCE: 181
ctttgaaatg gcagtattga taatgataaa ctcgagagct gagctcttcg agtttatcat 60
ta 62

<210> SEQ ID NO 182
<211> LENGTH: 67
<212> TYPE: DNA
<213> ORGANISM: Artificial sequence
<220> FEATURE:
<223> OTHER INFORMATION: PCR primer

<400> SEQUENCE: 182
gcgcaattaa ccctcactaa agggaacaaa agctggagct agtaagctac tatgaaagac 60
tttacaa 67

<210> SEQ ID NO 183
<211> LENGTH: 120
<212> TYPE: DNA
<213> ORGANISM: Artificial sequence
<220> FEATURE:
<223> OTHER INFORMATION: PCR primer

<400> SEQUENCE: 183
tgcgcatgtt tcggcgttcg aaacttctcc gcagtgaaag ataaatgatc tacatccaat 60
cttacaagaa gttttagagc tagaaatagc aagttaaaat aaggctagtc cgttatcaac 120

<210> SEQ ID NO 184
<211> LENGTH: 20
<212> TYPE: DNA
<213> ORGANISM: Artificial sequence
<220> FEATURE:
<223> OTHER INFORMATION: PCR primer

<400> SEQUENCE: 184
ctggggttaa gatagcaacg 20

<210> SEQ ID NO 185
<211> LENGTH: 53
<212> TYPE: DNA
<213> ORGANISM: Artificial sequence
<220> FEATURE:
<223> OTHER INFORMATION: PCR primer

<400> SEQUENCE: 185
cttagtatca cactaattgg cttttcgcga ctgtttatgt ttcgtaaaca aac 53

<210> SEQ ID NO 186
<211> LENGTH: 26
<212> TYPE: DNA
<213> ORGANISM: Artificial sequence
<220> FEATURE:
<223> OTHER INFORMATION: PCR primer

<400> SEQUENCE: 186
atttaactcc ttaagttact ttaatg 26

<210> SEQ ID NO 187
<211> LENGTH: 24
<212> TYPE: DNA
<213> ORGANISM: Artificial sequence
<220> FEATURE:
<223> OTHER INFORMATION: PCR primer

<400> SEQUENCE: 187
gcgaaaagcc aattagtgtg atac 24

<210> SEQ ID NO 188
<211> LENGTH: 57
<212> TYPE: DNA
<213> ORGANISM: Artificial sequence
<220> FEATURE:
<223> OTHER INFORMATION: PCR primer

<400> SEQUENCE: 188
ctaaatcatt aaagtaactt aaggagttaa atttaattgt ttttgttgat cttcttc 57

<210> SEQ ID NO 189
<211> LENGTH: 65
<212> TYPE: DNA
<213> ORGANISM: Artificial sequence
<220> FEATURE:
<223> OTHER INFORMATION: PCR primer

<400> SEQUENCE: 189
gataaaaaaa aacagttgaa tattccctca aaaaaaacaa tggtaagtga ttggaaaaat 60
ttttg 65

<210> SEQ ID NO 190

<211> LENGTH: 23
<212> TYPE: DNA
<213> ORGANISM: Artificial sequence
<220> FEATURE:
<223> OTHER INFORMATION: PCR primer

<400> SEQUENCE: 190
ttttgaggga atattcaact gtt 23

<210> SEQ ID NO 191
<211> LENGTH: 53
<212> TYPE: DNA
<213> ORGANISM: Artificial sequence
<220> FEATURE:
<223> OTHER INFORMATION: PCR primer

<400> SEQUENCE: 191
cgctcgaagg ctttaatttg cggccggtac cctttgccag cttactatcc ttc 53

<210> SEQ ID NO 192
<211> LENGTH: 20
<212> TYPE: DNA
<213> ORGANISM: Artificial sequence
<220> FEATURE:
<223> OTHER INFORMATION: PCR primer

<400> SEQUENCE: 192
gataccgtcg acctcgagtc 20

<210> SEQ ID NO 193
<211> LENGTH: 22
<212> TYPE: DNA
<213> ORGANISM: Artificial sequence
<220> FEATURE:
<223> OTHER INFORMATION: PCR primer

<400> SEQUENCE: 193
gggtaccggc cgcaaattaa ag 22

<210> SEQ ID NO 194
<211> LENGTH: 51
<212> TYPE: DNA
<213> ORGANISM: Artificial sequence
<220> FEATURE:
<223> OTHER INFORMATION: PCR primer

<400> SEQUENCE: 194
ctaattacat gactcgaggt cgacggtatc ttaccttttt cttctgtgtt g 51

<210> SEQ ID NO 195
<211> LENGTH: 62
<212> TYPE: DNA
<213> ORGANISM: Artificial sequence
<220> FEATURE:
<223> OTHER INFORMATION: PCR primer

<400> SEQUENCE: 195
caaaaaaaaa gtaagaattt ttgaaaattc aatataaaaa acaatgaatt cactcgttac 60
tc 62

<210> SEQ ID NO 196
<211> LENGTH: 22
<212> TYPE: DNA
<213> ORGANISM: Artificial sequence
<220> FEATURE:
<223> OTHER INFORMATION: PCR primer

<400> SEQUENCE: 196
ttatattgaa ttttcaaaaa tt 22

<210> SEQ ID NO 197
<211> LENGTH: 22
<212> TYPE: DNA
<213> ORGANISM: Artificial sequence
<220> FEATURE:
<223> OTHER INFORMATION: PCR primer

<400> SEQUENCE: 197
tatagttttt tctccttgac gt 22

<210> SEQ ID NO 198
<211> LENGTH: 62
<212> TYPE: DNA
<213> ORGANISM: Artificial sequence
<220> FEATURE:
<223> OTHER INFORMATION: PCR primer

<400> SEQUENCE: 198
ctatacttta acgtcaagga gaaaaaacta taaaaacaat ggaatctaat tgtgttcaat 60
tc 62

<210> SEQ ID NO 199
<211> LENGTH: 61
<212> TYPE: DNA
<213> ORGANISM: Artificial sequence
<220> FEATURE:
<223> OTHER INFORMATION: PCR primer

<400> SEQUENCE: 199
ctcattaaaa aactatatca attaatttga attaacttat tgtttcaaaa catgtgtgat 60
c 61

<210> SEQ ID NO 200
<211> LENGTH: 24
<212> TYPE: DNA
<213> ORGANISM: Artificial sequence
<220> FEATURE:
<223> OTHER INFORMATION: PCR primer

<400> SEQUENCE: 200
gttaattcaa attaattgat atag 24

<210> SEQ ID NO 201
<211> LENGTH: 25
<212> TYPE: DNA
<213> ORGANISM: Artificial sequence
<220> FEATURE:
<223> OTHER INFORMATION: PCR primer

<400> SEQUENCE: 201
agtaagctac tatgaaagac tttac 25

<210> SEQ ID NO 202
<211> LENGTH: 59
<212> TYPE: DNA
<213> ORGANISM: Artificial sequence
<220> FEATURE:
<223> OTHER INFORMATION: PCR primer

<400> SEQUENCE: 202

-continued

```
cggcttttt ccgtttgttt acgaaacata aacagtcata ggaagcgaga atttttgac      59


<210> SEQ ID NO 203
<211> LENGTH: 22
<212> TYPE: DNA
<213> ORGANISM: Artificial sequence
<220> FEATURE:
<223> OTHER INFORMATION: PCR primer

<400> SEQUENCE: 203

agttacttga tatccatgtt cc                                              22


<210> SEQ ID NO 204
<211> LENGTH: 120
<212> TYPE: DNA
<213> ORGANISM: Artificial sequence
<220> FEATURE:
<223> OTHER INFORMATION: PCR Primer

<400> SEQUENCE: 204

ctactcgtta ttattgcgta ttttgtgatg ctaaagttat gagtagaaaa aaatgagaag     60

ttgttctgaa caaagtaaaa aaaagaagta tacttatttc aaagtcttca acaatttttc    120


<210> SEQ ID NO 205
<211> LENGTH: 120
<212> TYPE: DNA
<213> ORGANISM: Artificial sequence
<220> FEATURE:
<223> OTHER INFORMATION: PCR Primer

<400> SEQUENCE: 205

tttcggtttg tattacttct tattcaaatg tcataaaagt atcaacaaaa aattgttaat     60

atacctctat actttaacgt caaggagaaa aaactataat gagcgaagaa agcttattcg    120
```